(12) United States Patent
Raker et al.

(10) Patent No.: US 9,029,536 B2
(45) Date of Patent: May 12, 2015

(54) FUSED HETEROCYCLIC COMPOUNDS

(75) Inventors: Joseph Raker, New York, NY (US);
Takahiko Taniguchi, Kanagawa (JP);
Masato Yoshikawa, Kanagawa (JP);
Tomoaki Hasui, Kanagawa (JP); Jun Kunitomo, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/814,073

(22) PCT Filed: Aug. 3, 2011

(86) PCT No.: PCT/US2011/046417
§ 371 (c)(1),
(2), (4) Date: Mar. 5, 2013

(87) PCT Pub. No.: WO2012/018909
PCT Pub. Date: Feb. 9, 2012

(65) Prior Publication Data
US 2013/0172292 A1  Jul. 4, 2013

Related U.S. Application Data

(60) Provisional application No. 61/427,271, filed on Dec. 27, 2010, provisional application No. 61/370,566, filed on Aug. 4, 2010.

(51) Int. Cl.
*C07D 471/04* (2006.01)
*C07D 471/14* (2006.01)
*C07D 519/00* (2006.01)

(52) U.S. Cl.
CPC ............ *C07D 471/04* (2013.01); *C07D 471/14* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 7,446,199 B2 | 11/2008 | Aronov et al. | |
| 8,318,793 B2 * | 11/2012 | Turner et al. | 514/412 |
| 8,383,624 B2 | 2/2013 | Penning et al. | |
| 2005/0137201 A1 | 6/2005 | Aronov et al. | |
| 2006/0122185 A1 | 6/2006 | Green et al. | |
| 2006/0258662 A1 | 11/2006 | Binch et al. | |
| 2007/0282101 A1 | 12/2007 | Ericsson et al. | |
| 2007/0287711 A1 * | 12/2007 | Arnold et al. | 514/249 |
| 2008/0045561 A1 | 2/2008 | Nemecek et al. | |
| 2008/0064719 A1 * | 3/2008 | Lanier et al. | 514/303 |

(Continued)

FOREIGN PATENT DOCUMENTS

| JP | 2007-504252 | 3/2007 |
|---|---|---|
| JP | 2010-111624 | 5/2010 |

(Continued)

OTHER PUBLICATIONS

Ye et al., 17(13) Bioorg. & Med. Chem. 4302-4312 (2009).*
Cacchi et al., 7(4) J. Combinatorial Chem. 510-512 (2005).*
International Search Report issued Oct. 17, 2011 in International (PCT) Application No. PCT/US2011/046417.
Y. M. Volovenko et al., "Synthesis and properties of 6-Amino-7-Hetaryl-5-R-5H-Pyrrolo-[2,3-*b*]Pyrazine-2,3-Dicarbonitriles", Chemistry of Heterocyclic Compounds, vol. 38, No. 3, pp. 336-343, 2002.
C. M. Harris et al., "2,4-Diaminopyrimidine MK2 Inhibitors. Part II: Structure-Based Inhibitor Optimization", Bioorganic & Medicinal Chemistry Letters, vol. 20, No. 1, pp. 334-337, 2010.
S. Cacchi et al., "The Aminopalladation-reductive Elimination Process as a Tool for the solution-Phase Synthesis of 2,3-Disubstituted Azaindole Libraries", Journal of Combinatorial Chemistry, vol. 7, No. 4, pp. 510-512, 2005.

(Continued)

*Primary Examiner* — Timothy R Rozof
(74) *Attorney, Agent, or Firm* — Wenderoth, Lind & Ponack, L.L.P.

(57) ABSTRACT

The present invention provides a compound which has the effect of PDE 10A inhibition, and which is useful as a medicament for preventing or treating schizophrenia or so on. A compound represented by the formula (1'): wherein, Ring A' represents an optionally substituted pyridine ring, an optionally substituted pyridazine ring, a pyrimidine ring, or 10 a pyrazine ring, R1' represents (1) wherein, $R^{1a'}$ represents an optionally substituted phenyl group, or an optionally substituted 5- to 10-membered heterocyclic group, Ring B2 represents a bond, —S—, -0-, —CO—, an optionally substituted methylene group, or —$NR^{a'}$— ($R^{a'}$ represents a hydrogen atom, or an optionally substituted $C_{1-6}$ alkyl group), and Ring $B^{1'}$ represents an optionally further substituted 6- to 10-membered aromatic hydrocarbon ring, or an optionally further substituted 5- to 10-membered aromatic heterocyclic ring, or alternatively, L' and $R^{1a'}$ may be taken together to form an optionally substituted bicyclic or tricyclic fused heterocyclic group, or (2), wherein, $R^{1b'}$ represents an optionally substituted phenyl group, or an optionally substituted 5- to 10-membered heterocyclic group, Ring $B^{2'}$ represents an optionally substituted benzene ring, an optionally substituted pyridine ring, an optionally substituted pyrimidine ring, an optionally substituted pyrazine ring, or an optionally substituted pyridazine ring, Ring D' represents an optionally further substituted 5- or 6-membered ring, $R^{2'}$ represents a hydrogen atom, or a substituent, X' represents =N— or =$CR^{b'}$— ($R^{b'}$ represents a hydrogen atom, or a substituent), - - - - - represents that $R^{b'}$ and $R^{2'}$ may form, taken together with the carbon atom and the nitrogen atom to which they are each adjacent, an optionally substituted 5- to 7-membered ring when X' is =$CR^{b'}$, or a salt thereof.

11 Claims, 1 Drawing Sheet

(56) References Cited

U.S. PATENT DOCUMENTS

| | | | |
|---|---|---|---|
| 2008/0090834 | A1 | 4/2008 | Hoover et al. |
| 2010/0125062 | A1 | 5/2010 | Allen et al. |
| 2010/0137278 | A1 | 6/2010 | Allen et al. |
| 2010/0152193 | A1 | 6/2010 | Alberati et al. |
| 2010/0197651 | A1 | 8/2010 | Taniguchi et al. |
| 2010/0256141 | A1 | 10/2010 | Nemecek et al. |
| 2011/0015172 | A1 | 1/2011 | Penning et al. |
| 2011/0081364 | A1 | 4/2011 | Binch et al. |
| 2011/0160182 | A1 | 6/2011 | Allen et al. |
| 2011/0160202 | A1 | 6/2011 | Allen et al. |
| 2011/0263541 | A1 | 10/2011 | Luo et al. |
| 2012/0028951 | A1 | 2/2012 | Taniguchi et al. |
| 2012/0053345 | A1 | 3/2012 | Ericson et al. |
| 2012/0277204 | A1 | 11/2012 | Taniguchi et al. |
| 2012/0277209 | A1 | 11/2012 | Allen et al. |
| 2012/0277430 | A1 | 11/2012 | Taniguchi et al. |
| 2012/0277431 | A1 | 11/2012 | Taniguchi et al. |

FOREIGN PATENT DOCUMENTS

| | | |
|---|---|---|
| WO | 2006/044821 | 4/2006 |
| WO | 2006/058074 | 6/2006 |
| WO | 2006/072828 | 7/2006 |
| WO | 2007/117465 | 10/2007 |
| WO | 2008/001182 | 1/2008 |
| WO | 2008/004117 | 1/2008 |
| WO | 2010/051781 | 5/2010 |
| WO | 2010/057121 | 5/2010 |
| WO | 2010/057126 | 5/2010 |
| WO | 2010/063610 | 6/2010 |
| WO | 2010/090737 | 8/2010 |
| WO | 2011/008830 | 1/2011 |

OTHER PUBLICATIONS

E. Merkul et al., "Rapid Preparation of Triazolyl Substituted NH-Heterocyclic Kinase Inhibitors *via* One-Pot Sonogashira Coupling—TMS Deprotection-CuAAC Sequence", Organic & Biomolecular Chemistry, vol. 9, No. 14, pp. 5129-5136, 2011.

F. S. Menniti et al., "Phosphodiesterases in the CNS: Targets for Drug Development", Nat. Rev. Drug. Disc., vol. 5, pp. 660-670, Aug. 2006.

M. D. Houslay et al., "cAMP-Specific Phosphodiesterase-4 Enzymes in the Cardiovasular System : A Molecular Toolbox for Generating Compartmentalized cAMP Signaling", Circulation Research, vol. 100, No. 7, pp. 950-966, 2007.

J. Nakayama et al., "Expression Cloning of a Human $\alpha 1,4$-$N$-Acetylglucosaminyltransferase that Forms GlcNA$\alpha$1→4Gal$\beta$→R, A Glycan Specifically Expressed in the Gastric Gland Mucous Cell-Type Mucin", Proc. Nat. Acad. Sci., vol. 96, pp. 8991-8996, Aug. 1999.

K. Loughney et al., "Isolation and Characterization of PDE10A, A Novel Human 3', 5' -cyclic Nucleotide Phosphodiesterase", Gene, vol. 234, pp. 109-117, 1999.

K. Fujishige et al., "Striatum- and Testis-Specific Phosphodiesterase PDE10A Isolation and Characterization of a Rat PDE10A", Eur. J. Biochem., vol. 266, pp. 1118-1127, 1999.

K. Fujishige et al., "Cloning and Characterization of A Novel Human Phosphodiesterase that Hydrolyzes both cAMP and cGMP (PDE10A)", The Journal of Biological Chemistry, vol. 274, No. 26, pp. 18438-18445, Jun. 25, 1999.

T. F. Seeger et al., "Immunohistochemical Localization of PDE10A in the Rat Brain", Brain Research, vol. 985, pp. 113-126, 2003.

English translation of Japanese Patent Application No. 2010-111624, published May 20, 2010.

\* cited by examiner

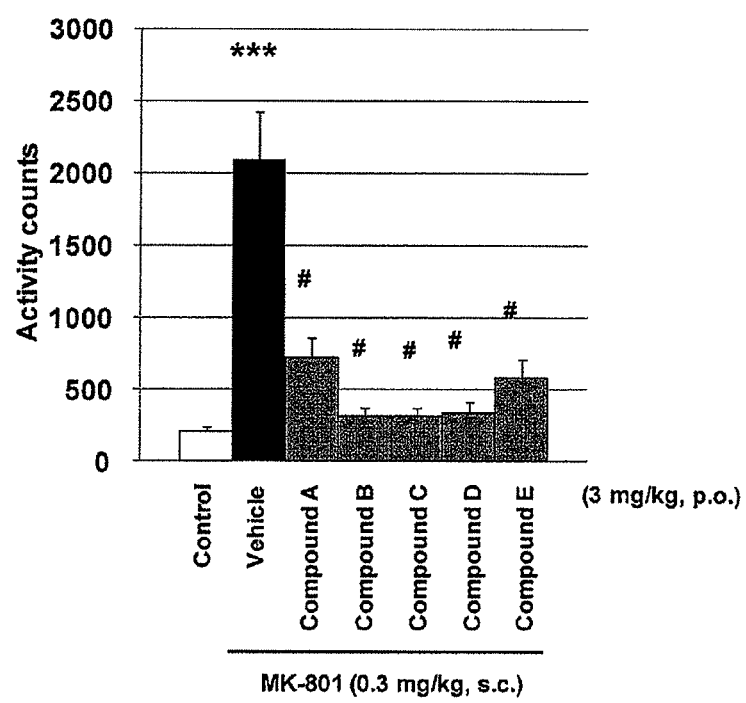

FUSED HETEROCYCLIC COMPOUNDS

This application is a U.S. national stage of International Application No. PCT/US2011/046417 filed Aug. 3, 2011, which claims the benefit of U.S. provisional application Ser. No. 61/370,566 filed Aug. 4, 2010 and Serial No. 61/427,271 filed Dec. 27, 2010.

TECHNICAL FIELD

The present invention relates to fused heterocyclic compounds.

BACKGROUND OF THE INVENTION

Phosphodiesterases (PDEs) are a superfamily of enzymes encoded by 21 genes and subdivided into 11 distinct families according to structural and functional properties. These enzymes metabolically inactivate the ubiquitous intracellular second messengers, cyclic adenosine monophosphate (cAMP) and cyclic guanosine monophosphate (cGMP); PDEs selectively catalyze the hydrolysis of the 3'-ester bond, forming the inactive 5'-monophosphate. On the basis of substrate specificity, the PDE families can be further classified into three groups: i) the cAMP-PDEs (PDE4, PDE7, PDE8), ii) the cGMP-PDEs (PDE5, PDE6 and PDE9), and iii) the dual-substrate PDEs (PDE1, PDE2, PDE3, PDE10 and PDE11).

The cAMP and cGMP are involved in the regulation of virtually every physiological process such as pro-inflammatory mediator production and action, ion channel function, muscle relaxation, learning and memory formation, differentiation, apoptosis, lipogenesis, glycogenolysis and gluconeogenesis. Especially, in neurons, these second messengers have important role in the regulation of synaptic transmission as well as in neuronal differentiation and survival (Nat. Rev. Drug Discov. 2006, vol. 5: 660-670). Regulation of these processes by cAMP and cGMP are accompanied by activation of protein kinase A (PKA) and protein kinase G (PKG), which in turn phosphorylate a variety of substrates, including transcription factors, ion channels and receptors that regulate a variety of physiological processes. Intracellular cAMP and cGMP concentrations seem to be temporally, spatially, and functionally compartmentalized by regulation of adenyl and guanyl cyclases in response to extracellular signaling and their degradation by PDEs (Circ. Res. 2007, vol. 100(7): 950-966). PDEs provide the only means of degrading the cyclic nucleotides cAMP and cGMP in cells, thus PDEs play an essential role in cyclic nucleotide signaling. Thereby, PDEs could be promising targets for various therapeutic drugs.

Phosphodiesterase 10A (PDE10A) was discovered in 1999 by three independent groups (Proc. Natl. Acad. Sci. USA 1999, vol. 96: 8991-8996, J. Biol. Chem. 1999, vol. 274: 18438-18445, Gene 1999, vol. 234: 109-117). Expression studies have shown that PDE10A has the most restricted distribution within the all known PDE families; the PDE10A mRNA is highly expressed only in brain and testes (Eur. J. Biochem. 1999, vol. 266: 1118-1127, J. Biol. Chem. 1999, vol. 274: 18438-18445). In the brain, mRNA and protein of PDE10A are highly enriched in medium spiny neurons (MSNs) of the striatum (Eur. J. Biochem. 1999, vol. 266: 1118-1127, Brain Res. 2003, vol. 985: 113-126). MSNs are classified into two groups: the MSN that express D1 dopamine receptors responsible for a direct (striatonigral) pathway and the MSN that express D2 dopamine receptors responsible for an indirect (striatopallidal) pathway. The function of direct pathway is to plan and execution, while indirect pathway is to act as a brake on behavioral activation. As PDE10A expresses in both MSNs, PDE10A inhibitors could activate both of these pathways. The antipsychotic efficacy of current medications, D2 or D2/5-HT2A antagonists, mainly derives from their activation of the indirect pathway in the striatum. As PDE10A inhibitors are able to activate this pathway, this suggests that PDE10A inhibitors are promising as antipsychotic drugs. The excessive D2 receptor antagonism in the brain by D2 antagonists causes problems of extrapyramidal side effects and hyperprolactinaemia. However the expression of PDE10A is limited to these striatal pathways in the brain, thus side effects by PDE10A inhibitors were expected to be weaker compared with current D2 antagonists. Regarding hyperprolactinaemia, PDE10A inhibitors would produce no prolactin elevation due to lack of D2 receptor antagonism in the pituitary. Moreover, the presence of PDE10A in a direct pathway makes it likely that PDE10A inhibition will have some advantage over current D2 antagonists; the direct pathway is thought to promote desired action, and activation of this pathway by PDE10A inhibitors may counteract extrapyramidal symptoms induced by excessive D2 receptor antagonism. In addition, activation of this pathway could facilitate striatal-thalamic outflow, promoting the execution of procedural strategies. Furthermore, enhancement of second messenger levels without blockade of dopamine and/or other neurotransmitter receptors may also provide therapeutic advantages with fewer adverse side-effects (e.g., hyperprolactinaemia and weight gain) compared with current antipsychotics. This unique distribution and function in the brain indicates that PDE10A represents an important new target for the treatment of neurological and psychiatric disorders, in particular psychotic disorders like schizophrenia.

Patent document 1 discloses, as PDE10A inhibitors, a compound of the following formula:

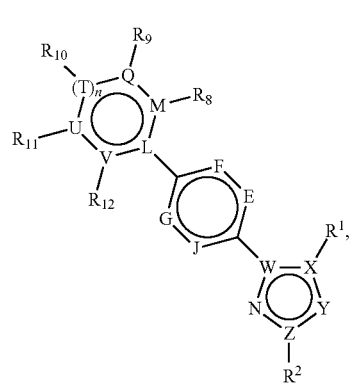

and the following compounds
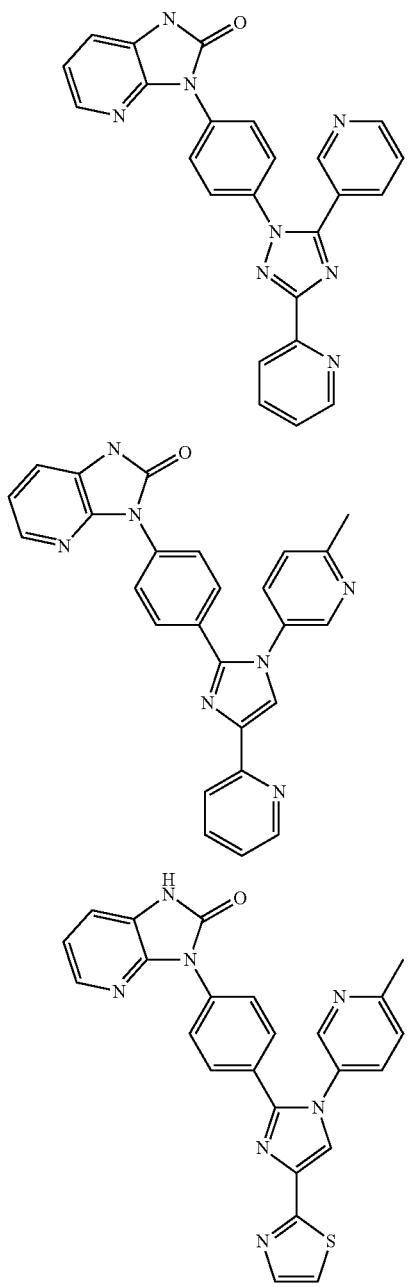
and
Patent document 2 discloses, as PDE10A inhibitors, a compound of the following formula:
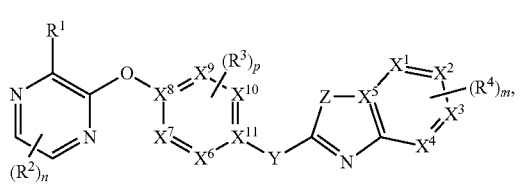
and the following compounds:
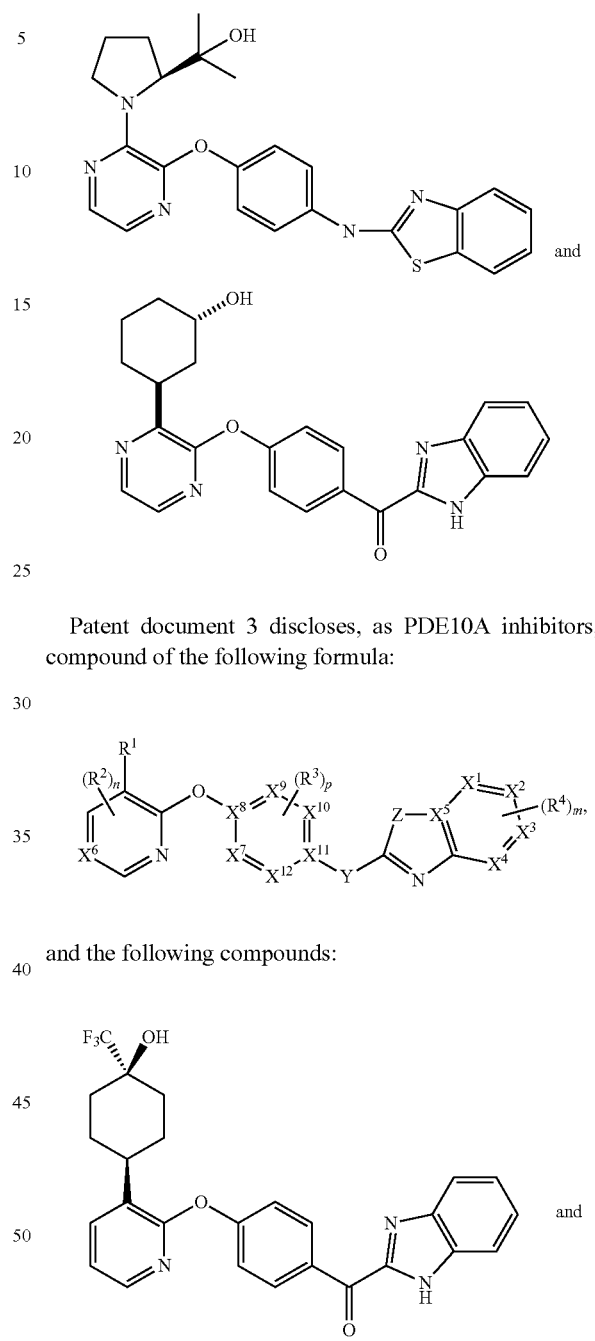
and
Patent document 3 discloses, as PDE10A inhibitors, a compound of the following formula:
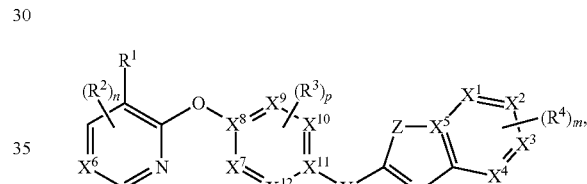
and the following compounds:
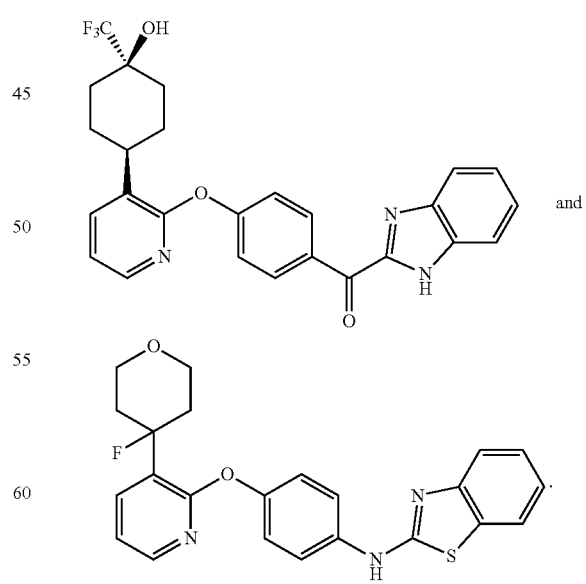
Patent document 4 discloses, as a PDE10A inhibitor, a compound of the following formula:

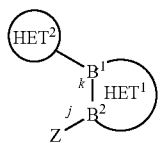
wherein Z is
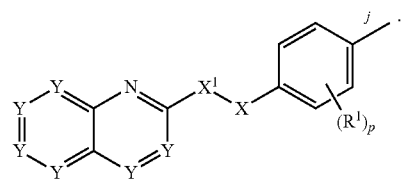
Patent document 5 discloses, as a PDE10A inhibitor, a compound of the following formula:
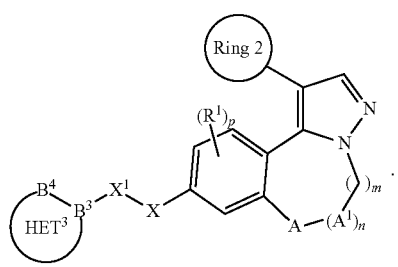
(I)
Patent document 6 discloses, as PDE10A inhibitors, a compound of the following formula:
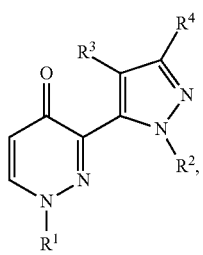
and the following compounds:
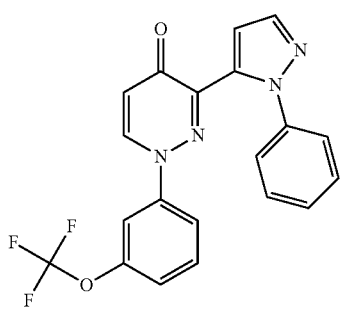
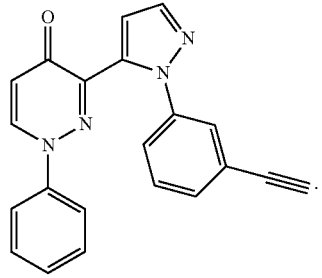
Patent document 7 discloses a compound of the following formula:
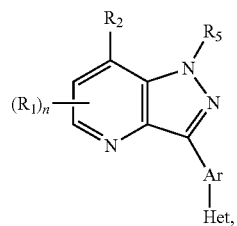
and the following compounds
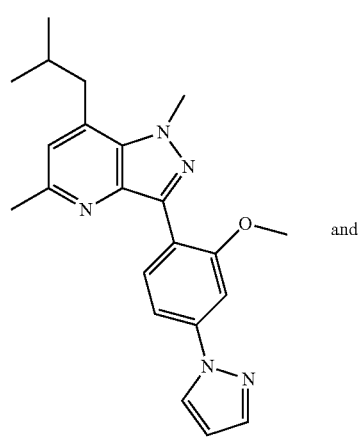
and
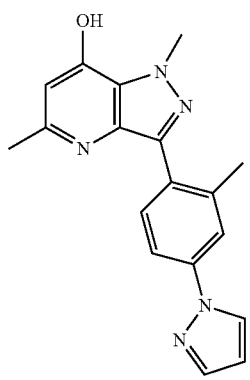

Patent document 8 discloses the following compounds:

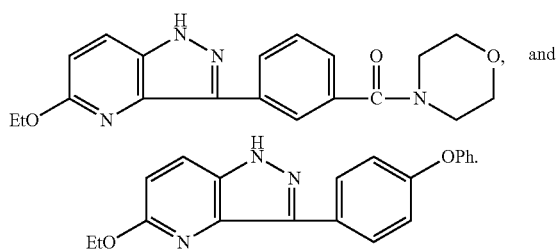

Patent document 9 discloses the following compound:

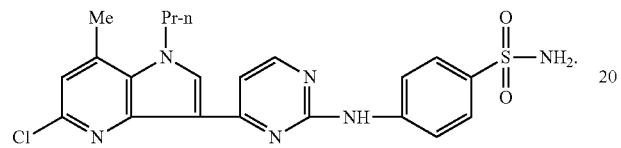

Patent document 10 discloses the following compound:

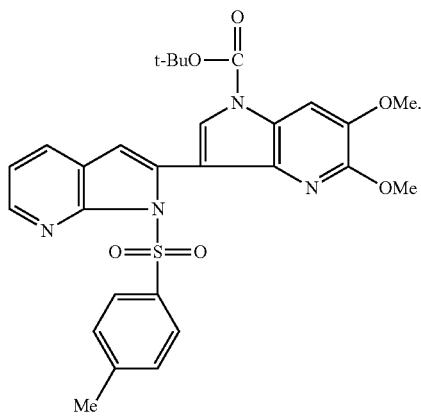 [SMILES: COc1cc2c(nc1OC)c(-c1cc3cccnc3n1S(=O)(=O)c1ccc(C)cc1)cn2C(=O)OC(C)(C)C]

Patent document 11 discloses, as a PDE10A inhibitor, the following compound:

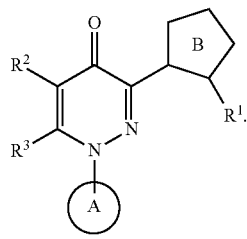

SUMMARY OF INVENTION

Technical Problem

However, development of new phosphodiesterase (PDE) 10A inhibitors is further requested.

Solution to Problem

The present inventors discovered that a compound expressed by the formula (1) or a salt thereof (referred to as compound (1) in this specification) has a PDE 10A inhibitory action and after extensive investigation, completed the present invention.

In this specification, the compound (1) or a prodrug thereof is also referred to the compound of the present invention.

That is, the present invention provides features of the following items, and so on.

[1] A compound represented by the formula (1'):

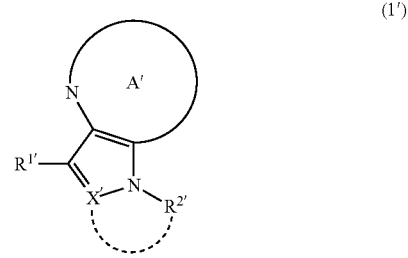

(1')

wherein,
Ring A' represents an optionally substituted pyridine ring, an optionally substituted pyridazine ring, a pyrimidine ring, or a pyrazine ring,
$R^{1'}$ represents

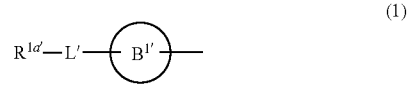

(1)

wherein,
$R^{1a'}$ represents an optionally substituted phenyl group, or an optionally substituted 5- to 10-membered heterocyclic group,
L' represents a bond, —S—, —O—, —CO—, an optionally substituted methylene group, or —$NR^{a'}$— wherein $R^{a'}$ represents a hydrogen atom, or an optionally substituted $C_{1-6}$ alkyl group, and
Ring $B^{1'}$ represents an optionally further substituted 6- to 10-membered aromatic hydrocarbon ring, or an optionally further substituted 5- to 10-membered aromatic heterocyclic ring, or alternatively, L' and $R^{1a'}$ may be taken together to form an optionally substituted bicyclic or tricyclic fused heterocyclic group, or

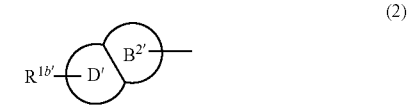

(2)

wherein,
$R^{1b'}$ represents an optionally substituted phenyl group, or an optionally substituted 5- to 10-membered heterocyclic group,
Ring $B^{2'}$ represents an optionally substituted benzene ring, an optionally substituted pyridine ring, an optionally substituted pyrimidine ring, an optionally substituted pyrazine ring, or an optionally substituted pyridazine ring,
Ring D' represents an optionally further substituted 5- or 6-membered ring, $R^{2'}$ represents a hydrogen atom, or a substituent, X' represents =N— or =$CR^{b'}$—($R^{b'}$ represents a hydrogen atom, or a substituent),

- - - - - represents that $R^{b'}$ and $R^{2'}$ may form, taken together with the carbon atom and the nitrogen atom to which they are each adjacent, an optionally substituted 5- to 7-membered ring when X' is =$CR^{b'}$—, provided that the following compounds:

(1) 5-ethoxy-3-[3-(morpholin-4-ylcarbonyl)phenyl]-1H-pyrazolo[4,3-b]pyridine (2) 5-ethoxy-3-(4-phenoxyphenyl)-1H-pyrazolo[4,3-b]pyridine (3) a compound represented by the formula:

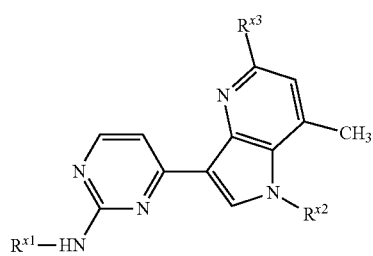

wherein, $R^{x1}$ represents a phenyl group which may be substituted by one or two substituents selected from an aminosulfonyl group, a hydroxy group, a methyl group, a morpholinosulfonyl group, a (1-piperazinyl)sulfonyl group, a 1-piperazinyl group, a 4-acetylpiperazine-1-yl group, a morpholino group, and morpholinocarbonyl group, $R^{x2}$ represents an ethyl group or a propyl group, and $R^{x3}$ represents a hydrogen atom or a chlorine atom, and, (4) a compound represented by the formula:

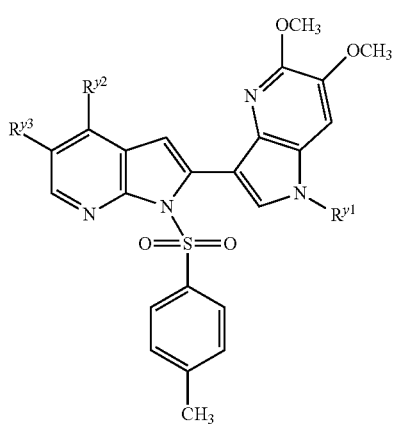

wherein, $R^{y1}$ represents a hydrogen atom, a methyl group, a tert-butoxycarbonyl group, a 2-chloroethyl group, a 2-iodoethyl group, a 2-morpholinoethyl group, or a 2-(4-methyl-1-piperazinyl)ethyl group, $R^{y2}$ represents a hydrogen atom or a chlorine atom, and $R^{y3}$ represents a hydrogen atom or a fluorine atom are excluded;

or a salt thereof.

[2] A compound represented by the formula (1):

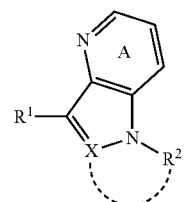

(1)

wherein,

Ring A represents an optionally substituted pyridine ring, $R^1$ represents

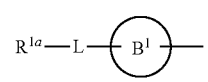

(1)

wherein, $R^{1a}$ represents an optionally substituted phenyl group, or an optionally substituted 5- to 10-membered heterocyclic group, L represents a bond, —S—, —O—, —CO—, an optionally substituted methylene group, or —$NR^a$— wherein $R^a$ represents a hydrogen atom, or an optionally substituted $C_{1-6}$ alkyl group, and Ring $B^1$ represents an optionally further substituted 6- to 10-membered aromatic hydrocarbon ring, or an optionally further substituted 5- to 10-membered aromatic heterocyclic ring, or alternatively, L and $R^{1a}$ may be taken together to form an optionally substituted bicyclic or tricyclic fused heterocyclic group, or

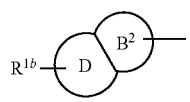

(2)

wherein, $R^{1b}$ represents an optionally substituted phenyl group, or an optionally substituted 5- to 10-membered heterocyclic group, Ring $B^2$ represents an optionally substituted benzene ring, an optionally substituted pyridine ring, an optionally substituted pyrimidine ring, an optionally substituted pyrazine ring, or an optionally substituted pyridazine ring, Ring D represents an optionally further substituted 5- or 6-membered ring, $R^2$ represents a hydrogen atom, or a substituent, X represents =N— or =$CR^b$— ($R^b$ represents a hydrogen atom, or a substituent),

- - - - - represents that $R^b$ and $R^2$ may form, taken together with the carbon atom and the nitrogen atom to which they are each adjacent, an optionally substituted 5- to 7-membered ring when X is =$CR^b$—, provided that the following compounds:

(1) 5-ethoxy-3-[3-(morpholin-4-ylcarbonyl)phenyl]-1H-pyrazolo[4,3-b]pyridine (2) 5-ethoxy-3-(4-phenoxyphenyl)-1H-pyrazolo[4,3-b]pyridine (3) a compound represented by the formula:

[Chemical structure with substituents $R^{x1}$—HN, $R^{x2}$, $R^{x3}$, and CH$_3$ on a pyrrolopyridine-pyrimidine scaffold]

wherein,
$R^{x1}$ represents a phenyl group which may be substituted by one or two substituents selected from an aminosulfonyl group, a hydroxy group, a methyl group, a morpholinosulfonyl group, a (1-piperazinyl)sulfonyl group, a 1-piperazinyl group, a 4-acetylpiperazine-1-yl group, a morpholino group, and a morpholinocarbonyl group,
$R^{X2}$ represents an ethyl group or a propyl group, and
$R^{X3}$ represents a hydrogen atom or a chlorine atom, and,
(4) a compound represented by the formula:

[Chemical structure with substituents $R^{y1}$, $R^{y2}$, $R^{y3}$, OCH$_3$ groups, and a tosyl (O=S=O with CH$_3$-phenyl) group on a bis-pyrrolopyridine scaffold]

wherein,
$R^{y1}$ represents a hydrogen atom, a methyl group, a tert-butoxycarbonyl group, a 2-chloroethyl group, a 2-iodoethyl group, a 2-morpholinoethyl group, or a 2-(4-methyl-1-piperazinyl)ethyl group,
$R^{y2}$ represents a hydrogen atom or a chlorine atom, and
$R^{y3}$ represents a hydrogen atom or a fluorine atom are excluded;
or a salt thereof.
[3] The compound according to the above-mentioned [2], wherein Ring A is a pyridine ring which may be substituted by substituent(s) selected from the group consisting of (i) an optionally substituted C$_{1-6}$ alkyl group, (ii) an optionally substituted C$_{1-6}$ alkoxy group, (iii) a halogen atom and (iv) a cyano group, or a salt thereof.
[4] The compound according to the above-mentioned [2], wherein Ring A is a pyridine ring which may be substituted by a halogen atom, or a salt thereof.
[5] The compound according to the above-mentioned [2], or a salt thereof, wherein R$^2$ is an optionally substituted C$_{1-6}$ alkyl group.
[6] The compound according to the above-mentioned [2], wherein R$^1$ is a group represented by

[Structure: $R^{1a}$—L—B$^1$—]

wherein $R^{1a}$ is a 5- to 10-membered heterocyclic group which may be substituted by 1 to 3 substituents selected from a group consisting of
(1) a C$_{1-6}$ alkyl group which may be substituted by 1-3 substituents selected from the group consisting of (a) a 2-(trimethylsilyl)ethoxy group, (b) a hydroxy group, (c) a C$_{1-6}$ alkoxy group and (d) a halogen atom;
(2) a halogen atom; and
(3) a cyano group;
B$^1$ is a benzene ring which may be substituted by a halogen atom, a pyridine ring, a dihydropyridine ring which may be substituted by an oxo group, or a pyrazole ring;
L is bond, —O—, —CO— or —NH—; or alternatively, L and $R^{1a}$ may be taken together to form

[Bicyclic benzimidazole-fused structure with methyl substituent]

or a salt thereof.
[7] The compound according to the above-mentioned [2] or [6], wherein L is —O—, or a salt thereof.
[8] 1-(2,2-Difluoroethyl)-3-{4-[(3-methyl-3H-imidazo[4,5-b]pyridin-2-yl)oxy]phenyl}-1H-pyrazolo[4,3-b]pyridine, or a salt thereof.
[9] 6-Fluoro-1-methyl-3-{4-[(3-methyl-3H-imidazo[4,5-b]pyridin-2-yl)oxy]phenyl}-1H-pyrazolo[4,3-b]pyridine, or a salt thereof.
[10] 1-Ethyl-6-fluoro-3-(4-{[3-(2-methoxyethyl)-3H-imidazo[4,5-b]pyridin-2-yl]oxy}phenyl)-1H-pyrazolo[4,3-b]pyridine, or a salt thereof.
[11] A medicament comprising the compound according to the above-mentioned [1] or [2], or a salt thereof.
[12] The medicament according to the above-mentioned [11] which is an agent for inhibiting phosphodiesterase 10A.
[13] The medicament according to the above-mentioned [1] which is for preventing or treating schizophrenia.
[14] A method of preventing or treating schizophrenia comprising administering an effective amount of the compound according to the above-mentioned [1] or [2], or a salt thereof to a mammal.
[15] Use of the compound according to the above-mentioned [1] or [2], or a salt thereof in the manufacture of a medicament for preventing or treating schizophrenia.
[16] The compound according to the above-mentioned [1] or [2], or a salt thereof for use in the prevention or treatment of schizophrenia.

Advantageous Effects of Invention

The compound of the present invention has a PDE10A inhibitory activity and is useful as a prophylactic or therapeutic drug for schizophrenia and the like.

BRIEF DESCRIPTION OF THE DRAWING

FIG. 1 is a graph showing an inhibition of MK-801-induced hyperlocomotion by compounds in mice.

DESCRIPTION OF EMBODIMENTS

The present invention is explained in detail in the following.

In the present specification, the hydrogen atoms in the chemical structural formulas are sometimes to be abbreviated according to convention in the chemical field.

In the present specification, unless otherwise specified, examples of the "halogen atom" include fluorine, chlorine, bromine, and iodine.

In the present specification, unless otherwise specified, "optionally halogenated" and "halogeno" mean optionally having one or more (e.g., 1 to 3) halogen atoms as substituents.

In the present specification, unless otherwise specified, examples of the "hydrocarbon ring having a carbon number of 5 to 7" include a $C_{5-7}$ cycloalkane (e.g., cyclopentane, cyclohexane, cycloheptane), a $C_{5-7}$ cycloalkene (e.g., cyclopentene, cyclohexene, cycloheptene), a $C_{5-7}$ cycloalkadiene (e.g., cyclopentadiene, cyclohexadiene, cycloheptadiene), and a benzene ring.

In the present specification, unless otherwise specified, examples of the "5- to 7-membered heterocyclic ring" include a 5- to 7-membered heterocyclic ring containing 1 to 4 hetero atoms selected from a nitrogen atom, a sulfur atom and an oxygen atom, specifically,
(1) a 5- to 7-membered nonaromatic heterocyclic ring containing 1 to 4 hetero atoms selected from a nitrogen atom, a sulfur atom and an oxygen atom such as pyrrolidine ring, pyrroline ring, dihydrofuran ring, tetrahydrofuran ring, tetrahydrothiophene ring, imidazolidine ring, imidazoline ring, oxazolidine ring, isoxazoline ring, piperidine ring, dihydropyran ring, tetrahydropyran ring, tetrahydrothiopyran ring, morpholine ring, thiomorpholine ring, piperazine ring, dihydrooxazine ring, tetrahydrooxazine ring, dihydropyrimidine ring, tetrahydropyrimidine ring, dihydropyridine ring, tetrahydropyridine ring, azepane ring, oxepane ring, thiepane ring, oxazepane ring, and thiazepane ring and the like; and
(2) a 5- to 7-membered aromatic heterocyclic ring containing 1 to 4 hetero atoms selected from a nitrogen atom, a sulfur atom and an oxygen atom such as furan ring, thiophene ring, pyrrole ring, oxazole ring, isoxazole ring, thiazole ring, isothiazole ring, imidazole ring, pyrazole ring, 1,2,3-oxadiazole ring, 1,2,4-oxadiazole ring, 1,3,4-oxadiazole ring, furazan ring, 1,2,3-thiadiazole ring, 1,2,4-thiadiazole ring, 1,3,4-thiadiazole ring, 1,2,3-triazole ring, 1,2,4-triazole ring, tetrazole ring, pyridine ring, pyridazine ring, pyrimidine ring, pyrazine ring, and triazine ring and the like.

In the present specification, unless otherwise specified, examples of the "alkyl (group)" include a $C_{1-6}$ alkyl (group).

In the present specification, unless otherwise specified, examples of the "$C_{1-6}$ alkyl (group)" include methyl, ethyl, propyl, isopropyl, butyl, isobutyl, sec-butyl, tert-butyl, pentyl, isopentyl, neopentyl, and hexyl.

In the present specification, unless otherwise specified, the "optionally halogenated $C_{1-6}$ alkyl (group)" means a $C_{1-6}$ alkyl (group) optionally substituted by a halogen atom, and examples thereof include trifluoromethyl, difluoromethyl, 2,2,2-trifluoroethyl, and 2,2-difluoroethyl.

In the present specification, unless otherwise specified, examples of the "alkenyl (group)" include a $C_{2-6}$ alkenyl (group).

In the present specification, unless otherwise specified, examples of the "$C_{2-6}$ alkenyl (group)" include vinyl, 1-propen-1-yl, 2-propen-1-yl, isopropenyl, 2-buten-1-yl, 4-penten-1-yl, and 5-hexen-1-yl.

In the present specification, unless otherwise specified, examples of the "alkynyl (group)" include a $C_{2-6}$ alkynyl group. Examples of the "$C_{2-6}$ alkynyl (group)" include ethynyl, 1-propyn-1-yl, 2-propyn-1-yl, 4-pentyn-1-yl, and 5-hexyn-1-yl.

In the present specification, unless otherwise specified, examples of the "$C_{3-7}$ cycloalkyl-$C_{2-6}$ alkynyl (group)" include cyclopropylethynyl.

In the present specification, unless otherwise specified, examples of the "$C_{3-7}$ cycloalkyl (group)" include cyclopropyl, cyclobutyl, cyclopentyl, and cyclohexyl.

In the present specification, unless otherwise specified, examples of the "$C_{6-14}$ aryl (group)" include phenyl, 1-naphthyl, 2-naphthyl, 2-biphenylyl, 3-biphenylyl, 4-biphenylyl, and 2-anthryl.

In the present specification, unless otherwise specified, examples of the "$C_{7-16}$ aralkyl (group)" include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, and 4-biphenylylmethyl.

In the present specification, unless otherwise specified, examples of the "$C_{6-14}$ aryl-$C_{2-6}$ alkenyl (group)" include styryl.

In the present specification, unless otherwise specified, the "heterocyclic group" (and heterocyclyl moiety in substituents) is a (saturated or unsaturated) nonaromatic heterocyclic group, or an aromatic heterocyclic group (i.e., heteroaryl group).

In the present specification, unless otherwise specified, the "heterocyclic group" may be monocyclic, bicyclic or tricyclic.

In the present specification, unless otherwise specified, the "heterocyclic group" is, for example, a 3- to 14-membered heterocyclic group containing, as a ring-constituting atom besides carbon atom, 1 to 5 hetero atoms selected from an oxygen atom, a sulfur atom and a nitrogen atom and the like, any may be a nonaromatic heterocyclic group or an aromatic heterocyclic group.

In the present specification, unless otherwise specified, the "nonaromatic heterocyclic group" (and nonaromatic heterocyclyl moiety in substituents) may be saturated or unsaturated and, for example, a 3- to 14-membered nonaromatic heterocyclic group can be mentioned. Concrete examples thereof include a 3- to 14-membered nonaromatic heterocyclic group containing 1 to 5 hetero atoms selected from an oxygen atom, a sulfur atom and a nitrogen atom besides a carbon atom such as tetrahydrofuryl, oxazolidinyl, imidazolinyl (e.g., 1-imidazolinyl, 2-imidazolinyl, 4-imidazolinyl), aziridinyl (e.g., 1-aziridinyl, 2-aziridinyl), azetidinyl (e.g., 1-azetidinyl, 2-azetidinyl), pyrrolidinyl (e.g., 1-pyrrolidinyl, 2-pyrrolidinyl, 3-pyrrolidinyl), piperidinyl (e.g., 1-piperidinyl, 2-piperidinyl, 3-piperidinyl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), piperazinyl (e.g., 1,4-piperazin-1-yl, 1,4-piperazin-2-yl), diazepinyl (e.g., 1,4-diazepin-1-yl, 1,4-diazepin-2-yl, 1,4-diazepin-5-yl, 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydroquinolyl, 5,6,7,8-tetrahydroimidazo[1,2-a]pyridyl (e.g., 5,6,7,8-tetrahydroimidazo[1,2-a]pyridin-2-yl, 5,6,7,8-tetrahydroimidazo[1,2-a]pyridin-3-yl, 5,6,7,8-tetrahydroimidazo[1,2-a]pyridin-5-yl, 5,6,7,8- tetrahydroimidazo[1,2-a]pyridin-6-yl, 5,6,7,8-tetrahydroimidazo[1,2-a]pyridin-7-yl, and imidazo[1,2-a]pyridin-8-yl), 2,3-dihydropyrrolo[1,2-a]benzimidazolyl (e.g., 2,3-dihydro-1H-pyrrolo[1,2-a]benzimidazol-2-yl), 2,3-dihydroimidazo[1,2-a]benzimidazolyl (e.g., 2,3-dihydro-1H-imidazo[1,2-a]benzimidazol-1-yl), 1,2,3,4-tetrahydroprimido[1,2-a]benzimidazolyl (e.g., 1,2,3,4-tetrahydroprimido[1,2-a]benzimidazol-1-yl), 6,7,8,9-tetrahydro-5H-4b,9,10-triazabenz[a]azulene (e.g., 6,7,8,9-tetrahydro-5H-4b,9,10-triazabenz[a]azulen-9-yl), pyrindinyl (e.g., 5H-1-pyrindin-7-yl), cyclopenta[b]pyrrolyl (e.g., cyclopenta[b]pyrrol-6-yl) and the like.

In the present specification, unless otherwise specified, examples of the "aromatic heterocyclic group" (and aromatic heterocyclyl moiety in substituents) include a 5- or 6-membered monocyclic aromatic heterocyclic group, and a 5- to 10-membered aromatic fused heterocyclic group.

In the present specification, unless otherwise specified, examples of the "5- or 6-membered monocyclic aromatic heterocyclic group" include a 5- or 6-membered monocyclic aromatic heterocyclic group containing 1 to 5 hetero atoms selected from an oxygen atom, a sulfur atom and a nitrogen atom besides a carbon atom, such as pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), pyrazolyl (e.g., 1-pyrazolyl, 3-pyrazolyl, 4-pyrazolyl), imidazolyl (e.g., 1-imidazolyl, 2-imidazolyl, 4-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), isothiazolyl (e.g., 3-isothiazolyl, 4-isothiazolyl, 5-isothiazolyl), thiazolyl (e.g., 2-thiazolyl, 4-thiazolyl, 5-thiazolyl), triazolyl (e.g., 1,2,3-triazol-4-yl, 1,2,4-triazol-3-yl), oxadiazolyl (e.g., 1,2,4-oxadiazol-3-yl, 1,2,4-oxadiazol-5-yl), thiadiazolyl (e.g., 1,2,4-thiadiazol-3-yl, 1,2,4-thiadiazol-5-yl), tetrazolyl, pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), and pyrazinyl and the like.

In the present specification, unless otherwise specified, examples of the "5- to 10-membered aromatic fused heterocyclic group" include a 5- to 10-membered aromatic fused heterocyclic group containing 1 to 5 hetero atoms selected from an oxygen atom, a sulfur atom and a nitrogen atom besides a carbon atom such as isoindolyl (e.g., 1-isoindolyl, 2-isoindolyl, 3-isoindolyl, 4-isoindolyl, 5-isoindolyl, 6-isoindolyl, 7-isoindolyl), indolyl (e.g., 1-indolyl, 2-indolyl, 3-indolyl, 4-indolyl, 5-indolyl, 6-indolyl, 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, 7-benzo[b]furanyl), benzo[c]furanyl (e.g., 1-benzo[c]furanyl, 4-benzo[c]furanyl, 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzo[c]thienyl (e.g., 1-benzo[c]thienyl, 4-benzo[c]thienyl, 5-benzo[c]thienyl), indazolyl (e.g., 1-indazolyl, 2-indazolyl, 3-indazolyl, 4-indazolyl, 5-indazolyl, 6-indazolyl, 7-indazolyl), benzimidazolyl (e.g., 1-benzimidazolyl, 2-benzimidazolyl, 4-benzimidazolyl, 5-benzimidazolyl), 1,2-benzoisooxazolyl (e.g., 1,2-benzoisoxazol-3-yl, 1,2-benzoisoxazol-4-yl, 1,2-benzoisoxazol-5-yl, 1,2-benzoisoxazol-6-yl, 1,2-benzoisoxazol-7-yl), benzoxazolyl (e.g., 2-benzoxazolyl, 4-benzoxazolyl, 5-benzoxazolyl, 6-benzoxazolyl, 7-benzoxazolyl), 1,2-benzoisothiazolyl (e.g., 1,2-benzoisothiazol-3-yl, 1,2-benzoisothiazol-4-yl, 1,2-benzoisothiazol-5-yl, 1,2-benzoisothiazol-6-yl, 1,2-benzoisothiazol-7-yl), benzothiazolyl (e.g., 2-benzothiazolyl, 4-benzothiazolyl, 5-benzothiazolyl, 6-benzothiazolyl, 7-benzothiazolyl), isoquinolyl (e.g., 1-isoquinolyl, 3-isoquinolyl, 4-isoquinolyl, 5-isoquinolyl), quinolyl (e.g., 2-quinolyl, 3-quinolyl, 4-quinolyl, 5-quinolyl, 8-quinolyl), cinnolinyl (e.g., 3-cinnolinyl, 4-cinnolinyl, 5-cinnolinyl, 6-cinnolinyl, 7-cinnolinyl, 8-cinnolinyl), phthalazinyl (e.g., 1-phthalazinyl, 4-phthalazinyl, 5-phthalazinyl, 6-phthalazinyl, 7-phthalazinyl, 8-phthalazinyl), quinazolinyl (e.g., 2-quinazolinyl, 4-quinazolinyl, 5-quinazolinyl, 6-quinazolinyl, 7-quinazolinyl, 8-quinazolinyl), quinoxalinyl (e.g., 2-quinoxalinyl, 3-quinoxalinyl, 5-quinoxalinyl, 6-quinoxalinyl, 7-quinoxalinyl, 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridin-7-yl), pyrazolo[4,5-b]pyridyl (e.g., pyrazolo[4,5-b]pyridin-1-yl, pyrazolo[4,5-b]pyridin-2-yl, pyrazolo[4,5-b]pyridin-3-yl, pyrazolo[4,5-b]pyridin-5-yl, pyrazolo[4,5-b]pyridin-6-yl, pyrazolo[4,5-b]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, and imidazo[1,2-a]pyridin-8-yl), imidazo[4,5-b]pyridyl (e.g., imidazo[4,5-b]pyridin-2-yl, imidazo[4,5-b]pyridin-3-yl, imidazo[4,5-b]pyridin-5-yl, imidazo[4,5-b]pyridin-6-yl, imidazo[4,5-b]pyridin-7-yl, and imidazo[4,5-b]pyridin-8-yl), imidazo[4,5-c]pyridyl (e.g., imidazo[4,5-c]pyridin-2-yl, imidazo[4,5-c]pyridin-3-yl, imidazo[4,5-c]pyridin-5-yl, imidazo[4,5-c]pyridin-6-yl, imidazo[4,5-c]pyridin-7-yl, and imidazo[4,5-c]pyridin-8-yl), pyrrolo[3,2-b]pyridyl (e.g., pyrrolo[3,2-b]pyridin-3-yl), furo[3,2-b]pyridyl (e.g., furo[3,2-b]pyridin-3-yl), thieno[3,2-b]pyridyl (e.g., thieno[3,2-b]pyridin-3-yl), pyrrolo[1,2-a]pyrimidinyl (e.g., pyrrolo[1,2-a]pyrimidin-8-yl), pyrrolo[3,2-b]pyrrolyl (e.g., pyrrolo[3,2-b]pyrrol-3-yl) and the like.

In the present specification, unless otherwise specified, examples of the "alkoxy (group)" include a $C_{1-6}$ alkoxy (group).

In the present specification, unless otherwise specified, examples of the "$C_{1-6}$ alkoxy (group)" include methoxy, ethoxy, propoxy, isopropoxy, butoxy, isobutoxy, sec-butoxy, pentyloxy, and hexyloxy.

In the present specification, unless otherwise specified, examples of the "$C_{3-7}$ cycloalkyloxy (group)" include cyclopropyloxy, cyclobutyloxy, cyclopentyloxy, and cyclohexyloxy.

In the present specification, unless otherwise specified, examples of the "$C_{6-14}$ aryloxy (group)" include phenyloxy, 1-naphthyloxy, and 2-naphthyloxy.

In the present specification, unless otherwise specified, examples of the "$C_{7-16}$ aralkyloxy (group)" include benzyloxy, and phenethyloxy.

In the present specification, unless otherwise specified, examples of the "alkyl-carbonyloxy (group)" include a $C_{1-6}$ alkyl-carbonyloxy (group).

In the present specification, unless otherwise specified, examples of the "$C_{1-6}$ alkyl-carbonyloxy (group)" include acetoxy, and propionyloxy.

In the present specification, unless otherwise specified, examples of the "alkoxy-carbonyloxy (group)" include a $C_{1-6}$ alkoxy-carbonyloxy (group).

In the present specification, unless otherwise specified, examples of the "$C_{1-6}$ alkoxy-carbonyloxy (group)" include methoxycarbonyloxy, ethoxycarbonyloxy, propoxycarbonyloxy, and butoxycarbonyloxy.

In the present specification, unless otherwise specified, examples of the "mono-alkyl-carbamoyloxy (group)" include a mono-$C_{1-6}$ alkyl-carbamoyloxy (group).

In the present specification, unless otherwise specified, examples of the "mono-$C_{1-6}$ alkyl-carbamoyloxy (group)" include methylcarbamoyloxy, and ethylcarbamoyloxy.

In the present specification, unless otherwise specified, examples of the "di-alkyl-carbamoyloxy (group)" include a di-$C_{1-6}$ alkyl-carbamoyloxy (group).

In the present specification, unless otherwise specified, examples of the "di-$C_{1-6}$ alkyl-carbamoyloxy (group)" include dimethylcarbamoyloxy, and diethylcarbamoyloxy.

In the present specification, unless otherwise specified, examples of the "$C_{6-14}$ aryl-carbonyloxy (group)" include benzoyloxy, 1-naphthylcarbonyloxy and 2-naphthylcarbonyloxy.

In the present specification, unless otherwise specified, examples of the "mono- or di-$C_{6-14}$ aryl-carbamoyloxy (group)" include phenylcarbamoyloxy, 1-naphthylcarbamoyloxy and 2-naphthylcarbamoyloxy.

In the present specification, unless otherwise specified, examples of the heterocyclyl moiety of the "heterocyclyl-oxy (group)" include those similar to the aforementioned "heterocyclic group". Specific examples of the "heterocyclyl-oxy (group)" include a 3- to 14-membered heterocyclyl-oxy (group) containing 1 to 5 hetero atoms selected from a nitrogen atom, a sulfur atom, and an oxygen atom.

In the present specification, unless otherwise specified, examples of the aromatic heterocyclyl moiety of the "aromatic heterocyclyl-oxy (group)" include those similar to the "aromatic heterocyclic group" as an example of the aforementioned "heterocyclic group". Specific example of the "aromatic heterocyclyl-oxy (group)" include a 5- to 10-membered aromatic heterocyclyl-oxy containing 1 to 5 hetero atoms selected from a nitrogen atom, a sulfur atom, and an oxygen atom.

In the present specification, unless otherwise specified, examples of the "$C_{1-6}$ alkylsulfonyloxy (group)" include methylsulfonyloxy, and ethylsulfonyloxy.

In the present specification, unless otherwise specified, examples of the "halogeno $C_{1-6}$ alkylsulfonyloxy (group)" include halogenomethylsulfonyloxy, and halogenoethylsulfonyloxy.

In the present specification, unless otherwise specified, examples of the "alkylsulfanyl (group)" include a $C_{1-6}$ alkylsulfanyl (group).

In the present specification, unless otherwise specified, examples of the "$C_{1-6}$ alkylsulfanyl (group)" include methylsulfanyl, ethylsulfanyl, propylsulfanyl, isopropylsulfanyl, butylsulfanyl, sec-butylsulfanyl, and tert-butylsulfanyl.

In the present specification, unless otherwise specified, examples of the "$C_{3-7}$ cycloalkylsulfanyl (group)" include cyclopropylsulfanyl, cyclobutylsulfanyl, cyclopentylsulfanyl, and cyclohexylsulfanyl.

In the present specification, unless otherwise specified, examples of the "$C_{6-14}$ arylsulfanyl (group)" include phenylsulfanyl, 1-naphthylsulfanyl, and 2-naphthylsulfanyl.

In the present specification, unless otherwise specified, examples of the "$C_{7-16}$ aralkylsulfanyl (group)" include benzylsulfanyl, and phenethylsulfanyl.

In the present specification, unless otherwise specified, examples of the heterocyclyl moiety of the "heterocyclyl-sulfanyl (group)" include those similar to the aforementioned "heterocyclic group". Specific examples of the "heterocyclyl-sulfanyl (group)" include a 3- to 14-membered heterocyclyl-sulfanyl (group) containing 1 to 5 hetero atoms selected from a nitrogen atom, a sulfur atom, and an oxygen atom.

In the present specification, unless otherwise specified, examples of the "alkyl-carbonyl (group)" include a $C_{1-6}$ alkyl-carbonyl (group).

In the present specification, unless otherwise specified, examples of the "$C_{1-6}$ alkyl-carbonyl (group)" include acetyl, propionyl, and pivaloyl.

In the present specification, unless otherwise specified, examples of the "$C_{3-7}$ cycloalkyl-carbonyl (group)" include cyclopropylcarbonyl, cyclopentylcarbonyl, and cyclohexylcarbonyl.

In the present specification, unless otherwise specified, examples of the "$C_{6-14}$ aryl-carbonyl (group)" include benzoyl, 1-naphthoyl, and 2-naphthoyl.

In the present specification, unless otherwise specified, examples of the "$C_{7-16}$ aralkyl-carbonyl (group)" include phenylacetyl, and 3-phenylpropionyl.

In the present specification, unless otherwise specified, examples of the heterocyclyl moiety of the "heterocyclyl-carbonyl (group)" include those similar to the aforementioned "heterocyclic group". Specifically, a 3- to 14-membered heterocyclyl-carbonyl (group) containing 1 to 5 hetero atoms selected from a nitrogen atom, a sulfur atom, and an oxygen atom can be mentioned, and more specifically, for example, picolinoyl, nicotinoyl, isonicotinoyl, 2-thenoyl, 3-thenoyl, 2-furoyl, 3-furoyl, 4-morpholinylcarbonyl, 4-thiomorpholinylcarbonyl, aziridin-1-ylcarbonyl, aziridin-2-ylcarbonyl, azetidin-1-ylcarbonyl, azetidin-2-ylcarbonyl, pyrrolidin-1-ylcarbonyl, pyrrolidin-2-ylcarbonyl, pyrrolidin-3-ylcarbonyl, piperidin-1-ylcarbonyl, piperidin-2-ylcarbonyl, piperidin-3-ylcarbonyl, azepan-1-ylcarbonyl, azepan-2-ylcarbonyl, azepane-3-ylcarbonyl, azepan-4-ylcarbonyl, azocan-1-ylcarbonyl, azocan-2-ylcarbonyl, azocan-3-ylcarbonyl, azocan-4-ylcarbonyl, 1,4-piperazin-1-ylcarbonyl, 1,4-piperazin-2-ylcarbonyl, 1,4-diazepan-1-ylcarbonyl, 1,4-diazepan-2-ylcarbonyl, 1,4-diazepane-5-ylcarbonyl, 1,4-diazepan-6-ylcarbonyl, 1,4-diazocan-1-ylcarbonyl, 1,4-diazocan-2-ylcarbonyl, 1,4-diazocan-5-ylcarbonyl, 1,4-diazocan-6-ylcarbonyl, 1,5-diazocan-1-ylcarbonyl, 1,5-diazocan-2-ylcarbonyl, and 1,5-diazocan-3-ylcarbonyl can be mentioned.

In the present specification, unless otherwise specified, examples of the "optionally esterified carboxy (group)" include carboxy, optionally substituted alkoxy-carbonyl, optionally substituted $C_{6-14}$ aryloxy-carbonyl, optionally substituted $C_{7-16}$ aralkyloxy-carbonyl, optionally substituted silyloxy-carbonyl (e.g., TMS-O—CO—, TES-O—CO—, TBS-O—CO—, TIPS—O—CO—, TBDPS-O—CO—) and the like.

In the present specification, unless otherwise specified, examples of the "alkoxy-carbonyl (group)" include a "$C_{1-6}$ alkoxy-carbonyl (group)".

In the present specification, unless otherwise specified, examples of the "$C_{1-6}$ alkoxy-carbonyl (group)" include methoxycarbonyl, ethoxycarbonyl, propoxycarbonyl, and tert-butoxycarbonyl.

In the present specification, unless otherwise specified, examples of the "$C_{6-14}$ aryloxy-carbonyl (group)" include phenoxycarbonyl, 1-naphthyloxycarbonyl, and 2-naphthyloxycarbonyl.

In the present specification, unless otherwise specified, examples of the "$C_{7-16}$ aralkyloxy-carbonyl (group)" include benzyloxycarbonyl, and phenethyloxycarbonyl.

In the present specification, unless otherwise specified, examples of the "alkylsulfonyl (group)" include a $C_{1-6}$ alkylsulfonyl (group).

In the present specification, unless otherwise specified, examples of the "$C_{1-6}$ alkylsulfonyl (group)" include methylsulfonyl, and ethylsulfonyl.

In the present specification, unless otherwise specified, examples of the "$C_{3-7}$ cycloalkylsulfonyl (group)" include cyclopropylsulfonyl, cyclobutylsulfonyl, cyclopentylsulfonyl, and cyclohexylsulfonyl.

In the present specification, unless otherwise specified, examples of the "$C_{6-14}$ arylsulfonyl (group)" include phenylsulfonyl, 1-naphthylsulfonyl, and 2-naphthylsulfonyl.

In the present specification, unless otherwise specified, examples of the heterocyclyl moiety of the "heterocyclylsulfonyl (group)" include those similar to the aforementioned "heterocyclic group". Specific examples of the "heterocyclylsulfonyl (group)" include a 3- to 14-membered heterocyclylsulfonyl (group) containing 1 to 5 hetero atoms selected from a nitrogen atom, a sulfur atom, and an oxygen atom.

In the present specification, unless otherwise specified, examples of the "alkylsulfinyl (group)" include a $C_{1-6}$ alkylsulfinyl (group).

In the present specification, unless otherwise specified, examples of the "$C_{1-6}$ alkylsulfinyl (group)" include methylsulfinyl, and ethylsulfinyl.

In the present specification, unless otherwise specified, examples of the "$C_{3-7}$ cycloalkylsulfinyl (group)" include cyclopropylsulfinyl, cyclobutylsulfinyl, cyclopentylsulfinyl, and cyclohexylsulfinyl.

In the present specification, unless otherwise specified, examples of the "$C_{6-14}$ arylsulfinyl (group)" include phenylsulfinyl, 1-naphthylsulfinyl, and 2-naphthylsulfinyl.

In the present specification, unless otherwise specified, examples of the heterocyclyl moiety of the "heterocyclylsulfinyl (group)" include those similar to the aforementioned "heterocyclic group". Specific examples of the "heterocyclylsulfinyl (group)" include a 3- to 14-membered heterocyclylsulfinyl (group) containing 1 to 5 hetero atoms selected from a nitrogen atom, a sulfur atom, and an oxygen atom.

In the present specification, unless otherwise specified, examples of the "optionally substituted carbamoyl (group)" include a carbamoyl (group), an optionally substituted mono- or di-alkyl-carbamoyl (group), a mono- or di-aryl-carbamoyl (group), and a mono- or di-heterocyclyl-carbamoyl (group).

In the present specification, unless otherwise specified, examples of the "mono- or di-alkyl-carbamoyl (group)" include a mono- or di-$C_{1-6}$ alkyl-carbamoyl (group).

In the present specification, unless otherwise specified, examples of the "mono- or di-$C_{1-6}$ alkyl-carbamoyl (group)" include methylcarbamoyl, ethylcarbamoyl, propylcarbamoyl, dimethylcarbamoyl, diethylcarbamoyl, and ethylmethylcarbamoyl.

In the present specification, unless otherwise specified, examples of the "mono- or di-aryl-carbamoyl (group)" include a mono- or di-$C_{6-14}$ aryl-carbamoyl (group).

In the present specification, unless otherwise specified, examples of the "mono- or di-$C_{6-14}$ aryl-carbamoyl (group)" include phenylcarbamoyl, 1-naphthylcarbamoyl, and 2-naphthylcarbamoyl.

In the present specification, unless otherwise specified, examples of the "mono- or di-heterocyclyl-carbamoyl (group)" include a mono- or di-5- to 7-membered heterocyclyl-carbamoyl (group) containing 1 to 5 hetero atoms selected from a nitrogen atom, a sulfur atom, and an oxygen atom.

In the present specification, unless otherwise specified, examples of the "mono- or di-5- to 7-membered heterocyclyl-carbamoyl (group) containing 1 to 5 hetero atoms selected from a nitrogen atom, a sulfur atom, and an oxygen atom" include 2-pyridylcarbamoyl, 3-pyridylcarbamoyl, 4-pyridylcarbamoyl, 2-thienylcarbamoyl, and 3-thienylcarbamoyl.

In the present specification, unless otherwise specified, examples of the "optionally substituted amino (group)" include an amino (group), an optionally substituted mono- or di-alkylamino (group), an optionally substituted mono- or di-$C_{3-7}$ cycloalkylamino (group), an optionally substituted mono- or di-$C_{6-14}$ arylamino (group), an optionally substituted mono- or di-$C_{7-16}$ aralkylamino (group), an optionally substituted heterocyclyl-amino (group), an optionally substituted $C_{6-14}$ aryl-carbonylamino (group), a formylamino (group), an optionally substituted alkyl-carbonylamino (group), an optionally substituted $C_{3-7}$ cycloalkyl-carbonylamino (group), an optionally substituted heterocyclyl-carbonylamino (group), an optionally substituted alkoxy-carbonylamino (group), an optionally substituted $C_{3-7}$ cycloalkyloxy-carbonylamino (group), an optionally substituted heterocyclyl-oxycarbonylamino (group), an optionally substituted carbamoylamino (group), an optionally substituted alkylsulfonylamino (group), an optionally substituted $C_{3-7}$ cycloalkylsulfonylamino (group), an optionally substituted heterocyclyl-sulfonylamino (group), and an optionally substituted $C_{6-14}$ arylsulfonylamino (group).

In the present specification, unless otherwise specified, examples of the "mono- or di-alkylamino (group)" include a mono- or di-$C_{1-6}$ alkylamino (group).

In the present specification, unless otherwise specified, examples of the "mono- or di-$C_{1-6}$ alkylamino (group)" include methylamino, ethylamino, propylamino, dimethylamino, and diethylamino.

In the present specification, unless otherwise specified, examples of the "alkyl-carbonylamino (group)" include a $C_{1-6}$ alkyl-carbonylamino (group).

In the present specification, unless otherwise specified, examples of the "$C_{1-6}$ alkyl-carbonylamino (group)" include acetylamino, propionylamino, and pivaloylamino.

In the present specification, unless otherwise specified, examples of the heterocyclyl moiety of the "heterocyclyl-amino (group)" include those similar to the aforementioned "heterocyclic group", and examples of the "heterocyclyl-amino (group)" include 2-pyridyl-amino.

In the present specification, unless otherwise specified, examples of the "heterocyclyl-carbonyl" of the "heterocyclyl-carbonylamino (group)" include those similar to the aforementioned "heterocyclyl-carbonyl", and examples of the "heterocyclyl-carbonylamino (group)" include 2-pyridyl-carbonylamino.

In the present specification, unless otherwise specified, examples of the heterocyclyl moiety of the "heterocyclyl-oxycarbonylamino (group)" include those similar to the aforementioned "heterocyclic group", and examples of the "heterocyclyl-oxycarbonylamino (group)" include 2-pyridyl-oxycarbonylamino.

In the present specification, unless otherwise specified, examples of the heterocyclyl moiety of the "heterocyclyl-sulfonylamino (group)" include those similar to the aforementioned "heterocyclic group", and examples of the "heterocyclyl-sulfonylamino (group)" include 2-pyridyl-sulfonylamino.

In the present specification, unless otherwise specified, examples of the "alkoxy-carbonylamino (group)" include a $C_{1-6}$ alkoxy-carbonylamino (group).

In the present specification, unless otherwise specified, examples of the "$C_{1-6}$ alkoxy-carbonylamino (group)" include methoxycarbonylamino, ethoxycarbonylamino, propoxycarbonylamino, and butoxycarbonylamino.

In the present specification, unless otherwise specified, examples of the "alkylsulfonylamino (group)" include a $C_{1-6}$ alkylsulfonylamino (group).

In the present specification, unless otherwise specified, examples of the "$C_{1-6}$ alkylsulfonylamino (group)" include methylsulfonylamino, and ethylsulfonylamino.

In the present specification, unless otherwise specified, examples of the "mono- or di-$C_{3-7}$ cycloalkylamino (group)" include cyclopropylamino, cyclopentylamino, and cyclohexylamino.

In the present specification, unless otherwise specified, examples of the "$C_{3-7}$ cycloalkyl-carbonylamino (group)" include cyclopropylcarbonylamino, cyclopentylcarbonylamino, and cyclohexylcarbonylamino.

In the present specification, unless otherwise specified, examples of the "$C_{3-7}$ cycloalkyloxy-carbonylamino (group)" include cyclopropoxycarbonylamino, cyclopentyloxycarbonylamino, and cyclohexyloxycarbonylamino.

In the present specification, unless otherwise specified, examples of the "$C_{3-7}$ cycloalkylsulfonylamino (group)" include cyclopropylsulfonylamino, cyclopentylsulfonylamino, and cyclohexylsulfonylamino.

In the present specification, unless otherwise specified, examples of the "mono- or di-$C_{6-14}$ arylamino (group)" include phenylamino, and diphenylamino.

In the present specification, unless otherwise specified, examples of the "mono- or di-$C_{7-16}$ aralkylamino (group)" include benzylamino.

In the present specification, unless otherwise specified, examples of the "$C_{6-14}$ aryl-carbonylamino (group)" include benzoylamino, 1-naphthoylamino, and 2-naphthoylamino.

In the present specification, unless otherwise specified, examples of the "$C_{6-14}$ arylsulfonylamino (group)" include phenylsulfonylamino, 2-naphthylsulfonylamino, and 1-naphthylsulfonylamino.

In the present specification, unless otherwise specified, examples of the "optionally substituted carbamoylamino (group)" include a carbamoylamino (group), an optionally substituted mono- or di-alkyl-carbamoylamino (group), a mono- or di-aryl-carbamoylamino (group), and a mono- or di-heterocyclyl-carbamoylamino (group).

In the present specification, unless otherwise specified, examples of the "mono- or di-alkyl-carbamoylamino (group)" include a mono- or di-$C_{1-6}$ alkyl-carbamoylamino (group).

In the present specification, unless otherwise specified, examples of the "mono- or di-$C_{1-6}$ alkyl-carbamoylamino (group)" include methylcarbamoylamino, ethylcarbamoylamino, propylcarbamoylamino, dimethylcarbamoylamino, diethylcarbamoylamino, and ethylmethylcarbamoylamino.

In the present specification, unless otherwise specified, examples of the "mono- or di-aryl-carbamoylamino (group)" include a mono- or di-$C_{6-14}$ aryl-carbamoylamino (group).

In the present specification, unless otherwise specified, examples of the "mono- or di-$C_{6-14}$ aryl-carbamoylamino (group)" include phenylcarbamoylamino, 1-naphthylcarbamoylamino, and 2-naphthylcarbamoylamino.

In the present specification, unless otherwise specified, examples of the "mono- or di-heterocyclyl-carbamoylamino (group)" include a mono- or di-5- to 7-membered heterocyclyl-carbamoylamino (group) containing 1 to 5 hetero atoms selected from a nitrogen atom, a sulfur atom, and an oxygen atom.

In the present specification, unless otherwise specified, examples of the "mono- or di-5- to 7-membered heterocyclyl-carbamoylamino (group) containing 1 to 5 hetero atoms selected from a nitrogen atom, a sulfur atom, and an oxygen atom" include 2-pyridylcarbamoylamino, 3-pyridylcarbamoylamino, 4-pyridylcarbamoylamino, 2-thienylcarbamoylamino, and 3-thienylcarbamoylamino.

[Substituent Group A]

In the present specification, substituent group A includes
(1) a halogen atom;
(2) a nitro group;
(3) a cyano group;
(4) an optionally esterified carboxy group
[e.g.,
a carboxy group,
an optionally substituted alkoxy-carbonyl group,
an optionally substituted $C_{6-14}$ aryloxy-carbonyl group,
an optionally substituted $C_{7-16}$ aralkyloxy-carbonyl group,
an optionally substituted silyloxy-carbonyl group and the like];
(5) an optionally substituted alkyl group;
(6) an optionally substituted alkenyl group;
(7) an optionally substituted alkynyl group;
(8) an optionally substituted $C_{3-7}$ cycloalkyl-$C_{2-6}$ alkynyl group;
(9) an optionally substituted $C_{3-7}$ cycloalkyl group;
(10) an optionally substituted $C_{6-14}$ aryl group;
(11) an optionally substituted $C_{7-16}$ aralkyl group;
(12) an optionally substituted $C_{6-14}$ aryl-$C_{2-6}$ alkenyl group;
(13) an optionally substituted heterocyclic group;
(14) a hydroxy group;
(15) an optionally substituted alkoxy group;
(16) an optionally substituted $C_{3-7}$ cycloalkyloxy group;
(17) an optionally substituted $C_{6-14}$ aryloxy group;
(18) an optionally substituted $C_{7-16}$ aralkyloxy group;
(19) an optionally substituted alkyl-carbonyloxy group;
(20) an optionally substituted alkoxy-carbonyloxy group;
(21) an optionally substituted mono-alkyl-carbamoyloxy group;
(22) an optionally substituted di-alkyl-carbamoyloxy group;
(23) an optionally substituted $C_{6-14}$ aryl-carbonyloxy group;
(24) an optionally substituted mono- or di-$C_{6-14}$ aryl-carbamoyloxy group;
(25) an optionally substituted heterocyclyl-oxy group (e.g., optionally substituted aromatic heterocyclyl-oxy group);
(26) an optionally substituted $C_{1-6}$ alkylsulfonyloxy group (e.g., optionally substituted halogeno $C_{1-6}$ alkylsulfonyloxy group),
(27) a mercapto group;
(28) an optionally substituted alkylsulfanyl group;
(29) an optionally substituted $C_{3-7}$ cycloalkylsulfanyl group;
(30) an optionally substituted $C_{6-14}$ arylsulfanyl group;
(31) an optionally substituted $C_{7-16}$ aralkylsulfanyl group;
(32) an optionally substituted heterocyclyl-sulfanyl group;
(33) a formyl group;
(34) an optionally substituted alkyl-carbonyl group;
(35) an optionally substituted $C_{3-7}$ cycloalkyl-carbonyl group;
(36) an optionally substituted $C_{6-14}$ aryl-carbonyl group;
(37) an optionally substituted $C_{7-16}$ aralkyl-carbonyl group;
(38) an optionally substituted heterocyclyl-carbonyl group;
(39) an optionally substituted alkylsulfonyl group;
(40) an optionally substituted $C_{3-7}$ cycloalkylsulfonyl group;
(41) an optionally substituted $C_{6-14}$ arylsulfonyl group;
(42) an optionally substituted heterocyclyl-sulfonyl group;
(43) an optionally substituted alkylsulfinyl group;
(44) an optionally substituted $C_{3-7}$ cycloalkylsulfinyl group;
(45) an optionally substituted $C_{6-14}$ arylsulfinyl group;
(46) an optionally substituted heterocyclyl-sulfinyl group;
(47) a sulfo group;
(48) a sulfamoyl group;
(49) a sulfinamoyl group;
(50) a sulfenamoyl group;
(51) a thiocarbamoyl group;

(52) an optionally substituted carbamoyl group
[e.g., a carbamoyl group,
an optionally substituted mono- or di-alkyl-carbamoyl group,
an optionally substituted mono- or di-$C_{6-14}$ aryl-carbamoyl group,
an optionally substituted mono- or di-heterocyclyl-carbamoyl group and the like];
(53) an optionally substituted amino group
[e.g.,
an amino,
an optionally substituted mono- or di-alkylamino group,
an optionally substituted mono- or di-$C_{3-7}$ cycloalkylamino group,
an optionally substituted mono- or di-$C_{6-14}$ arylamino group,
an optionally substituted mono- or di-$C_{7-16}$ aralkylamino group,
an optionally substituted heterocyclyl-amino group,
an optionally substituted $C_{6-14}$ aryl-carbonylamino group,
a formylamino group,
an optionally substituted alkyl-carbonylamino group (e.g., mono-($C_{1-6}$ alkyl-carbonyl)-amino group),
an optionally substituted $C_{3-7}$ cycloalkyl-carbonylamino group,
an optionally substituted heterocyclyl-carbonylamino group,
an optionally substituted alkoxy-carbonylamino group,
an optionally substituted $C_{3-7}$ cycloalkyloxy-carbonylamino group,
an optionally substituted heterocyclyl-oxycarbonylamino group,
an optionally substituted carbamoylamino group
[e.g., a carbamoylamino group,
an optionally substituted mono- or di-alkyl-carbamoylamino group,
an optionally substituted mono- or di-$C_{6-14}$ aryl-carbamoylamino group,
an optionally substituted mono- or di-heterocyclyl-carbamoylamino group and the like],
an optionally substituted alkylsulfonylamino group,
an optionally substituted $C_{3-7}$ cycloalkylsulfonylamino group,
an optionally substituted heterocyclyl-sulfonylamino group,
an optionally substituted $C_{6-14}$ arylsulfonylamino group]; and
(54) an oxo.

In the substituent group A, examples of each substituent of
"optionally substituted alkoxy-carbonyl group",
"optionally substituted alkyl group",
"optionally substituted alkenyl group",
"optionally substituted alkynyl group",
"optionally substituted alkoxy group",
"optionally substituted alkyl-carbonyloxy group",
"optionally substituted alkoxy-carbonyloxy group",
"optionally substituted mono-alkyl-carbamoyloxy group",
"optionally substituted di-alkyl-carbamoyloxy group",
"optionally substituted $C_{1-6}$ alkylsulfonyloxy group",
"optionally substituted halogeno $C_{1-6}$ alkylsulfonyloxy group",
"optionally substituted alkylsulfanyl group",
"optionally substituted alkyl-carbonyl group",
"optionally substituted alkylsulfonyl group",
"optionally substituted alkylsulfinyl group",
"optionally substituted Mono- or di-alkyl-carbamoyl group",
"optionally substituted mono- or di-alkylamino group",
"optionally substituted alkyl-carbonylamino group",
"optionally substituted mono- or di-$C_{1-6}$ alkyl-carbamoylamino group",
"optionally substituted mono-($C_{1-6}$ alkyl-carbonyl)-amino group",
"optionally substituted alkoxy-carbonylamino group",
"optionally substituted alkylsulfonylamino group", and
"optionally substituted silyloxy-carbonyl group" include substituents selected from the following substituent group B. The number of the substituents is 1 to the maximum substitutable number, more preferably 1 to 3, more preferably 1.

In substituent group A, examples of each substituent of
"optionally substituted $C_{6-14}$ aryloxy-carbonyl group",
"optionally substituted $C_{7-16}$ aralkyloxy-carbonyl group",
"optionally substituted $C_{3-7}$ cycloalkyl-$C_{2-6}$ alkynyl group",
"optionally substituted $C_{3-7}$ cycloalkyl group",
"optionally substituted $C_{6-14}$ aryl group",
"optionally substituted $C_{7-16}$ aralkyl group",
"optionally substituted $C_{6-14}$ aryl-$C_{2-6}$ alkenyl group",
"optionally substituted heterocyclic group",
"optionally substituted $C_{3-7}$ cycloalkyloxy group",
"optionally substituted $C_{6-14}$ aryloxy group",
"optionally substituted $C_{7-16}$ aralkyloxy group",
"optionally substituted $C_{6-14}$ aryl-carbonyloxy group",
"optionally substituted mono- or di-$C_{6-14}$ aryl-carbamoyloxy group",
"optionally substituted heterocyclyl-oxy group",
"optionally substituted aromatic heterocyclyl-oxy group",
"optionally substituted $C_{3-7}$ cycloalkylsulfanyl group",
"optionally substituted $C_{6-14}$ arylsulfanyl group",
"optionally substituted $C_{7-16}$ aralkylsulfanyl group",
"optionally substituted heterocyclyl-sulfanyl group",
"optionally substituted $C_{3-7}$ cycloalkyl-carbonyl group",
"optionally substituted $C_{6-14}$ aryl-carbonyl group",
"optionally substituted $C_{7-16}$ aralkyl-carbonyl group",
"optionally substituted heterocyclyl-carbonyl group",
"optionally substituted $C_{3-7}$ cycloalkylsulfonyl group",
"optionally substituted $C_{6-14}$ arylsulfonyl group",
"optionally substituted heterocyclyl-sulfonyl group",
"optionally substituted $C_{3-7}$ cycloalkylsulfinyl group",
"optionally substituted $C_{6-14}$ arylsulfinyl group",
"optionally substituted heterocyclyl-sulfinyl group",
"optionally substituted mono- or di-$C_{6-14}$ aryl-carbamoyl group",
"optionally substituted mono- or di-heterocyclyl-carbamoyl group",
"optionally substituted mono- or di-$C_{3-9}$ cycloalkylamino group",
"optionally substituted mono- or di-$C_{6-14}$ arylamino group",
"optionally substituted mono- or di-$C_{7-16}$ aralkylamino group",
"optionally substituted heterocyclyl-amino group",
"optionally substituted $C_{6-14}$ aryl-carbonylamino group",
"optionally substituted $C_{3-8}$ cycloalkyl-carbonylamino group",
"optionally substituted heterocyclyl-carbonylamino group",
"optionally substituted $C_{3-8}$ cycloalkyloxy-carbonylamino group",
"optionally substituted heterocyclyl-oxycarbonylamino group",
"optionally substituted mono- or di-$C_{6-14}$ aryl-carbamoylamino group",
"optionally substituted mono- or di-heterocyclyl-carbamoylamino group",
"optionally substituted $C_{3-8}$ cycloalkylsulfonylamino group",
"optionally substituted heterocyclyl-sulfonylamino group", and
"optionally substituted $C_{6-14}$ arylsulfonylamino group" include substituents selected from the following substituent group B and the following substituent group B'. The number of the substituents is 1 to the maximum substitutable number, more preferably 1 to 3, more preferably 1.
[Substituent Group B]
In the present specification, substituent group B includes
(a) a halogen atom;
(b) a hydroxy group;
(c) a nitro group;
(d) a cyano group;
(e) an optionally substituted $C_{6-14}$ aryl group [for example, a $C_{6-14}$ aryl group optionally substituted by one or more (e.g., 1 to 5) substituents selected from the group consisting of a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl and the like];
(f) an optionally substituted $C_{6-14}$ aryloxy group [for example, a $C_{6-14}$ aryloxy group optionally substituted by one or more (e.g., 1 to 5) substituents selected from the group consisting of a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl and the like];
(g) an optionally substituted $C_{7-16}$ aralkyloxy group [for example, a $C_{7-16}$ aralkyloxy group optionally substituted by one or more (e.g., 1 to 5) substituents selected from the group consisting of a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl and the like];
(h) an optionally substituted 5- to 10-membered heterocyclic group containing 1 to 5 hetero atoms selected from a nitrogen atom, a sulfur atom, and an oxygen atom [for example, a 5- to 10-membered heterocyclic group containing 1 to 5 hetero atoms selected from a nitrogen atom, a sulfur atom, and an oxygen atom (e.g., furyl, pyridyl, thienyl, pyrrolidino, 1-piperidinyl, 4-piperidyl, piperazinyl, 4-morpholinyl, 4-thiomorpholinyl, azepan-1-yl, azocan-1-yl, azonan-1-yl, 3,4-dihydroisoquinolin-2-yl), which is optionally substituted by one or more (e.g., 1 to 5) substituents selected from the group consisting of a halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl and the like];
(i) an optionally substituted amino group [for example, an amino group optionally substituted by 1 or 2 substituents selected from the group consisting of $C_{1-6}$ alkyl, $C_{2-6}$ alkenyl, $C_{6-14}$ aryl, $C_{7-16}$ aralkyl, a heterocyclic group, and heterocyclyl-alkyl, each of which is optionally substituted (examples of the substituent of the "$C_{1-6}$ alkyl, $C_{2-6}$ alkenyl, $C_{6-14}$ aryl, $C_{7-16}$ aralkyl, a heterocyclic group, and heterocyclyl-alkyl, each of which is optionally substituted" include a halogen atom, hydroxy, cyano, amino, optionally halogenated $C_{1-6}$ alkyl (which is not substituent of alkyl and alkenyl), mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{3-7}$ cycloalkyloxy-carbonyl, $C_{6-14}$ aryloxy-carbonyl, $C_{7-16}$ aralkyloxy-carbonyl, $C_{1-6}$ alkylsulfanyl, $C_{3-7}$ cycloalkylsulfanyl, $C_{1-6}$ alkylsulfinyl, $C_{3-7}$ cycloalkylsulfinyl, $C_{1-6}$ alkylsulfonyl, $C_{3-7}$ cycloalkylsulfonyl, carbamoyl, thiocarbamoyl, mono- or di-$C_{1-6}$ alkyl-carbamoyl, and mono- or di-$C_{6-14}$ aryl-carbamoyl and the like. The number of the substituents is one or more (e.g., 1 to 5). Examples of the "heterocyclyl-" of the "heterocyclic group" and "heterocyclyl-alkyl" include those similar to the aforementioned "heterocyclic group".)];
(j) a $C_{3-7}$ cycloalkyl;
(k) an optionally substituted $C_{1-6}$ alkoxy group [for example, a $C_{1-6}$ alkoxy group optionally substituted by one or more (e.g., 1 to 5) substituents selected from the group consisting of a halogen atom, hydroxy, amino, mono- or di-$C_{1-6}$ alkylamino, mono- or di-$C_{6-14}$ arylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{4-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl, trimethylsilyl (TMS) and the like];
(l) a formyl group;
(m) a $C_{1-6}$ alkyl-carbonyl group (e.g., acetyl);
(n) a $C_{3-7}$ cycloalkyl-carbonyl group;
(o) a $C_{6-14}$ aryl-carbonyl group;
(p) a $C_{7-16}$ aralkyl-carbonyl group;
(q) a $C_{1-6}$ alkoxy-carbonyl group;
(r) a $C_{6-14}$ aryloxy-carbonyl group;
(s) a $C_{7-16}$ aralkyloxy-carbonyl group;
(t) a $C_{1-6}$ alkylsulfanyl group;
(u) a $C_{1-6}$ alkylsulfinyl group;
(v) a $C_{1-6}$ alkylsulfonyl group;
(w) a carbamoyl group;
(x) a thiocarbamoyl group;
(y) a mono-$C_{1-6}$ alkyl-carbamoyl group (e.g., methylcarbamoyl, ethylcarbamoyl and the like);
(z) a di-$C_{1-6}$ alkyl-carbamoyl group (e.g., dimethylcarbamoyl, diethylcarbamoyl, ethylmethylcarbamoyl and the like);
(aa) a mono- or di-$C_{6-14}$ aryl-carbamoyl group (e.g., phenylcarbamoyl, 1-naphthylcarbamoyl, 2-naphthylcarbamoyl and the like);
(bb) a mono- or di-5- to 7-membered heterocyclyl-carbamoyl group containing 1 to 5 hetero atoms selected from a nitrogen atom, a sulfur atom, and an oxygen atom (e.g., 2-pyridylcarbamoyl, 3-pyridylcarbamoyl, 4-pyridylcarbamoyl, 2-thienylcarbamoyl, 3-thienylcarbamoyl and the like); and (cc) an oxo.
[Substituent Group B']
In the present specification, substituent group B' includes
(a) an optionally substituted $C_{1-6}$ alkyl group [for example, a $C_{1-6}$ alkyl group optionally substituted by one or more (e.g., 1 to 5) substituents selected from the group consisting of a halogen atom, hydroxy, cyano, amino, mono- or di-$C_{1-6}$ alkylamino, mono- or di-C$_{6-14}$ arylamino, mono- or di-C$_{7-16}$ aralkylamino, C$_{3-7}$ cycloalkyl, C$_{1-6}$ alkoxy, formyl, C$_{1-6}$ alkyl-carbonyl, C$_{3-7}$ cycloalkyl-carbonyl, C$_{6-14}$ aryl-carbonyl, C$_{7-16}$ aralkyl-carbonyl, C$_{1-6}$ alkoxy-carbonyl, C$_{6-14}$ aryloxy-carbonyl, C$_{7-16}$ aralkyloxy-carbonyl, C$_{1-6}$ alkylsulfanyl, C$_{1-6}$ alkylsulfinyl, C$_{1-6}$ alkylsulfonyl, carbamoyl, thiocarbamoyl, mono- or di-C$_{1-6}$ alkyl-carbamoyl, and mono- or di-C$_{6-14}$ aryl-carbamoyl and the like];

(b) an optionally substituted C$_{2-6}$ alkenyl group [for example, a C$_{2-6}$ alkenyl group optionally substituted by one or more (e.g., 1 to 5) substituents selected from the group consisting of a halogen atom, hydroxy, cyano, amino, mono- or di-C$_{1-6}$ alkylamino, mono- or di-C$_{6-14}$ arylamino, mono- or di-C$_{7-16}$ aralkylamino, C$_{3-7}$ cycloalkyl, C$_{1-6}$ alkoxy, formyl, C$_{1-6}$ alkyl-carbonyl, C$_{3-7}$ cycloalkyl-carbonyl, C$_{6-14}$ aryl-carbonyl, C$_{7-16}$ aralkyl-carbonyl, C$_{1-6}$ alkoxy-carbonyl, C$_{6-14}$ aryloxy-carbonyl, C$_{7-16}$ aralkyloxy-carbonyl, C$_{1-6}$ alkylsulfanyl, C$_{1-6}$ alkylsulfinyl, C$_{1-6}$ alkylsulfonyl, carbamoyl, thiocarbamoyl, mono- or di-C$_{1-6}$ alkyl-carbamoyl, and mono- or di-C$_{6-14}$ aryl-carbamoyl and the like]; and (c) an optionally substituted C$_{2-6}$ alkynyl group [for example, a C$_{2-6}$ alkynyl group optionally substituted by one or more (e.g., 1 to 5) substituents selected from the group consisting of a halogen atom, hydroxy, cyano, amino, mono- or di-C$_{1-6}$ alkylamino, mono- or di-C$_{6-14}$ arylamino, mono- or di-C$_{7-16}$ aralkylamino, C$_{3-7}$ cycloalkyl, C$_{1-6}$ alkoxy, formyl, C$_{1-6}$ alkyl-carbonyl, C$_{3-7}$ cycloalkyl-carbonyl, C$_{6-14}$ aryl-carbonyl, C$_{7-16}$ aralkyl-carbonyl, C$_{1-6}$ alkoxy-carbonyl, C$_{6-14}$ aryloxy-carbonyl, C$_{7-16}$ aralkyloxy-carbonyl, C$_{1-6}$ alkylsulfanyl, C$_{1-6}$ alkylsulfinyl, C$_{1-6}$ alkylsulfonyl, carbamoyl, thiocarbamoyl, mono- or di-C$_{1-6}$ alkyl-carbamoyl, and mono- or di-C$_{6-14}$ aryl-carbamoyl and the like].

The symbols in the following formula (1) and formula (1') are explained.

In the formula (1), Ring A is an optionally substituted pyridine ring.

In the formula (1'), Ring A' is an optionally substituted pyridine ring, an optionally substituted pyridazine ring, a pyrimidine ring or a pyrazine ring.

Examples of the substituent for "optionally substituted pyridine ring" for Ring A and Ring A', and the "optionally substituted pyridazine ring" for Ring A' include substituents selected from the aforementioned substituent group A.

The number of the substituent is preferably 0 (i.e., unsubstituted), or 1 to 5.

A compound wherein the "pyridine ring" of the "optionally substituted pyridine ring" for Ring A has a hydrogen atom (unsubstituted) at the 4-position, namely, a compound represented by the following formula:

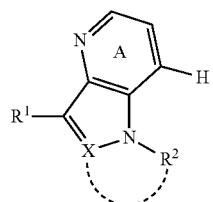

(1)

wherein each symbol is as defined above, is preferable.

Ring A is preferably a pyridine ring optionally substituted by substituent(s) selected from (i) an optionally substituted C$_{1-6}$ alkyl group, (ii) an optionally substituted C$_{1-6}$ alkoxy group, (iii) a halogen atom, and (iv) a cyano group, more preferably, a pyridine ring optionally substituted by substituent(s) selected from (i) a C$_{1-6}$ alkyl group, (ii) a C$_{1-6}$ alkoxy group, (iii) a halogen atom, and (iv) a cyano group, particularly preferably, a pyridine ring optionally substituted by 1 to 4 halogen atoms (e.g., fluorine atom).

Ring A' is preferably a pyridine ring optionally substituted by substituent(s) selected from (i) an optionally substituted C$_{1-6}$ alkyl group, (ii) an optionally substituted C$_{1-6}$ alkoxy group, (iii) a halogen atom, and (iv) a cyano group, an (unsubstituted) pyrimidine ring, or an (unsubstituted) pyrazine ring, more preferably, a pyridine ring optionally substituted by substituent(s) selected from (i) a C$_{1-6}$ alkyl group, (ii) a C$_{1-6}$ alkoxy group, (iii) a halogen atom, and (iv) a cyano group, an (unsubstituted) pyrimidine ring, or an (unsubstituted) pyrazine ring, particularly preferably, a pyridine ring optionally substituted by 1 to 4 halogen atoms (e.g., fluorine atom), an (unsubstituted) pyrimidine ring, or an (unsubstituted) pyrazine ring.

Examples of the substituent for the "optionally substituted C$_{2-6}$ alkyl group" and "optionally substituted C$_{1-6}$ alkoxy group" as substituents of the pyridine ring for Ring A and Ring A' include substituents selected from the aforementioned substituent group B. The number of the substituents is preferably 0 (i.e., unsubstituted), or 1 to 5.

In the formula (1), R$^1$ is

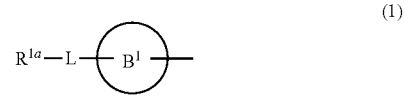

(1)

wherein R$^{1a}$ is an optionally substituted phenyl group, or an optionally substituted 5- to 10-membered heterocyclic group, L is a bond, —S—, —O—, —CO—, an optionally substituted methylene group, or —NR$^a$— wherein R$^a$ is a hydrogen atom or an optionally substituted C$_{1-6}$ alkyl group, and Ring B$^1$ is an optionally further substituted 6- to 10-membered aromatic hydrocarbon ring, or an optionally further substituted 5- to 10-membered aromatic heterocyclic ring, or alternatively, L and R$^{1a}$ may be taken together to form an optionally substituted bicyclic or tricyclic fused heterocyclic group), or,

(2)

wherein R$^{1b}$ is an optionally substituted phenyl group, or an optionally substituted 5- to 10-membered heterocyclic group, Ring B$^2$ is an optionally substituted benzene ring, an optionally substituted pyridine ring, an optionally substituted pyrimidine ring, an optionally substituted pyrazine ring, or an optionally substituted pyridazine ring, and Ring D is an optionally further substituted 5- or 6-membered ring.

In the formula (1'), R$^{1'}$ is

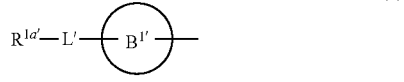

(1)

wherein R¹ᵃ' is an optionally substituted phenyl group, or an optionally substituted 5- to 10-membered heterocyclic group, L' is a bond, —S—, —O—, —CO—, an optionally substituted methylene group, or —NRᵃ'— wherein Rᵃ' is a hydrogen atom or an optionally substituted $C_{1-6}$ alkyl group, Ring B¹' is an optionally further substituted 6- to 10-membered aromatic hydrocarbon ring, or an optionally further substituted 5- to 10-membered aromatic heterocyclic ring, or alternatively, L' and R¹ᵃ' may be taken together to form an optionally substituted bicyclic or tricyclic fused heterocyclic group, or

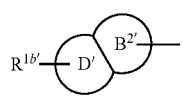
(2)

wherein R¹ᵇ' is an optionally substituted phenyl group, or an optionally substituted 5- to 10-membered heterocyclic group, Ring B²' is an optionally substituted benzene ring, an optionally substituted pyridine ring, an optionally substituted pyrimidine ring, an optionally substituted pyrazine ring, or an optionally substituted pyridazine ring, and Ring D' is an optionally further substituted 5- or 6-membered ring.

Examples of the substituent of the "optionally substituted phenyl group" for R¹ᵃ and R¹ᵃ' include substituents selected from the aforementioned substituent group A. The number of the substituent is preferably 0 (i.e., unsubstituted), or 1 to 5.

Examples of the "5- to 10-membered heterocyclic group" of the "optionally substituted 5- to 10-membered heterocyclic group" for R¹ᵃ and R¹ᵃ' include a 5- to 10-membered heterocyclic group from among the aforementioned "3- to 14-membered heterocyclic group containing 1 to 5 hetero atoms selected from a nitrogen atom, a sulfur atom, and an oxygen atom".

Particularly preferred are a 5- or 6-membered monocyclic heterocyclic group, a bicyclic fused heterocyclic group (preferably, 9- or 10-membered bicyclic fused heterocyclic group) and the like.

Examples of the "5- or 6-membered monocyclic heterocyclic group" include a 5- or 6-membered heterocyclic group (e.g., "5- or 6-membered monocyclic aromatic heterocyclic group" exemplified as the aforementioned "heterocyclic group"), from among the aforementioned "3- to 14-membered heterocyclic group containing 1 to 5 hetero atoms selected from a nitrogen atom, a sulfur atom, and an oxygen atom" and the like.

As the aforementioned "5- or 6-membered heterocyclic group", specifically preferred is pyridyl, and particularly preferred is 2-pyridyl.

Examples of the aforementioned "bicyclic fused heterocyclic group" include a bicyclic heterocyclic group (e.g., "5- to 10-membered aromatic fused heterocyclic group" exemplified as the aforementioned "heterocyclic group"), from among the aforementioned "3- to 14-membered heterocyclic group containing 1 to 5 hetero atoms selected from a nitrogen atom, a sulfur atom, and an oxygen atom" and the like.

As the aforementioned "bicyclic fused heterocyclic group", specifically preferred are the following groups:

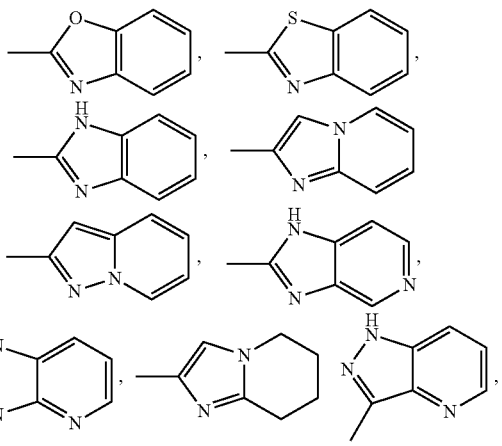

more preferred are 2-benzoxazolyl, 2-benzimidazolyl, azabenzoimidazol-2-yl (e.g., imidazo[4,5-b]pyridin-2-yl and the like), imidazo[1,2-a]pyridyl, tetrahydroimidazo[1,2-a]pyridyl, pyrazolo[4,5-b]pyridyl and the like.

Examples of the substituents of the "optionally substituted 5- to 10-membered heterocyclic group" for R¹ᵃ and R¹ᵃ' include the substituents selected from the aforementioned substituent group A. The number of the substituent is preferably 0 (i.e., unsubstituted), or 1 to 5.

Examples of the substituent of the "optionally substituted methylene group" for L and L' include the substituents selected from the aforementioned substituent group A.

The number of the substituent is preferably 0 (i.e., unsubstituted), or 1 or 2.

In —NRᵃ— for L and —NRᵃ'— for L', Rᵃ and Rᵃ' are each a hydrogen atom or an optionally substituted $C_{1-6}$ alkyl group.

Examples of the substituent of the "optionally substituted $C_{1-6}$ alkyl group" for Rᵃ and Rᵃ' include the substituents selected from the aforementioned substituent group B. The number of the substituent is preferably 0 (i.e., unsubstituted), or 1 to 5.

Rᵃ and Rᵃ' are each preferably a hydrogen atom and the like.

L is preferably a bond, —O—, —CO—, or —NH— and the like, more preferably —O—.

L and R¹ᵃ, or L' and R¹ᵃ' may be taken together to form an optionally substituted bicyclic or tricyclic fused heterocyclic group.

"L and R¹ᵃ may be taken together to form an optionally substituted bicyclic or tricyclic fused heterocyclic group" or "L' and R¹ᵃ' may be taken together to form an optionally substituted bicyclic or tricyclic fused heterocyclic group" means that a moiety represented by the formula:

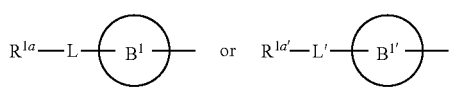

in the formula (1) or (1') is

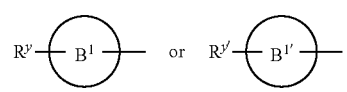

wherein R$^y$ and R$^{y'}$ are each an optionally substituted bicyclic or tricyclic fused heterocyclic group, and B$^1$ and B$^{1'}$ are as defined above.

In other words, a substituent on the ring-constituting atom of the "phenyl group" or "5- to 10-membered heterocyclic group" for R$^1$ or R$^{1'}$, and a substituent on the main chain-constituting atom for L or L' form a ring together with the ring-constituting atom or the main chain-constituting atom, respectively. In the present specification, such embodiment may be expressed by the following formula:

$$R^{1a}\!-\!L\!-\!\!\left(\!B^1\!\right)\!-\!\!\qquad\text{or}\qquad R^{1a'}\!-\!L'\!-\!\!\left(\!B^{1'}\!\right)\!-\!\!\quad.$$

Examples of the "bicyclic or tricyclic fused heterocyclic group" of the "optionally substituted bicyclic or tricyclic fused heterocyclic group" optionally formed by L and R$^{1a}$, or L' and R$^{1a'}$ in combination include a bicyclic or tricyclic heterocyclic group from among the aforementioned "3- to 14-membered heterocyclic group containing 1 to 5 hetero atoms selected from a nitrogen atom, a sulfur atom, and an oxygen atom".

The "bicyclic or tricyclic fused heterocyclic group" is preferably, for example, the following groups:

wherein
Y is —CH$_2$—, —NH—, an oxygen atom or a sulfur atom, and
Y' is =CH— or =N—, and the like.

Examples of the substituent of the "optionally substituted bicyclic or tricyclic fused heterocyclic group" optionally formed by L and R$^{1a}$, or L' and R$^{1a'}$ in combination include substituents selected from the aforementioned substituent group A.

The number of the substituent is preferably 0 (i.e., unsubstituted), or 1 to 3.

Ring B$^1$ and Ring B$^{1'}$ are each an optionally substituted 6- to 10-membered aromatic hydrocarbon ring, or an optionally substituted 5- to 10-membered aromatic heterocyclic ring.

Examples of the "6- to 10-membered aromatic hydrocarbon ring" of the "optionally substituted 6- to 10-membered aromatic hydrocarbon ring" for Ring B$^1$ or Ring B$^{1'}$ include a benzene ring, and a naphthalene ring.

Examples of the substituent of the "optionally substituted 6- to 10-membered aromatic hydrocarbon ring" for Ring B$^1$ or Ring B$^{1'}$ include the substituents selected from the aforementioned substituent group A.

The number of the substituent is preferably 0 (i.e., unsubstituted), or 1 to 3.

Examples of the "optionally substituted 5- to 10-membered aromatic heterocyclic ring" for Ring B$^1$ or Ring B$^{1'}$ include (1) a 5- or 6-membered heterocyclic ring, (2) 9- or 10-membered aromatic heterocyclic ring, which is a benzene ring condensed with the 5- or 6-membered heterocyclic ring, and (3) a bicyclic fused heterocyclic ring, which is a 5- or 6-membered heterocyclic ring condensed with the 5- or 6-membered heterocyclic ring.

Examples of the "5- or 6-membered heterocyclic ring" include 5- or 6-membered ones from the aforementioned "5- to 7-membered heterocyclic ring".

Examples of the substituent of the "optionally substituted 5- to 10-membered aromatic heterocyclic ring" for Ring B$^1$ or Ring B$^{1'}$ include the substituents selected from the aforementioned substituent group A.

The number of the substituent is preferably 0 (i.e., unsubstituted), or 1 to 3.

Ring B$^1$ and Ring are each particularly preferably a benzene ring, a pyridine ring, a dihydropyridine ring, a pyrazole ring and the like.

In the formula (1) or (1'), a moiety represented by $$-\!\!\left(\!B^1\!\right)\!-\!\!\qquad\text{or}\qquad -\!\!\left(\!B^{1'}\!\right)\!-$$

is particularly preferably and the like.

R$^{1b}$ and R$^{1b'}$ are each an optionally substituted phenyl group, or an optionally substituted 5- to 10-membered heterocyclic group.

Examples of the substituent of "optionally substituted phenyl group" for R$^{1b}$ or R$^{1b'}$ include the substituents selected from the aforementioned substituent group A. The number of the substituent is preferably 0 (i.e., unsubstituted), or 1 to 5.

Examples of the "5- to 10-membered heterocyclic group" of the "optionally substituted 5- to 10-membered heterocyclic group" for R$^{1b}$ or R$^{1b'}$ include a 5- to 10-membered heterocyclic group from the aforementioned "3- to 14-membered heterocyclic group containing 1 to 5 hetero atoms selected from a nitrogen atom, a sulfur atom, and an oxygen atom".

Particularly preferred is a 5- or 6-membered monocyclic heterocyclic group, a bicyclic fused heterocyclic group (preferably, 9- or 10-membered bicyclic fused heterocyclic group) and the like.

Examples of the "5- or 6-membered monocyclic heterocyclic group" include a 5- or 6-membered heterocyclic group (e.g., "5- or 6-membered monocyclic aromatic heterocyclic group" exemplified as the aforementioned "heterocyclic group"), from among the aforementioned "3- to 14-membered heterocyclic group to containing 1 to 5 hetero atoms selected from a nitrogen atom, a sulfur atom, and an oxygen atom" and the like.

Examples of the aforementioned "bicyclic fused heterocyclic group" include a bicyclic heterocyclic group (e.g., "5- to 10-membered aromatic fused heterocyclic group" exemplified as the aforementioned "heterocyclic group"), from among the aforementioned "3- to 14-membered heterocyclic group containing 1 to 5 hetero atoms selected from a nitrogen atom, a sulfur atom, and an oxygen atom" and the like.

Examples of the substituent of the "optionally substituted 5- to 10-membered heterocyclic group" for $R^{1b}$ or $R^{1b'}$ include the substituents selected from the aforementioned substituent group A. The number of the substituent is preferably 0 (i.e., unsubstituted), or 1 to 5.

Preferable embodiment of $R^{1b}$ and $R^{1b'}$ is the same as that of the above-mentioned $R^{1a}$ and $R^{1a'}$.

Ring $B^2$ and Ring $B^{2'}$ are each an optionally substituted benzene ring, an optionally substituted pyridine ring, an optionally substituted pyrimidine ring, an optionally substituted pyrazine ring, or an optionally substituted pyridazine ring.

Examples of the substituent of the "optionally substituted benzene ring", "optionally substituted pyridine ring", "optionally substituted pyrimidine ring", "optionally substituted pyrazine ring", and "optionally substituted pyridazine ring" for Ring $B^2$ or Ring $B^{2'}$ include the substituents selected from the aforementioned substituent group A. The number of the substituent is preferably 0 (i.e., unsubstituted), or 1 to 5.

Ring D and Ring D' are each an optionally further substituted 5- or 6-membered ring.

Examples of the "5- or 6-membered ring" of the "optionally further, substituted 5- or 6-membered ring" for Ring D or Ring D' include a hydrocarbon ring having a carbon number of 5 or 6, and 5- or 6-membered heterocyclic ring.

Examples of the "hydrocarbon ring having a carbon number of 5 or 6" include one having a carbon number of 5 or 6 from the aforementioned "hydrocarbon ring having a carbon number of 5 to 7".

Examples of the "5- or 6-membered heterocyclic ring" include a 5- or 6-membered one from the aforementioned "5- to 7-membered heterocyclic ring".

Further substituent of the "optionally further substituted 5- or 6-membered ring" for Ring D or Ring D' (i.e., substituents other than $R^{1b}$) includes the substituents selected from the aforementioned substituent group A. The number of the substituent is preferably 0 (i.e., unsubstituted), or 1 to 5.

In the formula (1), the moiety structure

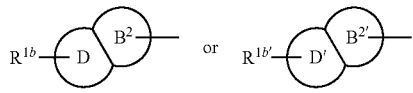

is preferably

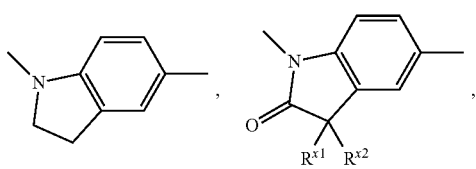

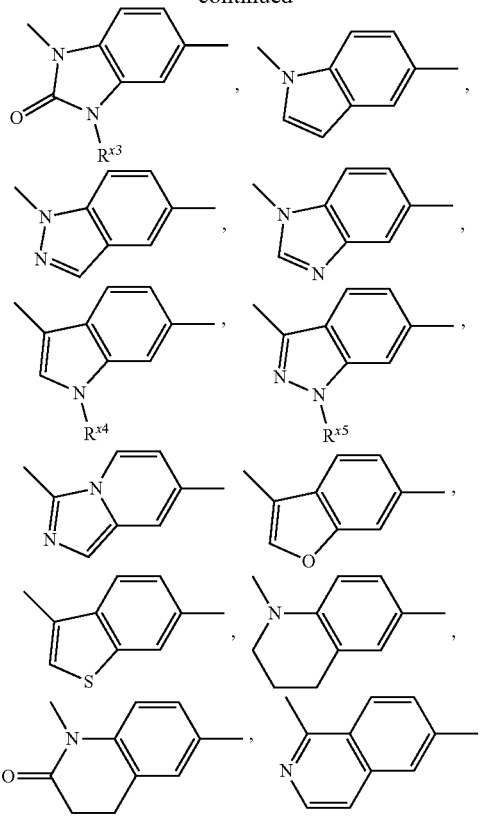

wherein
$R^{x1}$ and $R^{x2}$ are the same or different and each is a hydrogen atom or an optionally substituted $C_{1-6}$ alkyl group, $R^{x3}$, $R^{x3}$ and $R^{x5}$ are each a hydrogen atom or an optionally substituted alkyl group, and
the ring-constituting atom optionally has substituent(s), and the like.

Examples of the "substituent" of the "optionally substituted $C_{1-6}$ alkyl group" for $R^{x1}$ or $R^{x2}$ include the substituents selected from the aforementioned substituent group B. The number of the substituent is preferably 0 (i.e., unsubstituted), or 1 to 5.

Examples of the "substituent" of the "optionally substituted $C_{1-6}$ alkyl group" for $R^{x3}$, $R^{x3}$ or $R^{x5}$ include the substituents selected from the aforementioned substituent group B. The number of the substituent is preferably 0 (i.e., unsubstituted), or 1 to 5.

Examples of the substituent that the aforementioned ring-constituting atom further optionally has include the substituents selected from the aforementioned substituent group A. The number of the substituent is preferably 0 (i.e., unsubstituted), or 1 to 5.

$R^1$ is preferably a group represented by the formula:

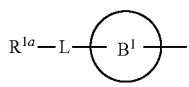

wherein
$R^{1a}$ is a 5- to 10-membered heterocyclic group optionally substituted by 1 to 3 substituents selected from
(1) a $C_{1-6}$ alkyl group optionally substituted by 1 to 3 substituents selected from (a) a 2-(trimethylsilyl)ethoxy group, (b) a hydroxy group, (c) a $C_{1-6}$ alkoxy group (e.g., methoxy) and (d) a halogen atom (e.g., fluorine atom), (2) a halogen atom (e.g., chlorine atom), and (3) a cyano group, Ring $B^1$ is a benzene ring optionally substituted by 1 to 3 halogen atoms, a pyridine ring, a dihydropyridine ring optionally substituted by an oxo group, or a pyrazole ring, L is a bond, —O—, —CO—, or —NH— (preferably, —O—), or alternatively, L and $R^{1a}$ are taken together to form

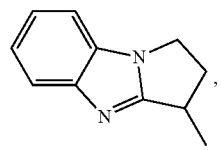

or a group represented by the formula:

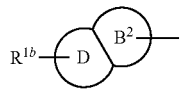

wherein $R^{1b}$ is a 5- to 10-membered heterocyclic group (e.g., benzimidazolyl group), Ring $B^2$ is a benzene ring, and Ring D is a 5- or 6-membered ring (e.g., pyrrolidine ring) and the like.

In another embodiment, $R^1$ is preferably a group represented by the formula:

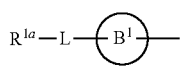

wherein $R^{1a}$ is a 5- to 10-membered heterocyclic group optionally substituted by 1 to 3 substituents selected from (1) a $C_{1-6}$ alkyl group optionally substituted by 1 to 3 substituents selected from (a) a 2-(trimethylsilyl)ethoxy group, (b) a hydroxy group, (c) a $C_{1-6}$ alkoxy group (e.g., methoxy) and (d) a halogen atom (e.g., fluorine atom), (2) a halogen atom (e.g., chlorine atom), and (3) a cyano group, Ring $B^1$ is a benzene ring optionally substituted by 1 to 3 halogen atoms, a pyridine ring, a dihydropyridine ring optionally substituted by an oxo group, or a pyrazole ring, L is a bond, —O—, —CO—, or —NH— (preferably —O—), or alternatively, L and $R^{1a}$ are taken together to form

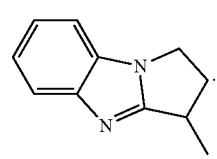

$R^{1'}$ is preferably a group represented by the formula:

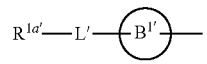

wherein $R^{1a'}$ is a 5- to 10-membered heterocyclic group optionally substituted by 1 to 3 substituents selected from (1) a $C_{1-6}$ alkyl group optionally substituted by 1 to 3 substituents selected from (a) a 2-(trimethylsilyl)ethoxy group, (b) a hydroxy group, (c) a $C_{1-6}$ alkoxy group and (d) a halogen atom (e.g., fluorine atom), (2) a halogen atom (e.g., chlorine atom), and (3) a cyano group, Ring $B^{1'}$ is a benzene ring optionally substituted by 1 to 3 halogen atoms, a pyridine ring, a dihydropyridine ring optionally substituted by oxo, or a pyrazole ring, L' is a bond, —O—, —CO—, or —NH— (preferably —O—), or alternatively, L' and $R^{1a'}$ are taken together to form

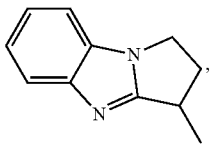

or a group represented by the formula:

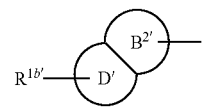

wherein $R^{1b'}$ is a 5- to 10-membered heterocyclic group (e.g., benzimidazolyl group), Ring $B^{2'}$ is a benzene ring, Ring D' is a 5- or 6-membered ring (e.g., pyrrolidine ring) and the like.

In the formula (1) and the formula (1'), $R^2$ and $R^{2'}$ are each a hydrogen atom, or a substituent.

Examples of the substituent for $R^2$ or $R^{2'}$ include the substituents selected from the aforementioned substituent group A. Particularly preferred are an optionally substituted alkyl group, or an optionally substituted cycloalkyl group and the like, more preferred area $C_{1-6}$ alkyl group optionally substituted by 1 to 3 halogen atoms (e.g., fluorine atom), $C_{3-7}$ cycloalkyl group (e.g., cyclobutyl group) and the like.

$R^2$ and $R^{2'}$ are each preferably a hydrogen atom, a $C_{1-6}$ alkyl group optionally substituted by 1 to 3 halogen atoms (e.g., fluorine atom) (e.g., methyl, ethyl, isopropyl, 2,2-difluoroethyl), or a $C_{3-7}$ cycloalkyl group (e.g., cyclobutyl) and the like.

In another embodiment, $R^2$ and $R^{2'}$ are each preferably an optionally substituted alkyl group, more preferably a alkyl group optionally substituted by 1 to 3 halogen atoms (e.g., fluorine atom).

In the formula (1), X is =N— or =$CR^b$— wherein $R^b$ is a hydrogen atom or a substituent.

In the formula (1'), X' is =N— or =$CR^{b'}$— wherein $R^{b'}$ is a hydrogen atom or a substituent.

Examples of the substituent for $R^b$ or $R^{b'}$ include the substituents selected from the aforementioned substituent group A.

X is preferably =N— or =CH— and the like.

X' is preferably =N— or =CH— and the like.

In the formula (1), - - - - - (i.e., dotted line connecting X and R²) means that, when X is =CR^b—, R^b and R² may form, taken together with the carbon atom and the nitrogen atom to which they are each adjacent, an optionally substituted 5- to 7-membered ring.

In the formula (1'), - - - - - (i.e., dotted line connecting X' and R²') means that, when X' is =CR^b'—, R^b' and R²' may form, taken together with the carbon atom and the nitrogen atom to which they are each adjacent, an optionally substituted 5- to 7-membered ring.

That is, in the formula (1), the moiety structural formula

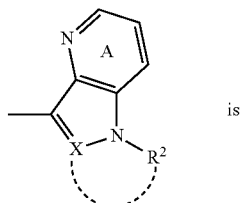

is

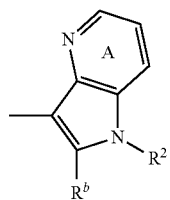

(1)

(2)

wherein each symbol is as defined above, provided R^b and R² do not form a ring, or

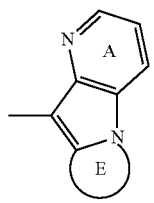

(2)

wherein Ring E is an optionally substituted 5- to 7-membered ring, and other symbols are as defined above.

Similarly, in the formula (1'),
the moiety structural formula

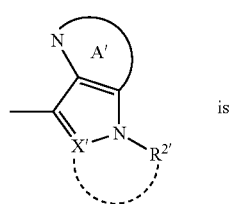

(1)

is

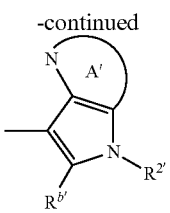

(1)

wherein each symbol is as defined above, provided R^b' and R²' do not form a ring, or

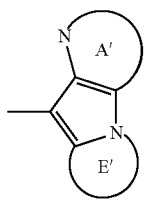

(2)

wherein Ring E' is an optionally substituted 5- to 7-membered ring, and other symbols are as defined above.

Examples of Ring E, namely, the "5- to 7-membered ring" of the "optionally substituted 5- to 7-membered ring" formed by R^b and R² taken together with the adjacent carbon atom and the nitrogen atom to which they are each adjacent include a 5- to 7-membered nitrogen-containing heterocyclic ring.

Examples of Ring E', namely, the "5- to 7-membered ring" of the "optionally substituted 5- to 7-membered ring" formed by R^b' and R²' taken together with the adjacent carbon atom and the nitrogen atom to which they are each adjacent include a 5- to 7-membered nitrogen-containing heterocyclic ring.

Examples of the "5- to 7-membered nitrogen-containing heterocyclic ring" include one containing at least one nitrogen atom as a ring-constituting atom from the aforementioned "5- to 7-membered heterocyclic ring".

Examples of the "5- to 7-membered nitrogen-containing heterocyclic ring" include pyrrolidine ring, pyrroline ring, imidazolidine ring, imidazoline ring, oxazolidine ring, isoxazoline ring, piperidine ring, morpholine ring, thiomorpholine ring, piperazine ring, dihydrooxazine ring, tetrahydrooxazine ring, dihydropyrimidine ring, tetrahydropyrimidine ring, dihydropyridine ring, tetrahydropyridine ring, azepane ring, oxazepane ring, thiazepane ring, pyrrole ring and the like, with preference given to a pyrrolidine ring or a piperidine ring.

Examples of the substituent of the "optionally substituted 5- to 7-membered ring" for Ring E or Ring E' include the substituents selected from the aforementioned substituent group A. The number of the substituent is preferably 0 (i.e., unsubstituted), or 1 to 5.

Preferable examples of the substituent, moiety, and ring and the like explained in the present specification are more preferably used in combination.

As compound (1), preferred is, for example, compound (1-A) below.

[Compound (1-A)]

The aforementioned compound (1), wherein

Ring A is a pyridine ring optionally substituted by 1 to 4 halogen atoms (e.g., fluorine atom), $R^1$ is a group represented by the formula:

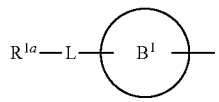

wherein
$R^{1a}$ is a 5- to 10-membered heterocyclic group optionally substituted by 1 to 3 substituents selected from
(1) a $C_{1-6}$ alkyl group optionally substituted by 1 to 3 substituents selected from (a) a 2-(trimethylsilyl)ethoxy group, (b) a hydroxy group, (c) a $C_{1-6}$ alkoxy group (e.g., methoxy) and (d) a halogen atom (e.g., fluorine atom),
(2) a halogen atom (e.g., chlorine atom), and
(3) a cyano group,
L is a bond, —O—, —CO—, or —NH—,
Ring $B^1$ is a benzene ring optionally substituted by 1 to 3 halogen atoms, a pyridine ring, a dihydropyridine ring optionally substituted by an oxo group, or a pyrazole ring, or alternatively, L and $R^{1a}$ are taken together to form

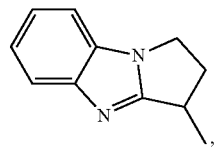

or a group represented by the formula:

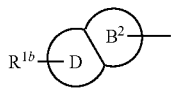

wherein
$R^{1b}$ is a 5- to 10-membered heterocyclic group (preferably, benzimidazolyl),
Ring $B^2$ is a benzene ring,
Ring D is a 5- or 6-membered ring (preferably, pyrrolidine ring), $R^2$ is a hydrogen atom, a $C_{1-6}$ alkyl group optionally substituted by 1 to 3 halogen atoms (e.g., fluorine atom) (e.g., methyl, ethyl, isopropyl, 2,2-difluoroethyl), or a $C_{3-7}$ cycloalkyl group (e.g., cyclobutyl), and
X is =N— or =CH—, or
when X is =$CR^b$—, $R^b$ and $R^2$ form a pyrrolidine ring or a piperidine ring taken together with the carbon atom and the nitrogen atom to which they are each adjacent.

As compound (1'), preferred is, for example, compound (1'-A) below.
[Compound (1'-A)]
The aforementioned compound (1'), wherein
Ring A' is a pyridine ring optionally substituted by 1 to 4 halogen atoms (e.g., fluorine atom), an (unsubstituted) pyrimidine ring, or an (unsubstituted) pyrazine ring,
$R^{1'}$ is a group represented by the formula:

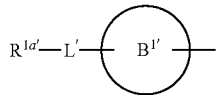

wherein
$R^{1a'}$ is a 5- to 10-membered heterocyclic group optionally substituted by 1 to 3 substituents selected from
(1) a $C_{1-6}$ alkyl group optionally substituted by 1 to 3 substituents selected from (a) a 2-(trimethylsilyl)ethoxy group, (b) a hydroxy group, (c) a $C_{1-6}$ alkoxy group (e.g., methoxy) and (d) a halogen atom (e.g., fluorine atom),
(2) a halogen atom (e.g., chlorine atom), and
(3) a cyano group,
L' is a bond, —O—, —CO—, or —NH—,
Ring $B^{1'}$ is a benzene ring optionally substituted by 1 to 3 halogen atoms, a pyridine ring, a dihydropyridine ring optionally substituted by an oxo group, or a pyrazole ring, or alternatively, L' and $R^{1a'}$ are taken together to form

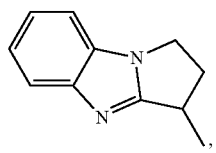

or a group represented by the formula:

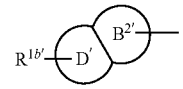

wherein
$R^{1b'}$ is a 5- to 10-membered heterocyclic group (preferably, benzimidazolyl),
Ring $B^{2'}$ is a benzene ring,
Ring D' is a 5- or 6-membered ring (preferably, pyrrolidine ring),
$R^{2'}$ is a hydrogen atom, a alkyl group optionally substituted by 1 to 3 halogen atoms (e.g., fluorine atom) (e.g., methyl, ethyl, isopropyl, 2,2-difluoroethyl), or a $C_{3-7}$ cycloalkyl group (e.g., cyclobutyl), and
X' is =N— or =CH—, or
when X' is =$CR^{b'}$—, $R^{b'}$, and $R^{2'}$ form a pyrrolidine ring or a piperidine ring together with the carbon atom and the nitrogen atom to which they are each adjacent.

Another preferable exemplary embodiment of compound (1') includes the following compound (1'-B).
[Compound (1'-B)]
The aforementioned compound (1'), wherein
Ring A' is a pyridine ring optionally substituted by 1 to 3 substituents selected from
(a) a $C_{1-5}$ alkyl group optionally substituted 1 to 5 substituents selected from the substituent group B,
(b) a $C_{1-5}$ alkoxy group optionally substituted 1 to 5 substituents selected from the substituent group B,
(c) a halogen atom, and
(d) a cyano group, $R^{1'}$ is a group represented by the formula:

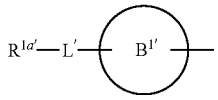

wherein
R$^{1a'}$ is the following formula

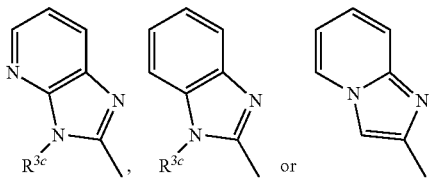

wherein R$^{3c}$ is a C$_{1-5}$ alkyl group optionally substituted by 1 to 5 substituents selected from the substituent group B,
L' is —O—,
Ring B$^{1'}$ is a group represented by

or a group represented by the formula:

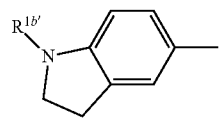

wherein
R$^{1b'}$ is as defined for R$^{1a'}$,
R$^{2'}$ is a C$_{1-5}$ alkyl group optionally substituted by 1 to 5 substituents selected from the substituent group B, and
X' is =N—.

When the compounds (1) and (1') are a salt, for example, metal salts, ammonium salts, salts with organic bases, salts with inorganic acids, salts with organic acids, salts with basic or acidic amino acids can be included. Preferable examples of metal salts, for example, include alkali metal salts such as sodium salts, potassium salts and the like; alkali earth metal salts such as calcium salts, magnesium salts, barium salts and the like; and aluminum salts. Preferable examples of salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acids include salts with hydrochloric acid, hydrobromic acid, nitric acid, sulfuric acid, phosphoric acid and the like. Preferable examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acids include salts with arginine, lysine, ornithine and the like. Preferable examples of salts with acidic amino acids include salts with aspartic acid, glutamic acid and the like. Among them, salts that are pharmacologically acceptable are preferable. For example, in the case when acidic functional group are present in the compound, for example, inorganic salts including alkali metal salts (e.g., sodium salts, etc.) and alkali earth metal salts (e.g., calcium salts, magnesium salts, barium salts, etc.) and ammonium salts are preferable. In contrast, in the case when basic functional group are present in the compound, for example, salts with inorganic acids such as hydrochloric acid, hydrobromic acid, nitric acid, sulfuric acid, phosphoric acid, etc. or salts with organic acid such as acetic acid, phthalic acid, fumaric acid, oxalic acid, tartaric acid, maleic acid, citric acid, succinic acid, methanesulfonic acid, p-toluenesulfonic acid, etc. are preferable.

If the compounds (1) and (1') include isomers such as tautomers, optical isomers, steric isomers, reverse isomers and rotational isomers, one of the other isomers or mixture are also included in the compound of the present invention. Further, if the compounds (1) and (1') have an optical isomer, the optical isomer separated from the racemate is included in the compound (1) or (1').

The compounds (1) and (1') can be obtained in the crystal form. Either single crystalline form or crystalline mixture can be included in the compound (1) or (1').

The compound of the formula (1) or (1') can be a pharmaceutically acceptable co-crystal or a co-crystal salt. The term "co-crystal" or "co-crystal salt" as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be obtained according to a per se known co-crystallization method.

The compounds (1) and (1') can be provided as a solvate (for example, hydrate) or as a non-solvate and both are included in the compound (1) or (1').

The compounds labeled with isotopes (e.g., $^2$H, $^3$H, $^{11}$C, $^{14}$C, $^{18}$F, $^{35}$S, $^{125}$I, etc.) are also included in the compound (1) or (1').

Compound (1) or (1') labeled with or substituted by an isotope can be used as a tracer (PET tracer) to be used for, for example, Positron Emission Tomography (PET), and is useful in the field of medical diagnosis and the like.

[Manufacturing Methods]

The production method of the compound of the present invention is explained in the following.

Compounds (1) and (1') can be produced according to a method known per se, for example, the production methods shown in reaction scheme 1 to reaction scheme 3, reaction scheme 6 to reaction scheme 8, reaction scheme 11, reaction scheme 12 and reaction scheme 14 described in detail below or a method analogous thereto.

Each starting compound to be used for the production of compound (1) and (1') in each production method below may form a salt. Examples of such salt include those similar to the salts of compounds (1) and (1').

In addition, each starting compound to be used for the production of compounds (1) and (1') can be used for the next reaction as a reaction mixture or a crude product. It can also be isolated from a reaction mixture according to a conventional method, and can be easily purified by a known means, for example, separation means such as extraction, concentration, neutralization, filtration, distillation, recrystallization, chromatography and the like. Examples of the solvent to be used for the above-mentioned recrystallization include water, alcohols, ethers, hydrocarbons, amides, halogenated hydrocarbons, nitriles, ketones, esters, sulfoxides, organic acids and the like. These solvents can be used alone or two or more kinds of the solvents may be used in a mixture at a suitable ratio, for example, at a ratio of 1:1 to 1:10. In addition, when a compound in the schemes is commercially available, the commercially available product can be directly used, or a compound produced by a method known per se, or a method analogous thereto can also be used.

When compound (1) or (1') has a convertible functional group (e.g., a carboxyl group, an amino group, a hydroxy group, a carbonyl group, a mercapto group, a $C_{1-6}$ alkoxy-carbonyl group, a $C_{6-14}$ aryloxy-carbonyl group, a $C_{7-16}$ aralkyloxy-carbonyl group, a sulfo group, a halogen atom etc.), various compounds can be produced by converting these functional groups according to a method known per se or a method analogous thereto.

A carboxyl group can be converted by, for example, reactions such as esterification, reduction, amidation, conversion reaction to an optionally protected amino group and the like.

An amino group can be converted by, for example, reactions such as acylation, sulfonylation, nitrosation, alkylation, arylation, imidation and the like.

A hydroxy group can be converted by, for example, reactions such as esterification, carbamoylation, sulfonylation, alkylation, arylation, oxidation, halogenation and the like.

A carbonyl group can be converted by, for example, reactions such as reduction, oxidation, amination (including oximation and hydrazonation), (thio)ketalation, alkylidenation, thiocarbonylation and the like.

A mercapto group can be converted by, for example, reactions such as alkylation, oxidation and the like.

A $C_{1-6}$ alkoxy-carbonyl group, a $C_{6-14}$ aryloxy-carbonyl group, or a $C_{7-16}$ aralkyloxy-carbonyl group can be converted by, for example, reactions such as reduction, hydrolysis and the like.

A sulfo group can be converted by, for example, reactions such as sulfonamidation, reduction and the like.

A halogen atom can be converted by, for example, various nucleophilic substitution reactions, various coupling reactions and the like.

In each of the aforementioned reactions, when a compound is obtained in a free form, the compound may be converted to a salt according to a conventional method, and when it is obtained as a salt, the salt can be converted to a free form or other salt according to a conventional method.

Conversion of these functional groups can be performed according to a method known per se, for example, the method described in "Comprehensive Organic Transformations" (Richard C. Larock) Wiley-VCH, 1999, and the like.

In addition, in each reaction in the production method of compounds (1) and (1') and each reaction of starting compound synthesis, when a starting compound has an amino group, a carboxyl group or a hydroxy group as a substituent, a protecting group as generally used in the peptide chemistry and the like may be introduced into these groups. The object compound can be obtained by removing the protecting group after the reaction where necessary.

As the amino-protecting group, for example, a formyl group, a $C_{1-6}$ alkyl-carbonyl group (e.g., acetyl, ethylcarbonyl etc.), a phenylcarbonyl group, a $C_{1-6}$ alkyl-oxycarbonyl group (e.g., methoxycarbonyl, ethoxycarbonyl, tert-butoxycarbonyl (Boc) etc.), an allyloxycarbonyl (Alloc) group, a phenyloxycarbonyl group, a fluorenylmethoxycarbonyl (Fmoc) group, a $C_{7-10}$ aralkyl-carbonyl group (e.g., benzylcarbonyl etc.), a $C_{7-10}$ aralkyl-oxycarbonyl group (e.g., benzyloxycarbonyl (Z) etc.), a $C_{7-10}$ aralkyl group (e.g., benzyl etc.), a 2-(trimethylsilyl)ethoxymethyl (SEM) group, a trityl group, a phthaloyl group and/or an N,N-dimethylaminomethylene group, each of which may have substituent(s), and the like are used. As these substituents, a phenyl group, a halogen atom (e.g., fluorine, chlorine, bromine, iodine etc.), a $C_{1-6}$ alkyl-carbonyl group (e.g., methylcarbonyl, ethylcarbonyl, butylcarbonyl etc.), a nitro group and the like are used, and the number of the substituents is about 1 to 3.

As the protecting group of the carboxyl group, for example, a $C_{1-6}$ alkyl group (e.g., methyl, ethyl, n-propyl, isopropyl, n-butyl, tert-butyl etc.), an allyl group, a benzyl group, a phenyl group, a trityl group and/or a trialkylsilyl group, each of which may have substituent(s), and the like are used. As these substituents, a halogen atom (e.g., fluorine, chlorine, bromine, iodine etc.), a formyl group, a $C_{1-6}$ alkyl-carbonyl group (e.g., acetyl, ethylcarbonyl, butylcarbonyl etc.), a nitro group and the like are used, and the number of the substituents is about 1 to 3.

As the protecting group of the hydroxy group, for example, a $C_{1-6}$ alkyl group (e.g., methyl, ethyl, n-propyl, isopropyl, n-butyl, tert-butyl etc.), a $C_{7-10}$ aralkyl group (e.g., benzyl etc.), a formyl group, a $C_{1-6}$ alkyl-carbonyl group (e.g., acetyl, ethylcarbonyl etc.), a benzoyl group, a $C_{7-10}$ aralkyl-carbonyl group (e.g., benzylcarbonyl etc.), a tetrahydropyranyl group, a furanyl group and/or a silyl group, each of which may have substituent(s), and the like are used. As these substituents, a halogen atom (e.g., fluorine, chlorine, bromine, iodine etc.), a $C_{1-6}$ alkyl group (e.g., methyl, ethyl, n-propyl etc.), a phenyl group, a $C_{7-10}$ aralkyl group (e.g., benzyl etc.), a $C_{1-6}$ alkoxy group (e.g., methoxy, ethoxy, n-propoxy etc.), a nitro group and the like are used, and the number of the substituent is about 1 to 4.

These protecting groups may be introduced or removed according to a method known per se, for example, the method described in "Protective Groups in Organic Synthesis, 3$^{rd}$ Ed." Wiley-Interscience, 1999, (Theodora W. Greene, Peter G. M. Wuts) and the like.

When compound (1) or (1') is present as a configurational isomer, diastereomer, conformer and the like, each can be isolated according to a known means. In addition, when compound (1) or (1') has an optically active form, the racemate can be separated into (+) form and (−) form according to a general optical resolution means.

When compound (1) or compound (1') contains an optical isomer, a stereoisomer, a regioisomer, a rotamer or a tautomer, these are also encompassed in compound (1) and compound (1'), and can be obtained as a single product according to synthesis and separation methods known per se.

The method of optical resolution may be a method known per se, such as a fractional recrystallization method, a chiral column method, a diastereomer method etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine etc.) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis and the like to separate an optically active reagent moiety, whereby an optical isomer is obtained. For example, when compound (1) or compound (1') contains hydroxy, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (1) or compound (1') has a carboxyl group, this compound and an optically active amine or an optically active alcohol reagent are subjected to condensation reaction to give diastereomers of the amide compound or the ester compound, respectively. The separated diastereomer is converted to an optical isomer of the original compound by acidic hydrolysis or basic hydrolysis.

The solvent, acid and base used in the production of the compound of the present invention are explained in the following.

Examples of the "solvent" include "alcohols", "ethers", "hydrocarbons", "amides", "halogenated hydrocarbons", "nitriles", "ketones", "esters", "sulfoxides" and the like.

Examples of the "alcohols" include methanol, ethanol, 1-propanol, 2-propanol, tert-butyl alcohol and the like.

Examples of the "ethers" include diethyl ether, diisopropyl ether, diphenylether, tetrahydrofuran, 1,4-dioxane, 1,2-dimethoxyethane, cyclopentyl methyl ether and the like.

Examples of the "hydrocarbons" include benzene, toluene, cyclohexane, hexane and the like.

Examples of the "amides" include N,N-dimethylformamide, N,N-dimethylacetamide, N-methylpyrrolidone, hexamethylphosphoric triamide and the like.

Examples of the "halogenated hydrocarbons" include dichloromethane, chloroform, carbon tetrachloride, 1,2-dichloroethane, chlorobenzene and the like.

Examples of the "nitriles" include acetonitrile, propionitrile and the like.

Examples of the "ketones" include acetone, ethylmethylketone and the like.

Examples of the "esters" include ethyl acetate and the like.

Examples of the "sulfoxides" include dimethylsulfoxide and the like.

Examples of the "acid" include "organic acids", "mineral acids", "Lewis acids" and the like.

Examples of the "organic acids" include formic acid, acetic acid, propionic acid, trifluoroacetic acid, citric acid, methanesulfonic acid, p-toluenesulfonic acid and the like.

Examples of the "mineral acids" include hydrochloric acid, sulfuric acid and the like.

Examples of the "Lewis acids" include boron trichloride, boron tribromide and the like.

Examples of the "base" include "inorganic bases", "basic salts", "aromatic amines", "tertiary amines", "alkali metal hydrides", "alkali metals", "metal amides", "alkylmetals", "arylmetals", "metal alkoxides" and the like.

Examples of the "inorganic bases" include sodium hydroxide, potassium hydroxide, lithium hydroxide, barium hydroxide and the like.

Examples of the "basic salts" include sodium carbonate, potassium carbonate, cesium carbonate, sodium hydrogen carbonate, sodium acetate, ammonium acetate and the like.

Examples of the "aromatic amines" include pyridine, lutidine and the like.

Examples of the "tertiary amines" include triethylamine, tripropylamine, tributylamine, diisopropylethylamine, cyclohexyldimethylamine, 4-dimethylaminopyridine, N,N-dimethylaniline, N-methylpiperidine, N-methylpyrrolidine, N-methylmorpholine, 1,8-diazabicyclo[5,4,0]undec-7-ene and the like.

Examples of the "alkali metal hydrides" include sodium hydride, potassium hydride and the like.

Examples of the "alkali metals" include sodium, lithium, potassium and the like.

Examples of the "metal amides" include sodium amide, lithium diisopropylamide, lithium hexamethyldisilazide and the like.

Examples of the "alkyl metals" include butyllithium, sec-butyllithium, tert-butyllithium and the like.

Examples of the "aryl metals" include phenyllithium and the like.

Examples of the "metal alkoxides" include sodium methoxide, sodium ethoxide, sodium tert-butoxide, potassium tert-butoxide and the like.

The production method of compound (1) and compound (1') is explained in the following.

In compound (1), compound (1a) wherein $R^1$ is

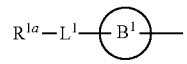

wherein $L^1$ is an optionally substituted nitrogen atom, an oxygen atom, a sulfur atom, and other symbols are as defined above, can be produced by, for example, the method shown in the following reaction scheme 1 or a method analogous thereto.

Reaction scheme 1

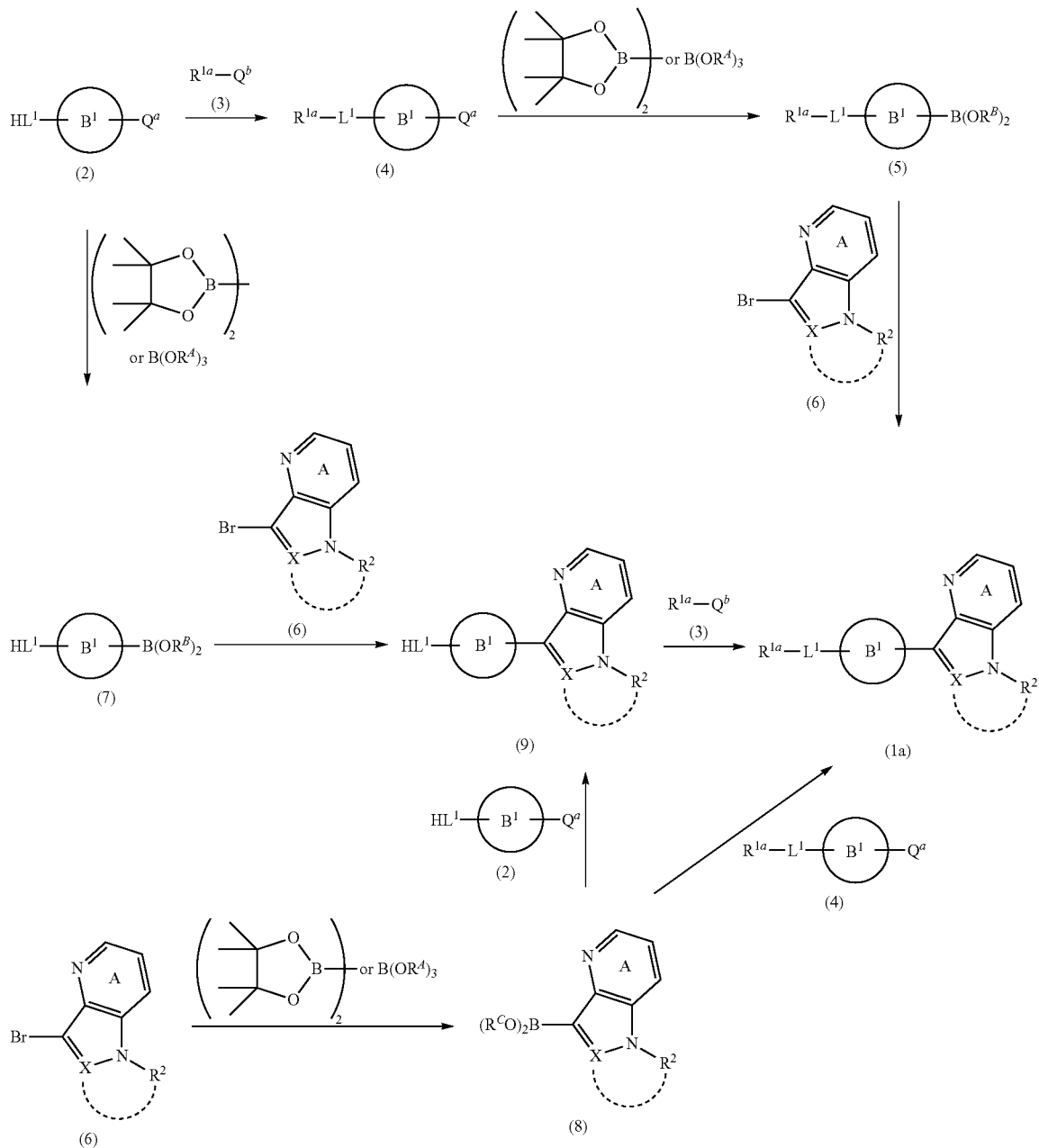

wherein $R^A$ is an optionally substituted hydrocarbon group, $R^B$ and $R^C$ are each independently a hydrogen atom or an optionally substituted hydrocarbon group, the two $R^B$s and two $R^C$s may be connected to form a 4,4,5,5-tetramethyl-1, 3,2-dioxaborolane ring, $Q^a$ and $Q^b$ are each a leaving group, and other symbols are as defined above.

Examples of the leaving group for $Q^a$ or $Q^b$ include a halogen atom (e.g., fluorine, chlorine, bromine, iodine), an optionally halogenated $C_{1-6}$ alkylsulfonyloxy group (e.g., methylsulfonyloxy, ethylsulfonyloxy, trifluoromethylsulfonyloxy), a $C_{6-10}$ arylsulfonyloxy group optionally substituted by a $C_{1-6}$ alkyl group (e.g., benzenesulfonyloxy, p-toluenesulfonyloxy), a methanesulfonyl group and the like. Preferred are a halogen atom and an optionally halogenated $C_{1-6}$ alkylsulfonyloxy group.

Compounds (2) and (3) can be easily obtained as commercially available products, and can also be produced according to a method known per se or a method analogous thereto.

Compound (6) can be produced by, for example, the method shown in the following reaction schemes 4 and 5 or a method analogous thereto.

Compound (4) can be produced by reacting compound (2) with compound (3).

Compound (3) is generally used in about 0.1 to 10 mol, preferably 0.2 to 5 mol, per 1 mol of compound (2).

This reaction is generally performed in the presence of a base. Examples of the base include inorganic bases, basic salts, aromatic amines, tertiary amines, alkali metal hydrides, metal amides, alkylmetals, arylmetals, metal alkoxides and the like. These bases are generally used in about 1 to 10 mol, preferably 1 to 3 mol, per 1 mol of compound (2).

This reaction can be performed in a solvent inert to the reaction or without a solvent. Such solvent is not particularly limited as long as the reaction proceeds and, for example, solvents such as ethers, hydrocarbons, amides, halogenated hydrocarbons, sulfoxides and the like or a mixed solvent thereof and the like are preferable.

While the reaction time varies depending on the reagent and solvent to be used, it is generally 0.5 to 12 hr, preferably 1 to 5 hr.

The reaction temperature is generally −20 to 300° C., preferably 0 to 150° C.

Compound (5) can be produced by reacting compound (4) with bis(pinacolato)diboron or a borate.

The bis(pinacolato)diboron or a borate is generally used in about 1 to 10 mol, preferably 1 to 5 mol, per 1 mol of compound (4).

When bis(pinacolato)diboron is used, this reaction is generally performed in the presence of a palladium catalyst and a base. Examples of the palladium catalyst include [1,1'-bis(diphenylphosphino)ferrocene]dichloropalladium(II), dichlorobis(triphenylphosphine)palladium(II), tetrakis(triphenylphosphine)palladium(0), palladium(II) acetate and the like. These palladium catalysts are generally used in 0.001 to 1 mol, preferably 0.01 to 0.1 mol, per 1 mol of compound (4). Examples of the base include inorganic bases, basic salts, metal alkoxides and the like. These bases are generally used in 1 to 10 mol, preferably 2 to 5 mol, per 1 mol of compound (4).

This reaction can be performed by adding a phosphine ligand when desired. Examples of the phosphine ligand include tri-tert-butylphosphine, 2-(di-tert-butylphosphino)biphenyl, 2-(dicyclohexylphosphino)biphenyl, triphenylphosphine and the like. These phosphine ligands are generally used in 2 mol per 1 mol of a palladium catalyst.

This reaction is advantageously performed in a solvent inert to the reaction. Such solvent is not particularly limited as long as the reaction proceeds and, for example, solvents such as ethers, hydrocarbons, amides, halogenated hydrocarbons, nitriles, ketones, esters, sulfoxides and the like or a mixed solvent thereof and the like are preferable.

While the reaction time varies depending on the reagent and solvent to be used, it is generally 0.5 to 72 hr, preferably 1 to 24 hr.

The reaction temperature is generally 0 to 200° C., preferably 20 to 100° C.

When a borate is used, this reaction is generally performed in the presence of alkylmetals and arylmetals. These alkylmetals and arylmetals are generally used in about 1 to 10 mol, preferably 1 to 5 mol, per 1 mol of compound (4).

This reaction is advantageously performed in a solvent inert to the reaction. Such solvent is not particularly limited as long as the reaction proceeds and, for example, ethers, hydrocarbons and the like solvent or a mixed solvent thereof and the like are preferable.

While the reaction time varies depending on the reagent and solvent to be used, it is generally 0.5 to 24 hr, preferably 0.5 to 4 hr.

The reaction temperature is generally −100 to 100° C., preferably −80 to 40° C.

Compound (7) can be produced by reacting compound (2) with bis(pinacolato)diboron or a borate.

This reaction is performed in the same manner as in the reaction of compound (4) with bis(pinacolato)diboron or a borate.

Compound (8) can be produced by reacting compound (6) with bis(pinacolato)diboron or a borate.

This reaction is performed in the same manner as in the reaction of compound (4) with bis(pinacolato)diboron or a borate.

Compound (9) can be produced by reacting compound (7) with compound (6).

This reaction is performed in the same manner as in the reaction of compound (5) with compound (6) to be mentioned below.

In addition, compound (9) can also be produced by reacting compound (8) with compound (2).

This reaction is performed in the same manner as in the reaction of compound (5) with compound (6) to be mentioned below.

Compound (1a) can be produced by reacting compound (5) with compound (6).

Compound (6) is generally used in about 0.1 to 10 mol, preferably 0.2 to 5 mol, per 1 mol of compound (5).

This reaction is generally performed in the presence of a palladium catalyst and a base. Examples of the palladium catalyst include tetrakis(triphenylphosphine)palladium(0), dichlorobis(triphenylphosphine)palladium(II), palladium(II) acetate and the like. These palladium catalysts are generally used in 0.001 to 1 mol, preferably 0.01 to 0.1 mol, per 1 mol of compound (5). Examples of the base include inorganic bases, basic salts, metal alkoxides and the like. These bases are generally used in 1 to 10 mol, preferably 2 to 5 mol, per 1 mol of compound (5).

This reaction can be performed by adding, when desired, a phosphine ligand. Examples of the phosphine ligand include tri-tert-butylphosphine, 2-(di-tert-butylphosphino)biphenyl, 2-(dicyclohexylphosphino)biphenyl, triphenylphosphine and the like. These phosphine ligands are generally used in 2 mol per 1 mol of palladium catalyst.

This reaction is advantageously performed in a solvent inert to the reaction. Such solvent is not particularly limited as long as the reaction proceeds and, for example, solvents such as alcohols, ethers, hydrocarbons, amides, halogenated hydrocarbons, nitriles, ketones, esters, sulfoxides, water and the like or a mixed solvent thereof and the like are preferable.

While the reaction time varies depending on the reagent and solvent to be used, it is generally 0.5 to 72 hr, preferably 1 to 24 hr.

The reaction temperature is generally −20 to 300° C., preferably 0 to 150° C.

In addition, compound (1a) can also be produced by reacting compound (9) with compound (3).

This reaction is performed in the same manner as in the reaction of compound (2) with compound (3).

In addition, compound (1a) can also be produced by reacting compound (8) with compound (4).

This reaction is performed in the same manner as in the reaction of compound (5) with compound (6).

When L and $R^{1a}$ in compound (1) are taken together to form an optionally substituted bicyclic or tricyclic fused heterocyclic group, that is, when a group represented by "$R^{1a}$-$L^1$-" is an "optionally substituted bicyclic or tricyclic fused heterocyclic group", compound (1) can be produced by forming "optionally substituted bicyclic or tricyclic fused heterocyclic group" on the moiety of a group represented by "$R^{1a}$-$L^1$-" in compound (4), compound (5) or compound (1a) in the above-mentioned reaction scheme 1, according to a method known per se or a method analogous thereto.

In compound (1), compound (1b) wherein $R^1$ is

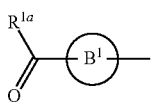

wherein each symbol is as defined above,
can be produced, for example, by the method shown in the following reaction scheme 2 or a method analogous thereto.

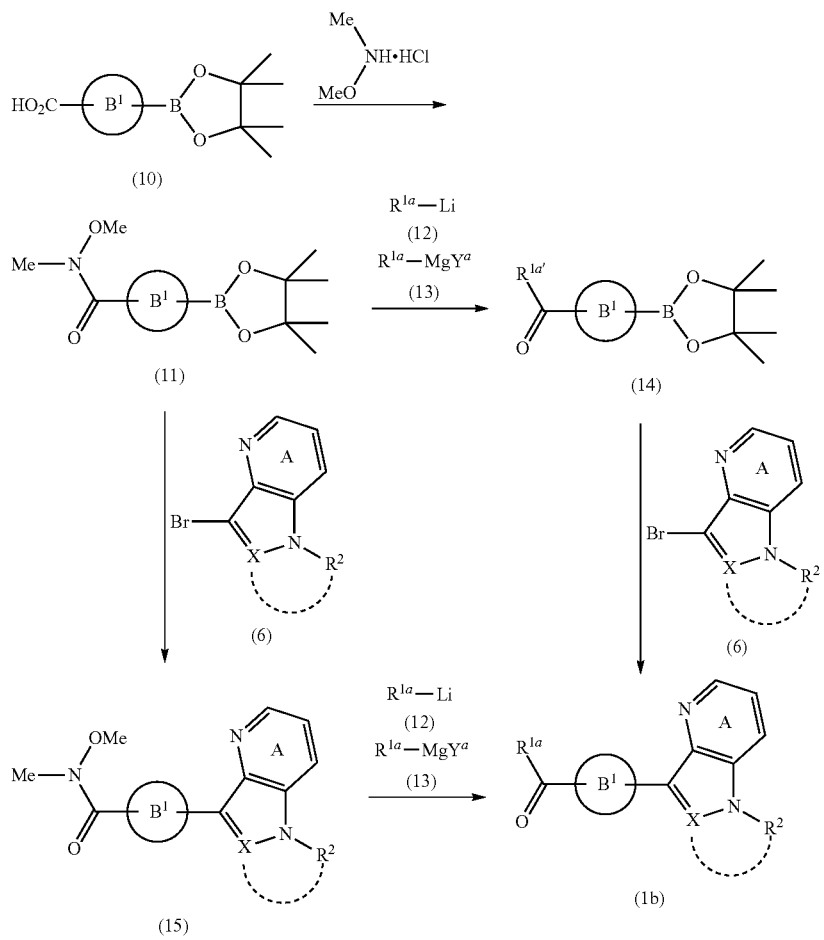

wherein $Y^a$ is a halogen atom, and other symbols are as defined above.

Compounds (10), (12) and (13) can be easily obtained as commercially available products, and can also be produced according to a method known per se or a method analogous thereto.

Compound (11) can be produced by condensing compound (10) or a reactive derivative thereof with N,O-dimethylhydroxylamine or a salt thereof.

Examples of the reactive derivative of compound (10) include acid halides (e.g., acid chloride, acid bromide), acid amides (e.g., acid amide with pyrazole, imidazole, benzotriazole etc.), acid anhydrides (e.g., acid anhydride with $C_{1-6}$ aliphatic carboxylic acid such as acetic acid, propionic acid, butyric acid etc.), acid azide, active esters (e.g., diethoxyphosphate ester, diphenoxyphosphate ester, p-nitrophenyl ester, 2,4-dinitrophenyl ester, cyanomethyl ester, pentachlorophenyl ester, ester with N-hydroxysuccinimide, ester with N-hydroxyphthalimide, ester with 1-hydroxybenzotriazole, ester with 6-chloro-1-hydroxybenzotriazole, ester with 1-hydroxy-1H-2-pyridone), active thioesters (e.g., 2-pyridyl thioester, 2-benzothiazolyl thioester) and the like.

N,O-dimethylhydroxylamine or a salt thereof is generally used in 1 to 10 mol, preferably 1 to 3 mol, per 1 mol of compound (10).

When acid halide is used as a reactive derivative of compound (10), the reaction can be performed in the presence of a deacidifying agent to remove generated hydrogen halide from the reaction system. Preferable examples of the deacidifying agent include basic salts, aromatic amines, tertiary amines and the like. These deacidifying agents are generally used in 1 to 50 mol, preferably 1 to 5 mol, per 1 mol of compound (10).

In addition, compound (11) can also be produced by directly reacting compound (10) with N,O-dimethylhydroxylamine or a salt thereof in the presence of a suitable condensing agent.

As the condensing agent, N,N'-disubstituted carbodiimides such as N,N'-dicyclohexylcarbodiimide, N,N'-diisopropylcarbodiimide, 3-(3-dimethylaminopropyl)-1-ethylcarbodiimide or a hydrochloride thereof and the like; azolides such as N,N'-carbonyldiimidazole and the like; dehydrating agents such as 2-ethoxy-N-ethoxycarbonyl-1,2-dihydroquinoline, phosphorus oxychloride, alkoxyacetylene and the like; 2-halogenopyridinium salts such as 2-chloromethylpyridinium iodide, 2-fluoro-1-methylpyridinium iodide and the like; phosphate esters such as diethyl cyanophosphate, diphenylphosphoryl azide and the like; and the like are used. When these condensing agents are used, the reaction is considered to proceed via a reactive derivative of compound (10). The condensing agent is generally used in 1 to mol, preferably 1 to 5 mol, per 1 mol of compound (10).

When the aforementioned N,N'-disubstituted carbodiimides are used as condensing agents, the reaction efficiency can be improved by using a suitable condensation promoter (e.g., 1-hydroxy-7-azabenzotriazole, 1-hydroxybenzotriazole, N-hydroxysuccinimide, N-hydroxyphthalimide) as necessary. In addition, when the aforementioned phosphate esters are used as condensing agents, the reaction efficiency can be generally improved by adding aromatic amines, tertiary amines and the like. These condensation promoters, aromatic amines, tertiary amines and the like are generally used in 0.1 to 10 mol, preferably 0.3 to 3 mol, per 1 mol of compound (10).

This reaction is advantageously performed in a solvent inert to the reaction. Such solvent is not particularly limited as long as the reaction proceeds and, for example, solvents such as ethers, hydrocarbons, amides, halogenated hydrocarbons, nitriles, ketones, esters, water and the like or a mixed solvent thereof and the like are preferable.

While the reaction time varies depending on the reagent and solvent to be used, it is generally 0.5 to 72 hr, preferably 0.5 to 24 hr.

The reaction temperature is generally 0 to 100° C., preferably 0 to 60° C.

Compound (14) can be produced by reacting compound (11) with compound (12) or compound (13).

Compound (12) or compound (13) is generally used in 1 to 10 mol, preferably 1 to 5 mol, per 1 mol of compound (11).

This reaction is advantageously performed in a solvent inert to the reaction. Such solvent is not particularly limited as long as the reaction proceeds and, for example, solvents such as ethers, hydrocarbons and the like or a mixed solvent thereof and the like are preferable.

While the reaction time varies depending on the reagent and solvent to be used, it is generally 0.5 to 24 hr, preferably 0.5 to 6 hr.

The reaction temperature is generally −100 to 100° C., preferably −80 to 40° C.

Compound (15) can be produced by reacting compound (11) with compound (6).

This reaction is performed in the same manner as in the reaction of compound (5) with compound (6).

Compound (1b) can be produced by reacting compound (14) with compound (6).

This reaction is performed in the same Manner as in the reaction of compound (5) with compound (6).

In addition, compound (1b) can be produced by reacting compound (15) with compound (12) or compound (13).

This reaction is performed in the same manner as in the reaction of compound (11) with compound (12) or compound (13).

In compound (1), compound (1c) wherein $R^1$ is

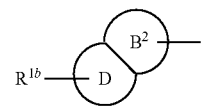

wherein each symbol is as defined above, can be produced, for example, according to the method shown in the following reaction scheme 3 or a method analogous thereto.

Reaction scheme 3

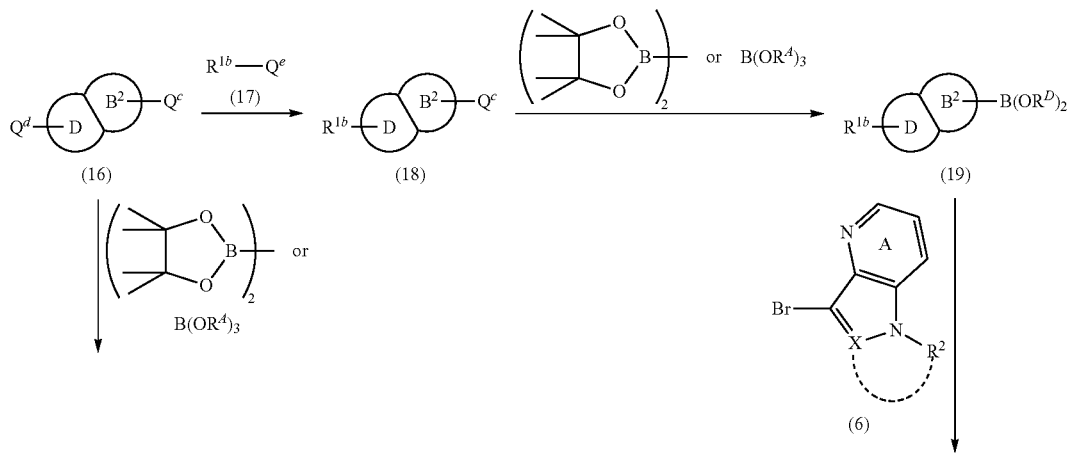

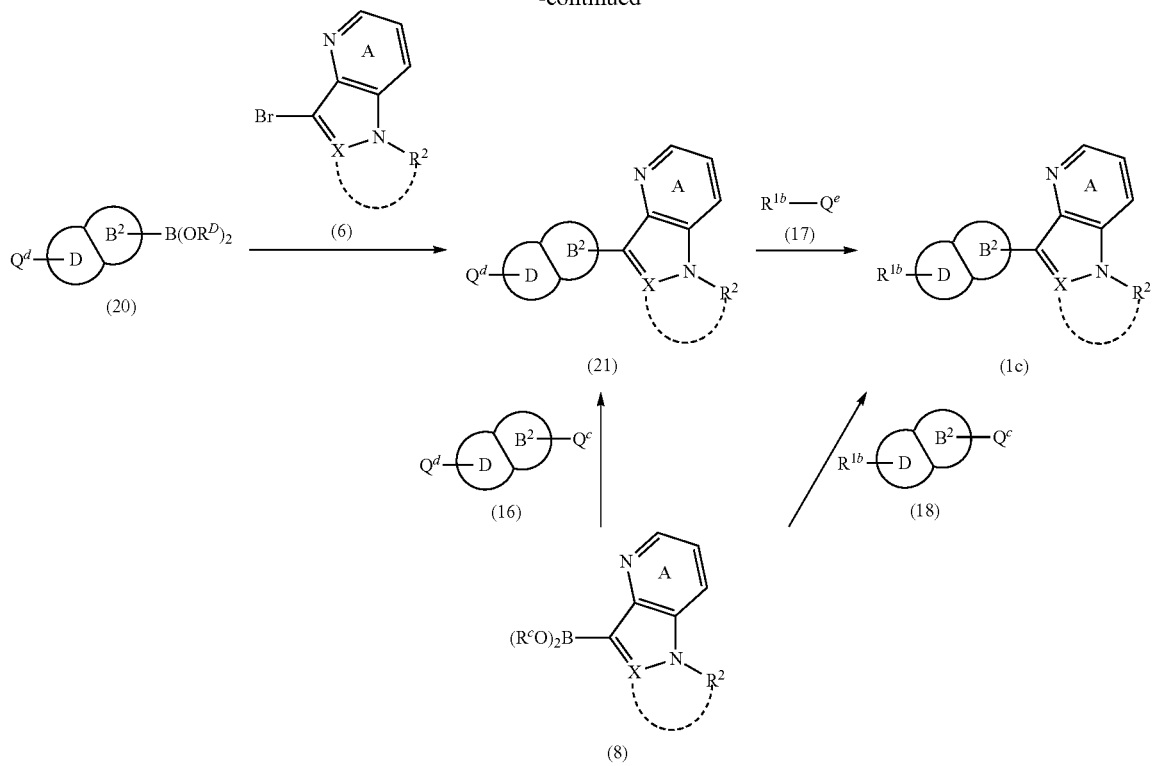

wherein $R^D$ is a hydrogen atom or an optionally substituted hydrocarbon group, two $R^d$ optionally form, together with the adjacent oxygen atom, a 4,4,5,5-tetramethyl-1,3,2-dioxaborolane ring, $Q^c$ is a leaving group, $Q^d$ and $Q^e$ are each independently a leaving group, a hydrogen atom or a metal-containing group (one of $Q^d$ and $Q^e$ is a hydrogen atom or a metal-containing group, and the other is a leaving group), and other symbols are as defined above.

Examples of the leaving group for $Q^c$, $Q^d$ or $Q^e$ include those exemplified as the aforementioned $Q^a$.

Examples of the metal-containing group include lithium, boron-containing groups (e.g., $B(OH)_2$, 4,4,5,5-tetramethyl-1,3,2-dioxaborolan-2-yl etc.), magnesium-containing groups (e.g., MgCl, MgBr, MgI etc.), zinc-containing groups (e.g., ZnCl, ZnBr, ZnI etc.), tin-containing groups (e.g., $Sn(n\text{-}Bu)_3$ etc.) and the like.

Compounds (16) and (17) can be easily obtained as commercially available products, and can also be produced according to a method known per se or a method analogous thereto.

Compound (18) can be produced by reacting compound (16) with compound (17).

When a compound having a leaving group is reacted with other compound, the compound having a leaving group is generally used in 1 to 10 mol, preferably 1 to 3 mol, per 1 mol of the "other compound".

This reaction is generally performed in the presence of a palladium catalyst and a base. Examples of the palladium catalyst include [1,1'-bis(diphenylphosphino)ferrocene]dichloropalladium(II), dichlorobis(triphenylphosphine)palladium(II), tetrakis(triphenylphosphine)palladium(0), palladium(II) acetate and the like. These palladium catalysts are generally used in 0.001 to 1 mol, preferably 0.01 to 0.1 mol, per 1 mol of compound (16) or compound (17). Examples of the base include inorganic bases, basic salts, metal alkoxides and the like. These bases are generally used in 1 to 10 mol, preferably 2 to 5 mol, per 1 mol of compound (16) or compound (17).

When desired, this reaction can be performed by adding a phosphine ligand. Examples of the phosphine ligand include tri-tert-butylphosphine, 2-(di-tert-butylphosphino)biphenyl, 2-(dicyclohexylphosphino)biphenyl, triphenylphosphine and the like. These phosphine ligands are generally used in 2 mol per 1 mol of the palladium catalyst.

This reaction is advantageously performed in a solvent inert to the reaction. Such solvent is not particularly limited as long as the reaction proceeds and, for example, solvents such as alcohols, ethers, hydrocarbons, amides, halogenated hydrocarbons, nitriles, ketones, esters, sulfoxides, water and the like or a mixed solvent thereof and the like are preferable.

While the reaction time varies depending on the reagent and solvent to be used, it is generally 0.5 to 72 hr, preferably 1 to 24 hr.

The reaction temperature is generally 0 to 200° C., preferably 20 to 100° C.

When one of $Q^d$ and $Q^e$ is a hydrogen atom and the other is a leaving group, this reaction can also be performed in the absence of a palladium catalyst. In this case, the compound having a leaving group is generally used in 1 to 10 mol, preferably 1 to 3 mol, per 1 mol of the other compound.

This reaction is generally performed in the presence of a base when desired. Examples of the base include inorganic bases, basic salts, aromatic amines, tertiary amines, alkali metal hydrides, metal amides, alkylmetals, arylmetals, metal alkoxides and the like. These bases are generally used in about 1 to 20 mol, preferably 1 to 5 mol, per 1 mol of compound (16) or compound (17).

This reaction can be performed in a solvent inert to the reaction. Such solvent is not particularly limited as long as the reaction proceeds and, for example, solvents such as alcohols, ethers, hydrocarbons, amides, halogenated hydrocarbons, nitriles, ketones, esters, sulfoxides and the like or a mixed solvent thereof and the like are preferable.

While the reaction time varies depending on the reagent and solvent to be used, it is generally 0.1 to 72 hr, preferably 0.5 to 24 hr.

The reaction temperature is generally 0 to 300° C., preferably 20 to 200° C.

Compound (19) can be produced by reacting compound (18) with bis(pinacolato)diboron or a borate.

This reaction is performed in the same manner as in the reaction of compound (4) with bis(pinacolato)diboron or a borate.

Compound (20) can be produced by reacting compound (16) with bis(pinacolato)diboron or a borate.

This reaction is performed in the same manner as in the reaction of compound (4) with bis(pinacolato)diboron or a borate.

Compound (21) can be produced by reacting compound (20) with compound (6).

This reaction is performed in the same manner as in the reaction of compound (5) with compound (6).

In addition, compound (21) can be produced by reacting compound (8) with compound (16).

This reaction is performed in the same manner as in the reaction of compound (5) with compound (6).

Compound (1c) can be produced by reacting compound (19) with compound (6).

This reaction is performed in the same manner as in the reaction of compound (5) with compound (6).

In addition, compound (1c) can also be produced by reacting compound (21) with compound (17).

This reaction is performed in the same manner as in the reaction of compound (16) with compound (17).

In addition, compound (1c) can also be produced by reacting compound (8) with compound (18).

This reaction is performed in the same manner as in the reaction of compound (5) with compound (6).

In compound (6), compounds (6a) and (6b) wherein X is =N— or =$CR^b$— ($R^b$ is a hydrogen atom or a substituent and $R^b$ and $R^2$ do not feint a ring) can be produced by, for example, the method shown in the following reaction scheme 4 or a method analogous thereto.

Reaction scheme 4

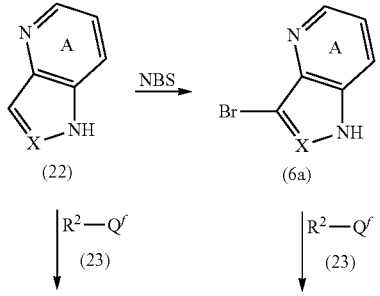

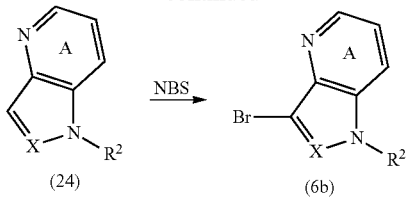

wherein $Q^f$ is a leaving group, and other symbols are as defined above.

As the leaving group for $Q^f$, those exemplified as the aforementioned $Q^a$ can be mentioned.

Compounds (22) and (23) can be easily obtained as is commercially available products, and can also be produced according to a method known per se or a method analogous thereto.

Compound (24) can be produced by reacting compound (22) with compound (23).

This reaction is generally performed in the presence of a base. Examples of the base include inorganic bases, basic salts, aromatic amines, tertiary amines, alkali metal hydrides, metal amides, alkylmetals, arylmetals, metal alkoxides and the like. These bases are generally used in 1 to 10 mol, preferably 1 to 3 mol, per 1 mol of compound (22).

This reaction is advantageously performed in a solvent inert to the reaction. Such solvent is not particularly limited as long as the reaction proceeds and, for example, solvents such as ethers, hydrocarbons, amides, halogenated hydrocarbons, nitriles, ketones, esters, sulfoxides and the like or a mixed solvent thereof and the like are preferable.

While the reaction time varies depending on the reagent and solvent to be used, it is generally 0.1 to 72 hr, preferably 1 to 24 hr.

The reaction temperature is generally −20 to 200° C., preferably 0 to 100° C.

Compound (6a) can be produced by reacting compound (22) with N-bromosuccinimide (NBS).

N-bromosuccinimide is generally used in about 1 to 5 mol, preferably 1 to 2 mol, per 1 mol of compound (22).

This reaction is advantageously performed in a solvent inert to the reaction. Such solvent is not particularly limited as long as the reaction proceeds and, for example, solvents such as ethers, hydrocarbons, amides, halogenated hydrocarbons, nitriles, esters, sulfoxides and the like or a mixed solvent thereof and the like are preferable.

While the reaction time varies depending on the reagent and solvent to be used, it is generally 0.1 to 24 hr, preferably 0.1 to 4 hr.

The reaction temperature is generally −20 to 200° C., preferably 0 to 100° C.

Compound (6b) can be produced by reacting compound (24) with N-bromosuccinimide.

This reaction is performed in the same manner as in the reaction of compound (22) with N-bromosuccinimide.

In addition, compound (6b) can also be produced by reacting compound (6a) with compound (23).

This reaction is performed in the same manner as in the reaction of compound (22) with compound (23).

In compound (6), compound (6c) wherein

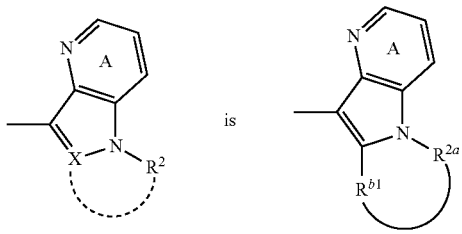

is wherein $R^{b1}$ and $R^{2a}$ are each independently an optionally substituted carbon atom, and other symbols are as defined above,
can be produced by, for example, the method shown in the following reaction scheme 5 or a method analogous thereto.

Reaction scheme 5

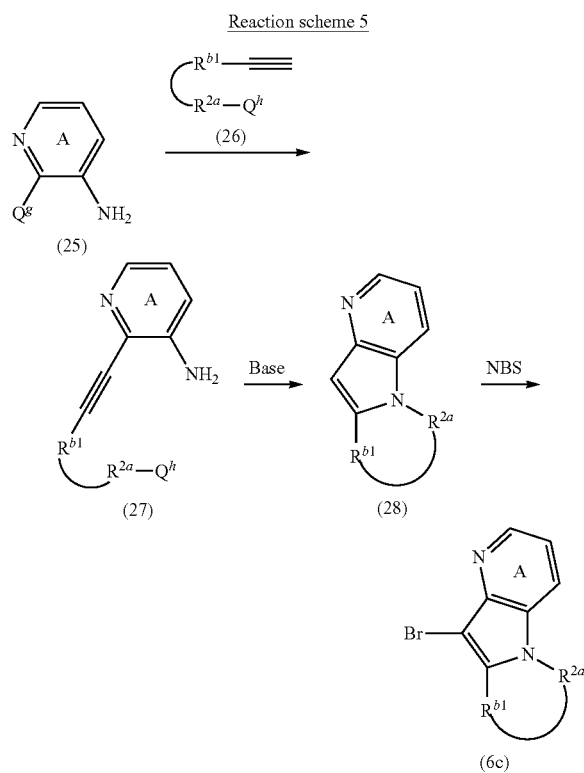

wherein $Q^g$ and $Q^h$ are each a leaving group, and other symbols are as defined above.

As the leaving group for $Q^g$ or $Q^h$, those exemplified as the aforementioned $Q^a$ can be mentioned.

Compounds (25) and (26) can be easily obtained as commercially available products, and can also be produced according to a method known per se or a method analogous thereto.

Compound (27) can be produced by reacting compound (25) with compound (26).

Compound (26) is generally used in 1 to 10 mol, preferably 1 to 3 mol, per 1 mol of compound (25).

This reaction is generally performed in the presence of a palladium catalyst. Examples of the palladium catalyst include [1,1'-bis(diphenylphosphino)ferrocene]dichloropalladium(II), dichlorobis(triphenylphosphine)palladium(II), tetrakis(triphenylphosphine)palladium(0), palladium(II) acetate and the like. These palladium catalysts are generally used in 0.001 to 1 mol, preferably 0.01 to 0.1 mol, per 1 mol of compound (25).

When desired, this reaction can be performed by adding a phosphine ligand or a copper catalyst. Examples of the phosphine ligand include tri-tert-butylphosphine, 2-(di-tert-butylphosphino)biphenyl, 2-(dicyclohexylphosphino)biphenyl, triphenylphosphine and the like. These phosphine ligands are generally used in 2 mol per 1 mol of the palladium catalyst. Examples of the copper catalyst include copper(I) bromide, copper(I) iodide, copper(I) oxide and the like. These copper catalysts are generally used in 0.001 to 1 mol, preferably 0.01 to 0.1 mol, per 1 mol of compound (25).

This reaction is advantageously performed in a solvent inert to the reaction. Such solvent is not particularly limited as long as the reaction proceeds and, for example, solvents such as alcohols, ethers, hydrocarbons, amides, halogenated hydrocarbons, nitriles, ketones, esters, sulfoxides, tertiary amines and the like or a mixed solvent thereof and the like are preferable.

While the reaction time varies depending on the reagent and solvent to be used, it is generally 1 to 96 hr, preferably 2 to 48' hr.

The reaction temperature is generally 0 to 200° C., preferably 0 to 150° C.

Compound (28) can be produced by reacting compound (27) with a base.

Examples of the base include inorganic bases, basic salts, aromatic amines, tertiary amines, alkali metal hydrides, metal amides, alkylmetals, arylmetals, metal alkoxides and the like. These bases are generally used in about 1 to 10 mol, preferably 1 to 3 mol, per 1 mol of compound (27).

This reaction is advantageously performed in a solvent inert to the reaction. Such solvent is not particularly limited as long as the reaction proceeds and, for example, solvents such as ethers, hydrocarbons, amides, halogenated hydrocarbons, nitriles, ketones, esters, sulfoxides and the like or a mixed solvent thereof and the like are preferable.

While the reaction time varies depending on the reagent and solvent to be used, it is generally 0.1 to 48 hr, preferably 1 to 24 hr.

The reaction temperature is generally −20 to 200° C., preferably 0 to 100° C.

Compound (6c) can be produced by reacting compound (28) with N-bromosuccinimide.

This reaction is performed in the same manner as in the reaction of compound (22) with N-bromosuccinimide.

In compound (1'), compound (1a') wherein $R^{1'}$ is

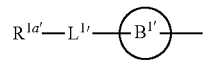

wherein $L^{1'}$ is an optionally substituted nitrogen atom, an oxygen atom, a sulfur atom, and other symbols are as defined above,
can be produced by, for example, the method shown in the following reaction scheme 6 or a method analogous thereto.

Reaction scheme 6

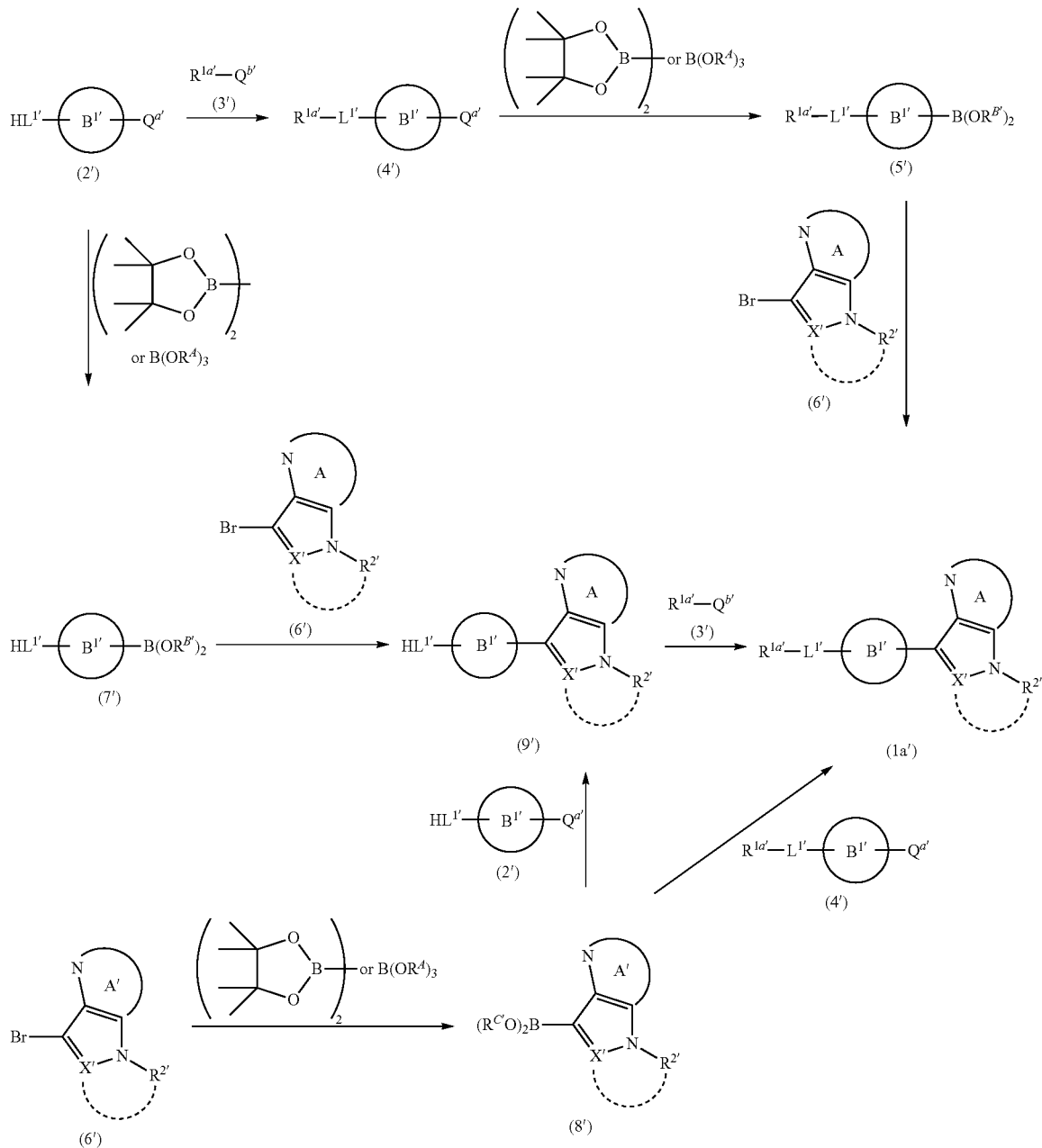

wherein $R^{B'}$ and $R^{C'}$ are each independently a hydrogen atom or an optionally substituted hydrocarbon group, two $R^{B'}$ or two $R^{C'}$ may be joined to form a 4,4,5,5-tetramethyl-1,3,2-dioxaborolane ring, $Q^{a'}$ and $Q^{b'}$ are each a leaving group, and other symbols are as defined above.

As the leaving group for $Q^{a'}$ or $Q^{b'}$, those exemplified as the aforementioned $Q^a$ or $Q^b$ can be mentioned.

Compounds (2') and (3') can be easily obtained as commercially available products, and can also be produced according to a method known per se or a method analogous thereto.

Compound (6') can be produced by, for example, the method shown in the following reaction schemes 9, 10 and 15 or a method analogous thereto.

Compound (4') can be produced by reacting compound (2') with compound (3').

This reaction is performed in the same manner as in the reaction of compound (2) with compound (3).

Compound (5') can be produced by reacting compound (4') with bis(pinacolato)diboron or a borate.

This reaction is performed in the same manner as in the reaction of compound (4) with bis(pinacolato)diboron or a borate.

Compound (7') can be produced by reacting compound (2') with bis(pinacolato)diboron or a borate.

This reaction is performed in the same manner as in the reaction of compound (4) with bis(pinacolato)diboron or a borate.

Compound (8') can be produced by reacting compound (6') with bis(pinacolato)diboron or a borate.

This reaction is performed in the same manner as in the reaction of compound (4) with bis(pinacolato)diboron or a borate.

Compound (9') can be produced by reacting compound (7') with compound (6').

This reaction is performed in the same manner as in the reaction of compound (5) with compound (6).

In addition, compound (9') can also be produced by reacting compound (8') with compound (2').

In compound (1'), compound (1b') wherein $R^{1'}$ is

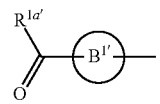

wherein each symbol is as defined above, can be produced by, for example, the method shown in the following reaction scheme 7 or a method analogous thereto.

Reaction scheme 7

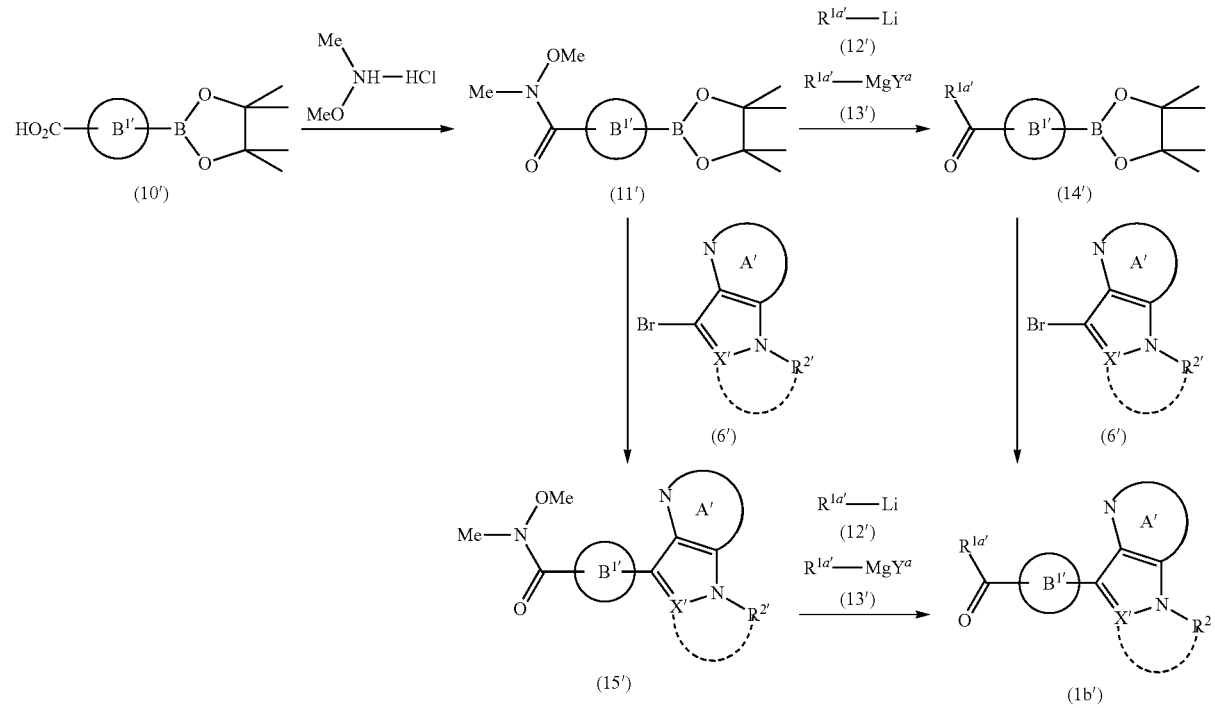

This reaction is performed in the same manner as in the reaction of compound (5) with compound (6).

Compound (1a') can be produced by reacting compound (5') with compound (6').

This reaction is performed in the same manner as in the reaction of compound (5) with compound (6).

In addition, compound (1a') can also be produced by reacting compound (9') with compound (3').

This reaction is performed in the same manner as in the reaction of compound (2) with compound (3).

In addition, compound (1a') can also be produced by reacting compound (8') with compound (4').

This reaction is performed in the same manner as in the reaction of compound (5) with compound (6).

When L' and $R^{1a'}$ of compound (1') are taken together to form an optionally substituted bicyclic or tricyclic fused heterocyclic group, that is, when a group represented by "$R^{1a'}$-L'—" is an "optionally substituted bicyclic or tricyclic fused heterocyclic group", compound (1') can be produced by forming "optionally substituted bicyclic or tricyclic fused heterocyclic group" on the moiety of a group represented by "$R^{1a'}$-L$^{1'}$—" in compound (4'), compound (5') or compound (1a') in the above-mentioned reaction scheme 6, according to a method known per se or a method analogous thereto.

wherein each symbol is as defined above.

Compounds (10'), (12') and (13') can be easily obtained as commercially available products, and can also be produced according to a method known per se or a method analogous thereto.

Compound (11') can be produced by condensing compound (10') or a reactive derivative thereof and N,O-dimethylhydroxylamine or a salt thereof.

This reaction is performed in the same manner as in the reaction of compound (10) or a reactive derivative thereof with N,O-dimethylhydroxylamine or a salt thereof.

Compound (14') can be produced by reacting compound (11') with compound (12') or compound (13').

This reaction is performed in the same manner as in the reaction of compound (11) with compound (12) or compound (13).

Compound (15') can be produced by reacting compound (11') with compound (6').

This reaction is performed in the same manner as in the reaction of compound (5) with compound (6).

Compound (1b') can be produced by reacting compound (14') with compound (6').

This reaction is performed in the same manner as in the reaction of compound (5) with compound (6).

In addition, compound (1b') can be produced by reacting compound (15') with compound (12') or compound (13').

This reaction is performed in the same manner as in the reaction of compound (11) with compound (12) or compound (13).

In compound (1'), compound (1c') wherein $R^{1'}$ is

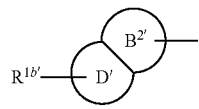

wherein each symbol is as defined above,
can be produced by, for example, the method shown in the following reaction scheme 8 or a method analogous thereto.

wherein $R^{D'}$ is a hydrogen atom or an optionally substituted hydrocarbon group, two $R^{D'}$ optionally form, together with the adjacent oxygen atom, a 4,4,5,5-tetramethyl-1,3,2-dioxaborolane ring, $Q^{c'}$ is a leaving group, $Q^{d'}$ and $Q^{e'}$ are each independently a leaving group, a hydrogen atom or a metal-containing group (when one of $Q^{d'}$ and $Q^{e'}$ is a hydrogen atom or a metal-containing group, the other is a leaving group), and other symbols are as defined above.

As the leaving group for $Q^{c'}$, $Q^{d'}$ or $Q^{e'}$, those exemplified as the aforementioned $Q^a$ can be mentioned.

Compounds (16') and (17') can be easily Obtained as commercially available products, and can also be produced according to a method known per se or a method analogous thereto.

Compound (18') can be produced by reacting compound (16') with compound (17').

Reaction scheme 8

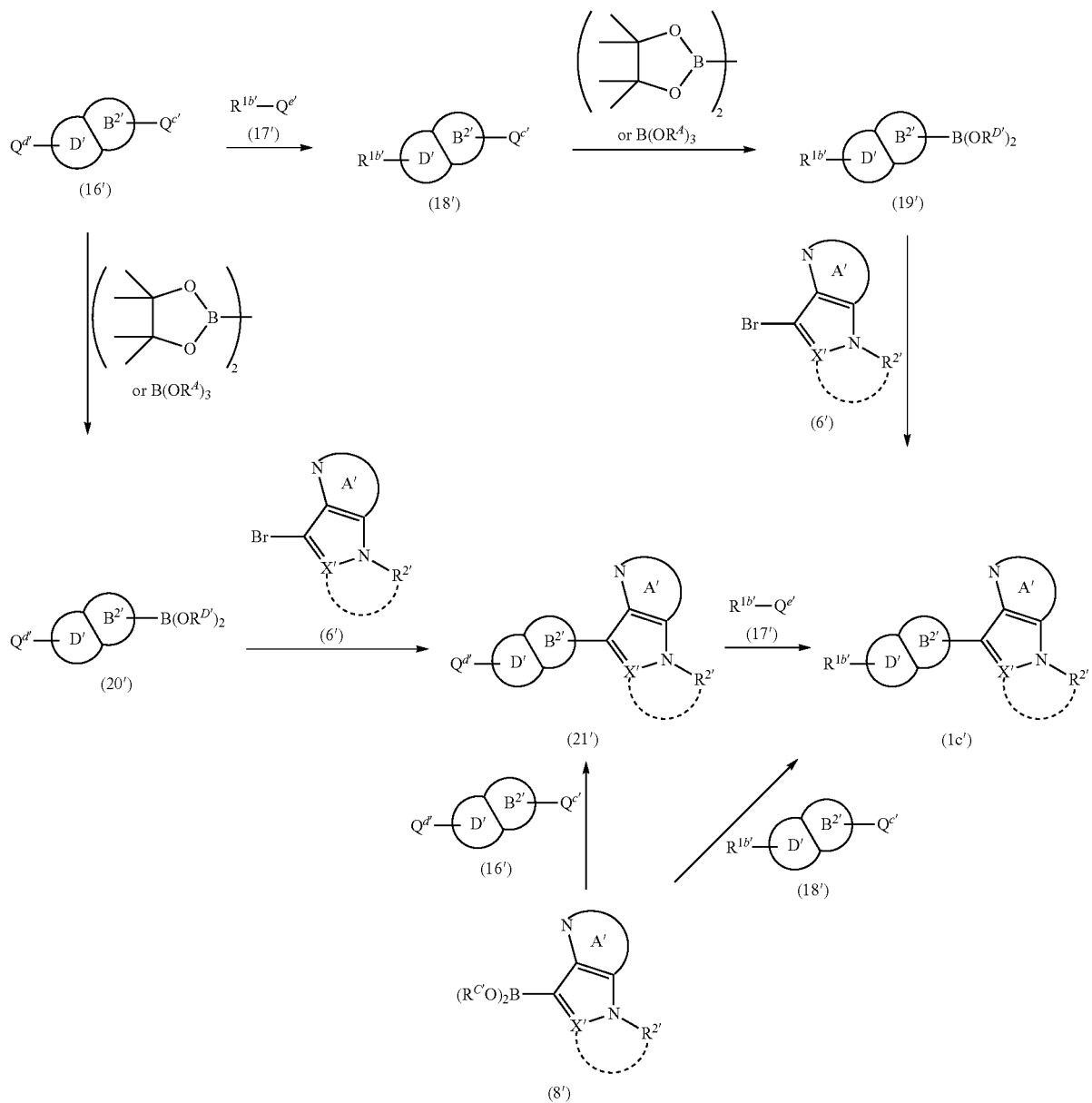

This reaction is performed in the same manner as in the reaction of compound (16) with compound (17).

Compound (19') can be produced by reacting compound (18') with bis(pinacolato)diboron or a borate.

This reaction is performed in the same manner as in the reaction of compound (4) with bis(pinacolato)diboron or a borate.

Compound (20') can be produced by reacting compound (16') with bis(pinacolato)diboron or a borate.

This reaction is performed in the same manner as in the reaction of compound (4) with bis(pinacolato)diboron or a borate.

Compound (21') can be produced by reacting compound (20') with compound (6').

This reaction is performed in the same manner as in the reaction of compound (5) with compound (6).

In addition, compound (21') can be produced by reacting compound (8') with compound (16').

This reaction is performed in the same manner as in the reaction of compound (5) with compound (6).

Compound (1c') can be produced by reacting compound (19') with compound (6').

This reaction is performed in the same manner as in the reaction of compound (5) with compound (6).

In addition, compound (1c') can also be produced by reacting compound (21') with compound (17').

This reaction is performed in the same manner as in the reaction of compound (16) with compound (17).

In addition, compound (1c') can also be produced by reacting compound (8') with compound (18').

This reaction is performed in the same manner as in the reaction of compound (5) with compound (6).

In compound (6'), compounds (6a') and (6b') wherein X' is =N— or (e is a hydrogen atom or a substituent and $R^{b'}$ and $R^{2'}$ do not form a ring) can be produced by, for example, the method shown in the following reaction scheme 9 or a method analogous thereto.

Compound (24') can be produced by reacting compound (22') with compound (23').

This reaction is performed in the same manner as in the reaction of compound (22) with compound (23).

Compound (6a') can be produced by reacting compound (22') with N-bromosuccinimide (NBS).

This reaction is performed in the same manner as in the reaction of compound (22) with N-bromosuccinimide.

Compound (6b') can be produced by reacting compound (24') with N-bromosuccinimide.

This reaction is performed in the same manner as in the reaction of compound (22) with N-bromosuccinimide.

In addition, compound (6b') can also be produced by reacting compound (6a') with compound (23').

This reaction is performed in the same manner as in the reaction of compound (22) with compound (23).

In compound (6'), compound (6c') wherein

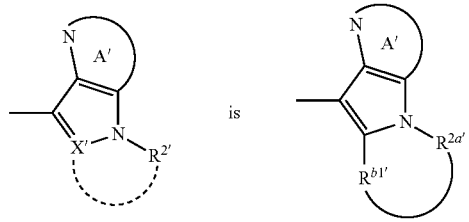

is wherein $R^{b1'}$ and $R^{2a'}$ are each independently an optionally substituted carbon atom, and other symbols are as defined above, can be produced by, for example, the method shown in the following reaction scheme 10 or a method analogous thereto.

Reaction scheme 9

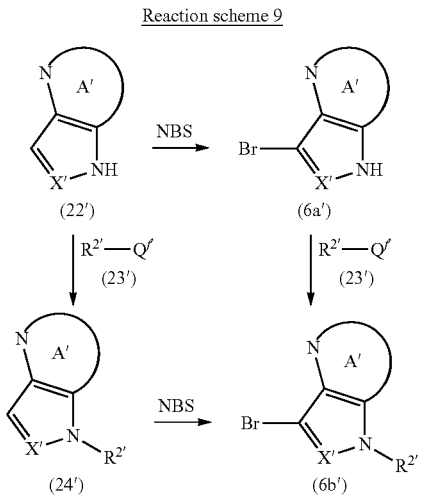

wherein $Q'$ is a leaving group, and other symbols are as defined above.

As the leaving group for $Q'$, those exemplified as the aforementioned $Q^a$ can be mentioned.

Compounds (22') and (23') can be easily obtained as commercially available products, and can also be produced according to a method known per se or a method analogous thereto.

Reaction scheme 10

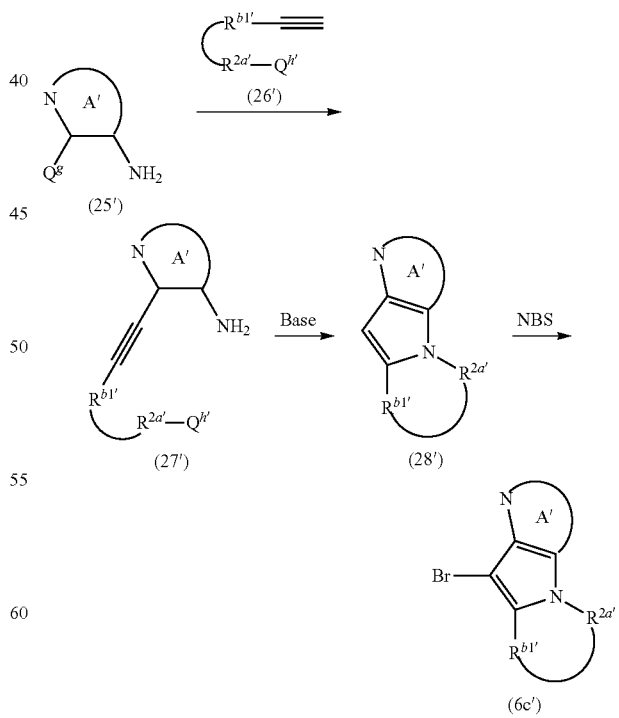

wherein $Q^{g'}$ and $Q^{h'}$ are each a leaving group, and other symbols are as defined above.

As the leaving group for $Q^{g'}$ or $Q^{h'}$, those exemplified as the aforementioned $Q^a$ can be mentioned.

Compounds (25') and (26') can be easily obtained as commercially available products, and can also be produced according to a method known per se or a method analogous thereto.

Compound (27') can be produced by reacting compound (25') with compound (26').

This reaction is performed in the same manner as in the reaction of compound (25) with compound (26).

Compound (28') can be produced by reacting compound (27') with a base.

This reaction is performed in the same manner as in the reaction of compound (27) with a base.

Compound (6c') can be produced by reacting compound (28') with N-bromosuccinimide.

This reaction is performed in the same manner as in the reaction of compound (22) with N-bromosuccinimide.

In compound (1'), compound (1d') wherein X' is N can be produced by, for example, the method shown in the following reaction scheme 11 or a method analogous thereto.

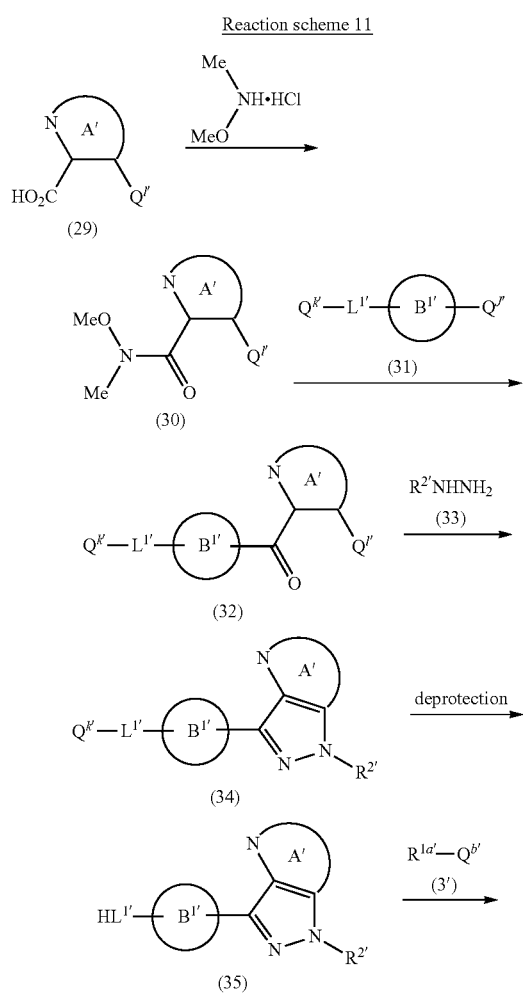

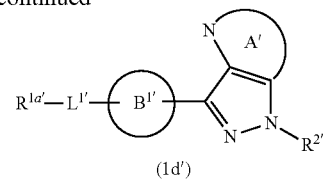

wherein $Q^{i'}$ and $Q^{j'}$ are each a leaving group, $Q^{k'}$ is a protecting group, and other symbols are as defined above.

As the leaving group for or $Q^{i'}$ or $Q^{j'}$, those exemplified as the aforementioned $Q^a$ can be mentioned. As the protecting group for $Q^{k'}$, those exemplified as the aforementioned protecting group can be mentioned.

Compounds (29), (31) and (33) can be easily obtained as commercially available products, and can also be produced according to a method known per se or a method analogous thereto.

Compound (30) can be produced by condensing compound (29) or a reactive derivative thereof and N,O-dimethylhydroxylamine or a salt thereof.

This reaction is performed in the same manner as in the reaction of compound (10) or a reactive derivative thereof with N,O-dimethylhydroxylamine or a salt thereof.

Compound (32) can be produced by reacting compound (30) with compound (31).

Compound (31) is generally used in 1 to 15 mol, preferably 1 to 5 mol, per 1 mol of compound (30).

This reaction is generally performed in the presence of a base. Examples of the base include metal amides, alkylmetals and the like. These bases are generally used in 1 to 15 mol, preferably 1 to 5 mol, per 1 mol of compound (30).

This reaction is advantageously performed in a solvent inert to the reaction. Such solvent is not particularly limited as long as the reaction proceeds and, for example, solvents such as ethers, hydrocarbons and the like or a mixed solvent thereof and the like are preferable.

While the reaction time varies depending on the reagent and solvent to be used, it is generally 0.1 to 24 hr, preferably 1 to 5 hr.

The reaction temperature is generally −100 to 100° C., preferably −100 to 30° C.

Compound (34) can be produced by reacting compound (32) with compound (33).

Compound (33) is generally used in 1 to 15 mol, preferably 1 to 5 mol, per 1 mol of compound (32).

This reaction can be performed in a solvent when desired. Such solvent is not particularly limited as long as the reaction proceeds and, for example, solvents such as alcohols, ethers, hydrocarbons, amides, halogenated hydrocarbons, sulfoxides, aromatic amines, tertiary amines and the like or a mixed solvent thereof and the like are preferable.

While the reaction time varies depending on the reagent and solvent to be used, it is generally 1 to 72 hr, preferably 1 to 24 hr.

The reaction temperature is generally 0 to 250° C., preferably 50 to 250° C.

Compound (35) can be produced by subjecting compound (34) to deprotection.

This reaction can be performed according to a method known per se, for example, the method described in Protective Groups in Organic Synthesis, $3^{rd}$ ed." Theodora W. Greene, Peter G. M. Wuts, Wiley-Interscience (1999) and the like.

Compound (1d') can be produced by reacting compound (35) with compound (3').

This reaction is performed in the same manner as in the reaction of compound (2) with compound (3).

In compound (1'), compound (1e') wherein $R^{1'}$ is

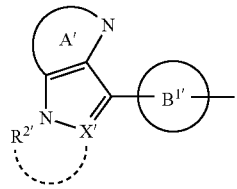

wherein each symbol is as defined above,
can be produced by, for example, the method shown in the following reaction scheme 12 or a method analogous thereto.

Reaction scheme 12

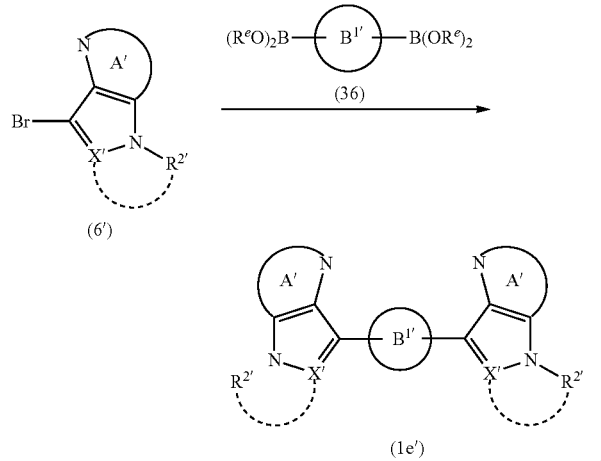

wherein each $R^e$ independently shows a hydrogen atom or an optionally substituted hydrocarbon group, two $R^e$ are optionally joined to form a 4,4,5,5-tetramethyl-1,3,2-dioxaborolane ring, and other symbols are as defined above.

Compound (36) can be easily obtained as a commercially available product, and can also be produced according to a method known per se or a method analogous thereto.

Compound (1e') can be produced by reacting compound (6') with compound (36).

This reaction is performed in the same manner as in the reaction of compound (5) with compound (6).

In compound (9'), compound (9a') wherein

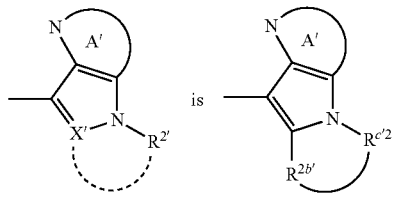

wherein $R^{b2'}$ and $R^{2c'}$ are each independently an optionally substituted carbon atom, and other symbols are as defined above, can be produced by, for example, the method shown in the following reaction scheme 13 or a method analogous thereto.

Reaction scheme 13

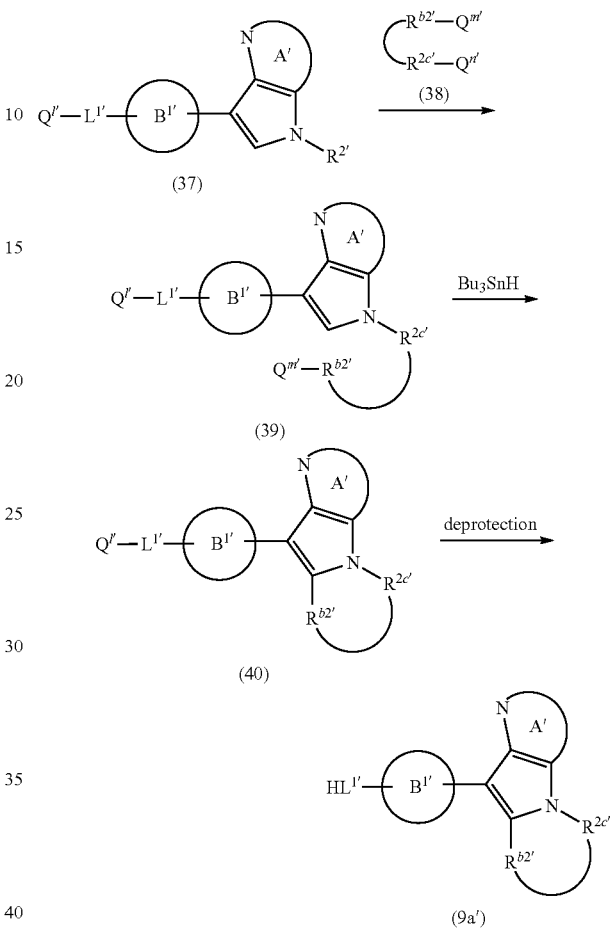

wherein $Q^{1'}$ is a protecting group, $Q^{m'}$ and $Q^{n'}$ are each a leaving group, and other symbols are as defined above.

As the protecting group for $Q^{1'}$, those exemplified as the aforementioned protecting group can be mentioned.

As the leaving group for $Q^{m'}$ or $Q^{n'}$, those exemplified as the aforementioned $Q^a$ can be mentioned.

Compound (37) can be easily obtained as a commercially available product, and can also be produced according to a method known per se or a method analogous thereto.

Compound (39) can be produced by reacting compound (37) with compound (38).

This reaction is performed in the same manner as in the reaction of compound (22) with compound (23).

Compound (40) can be produced by reacting compound (39) with tributyltin.

The tributyltin is generally used in 1 to 10 mol, preferably 1 to 3 mol, per 1 mol of compound (39).

This reaction is generally performed in the presence of a radical initiator. Examples of the radical initiator include 2,2'-azobis(isobutyronitrile), 1,1'-azobis(cyclohexanecarbonitrile), benzoyl peroxide and the like. These radical initiators are generally used in 0.01 to 0.5 mol, preferably 0.05 to 0.25 mol, per 1 mol of compound (39).

This reaction is advantageously performed in a solvent inert to the reaction. Such solvent is not particularly limited as long as the reaction proceeds and, for example, hydrocarbons, halogenated hydrocarbons and the like solvent or a mixed solvent thereof and the like are preferable.

While the reaction time varies depending on the reagent and solvent to be used, it is generally 1 to 96 hr, preferably 2 to 24 hr.

The reaction temperature is generally 20 to 200° C., preferably 50 to 150° C.

Compound (9a') can be produced by subjecting compound (40) to deprotection.

This reaction can be performed according to a method known per se, for example, the method described in Protective Groups in Organic Synthesis, 3$^{rd}$ ed." Theodora W. Greene, Peter G. M. Wuts, Wiley-Interscience (1999) and the like.

In compound (1), compound (1j') wherein R$^1$ is

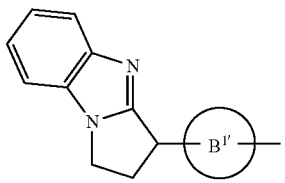

wherein each symbol is as defined above,
can be produced by, for example, the method shown in the following reaction scheme 14 or a method analogous thereto.

Reaction scheme 14

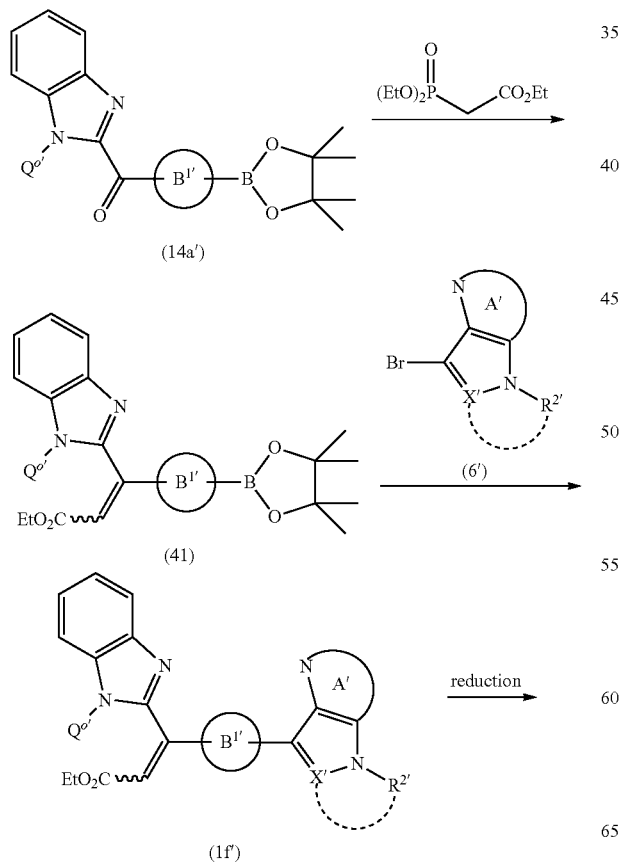

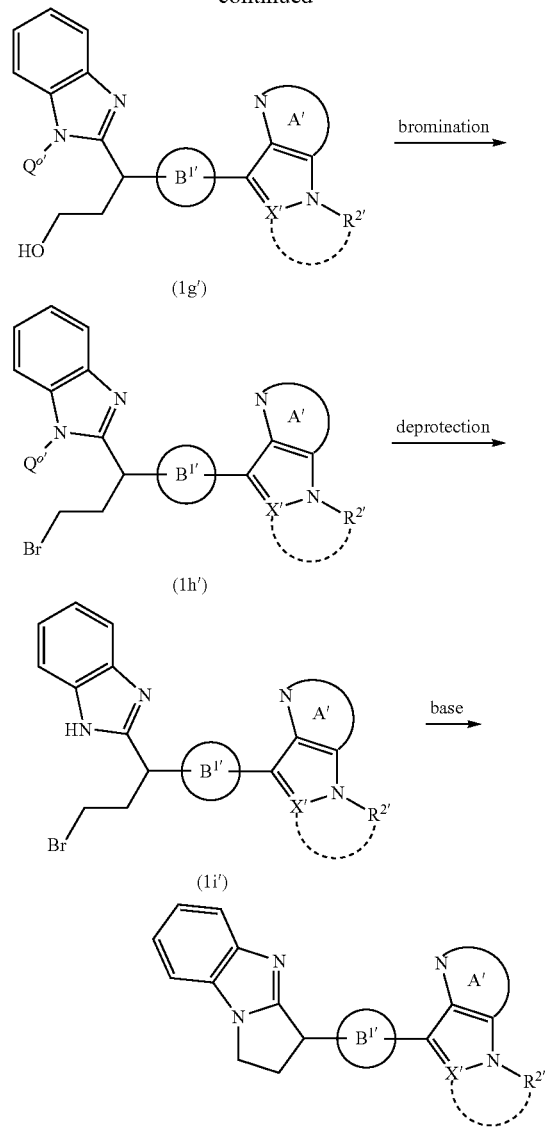

wherein Q$^{o'}$ is a protecting group, and other symbols are as defined above.

As the protecting group for Q$^{o'}$, those exemplified as the aforementioned protecting group can be mentioned.

Compound (14a') can be produced by, for example, the method shown in reaction scheme 7 or a method analogous thereto.

Compound (41) can be produced by reacting compound (14a') with triethyl phosphonoacetate.

The triethyl phosphonoacetate is generally used in 1 to 5 mol, preferably 1 to 2 mol, per 1 mol of compound (14a').

This reaction is generally performed in the presence of a base. Examples of the base include basic salts, aromatic amines, tertiary amines, alkali metal hydrides, metal alkoxides and the like. These bases are generally used in 1 to 10 mol, preferably 1 to 3 mol, per 1 mol of compound (14a').

This reaction is advantageously performed in a solvent inert to the reaction. Such solvent is not particularly limited as long as the reaction proceeds and, for example, solvents such as alcohols, ethers, hydrocarbons, amides, halogenated hydrocarbons, nitriles, sulfoxides and the like or a mixed solvent thereof and the like are preferable.

While the reaction time varies depending on the reagent and solvent to be used, it is generally 0.1 to 96 hr, preferably 0.5 to 24 hr.

The reaction temperature is generally −100 to 200° C., preferably −50 to 100° C.

Compound (1P) can be produced by reacting compound (41) with compound (6′).

This reaction is performed in the same manner as in the reaction of compound (5) with compound (6).

Compound (1g′) can be produced by reacting compound (1f′) with a reducing agent.

Examples of the reducing agent include lithium aluminum hydride, diisobutyl aluminum hydride, sodium borohydride, lithium borohydride and the like. These reducing agents are generally used in 0.5 to 10 mol, preferably 1 to 5 mol, per 1 mol of compound (1f′).

This reaction is advantageously performed in a solvent inert to the reaction. Such solvent is not particularly limited as long as the reaction proceeds and, for example, solvents such as ethers, hydrocarbons, halogenated hydrocarbons and the like or a mixed solvent thereof and the like are preferable.

While the reaction time varies depending on the reagent and solvent to be used, it is generally 0.1 to 24 hr, preferably 0.5 to 4 hr.

The reaction temperature is generally −100 to 200° C., preferably −50 to 100° C.

Compound (1 h′) can be produced by reacting compound (1g′) with a brominating agent.

Examples of the brominating agent include N-bromosuccinimide, carbon tetrabromide and the like. These brominating agents are generally used in 1 to 10 mol, preferably 1 to 5 mol, per 1 mol of compound (1f′).

This reaction is generally performed in the presence of triphenylphosphine. Triphenylphosphine is generally used in 1 to 10 mol, preferably 1 to 5 mol, per 1 mol of compound (1f′).

This reaction is advantageously performed in a solvent inert to the reaction. Such solvent is not particularly limited as long as the reaction proceeds and, for example, solvents such as ethers, hydrocarbons, amides, nitriles, sulfoxides and the like or a mixed solvent thereof and the like are preferable.

While the reaction time varies depending on the reagent and solvent to be used, it is generally 0.1 to 24 hr, preferably 0.5 to 4 hr.

The reaction temperature is generally 0 to 100° C., preferably 0 to 40° C.

Compound (1i′) can be produced by subjecting compound (1 h′) to deprotection.

This reaction can be performed according to a method known per se, for example, the method described in Protective Groups in Organic Synthesis, $3^{rd}$ ed." Theodora W. Greene, Peter G. M. Wuts, Wiley-Interscience (1999) and the like.

Compound (1j′) can be produced by reacting compound (1i′) with a base.

Examples of the base include inorganic bases, basic salts, aromatic amines, tertiary amines, alkali metal hydrides, metal alkoxides and the like. These bases are generally used in 1 to 10 mol, preferably 1 to 3 mol, per 1 mol of compound (1i′).

This reaction is advantageously performed in a solvent inert to the reaction. Such solvent is not particularly limited as long as the reaction proceeds and, for example, solvents such as ethers, hydrocarbons, amides, halogenated hydrocarbons, nitriles, sulfoxides and the like or a mixed solvent thereof and the like are preferable.

While the reaction time varies depending on the reagent and solvent to be used, it is generally 0.1 to 96 hr, preferably 0.5 to 24 hr.

The reaction temperature is generally 0 to 200° C., preferably 0 to 100° C.

In compound (6′), compound (6d′) wherein

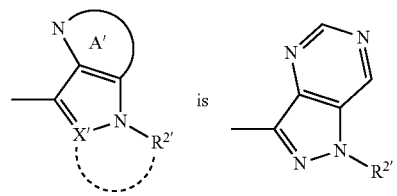

is wherein each symbol is as defined above,
can be produced by, for example, the method shown in the following reaction scheme 15 or a method analogous thereto.

Reaction scheme 15

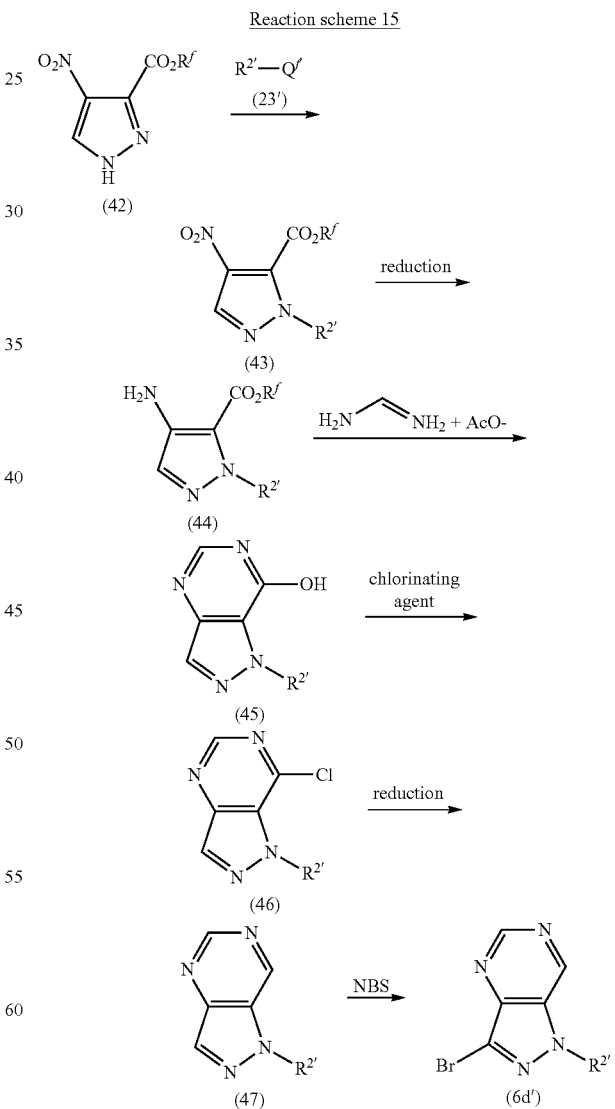

wherein $R^f$ is an optionally substituted hydrocarbon group, and other symbols are as defined above.

Compound (43) can be produced by reacting compound (42) with compound (23').

This reaction is performed in the same manner as in the reaction of compound (22) with compound (23).

Compound (44) can be produced by reducing compound (43).

Examples of the reducing agent include hydrogen source, metal, sodium dithonite and the like. Examples of the hydrogen source include hydrogen, hydrazine, formic acid, ammonium formate, 1,4-cyclohexadiene and the like. Examples of the metal include iron, zinc and the like.

When hydrogen source is used as a reducing agent, this reaction is generally performed in the presence of a catalyst. Examples of the catalyst include platinum oxide, palladium, or palladium, ruthenium, rhodium, iridium, Raney-nickel and the like supported by activated carbon, barium sulfate, calcium carbonate and the like. These catalysts are generally used in 0.01 to 1 g, preferably 0.1 to 0.5 g, per 1 g of compound (43).

When hydrogen is used as a hydrogen source, the pressure thereof is generally 1 to 10 atom, preferably 1 to 3 atom. When hydrazine, formic acid or ammonium formate is used as a hydrogen source, these hydrogen sources are generally used in 1 to 500 g, preferably 5 to 100 g, per 1 g of compound (43).

This reaction is advantageously performed in a solvent inert to the reaction. Such solvent is not particularly limited as long as the reaction proceeds and, for example, solvents such as alcohols, ethers, hydrocarbons, amides, nitriles, esters, organic acids, water and the like or a mixed solvent thereof and the like are preferable.

The reaction temperature is generally 0 to 100° C., preferably 20 to 60° C.

The reaction time is generally 0.5 to 100 hr, preferably 1 to 24 hr.

When the metal is used as a reducing agent, these metals are generally used in 1 to 100 mol, preferably 1 to 20 mol, per 1 mol of compound (43).

This reaction is generally performed in the presence of an acid. Examples of the acid include organic acids, mineral acids and the like. These acids are generally used in 1 to 100 1 g, preferably 5 to 30 g, per 1 g of compound (43).

This reaction is advantageously performed in a solvent inert to the reaction. Such solvent is not particularly limited as long as the reaction proceeds and, for example, solvents such as alcohols, ethers, hydrocarbons, amides, halogenated hydrocarbons, nitriles, esters, water and the like or a mixed solvent thereof and the like are preferable.

The reaction temperature is generally 0 to 100° C., preferably 20 to 60° C.

The reaction time is generally 30 min to 100 hr, preferably 1 to 24 hr.

When sodium dithonite is used as a reducing agent, it is generally used in 1 to 100 mol, preferably 10 to 30 mol, per 1 mol of compound (43).

This reaction is advantageously performed in a solvent inert to the reaction. Such solvent is not particularly limited as long as the reaction proceeds and, for example, solvents such as alcohols, ethers, hydrocarbons, amides, halogenated hydrocarbons, nitriles, esters, water and the like or a mixed solvent thereof and the like are preferable.

The reaction temperature is generally 0 to 100° C., preferably 20 to 60° C.

The reaction time is generally 30 min to 100 hr, preferably 1 to 24 hr.

Compound (45) can be produced by reacting compound (44) with formamidine acetate.

The formamidine acetate is generally used in 1 to 20 mol, preferably 1 to 5 mol, per 1 mol of compound (44).

This reaction is generally performed in the presence of a base. Examples of the base include basic salts, aromatic amines, tertiary amines, alkali metal hydrides, metal alkoxides and the like. These bases are generally used in 1 to 10 mol, preferably 1 to 5 mol, per 1 mol of compound (44).

This reaction is advantageously performed in a solvent inert to the reaction. Such solvent is not particularly limited as long as the reaction proceeds and, for example, solvents such as alcohols, ethers, hydrocarbons, amides, halogenated hydrocarbons, sulfoxides and the like or a mixed solvent thereof and the like are preferable.

While the reaction time varies depending on the reagent and solvent to be used, it is generally 0.5 to 24 hr, preferably 1 to 5 hr.

The reaction temperature is generally 0 to 200° C., preferably 50 to 150° C.

Compound (46) can be produced by reacting compound (45) with a chlorinating agent.

Examples of the chlorinating agent include phosphorus oxychloride, phosphorus trichloride, phosphorus pentachloride and the like. These chlorinating agents are generally used in 1 to 100 mol, preferably 1 to 20 mol, per 1 mol of compound (45).

This reaction can be performed in a solvent when desired. Such solvent is not particularly limited as long as the reaction proceeds and, for example, solvents such as ethers, hydrocarbons, amides, halogenated hydrocarbons, sulfoxides and the like or a mixed solvent thereof and the like are preferable.

While the reaction time varies depending on the reagent and solvent to be used, it is generally 1 to 48 hr, preferably 1 to 24 hr.

The reaction temperature is generally 0 to 200° C., preferably 50 to 150° C.

Compound (47) can be produced by subjecting compound (46) to a catalytic hydrogenation reaction.

This reaction is performed in the same manner as in the reduction reaction of compound (43) using a hydrogen source.

Compound (6d') can be produced by reacting compound (47) with N-bromosuccinimide.

This reaction is performed in the same manner as in the reaction of compound (22) with N-bromosuccinimide.

As in the case of the compound (1) or (1'), a prodrug of the compound (1) or (1') can be used. The prodrug of the compound (1) or (1') is a compound that is converted to a compound (1) or (1') by reactions using enzymes or gastric acid under physiological conditions in vivo. Namely, it includes a compound that is converted to a compound (1) or (1') by enzymatic oxidation, reduction and hydrolysis or a compound that is converted to a compound (1) or (1') by hydrolysis using gastric acid.

Prodrugs of the compound (1) or (1') include compounds wherein an amino group in the compound (1) or (1') is acylated, alkylated or phosphorylated (e.g., the amino group in the compound (1) or (1') is eicosanoylated, alanylated, pentylaminocarbonylated, (5-methyl-2-oxo-1,3-dioxolen-4-yl) methoxycarbonylated, tetrahydrofuranylated, pyrrolidylmethylated, pivaloyloxymethylated or tert-butylated); the hydroxy group in the compound (1) or (1') is acylated, alkylated, phosphorylated or borated (e.g., the hydroxy group in the compound (1) or (1') is acetylated, palmitoylated, propanoylated, pivaloylated, succinylated, fumarylated, alanylated, dimethylaminomethylcarbonylated); the carboxyl group in the compound (1) or (1') is esterified or amidated (e.g., the carboxyl group in the compound (1) or (1') ethyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, or methylamidated). These compounds can be produced from the compound (1) or (1') by the known methods. Prodrugs of the compound (1) or (1') can be converted to the compound (1) or (1') under the physiological conditions as described in "Development of Drugs" Vol. 7 Molecular Design published in 1990 by Hirokawa Shoten, page 163 to 198.

The compound of the present invention has an excellent PDE10A inhibitory activity and is useful for the following diseases and symptoms in mammals (e.g., humans, cows, horses, dogs, cats, monkeys, mice, rats, etc. particularly in humans):

psychotic disorder (e.g., brief psychotic disorder, shared psychotic disorder);
psychosis induced by alcohol, amphetamine, cannabis, cocaine, hallucinogens, obesity, inhalants, opioids, or phencyclidine;
delusional disorder;
anxiety disorder;
movement disorder;
mood disorder;
major depressive disorder;
a major depressive disorder superimposed on a psychotic disorder comprising a delusional disorder or schizophrenia;
major depressive episode of the mild, moderate or severe type;
manic or mixed mood episode;
hypomanic mood episode;
depressive episode with atypical features;
depressive episode with melancholic features;
depressive episode with catatonic features;
mood episode with postpartum onset;
post-stroke depression;
dysthymic disorder;
minor depressive disorder;
autism
drug addiction
neurodegenerative disorder;
neurodegeneration associated with cerebral trauma;
neurodegeneration associated with stroke;
neurodegeneration associated with cerebral infarct;
hypoglycemia-induced neurodegeneration;
neurodegeneration associated with epileptic seizure;
neurodegeneration associated with neurotoxin poisoning;
multi-system atrophy;
Alzheimer's disease;
dementia;
multi-infarct dementia;
alcoholic dementia or other drug-related dementia;
dementia associated with intracranial tumors or cerebral trauma;
dementia associated with Huntington's disease or Parkinson's disease;
AIDS-related dementia;
Frontotemporal dementia;
delirium;
amnestic disorder;
post-traumatic stress disorder;
mental retardation;
learning disorder (e.g., reading disorder, mathematics disorder, or a disorder of written expression);
attention-deficit/hyperactivity disorder;
age-related cognitive decline;
premenstrual dysphoric disorder;
post-psychotic depressive disorder of schizophrenia;
bipolar disorder comprising bipolar I disorder, bipolar II disorder;
cyclothymic disorder;
Parkinson's disease;
Huntington's disease;
paranoid;
schizophrenia (e.g., paranoid schizophrenia, disorganized schizophrenia, disorganized schizophrenia, catatonic schizophrenia, undifferentiated schizophrenia, residual schizophrenia);
schizophreniform disorder;
schizoaffective disorder of the delusional type or the depressive type;
personality disorder of the paranoid type;
personality disorder of the schizoid type;
obesity;
metabolic syndrome;
non-insulin dependent diabetes (NIDDM);
glucose intolerance;

In particular, the compound of the present invention is useful for preventing or treating schizophrenia.

Since the compound of the present invention demonstrates excellent metabolic stability, superior therapeutic effects on the aforementioned diseases are expected even at a low dosage.

The compound of the present invention shows low toxicity and can be administered safely, as it is, or in a dosage form which is manufactured according to a per se known method for manufacturing pharmaceutical formulations (e.g., methods described in Japanese Pharmacopoeia) such as tablets (inclusive of sugar coated tablet, film coated tablet, sublingual tablet, orally disintegrable tablet, and buccal), pills, powders, granules, capsules (inclusive of soft capsule, and microcapsule), troches, syrups, liquid dosage forms, emulsions, controlled-release preparations (e.g., quick-release preparation, sustained-release preparation, sustained-release microcapsule), aerosols, films (e.g., orally disintegrable film, adhesive film for application to oral-cavity mucosa), injections (e.g., subcutaneous injection, intravenous injection, intramuscular injection, intraperitoneal injection), drip infusion, percutaneous absorbent, ointment, lotion, patch, suppositories (e.g., rectal suppository, vaginal suppository), pellets, transnasal preparations, pulmonary preparations (inhalant), eye drops and the like, in an oral or parenteral route (e.g., intravenous, intramuscular, subcutaneous, intraorgan, intranasal, intradermal, ophthalmic instillation, intracerebral, intrarectal, intravaginal, intraperitoneal, directly to lesion).

The compound of the present invention can be administered orally or non-orally (e.g., including local, rectal and venous routes).

Here, as a pharmaceutical acceptable carrier, common organic or inorganic carrier substances are used as formulation raw materials. Carriers are added as vehicles, lubricants, binders and disintegrants in the solid formulations; and as solubilizing agents, suspending agents, isotonization agents, buffers and soothing agents in the liquid formulations. If desired, formulation additives such as antiseptics, antioxidants, colorants, sweeteners, etc. can be used.

Favorable examples of the vehicles are as follows: lactose, sucrose, D-mannitol, D-sorbitol, starch, α-starch, dextrin, crystalline cellulose, low-substituted hydroxypropyl cellulose, sodium carboxymethylcellulose, gum Arabic, pullulan, light silicic anhydride, synthetic aluminum silicate and magnesium metasilicic aluminate.

Favorable examples of the lubricants include magnesium stearate, calcium stearate, talc and colloidal silica.

Favorable examples of the binders are as follows: α-starch, sucrose, gelatin, gum Arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropyl methyl cellulose and polyvinylpyrrolidone.

Favorable examples of the disintegrants are as follows: lactose, sucrose, starch, carboxymethylcellulose, calcium carboxymethylcellulose, croscarmellose sodium, sodium carboxymethyl starch, light silicic anhydride and low-substituted hydroxypropylcellulose.

Favorable examples of the solvents are as follows: water for injection, physiological saline, Linger solution, alcohol, propylene glycol, polyethylene glycol, sesame oil, corn oil, olive oil and cottonseed oil.

Favorable examples of the solubilizing agents are as follows: polyethylene glycol, propylene glycol, D-mannitol, trehalose, benzylbenzoate, ethanol, tris-aminomethane, cholesterol, triethanolamine, sodium carbonate, sodium citrate, sodium salicylate and sodium acetate.

Favorable examples of the suspending agents are as follows: surfactants such as stearyl triethanolamine, sodium lauryl sulfate, laurylamino propionic acid, lecithin, benzalkonium chloride, benzethonium chloride, and glycerin monostearate; hydrophilic polymers such as polyvinyl alcohol, polyvinyl pyrrolidone, sodium carboxymethylcellulose, methylcellulose, hydroxymethyl cellulose, hydroxyethyl cellulose and hydroxypropyl cellulose; polysorbates, and polyoxyethylene-hardened castor oil.

Favorable examples of the isotonization agents include sodium chloride, glycerin, D-mannitol, D-sorbitol and glucose.

Favorable examples of the buffers include buffer solutions of phosphates, acetates, carbonates and citrates.

Favorable examples of the soothing agents include benzyl alcohol.

Favorable examples of antiseptics include para-oxybenzoic acid esters, chlorobutanol, benzyl alcohol, phenethyl alcohol, dehydroacetic acid and sorbic acid.

Favorable examples of antioxidants include sulfites and ascorbates.

Favorable examples of the colorants include water soluble edible tar dyes (e.g., edible dyes such as Food Red No. 2 and No. 3, Food Yellow No. 4 and No. 5, Food Blue No. 1 and 2); water insoluble lake dyes (e.g., aluminum salts of the aforementioned water soluble edible tar dyes), natural dyes (e.g., β-carotene, chlorophyll, red iron oxide).

Favorable examples of the sweeteners include sodium saccharin, dipotassium glycyrrhizate, aspartame and stevia.

The medical compositions of the present invention can be manufactured by the common methods in the field of formulation technology, for example, methods listed in the Japanese pharmacopoeia. Specific manufacturing methods for formulations are described in detail below.

The content of the compound of the present invention in the medical compositions of the present invention varies based on the dosage forms, dosages of the compound of the present invention, etc. For example, the content approximately ranges from 0.01 to 100 wt % and preferably from 0.1 to 95 wt % relative to the entire amount of the composition.

The dosage of the compound of the present invention depends upon injection targets, administration routes, target diseases, symptoms, etc. For example, in the case of oral administration in patients with schizophrenia (adults, bodyweight of approximately 60 kg), generally a single dose ranges from approximately 0.1 to 20 mg/kg bodyweight, preferably from approximately 0.2 to 10 mg/kg bodyweight, further preferably from approximately 0.5 to 10 mg/kg bodyweight, and this dosage is preferably administered once daily or several times daily (e.g., 3 times).

The compounds can be administered as the sole active agent or in combination with other pharmaceutical agents such as other agents used in the treatment of psychosis, especially schizophrenia and bipolar disorder, obsessive-compulsive disorder, major depression, Parkinson's disease, Alzheimer's disease, cognitive impairment and/or memory loss, e.g., nicotinic α7 agonists, nicotinic α7 partial agonists, nicotinic α7 positive allosteric modulators, PDE2 inhibitors, PDE4 inhibitors, PDE5 inhibitors, other PDE inhibitors, calcium channel blockers, muscarinic m1 and m2 modulators, adenosine receptor modulators, ampakines, Glycine transporter 1 inhibitors, NMDA-R modulators, mGluR modulators, dopamine modulators, serotonin modulators, selective serotonin reuptake inhibitors, serotonin and norepinephrine reuptake inhibitors, norepinephrine and dopamine reuptake inhibitors, triple reuptake inhibitors, cannabinoid modulators, and cholinesterase inhibitors (e.g., donepezil, rivastigimine, and galantamine). In such combinations, each active ingredient can be administered either in accordance with their usual dosage range or a dose below their usual dosage range, and can be administered either simultaneously or sequentially.

Drugs suitable in combination with the compounds of the present invention include, but are not limited to, other suitable schizophrenia drugs such as Haloperidol, Clozapine, Olanzapine, Risperidone, Aripiprazole, Ziprasidone, Paliperidone, and Quetiapine fumarate; bipolar disorder drug, including, but not limited to, Lithium, Olanzapine, Aripiprazole, and Valproic acid; Parkinson's disease drugs, including, but not limited to, Levodopa, Bromocriptine, Pergolide, Pramipexole, Tolcapone, Procyclidine, Trihexyphenidyl, and Benztropine; agents used in the treatment of major depression, including, but not limited to, Amitriptyline, Protriptyline, Desipramine, Nortriptyline, Paroxetine, Fluoxetine, Sertraline, Bupropion, Escitalopram, Mirtazapine, Venlafaxine, Duloxetine; agents used in the treatment of Alzheimer's disease, including, but not limited to, Galantamine, Tacrine, Donepezil, Rivastigmine, Memantine, Neotropin, Selegiline, Estrogen and Iodoquinol; agents used in the treatment of dementia, including, but not limited to, Thioridazine, Haloperidol, Risperidone, Tacrine, Donepezil, and Rivastigmine; agents used in the treatment of epilepsy, including, but not limited to, Phenyloin, Phenobarbital, Carbamazepine, Valproic acid, Ethosuximide, Gabapentin, Phenobarbital, Solfeton and Felbatol; agents used in the treatment of multiple sclerosis, including, but not limited to, Tolterodine, Oxybutynin, Oxycodone, Interferon beta-1b, Interferon beta-1a, Azathioprine, Methotrexate and Glatiramer; agents used in the treatment of Huntington's disease, including, but not limited to, Amitriptyline, Protripthline, Desipramine, Nortriptyline, Paroxetine, Fluoxetine, Setraline, Tetrabenazine, Haloperidol, Chlorpromazine, Thioridazine, Sulpiride, Quetiapine, Clozapine, and Risperidone; agents useful in the treatment of diabetes, including, but not limited to, PPAR ligands (e.g. agonists, antagonists, such as Rosiglitazone, Troglitazone and Pioglitazone), insulin secretagogues (e.g., sulfonylurea drugs, such as Glyburide, Glimepiride, Chlopropamide, Tolbutamide, and Glipizide, and non-sulfonyl secretagogues), α-glucosidase inhibitors (such as Acarbose, Miglitol, and Voglibose), insulin sensitizers (such as the PPAR-γ agonists, e.g., the glitazones; biguanides, PTP-1B inhibitors, DPP-IV inhibitors, and 11beta-HSD inhibitors), hepatic glucose output lowering compounds (such as glucagon antagonists and metformin, e.g., Glucophage and Glucophage XR), insulin and insulin derivatives (both long and short acting forms and formulations of insulin); and antiobesity drugs, including, but not limited to, β-3 agonists, CB-1 agonists, neuropeptide Y5 inhibitors, Ciliary Neurotrophic Factor and derivatives (e.g., Axokine), appetite suppressants (e.g., Sibutramine), and lipase inhibitors (e.g., Orlistat).

The form of administration of concomitant drugs with the compound of the present invention is not particularly limited and is acceptable as long as the compound of the present invention is combined with concomitant drugs at the time of administration. Examples of such forms of administration are as follows:

(1) Administration of a single formula obtained simultaneous formulation of the compound of the present invention with a concomitant drug, (2) Simultaneous administration via the same administration route for two kinds of formulas obtained by independent formulations of the compound of the present invention and a concomitant drug, (3) Administrations at different times via the same administration route for two kings of formulas obtained by independent formulations of the compound of the present invention and a concomitant drug, (4) Simultaneous administration via different administration routes for two kinds of formulas obtained by independent formulations of the compound of the present invention and a concomitant drug, (5) Administrations at different times via different administration routes for two kinds of formulas obtained by independent formulations of the compound of the present invention and a concomitant drug. (For example, administration in the order of the composition of the present invention a concomitant drug, or administration in the reversed order). These forms of administration are summarized below and abbreviated as a concomitant agent of the present invention.

When administering the concomitant agent of the present invention, a concomitant drug and the compound of the present invention can be administered at the same time, but the compound of the present invention can be administered after a concomitant drug is administered or after the compound of the present invention is administered, a concomitant drug can be administered. When administering at different times, the time difference depends upon the active ingredients to be administered, drug forms and methods of administration. For example, when a concomitant drug is administered first, the compound of the present invention can be administered within 1 min. to 3 days, preferably within 10 min. to 1 day and more preferably within 15 min. to 1 hour after the concomitant drug is administered. However, if the compound of the present invention is administered first, a concomitant drug can be administered within 1 min. to 1 day, preferably within 10 min. to 6 hours and more preferably within 15 min. to 1 hour after the compound of the present invention is administered.

If there are no problems with side effects of the concomitant drugs, any dosages can be set. A daily dosage as a concomitant drug depends upon dosages, administration subjects, administration routes, target diseases, symptoms, etc. For example, in the case of oral administration in patients with m schizophrenia (adults, bodyweight of approximately 60 kg), a normal daily dosage ranges from about 0.1 to 20 mg/kg bodyweight, preferably from about 0.2 to 10 mg/kg bodyweight and more preferably from about 0.5 to 10 mg/kg bodyweight. It is preferable that this dosage is administered once daily to several times daily (e.g., 3 times).

If the compound of the present invention is used in combination with a concomitant drug, the respective dosages can be reduced within a safe range with consideration of the opposite effects of the respective drugs.

The concomitant agent of the present invention exhibits low toxicity. For example, the compound of the present invention or(and) the aforementioned concomitant drug can be combined with a pharmaceutically acceptable carrier according to the known method to prepare a medical composition such as tablets (including sugar-coated tablets and film-coated tablets), powder agents, granular agents, capsules (including soft capsules), liquids, injection solutions, suppositories, sustained-release agents, etc. These compositions can be administered safely orally or non-orally (e.g., including local, rectal and venous routes).

The pharmaceutically acceptable carriers that can be used for manufacturing the concomitant agent of the present invention can be the same as those used in the medical composition of the present invention as mentioned above.

A mixing ratio between the compound of the present invention and a concomitant drug in the concomitant agent of the present invention can be selected appropriately based on the administration subjects, administration routes and diseases.

The aforementioned concomitant drugs can be combined at an appropriate proportion if two or more drugs are combined.

A dosage of the concomitant drug can be selected appropriately based on the dosages used clinically. In addition, a mixing ratio between the compound of the present invention and a concomitant drug can be selected appropriately based on the administration subjects, administration routes, as target diseases, symptoms, combinations, etc. For example, if the administration subject is humans, a concomitant drug can be used in an amount ranging from 0.01 to 100 parts by weight relative to 1 part by weight of the compound of the present invention.

For example, the content of the compound of the present invention in the concomitant agent of the present invention varies with the drug form of formulations. Generally, it is present in a range from about 0.01 to 99.9 wt %, preferably from about 0.1 to 50 wt % and more preferably from about 0.5 to wt % relative to the entire formula.

The content of a concomitant drug in the concomitant agent of the present invention varies with the drug form of formulations. Generally it is present in a range from about 0.01 to 99.9 wt %, preferably from about 0.1 to 50 wt % and more preferably from about 0.5 to 20 wt % relative to the entire formula.

The content of an additive such as carriers in the concomitant agent of the present invention varies with the drug form of formulations. Generally it is present in a range from about 1 to 99.99 wt % and preferably from about 10 to 90 wt % relative to the entire formula.

When the compound of the present invention and a concomitant drug are formulated independently, the same contents can be applied.

Since the dosages may fluctuate under various conditions as mentioned above, a dosage less than the aforementioned dosages may be sufficient or it may be necessary to administer at a dosage exceeding the range.

EXAMPLES

The present invention will be explained in detail below with reference to the reference examples, embodiments, formulation examples and experimental examples. Since these are simply examples, the present invention will not be limited to these examples and the present invention can be modified in the range not deviating from the scope of the present invention.

In the following reference examples and embodiments, "room temperature" indicates generally approximately 10° C. to 35° C. As for %, % in terms of yields indicates mol/mol %, % in terms of the solvent used for chromatography indicates vol %, and % in other cases indicates wt %. In the proton NMR spectrum, OH and NH protons that cannot be identified due to broad bands are not recorded in the data. Kieselgel 60 by Merck & Co., Inc. was used in silica gel chromatography and Chromatorex NH by Fuji Silysia Chemical Ltd. was used in basic silica gel chromatography.

Abbreviations used in other sections of the text imply the following meanings.

$^1$H NMR: proton nuclear magnetic resonance
CDCl$_3$: deuterochloroform
DMSO-d$_6$: deutero-dimethyl sulfoxide
s: singlet
d: doublet
dd: doublet of doublets
dt: doublet of triplets
t: triplet
tt: triplet of triplets
td: triplet of doublets
q: quartet
spt: septet
m: multiplet
br: broad
J: coupling constant
Hz: hertz
LC-MS: liquid chromatography/mass spectroscopy
API: atmospheric pressure ionization
ESI: electrospray ionization
HPLC: high performance liquid chromatography
Rt: retention time
dec.: decomposition
AcOEt: ethyl acetate
AIBN: 2,2'-azobis(isobutyronitrile)
CDI: 1,1'-carbonyldiimidazole
CH$_3$CN: acetonitrile
DBU: 1,8-diazabicyclo[5.4.0]-7-undecene
DIBAL: diisobutylaluminium hydride
DIPEA: N-ethyldiisopropylamine
DME: 1,2-dimethoxyethane
DMF: N,N-dimethylformamide
DMSO: dimethylsulfoxide
DMTMM: 4-(4,6-dimethoxy-1,3,5-triazin-2-yl)-4-methylmorpholinium chloride n-hydrate
DPPA: diphenylphosphoryl azide
dppb: 1,4-bis(diphenylphosphino)butane
dppf: 1,1'-bis(diphenylphosphino)ferrocene
Et$_3$N: triethylamine
EtOH: ethanol
HATU: hexafluorophosphate 2-(7-aza-1H-benzotriazole-1-yl)-1,1,3,3-tetramethyluronium
HMPA: hexamethylphosphoric triamide
HOBt: 1-hydroxybenzotriazole
IPE: diisopropyl ether
LiHMDS: lithium bis(trimethylsilyl)amide
KOAc: potassium acetate
KOtBu: potassium tert-butoxide
mCPBA: m-chloroperbenzoic acid
MeOH: methanol
MOMCl: chloromethyl methyl ether
NaH: sodium hydride
NBS: N-bromosuccinimide
NMP: N-methylpyrrolidone
Pd—C: palladium on carbon
Pd$_2$(dba)$_3$: tris(dibenzylideneacetone)dipalladium(0)
Pd(dppf)$_2$Cl$_2$: [1,1'-bis(diphenylphosphino)ferrocene]dichloropalladium(0)
Pd(OAc)$_2$: palladium(II) acetate
Pd(PPh$_3$)$_4$: tetrakis(triphenylphosphine)palladium(0)
POCl$_3$: phosphoryl chloride
Selectfluor: 1-chloromethyl-4-fluoro-1,4-diazoniabicyclo[2.2.2]octane bis(tetrafluoroborate)
SEMCl: chloromethyl 2-(trimethylsilyl)ethyl ether
TBAF: tetrabutylammonium fluoride
TEA: triethylamine
TFA: trifluoroacetic acid
THF: tetrahydrofuran
TMSCl: trimethylsilyl chloride
WSC: 1-ethyl-3-(3-dimethylaminopropyl)-carbodiimide hydrochloride
Xantphos: 4,5-bis(diphenylphosphino)-9,9-dimethylxanthene
Xphos: 2-(dicyclohexylphosphino)-2',4',6'-triisopropyl-1,1'-biphenyl
EGTA: ethylene glycol tetraacetic acid
BSA: bovine serum albumin All reagents and solvents were of commercial quality and used without further purification. Column chromatography was performed using Merck silica gel 60 (230-400 mesh). The compounds and/or intermediates were purified by preparative high performance liquid chromatography (prep. HPLC) using a Gilson High through Put purification system.

The columns were reversed phase YMC CombiPrep Pro C18, S-5 µm, 19×50 mm or L-Column 2, S-5 µm, 20×150 mm.

Massspectrometric analysis was performed according to liquid chromatography/mass spectroscopy (LCMS) methods. The method employed a Waters LC-MS System (Agilent HP1100 HPLC and a Micromass ZMD mass spectrometer for the LCMS instrument, a CAPCELL PAK C18, UG120, S-3 µm, 1.5×35 mm for the chromatography column, and a solvent system that was a 5-95% gradient of CH$_3$CN in water with 0.04% TFA over a 3.60 min period (flow rate 0.5 mL/min molecular weight range 200-800; cone Voltage 20 V; column temperature 40° C.). All masses were reported as those of the protonated parent ions.

Example 1

N-[4-(1-Methyl-1H-pyrrolo[3,2-b]pyridin-3-yl)phenyl]-1,3-benzoxazol-2-amine hydrochloride A) 3-Bromo-1-methyl-1H-pyrrolo[3,2-b]pyridine A mixture of 3-bromo-1H-pyrrolo[3,2-b]pyridine (450 mg) in DMF (5 mL) was treated with a NaH (60% in oil, 100 mg) and the resulting mixture stirred at room temperature for 5 min. The mixture was cooled to 0° C., treated with MeI (324 mg) then allowed to warm to room temperature over a period of 1 h. After this time, the reaction was diluted with water (100 mL) and extracted with AcOEt (3×50 mL). The combined organics were washed with water (50 mL), 5% LiCl aqueous solution (50 mL) then brine (50 mL), dried over Na$_2$SO$_4$, filtered and the filtrate was concentrated under reduced pressure. The residue obtained was purified by silica gel column chromatography (heptane to AcOEt) to give the title compound (408 mg).

$^1$H NMR (300 MHz, DMSO-d$_6$) δ 3.82 (3H, s), 7.19 (1H, dd, J=8.4, 4.8 Hz), 7.33 (1H, s), 7.63 (1H, dd, J=8.4, 1.5 Hz), 8.55 (1H, dd, J=4.8, 1.5 Hz).

B) 1-Methyl-3-(4-nitrophenyl)-1H-pyrrolo[3,2-b]pyridine

A mixture of 3-bromo-1-methyl-1H-pyrrolo[3,2-b]pyridine (200 mg), (4-nitrophenyl)boronic acid (175 mg), Pd(PPh$_3$)$_4$ (95 mg) and Na$_2$CO$_3$ (201 mg) in DME (4 mL) and water (2 mL) was heated at 100° C. for 19 h. After this time, the reaction was cooled to room temperature, diluted with AcOEt (100 mL), washed with water (100 mL) and brine (100 mL), dried over Na$_2$SO$_4$, filtered and the filtrate was concentrated under reduced pressure. The residue obtained was purified by silica gel column chromatography (heptane to 1:1 AcOEt/heptane) to give the title compound (89 mg).

$^1$H NMR (500 MHz, DMSO-d$_6$) δ 3.92 (3H, s), 7.30 (1H, dd, J=8.5, 4.5 Hz), 8.02 (1H, dd, J=8.0, 1.0 Hz), 8.27-8.29 (2H, m), 8.49 (1H, s), 8.54 (1H, dd, J=4.5, 1.5 Hz), 8.56-8.59 (2H, m).

C) 4-(1-Methyl-1H-pyrrolo[3,2-b]pyridin-3-yl)aniline

A mixture of 1-methyl-3-(4-nitrophenyl)-1H-pyrrolo[3,2-b]pyridine (85 mg) and 10% Pd—C (50% wet, 100 mg) in MeOH (4 mL) and AcOEt (4 ml) was stirred under H$_2$ atmosphere (balloon) for 4 h. After this time, the reaction was filtered and the filtrate was concentrated under reduced pressure to give the title compound (74 mg).

MS (ESI+): [M+H]$^+$224.

D) N-[4-(1-Methyl-1H-pyrrolo[3,2-b]pyridin-3-yl)phenyl]-1,3-benzoxazol-2-amine hydrochloride A mixture of 4-(1-methyl-1H-pyrrolo[3,2-b]pyridin-3-yl)aniline (70 mg) and 2-chlorobenzo[d]oxazole (57 mg) in 1-methylpyrrolidinone (2 mL) was stirred at 120° C. for 30 min. After this time, the reaction was cooled to room temperature, diluted with AcOEt (50 mL), washed with saturated NaHCO$_3$ aqueous solution (50 mL), water (2×50 mL) then brine (50 mL), dried over Na$_2$SO$_4$, filtered and the filtrate was concentrated under reduced pressure. The residue obtained was purified by silica gel column chromatography (CH$_2$Cl$_2$ to 1:19 MeOH/CH$_2$Cl$_2$), dissolved in 1,4-dioxane (2 ml), treated with 4 M HCl in 1,4-dioxane (0.500 mL, 2.00 mmol) and concentrated under reduced pressure. The residue obtained was triturated with boiling is CH$_3$CN to give the title compound (60 mg).

MS (ESI+): [M+H]$^+$341.

Example 2

1-Ethyl-3-{4-[(1-{[2-(trimethylsilyl)ethoxy]methyl}-1H-benzimidazol-2-yl)oxy]phenyl}-1H-pyrazolo[4,3-b]pyridine

A) 3-Bromo-1-ethyl-1H-pyrazolo[4,3-b]pyridine

A suspension of 3-bromo-1H-pyrazolo[4,3-b]pyridine (2.22 g), EtI (1.08 mL), and K$_2$CO$_3$ (2.32 g) in DMF (15 mL) was stirred overnight at room temperature. The reaction mixture was poured into water and extracted with AcOEt. The extract was washed with water and brine, dried over MgSO$_4$, and concentrated under reduced pressure. The residue purified by basic silica gel column chromatography (hexane/AcOEt) and crystallized from hexane/AcOEt to give the title compound (1.90 g).

MS (ESI+): [M+H]$^+$227.0.

B) 4-(1-Ethyl-1H-pyrazolo[4,3-b]pyridin-3-yl)phenol

A mixture of 3-bromo-1-ethyl-1H-pyrazolo[4,3-b]pyridine (904 mg), (4-hydroxyphenyl)boronic acid (690 mg), Pd(PPh$_3$)$_4$ (139 mg), Na$_2$CO$_3$ (1.48 g), DME (17.5 mL), and H$_2$O (3.5 mL) was refluxed overnight under Ar atmosphere. The reaction mixture was poured into water and extracted with AcOEt. The extract was washed with brine, dried over MgSO$_4$, and concentrated under reduced pressure. The residue purified by basic silica gel column chromatography (AcOEt) and crystallized from hexane/AcOEt to give the title compound (353 mg).

MS (ESI+): [M+H]$^+$240.2.

C) 1-Ethyl-3-{4-[(1-{[2-(trimethylsilyl)ethoxy]methyl}-1H-benzimidazol-2-yl)oxy]phenyl}-1H-pyrazolo[4,3-b]pyridine NaH (60% in oil, 59 mg) was added portionwise at room temperature to a solution of 4-(1-ethyl-1H-pyrazolo[4,3-b]pyridin-3-yl)phenol (335 mg) in DMF (3.5 mL). After stirring for 30 min, 2-chloro-1-{[2-(trimethylsilyl)ethoxy]methyl}-1H-benzimidazole (416 mg) was added, and the mixture was heated for 2 h at 150° C. under microwave irradiation. The reaction mixture was poured into water and extracted with AcOEt. The extract was washed with brine, dried over MgSO$_4$, and concentrated under reduced pressure. The residue was purified by basic silica gel column chromatography (hexane/AcOEt) and crystallized from hexane/AcOEt to give the title compound (530 mg).

MS (ESI+): [M+H]$^+$ 486.6.

Example 3

3-[4-(1H-Benzimidazol-2-yloxy)phenyl]-1-ethyl-1H-pyrazolo[4,3-b]pyridine

A mixture of 1-ethyl-3-{4-[(1-{[2-(trimethylsilyl)ethoxy]methyl}-1H-benzimidazol-2-yl)oxy]phenyl}-1H-pyrazolo[4,3-b]pyridine (510 mg), 6 M HCl aqueous solution (5 mL), and EtOH (5 mL) was refluxed for 2 h. The reaction mixture was poured into 1 M NaOH aqueous solution and extracted with AcOEt. The extract was washed with brine, dried over MgSO$_4$, and concentrated under reduced pressure. The residue was washed with hexane/AcOEt (1/1) and recrystallized from MeOH to give the title compound (294 mg).

MS (ESI+): [M+H]$^+$356.1.

Example 4

1-Ethyl-3-{4-[(1-methyl-1H-benzimidazol-2-yl)oxy]phenyl}-1H-pyrazolo[4,3-b]pyridine A suspension of 3-[4-(1H-benzimidazol-2-yloxy)phenyl]-1-ethyl-1H-pyrazolo[4,3-b]pyridine (150 mg), MeI (0.039 mL), and K$_2$CO$_3$ (117 mg) in DMF (1.5 ml) was stirred overnight at 40° C. The reaction mixture was poured into water and extracted with AcOEt. The extract was washed with brine, dried over MgSO$_4$, and concentrated under reduced pressure. The residue was crystallized from hexane/AcOEt to give the title compound (128 mg).

MS (ESI+): [M+H]$^+$370.2.

Example 5

(1H-Benzimidazol-2-yl)[4-(1-ethyl-1H-pyrazolo[4,3-b]pyridin-3-yl)phenyl]methanone

A) N-Methoxy-N-methyl-4-(4,4,5,5-tetramethyl-1,3,2-dioxaborolan-2-yl)benzamide A suspension of 4-(4,4,5,5-tetramethyl-1,3,2-dioxaborolan-2-yl)benzoic acid (10.05 g), N,O-dimethylhydroxylamine hydrochloride (4.35 g), WSC (9.32 g), HOBt (6.57 g), and TEA (6.21 ml) in DMF (80 ml) was stirred overnight at room temperature. The reaction mixture was poured into water and extracted with AcOEt. The extract was washed with water and brine, dried over $MgSO_4$, and concentrated under reduced pressure. The residue was purified by silica gel column chromatography (hexane/AcOEt) and crystallized from hexane to give the title compound (7.60 g).
MS (ESI+): [M+H]$^+$292.2.

B) [4-(4,4,5,5-Tetramethyl-1,3,2-dioxaborolan-2-yl)phenyl](1-{[2-(trimethylsilyl)ethoxy]methyl}-1H-benzimidazol-2-yl)methanone To a solution of 1-{[2-(trimethylsilyl)ethoxy]methyl}-1H-benzo[d]imidazole (6.06 g) in THF (50 mL) was added LiHMDS (1 M solution in THF, 30 ml) dropwise at 0° C. After stirring for 1 h, a solution of N-methoxy-N-methyl-4-(4,4,5,5-tetramethyl-1,3,2-dioxaborolan-2-yl)benzamide (7.10 g) in THF (50 mL) was added dropwise, and the mixture was stirred for 1 h at 0° C. The reaction mixture was poured into water and extracted with AcOEt. The extract was washed with brine, dried over $MgSO_4$, and concentrated under reduced pressure. The residue was purified by silica gel column chromatography (hexane/AcOEt) and crystallized from hexane to give the title compound (6.20 g). $^1$H NMR (300 MHz, CDCl$_3$) δ −0.11 (9H, s), 0.84-0.91 (2H, m), 1.37 (12H, s), 3.55-3.62 (2H, m), 6.03 (2H, s), 7.37-7.43 (1H, m), 7.45-7.50 (1H, m), 7.65-7.70 (1H, m), 7.91-7.98 (3H, m), 8.22-8.26 (2H, m).

C) (1H-Benzimidazol-2-yl)[4-(1-ethyl-1H-pyrazolo[4,3-b]pyridin-3-yl)phenyl]methanone A mixture of [4-(4,4,5,5-tetramethyl-1,3,2-dioxaborolan-2-yl)phenyl](1-{[2-(trimethylsilylepthoxy]methyl}-1H-benzimidazol-2-yl)methanone (478 mg), 3-bromo-1-ethyl-1H-pyrazolo[4,3-b]pyridine (225 mg), Pd(PPh$_3$)$_4$ (57.8 mg), Na$_2$CO$_3$ (212 g), DME (5 mL), and H$_2$O (1 mL) was refluxed overnight under Ar atmosphere. The reaction mixture was poured into water and extracted with AcOEt. The extract was washed with brine, dried over MgSO$_4$, and concentrated under reduced pressure. The residue was purified by basic silica gel column chromatography (hexane/AcOEt) to give crude[4-(1-ethyl-1H-pyrazolo[4,3-b]pyridin-3-yl)phenyl](1-{[2-(trimethylsilyl)ethoxy]methyl}-1H-benzimidazol-2-yl)methanone as a yellow oil.
A mixture of [4-(1-ethyl-1H-pyrazolo[4,3-b]pyridin-3-yl)phenyl](1-{[2-(trimethylsilyl)ethoxy]methyl}-1H-benzimidazol-2-yl)methanone obtained, EtOH (5 mL), and 6 M HCl aqueous solution (5 mL) was refluxed for 2 h. The reaction mixture was poured into water, alkalized with 1 M NaOH aqueous solution, and extracted with AcOEt. The extract was washed with brine, dried over MgSO$_4$, and concentrated under reduced pressure. The residue was recrystallized from THF to give the title compound (285 mg).
MS (ESI+): [M+H]$^+$368.2.

Example 6

[4-(1-Ethyl-1H-pyrazolo[4,3-b]pyridin-3-yl)phenyl](1-methyl-1H-benzimidazol-2-yl)methanone A suspension of 1H-benzimidazol-2-yl[4-(1-ethyl-1H-pyrazolo[4,3-b]pyridin-3-yl)phenyl]methanone (147 mg), MeI (0.037 mL), and K$_2$CO$_3$ (111 mg) in DMF (1.5 ml) was stirred overnight at 40° C. The reaction mixture was poured into water and extracted with AcOEt. The extract was washed with brine, dried over MgSO$_4$, and concentrated under reduced pressure. The residue was purified by basic silica gel column chromatography (hexane/AcOEt) and crystallized from hexane/AcOEt to give the title compound (139 mg).
MS (ESI+): [M+H]$^+$382.2.

Example 7

3-[1-(1H-Benzimidazol-2-yl)-2,3-dihydro-1H-indol-5-yl]-1-ethyl-1H-pyrazolo[4,3-b]pyridine

A) 2-(5-Bromo-2,3-dihydro-1H-indol-1-yl)-1H-benzimidazole

A mixture of 5-bromoindoline (1 g) and 2-chloro-1H-benzo[d]imidazole (0.770 g) in DMA/DMF (5 mL, 3/2) was stirred at 150° C. for 12 h, treated with water, and extracted with AcOEt. The organic layer was dried over MgSO$_4$ and concentrated under reduced pressure. The residue was purified by silica gel column chromatography (AcOEt/hexane) to give the title compound (1.1 g).
MS (API+): [M+H]$^+$314.0.

B) 3-[1-(1H-Benzimidazol-2-yl)-2,3-dihydro-1H-indol-5-yl]-1-ethyl-1H-pyrazolo[4,3-b]pyridine A mixture of 2-(5-Bromo-2,3-dihydro-1H-indol-1-yl)-1H-benzimidazole (200 mg), 4,4,4',4',5,5,5',5'-octamethyl-2,2'-bi(1,3,2-dioxaborolane) (162 mg), Pd(dppf)$_2$Cl$_2$ (46.6 mg) and KOAc (187 mg) in 1,4-dioxane (3 mL) was stirred at 90° C. for 12 h under Ar atmosphere, treated with water, and extracted with AcOEt. The organic layer was dried over MgSO$_4$, passed through a silica gel pad covered with activated carbon, and concentrated under reduced pressure. The residue was dissolved in DME (4 mL) and 3-bromo-1-ethyl-1H-pyrazolo[4,3-b]pyridine (145 mg), Pd(PPh$_3$)$_4$ (37.0 mg), Na$_2$CO$_3$ (136 mg) and water (1 mL) were added. The mixture was exposed to microwave irradiation at 150° C. for 1 h, treated with water and extracted with AcOEt. The organic layer was separated, dried over MgSO$_4$ and concentrated under reduced pressure. The residue was purified by silica gel column chromatography (AcOEt/hexane) and crystallized from AcOEt/IPE to give the title compound (73 mg).
MS (API+): [M+H]$^+$381.2.

Example 8

1-Ethyl-3-[4-(imidazo[1,2-a]pyridin-2-yloxy)phenyl]-1H-pyrazolo[4,3-b]pyridine hydrochloride

A) 2-(4-Bromophenoxy)imidazo[1,2-a]pyridine

Ethyl 2-chloroimidazo[1,2-a]pyridine-3-carboxylate (2.00 g) was added to a solution of p-bromophenol (1.617 g) and NaH (0.427 g) in DMF (10 mL) at 100° C. The mixture was stirred at 100° C. under a dry atmosphere (CaCl$_2$ tube) overnight. The reaction mixture was diluted with MeOH, and concentrated under reduced pressure. The residue was purified by silica gel column chromatography (AcOEt/hexane) to give the title compound (530 mg).

$^1$H NMR (300 MHz, DMSO-d$_6$) δ 6.88-7.03 (1H, m), 7.08-7.20 (2H, m), 7.23-7.39 (1H, m), 7.41-7.71 (4H, m), 8.42-8.56 (1H, m).

MS (API+): [M+H]$^+$289.0.

B) 2-[4-(4,4,5,5-Tetramethyl-1,3,2-dioxaborolan-2-yl)phenoxy]imidazo[1,2-a]pyridine A mixture of 2-(4-bromophenoxy)imidazo[1,2-a]pyridine (370 mg), 4,4,4',4',5,5,5',5'-octamethyl-2,2'-bi(1,3,2-dioxaborolane) (487 mg), Pd(dppf)$_2$Cl$_2$ dichloromethane adduct (52.6 mg) and KOAc (377 mg) in THF (10 mL)-DMSO (0.500 mL) was stirred at 80° C. under Ar for 3 h. The mixture was poured into water at room temperature and extracted with AcOEt. The organic layer was separated, washed with water and brine, dried over MgSO$_4$ and concentrated under reduced pressure. The residue was purified by silica gel column chromatography (AcOEt/hexane) to give the title compound (280 mg). $^1$H NMR (300 MHz, DMSO-d$_5$) δ 1.29 (12H, s), 6.88-7.01 (1H, m), 7.07-7.19 (2H, m), 7.22-7.33 (1H, m), 7.41-7.56 (1H, m), 7.63 (3H, s), 8.41-8.56 (1H, m).

MS (API+): [M+H]$^+$337.1.

C) 1-Ethyl-3-[4-(imidazo[1,2-a]pyridin-2-yloxy)phenyl]-1H-pyrazolo[4,3-b]pyridine hydrochloride A mixture of 2-[4-(4,4,5,5-tetramethyl-1,3,2-dioxaborolan-2-yl)phenoxy]imidazo[1,2-a]pyridine (232 mg), 3-bromo-1-ethyl-1H-pyrazolo[4,3-b]pyridine (130 mg), Pd(PPh$_3$)$_4$ (33.2 mg), 2 M Na$_2$CO$_3$ aqueous solution (0.288 mL) and THF (4 mL) was heated at 150° C. for 1 h. The residue was purified with basic silica gel column chromatography (AcOEt/hexane) followed by recrystallization from 2 M HCl in AcOEt to give the title compound (170 mg).

$^1$H NMR (300 MHz, DMSO-d$_6$) δ 1.47 (3H, t, J=7.2 Hz), 4.55 (2H, q, J=7.2 Hz), 7.15-7.29 (1H, m), 7.36-7.94 (6H, m), 8.22-8.35 (1H, m), 8.46-8.75 (4H, m).

MS (API+): [M+H]$^+$356.2.

Example 9

1-Ethyl-3-[4-(5,6,7,8-tetrahydroimidazo[1,2-a]pyridin-2-yloxy)phenyl]-1H-pyrazolo[4,3-b]pyridine hydrochloride A mixture of 1-ethyl-3-[4-(imidazo[1,2-a]pyridin-2-yloxy)phenyl]-1H-pyrazolo[4,3-b]pyridine (100 mg) and 10% Pd—C (29.9 mg) in AcOEt (2 ml) was hydrogenated under balloon pressure at room temperature for 5 h. The catalyst was removed by filtration and the filtrate was concentrated under reduced pressure. The residue was purified with silica gel column chromatography (AcOEt/hexane) followed by recrystallization from 2 M HCl in AcOEt to give the title compound (37 mg).

$^1$H NMR (300 MHz, CDCl$_3$) δ 1.55 (3H, t, J=7.2 Hz), 1.88-2.07 (4H, m), 2.82 (2H, t, J=6.0 Hz), 3.89 (2H, t, J=5.7 Hz), 4.46 (2H, q, J=7.2 Hz), 6.31 (1H, s), 7.14-7.34 (3H, m), 7.67-7.84 (1H, m), 8.36-8.49 (2H, m), 8.58-8.69 (1H, m).

MS (API+): [M+H]$^+$360.2.

Example 10

3-[6-(1H-Benzimidazol-2-yloxy)pyridin-3-yl]-1-ethyl-1H-pyrazolo[4,3-b]pyridine

A) 2-[(5-Bromopyridin-2-yl)oxy]-1-{[2-(trimethylsilyl)ethoxy]methyl}-1H-benzimidazole and 5-bromo-1-(1-{[2-(trimethylsilyl)ethoxy]methyl}-1H-benzimidazol-2-yl)pyridin-2(1H)-one To a stirred mixture of 5-bromopyridin-2-ol (500 mg) in DMF (10 mL) was added NaH (60% in oil, 115 mg) at room temperature. The mixture was stirred at room temperature for 30 min and then 2-chloro-1-{[2-(trimethylsilyl)ethoxy]methyl}-1H-benzo[d]imidazole (813 mg) was added. The mixture was exposed to microwave irradiation at 200° C. for 1 h, treated with water, and extracted with AcOEt. The organic layer was dried over MgSO$_4$ and concentrated under reduced pressure. The residue was purified by silica gel column chromatography (AcOEt/MeOH) and crystallized from AcOEt/hexane to give 2-(5-bromopyridin-2-yloxy)-1-((2-(trimethylsilyl)methyl)-1H-benzo[d]imidazole (336 mg) and 5-bromo-1-(1-{[2-(trimethylsilyl)ethoxy]methyl}-1H-benzo[d]imidazol-2-yl)pyridin-2(1H)-one (170 mg).

2-[(5-Bromopyridin-2-yl)oxy]-1-{[2-(trimethylsilyl)ethoxy]methyl}-1H-benzo[d]imidazole $^1$H NMR (300 MHz, DMSO-d$_6$) δ 0.11 (9H, s), 0.78-0.87 (2H, m), 3.50-3.62 (2H, m), 5.55 (2H, s), 7.15-7.33 (2H, m), 7.41-7.53 (2H, m), 7.59 (1H, d, J=6.4 Hz), 8.19-8.31 (1H, m), 8.45 (1H, d, J=2.3 Hz).

5-Bromo-1-(1-{[2-(trimethylsilyl)ethoxy]methyl}-1H-benzimidazol-2-yl)pyridin-2(1H)-one $^1$H NMR (300 MHz, DMSO-d$_6$) δ −0.09 (9H, s), 0.69-0.86 (2H, m), 3.35-3.48 (2H, m), 5.47 (2H, brs), 6.60 (1H, d, J=9.8 Hz), 7.28-7.47 (2H, m), 7.68-7.91 (3H, m), 8.21 (1H, d, J=2.6 Hz).

B) 3-[6-(1H-Benzimidazol-2-yloxy)pyridin-3-yl]-1-ethyl-1H-pyrazolo[4,3-b]pyridine A mixture of 2-[(5-bromopyridin-2-yl)oxy]-1-{[2-(trimethylsilyl)ethoxy]methyl}-1H-benzimidazole (336 mg), 4,4,4',4',5,5,5',5'-octamethyl-2,2'-bi(1,3,2-dioxaborolane) (203 mg), Pd(dppf)$_2$Cl$_2$ (58.5 mg) and KOAc (235 mg) in 1,4-dioxane (5 mL) was stirred at 90° C. for 12 h under Ar atmosphere, treated with water, and extracted with AcOEt. The organic layer was dried over MgSO$_4$ and passed through a silica gel pad covered with activated carbon, and concentrated under reduced pressure. The residue was dissolved in DME (4 mL) and 3-bromo-1-ethyl-1H-pyrazolo[4,3-b]pyridine (181 mg), Pd(PPh$_3$)$_4$ (92.0 mg), Cs$_2$CO$_3$ (521 mg) and water (1 mL) were added. The mixture was exposed to microwave irradiation at 120° C. for 40 min, treated with water and extracted with AcOEt. The organic layer was separated, dried over MgSO$_4$ and concentrated under reduced pressure. The residue was dissolved in AcOEt/EtOH (5 mL, 3/2) and 4 M HCl in AcOEt (1.5 mL) was added. The mixture was stirred at 70° C. for 4 h, evaporated, treated with NaHCO$_3$ aqueous solution and extracted with AcOEt. The organic layer was separated, dried over MgSO$_4$ and concentrated under reduced pressure. The residue was purified by silica gel column chromatography (AcOEt/hexane) and crystallized from AcOEt/hexane to give the title compound (16 mg).

MS (API+): [M+H]$^+$357.4

Example 11

1-(1H-Benzimidazol-2-yl)-5-(1-ethyl-1H-pyrazolo[4,3-b]pyridin-3-yl)pyridin-2(1H)-one A mixture of 5-bromo-1-(1-{([2-(trimethylsilyl)ethoxy]methyl}-1H-benzimidazol-2-yl)pyridin-2(1H)-one (170 mg), 4,4,4',4',5,5,5',5'-octamethyl-2,2'-bi(1,3,2-dioxaborolane) (103 mg), Pd(dppf)$_2$Cl$_2$ (29.6 mg) and KOAc (79 mg) in 1,4-dioxane (3 ml) was stirred at 90° C. for 12 h under Ar atmosphere, treated with water, and extracted with AcOEt. The organic layer was dried over MgSO$_4$ and passed through a silica gel pad covered with activated carbon, and concentrated under reduced pressure. The residue was dissolved in DME (3 ml) and 3-bromo-1-ethyl-1H-pyrazolo[4,3-b]pyridine (90 mg), Pd(PPh$_3$)$_4$ (46.0 mg), Cs$_2$CO$_3$ (261 mg) and water (1 mL) were added. The mixture was exposed to microwave irradiation at 120° C. for 40 min, treated with water and extracted with AcOEt. The organic layer was separated, dried over MgSO$_4$ and concentrated under reduced pressure. The residue was dissolved in THF (2 mL) and 1 M TBAF in THF (1.0 mL) was added. The mixture was stirred at reflux for 4 h, and then exposed to microwave irradiation at 100° C. for 1 h. After cooling to room temperature, the mixture was evaporated, treated with water and extracted with AcOEt. The organic layer was separated, dried over MgSO$_4$ and concentrated under reduced pressure. The residue was purified by silica gel column chromatography (AcOEt/hexane) and crystallized from AcOEt/hexane to give the title compound (40 mg).

MS (API+): [M+H]$^+$357.4

Example 12

5-(1-Ethyl-1H-pyrazolo[4,3-b]pyridin-3-yl)-1-(1-methyl-1H-benzimidazol-2-yl)pyridin-2(1H)-one A mixture of 1-(1H-benzimidazol-2-yl)-5-(1-ethyl-1H-pyrazolo[4,3-b]pyridin-3-yl)pyridin-2(1H)-one (20 mg), MeI (11.95 mg) and Cs$_2$CO$_3$ (36.6 mg) in DMF (1 mL) was stirred at room temperature for 12 h, treated with water, and extracted with AcOEt. The organic layer was dried over MgSO$_4$ and concentrated under reduced pressure. The residue was purified by silica gel column chromatography (AcOEt/hexane) and crystallized from hexane/AcOEt to give the title compound (12 mg).

MS (API+): [M+H]$^+$371.3.

Example 13

10-[4-(1H-Benzimidazol-2-yloxy)phenyl]-6,7,8,9-tetrahydropyrido[2,3-b]indolizine A) 2-(6-Chlorohex-1-ynyl)pyridin-3-amine A mixture of 2-chloropyridin-3-amine (2571 mg), K$_2$CO$_3$ (8292 mg), Pd(OAc)$_2$ (180 mg), dppb (682 mg) and CH$_3$CN (25 mL) was stirred at room temperature under Ar atmosphere for 30 min. 6-Chlorohex-1-yne (2565 mg) was added to the mixture, and the mixture was stirred at 80° C. under Ar atmosphere for 24 h. The mixture was filtrated and insoluble material was washed with CH$_3$CN. The filtrate was concentrated under reduced pressure, and the residue was purified by silica gel column chromatography (AcOEt/hexane) to give the title compound (600 mg).

MS (API+): [M+H]$^+$209.3.

B) 6,7,8,9-Tetrahydropyrido[2,3-b]indolizine

A solution of 2-(6-chlorohex-1-ynyl)pyridin-3-amine (300 mg) in CH$_3$CN (3 ml) was added a solution of KOtBu (387 mg) in THF (3.5 mL) at 0.0° C. The mixture was stirred at 0° C. for 30 min. The mixture was quenched with water at 0° C. and extracted with AcOEt. The organic layer was separated, washed with brine, dried over Na$_2$SO$_4$ and concentrated under reduced pressure. The residue was purified by silica gel column chromatography (AcOEt/hexane) to give the title compound (170 mg).

MS (API+): [M+H]$^+$173.0.

C) 10-Bromo-6,7,8,9-tetrahydropyrido[2,3-b]indolizine

To a solution of 6,7,8,9-tetrahydropyrido[2,3-b]indolizine (170 mg) in DMF (3 mL) was added NBS (193 mg) at 0° C. The mixture was stirred at 0° C. for 30 min. The mixture was added saturated NaHCO$_3$ aqueous solution at 0° C. and extracted with AcOEt. The organic layer was separated, washed with brine, dried over Na$_2$SO$_4$ and concentrated under reduced pressure. The residue was purified by silica gel column chromatography (AcOEt/hexane) to give the title compound (217 mg).

MS (API+): [M+H]$^+$250.9.

D) 2-(4-Bromophenoxy)-1H-benzo[d]imidazole

A mixture of 2-(methylsulfonyl)-1H-benzo[d]imidazole (5.6 g), 4-bromophenol (24.69 g) and TEA (19.89 mL) was stirred at 120° C. for 15 h. The mixture was added with 8 M NaOH aqueous solution and extracted with AcOEt. The organic layer was separated, washed with water and brine, dried over Na$_2$SO$_4$ and concentrated under reduced pressure. The precipitate was collected by filtration to give the first lot of the titled compound (5.77 g). The filtrate was evaporated, and the precipitate was collected by filtration to give the second lot of the titled compound (0.92 g).

MS (API+): [M+H]$^+$289.0.

E) 2-[4-(4,4,5,5-Tetramethyl-1,3,2-dioxaborolan-2-yl)phenoxy]-1H-benzo[d]imidazole To a mixture of 4,4,4',4',5,5,5',5'-octamethyl-2,2'-bi(1,3,2-dioxaborolane) (8.81 g), KOAc (6.81 g) and 2-(4-bromophenoxy)-1H-benzo[d]imidazole (6.69 g) in THF (180 mL) and DMSO (9 mL) was added Pd(dppf)$_2$Cl$_2$ dichloromethane complex (0.945 g, 1.16 mmol). The mixture was stirred at 80° C. under Ar atmosphere for 15 h. The mixture was poured into water and extracted with AcOEt. The organic layer was separated, washed with brine, dried over Na$_2$SO$_4$ and concentrated under reduced pressure. The residue was purified by silica gel column chromatography (THF/hexane) and recrystallized from hexane/THF to give the title compound (1.32 g).

MS (API+): [M+H]$^+$337.1.

F) 10-[4-(1H-Benzimidazol-2-yloxy)phenyl]-6,7,8,9-tetrahydropyrido[2,3-b]indolizine To a suspension of 2-[4-(4,4,5,5-tetramethyl-1,3,2-dioxaborolan-2-yl)phenoxy]-1H-benzo[d]imidazole (320 mg), 10-bromo-6,7,8,9-tetrahydropyrido[2,3-b]indolizine (217 mg) and K$_2$CO$_3$ (119 mg) in DME (4 mL) and water (1 mL) was added Pd(PPh$_3$)$_4$ (100 mg). The mixture was heated at 150° C. for 40 min under microwave irradiation. The mixture was poured into water and extracted with AcOEt. The organic layer was separated, washed with brine, dried over $Na_2SO_4$ and concentrated under reduced pressure. The residue was purified by silica gel column chromatography (AcOEt/hexane) to give the title compound (43.4 mg).

mp 264° C. (dec.)

$^1$H NMR (300 MHz, DMSO-$d_6$) δ 1.74-1.96 (2H, m), 2.02-2.19 (2H, m), 3.16 (2H, t, J=6.2 Hz), 4.16 (2H, t, J=6.0 Hz), 7.05-7.19 (3H, m), 7.30-7.49 (4H, m), 7.81-7.98 (3H, m), 8.38 (1H, dd, J=4.5, 1.5 Hz), 12.34 (1H, s).

MS (API+): [M+H]$^+$381.2.

Anal. Calcd for $C_{24}H_{20}N_4O \cdot 0.1H_2O$: C, 75.41; H, 5.44; N, 14.66.

Found: C, 75.29; H, 5.41; N, 14.43.

Example 14

1-Ethyl-3-{4-[(3-methyl-3H-imidazo[4,5-b]pyridin-2-yl)oxy]phenyl}-1H-pyrazolo[4,3-b]pyridine A) 3-Methyl-2-(methylsulfanyl)-3H-imidazo[4,5-b]pyridine To a solution of 1H-imidazo[4,5-b]pyridine-2-thiol (13 g) in acetone (200 mL) were added MeI (5.8 ml) and $K_2CO_3$ (35 g) at room temperature. After stirring for 10 h, the mixture was concentrated under reduced pressure. The residue was purified by basic silica gel column chromatography (AcOEt/hexane) to give the title compound (3.0 g).

MS (API+): [M+H]$^+$180.2.

B) 3-Methyl-2-(methylsulfonyl)-3H-imidazo[4,5-b]pyridine

To a solution of 3-methyl-2-(methylsulfanyl)-3H-imidazo[4,5-b]pyridine (3.0 g) in AcOEt (50 mL) was added mCPBA (7.7 g) at 0° C. After stirring for 1 day, the solution was purified by basic silica gel column chromatography (AcOEt) to give the title compound (3.1 g).

MS (API+): [M+H]$^+$212.0.

C) 2-(4-Bromophenoxy)-3-methyl-3H-imidazo[4,5-b]pyridine

A mixture of 3-methyl-2-(methylsulfonyl)-3H-imidazo[4,5-b]pyridine (2.0 g), 4-bromophenol (4.9 g) and TEA (4.0 ml) was stirred at 120° C. for 3 h. The reaction mixture was poured into water and extracted with AcOEt. The extract was washed with 1 M NaOH aqueous solution, dried over $Na_2SO_4$, filtered and concentrated under reduced pressure. The residual crystals were recrystallized from AcOEt to give the title compound (1.7 g).

$^1$H NMR (300 MHz, DMSO-$d_6$) δ 3.73 (3H, s), 7.20 (1H, dd, J=7.9, 4.9 Hz), 7.43-7.50 (2H, m), 7.65-7.72 (2H, m), 7.79 (1H, dd, J=7.9, 1.5 Hz), 8.21 (1H, dd, J=4.9, 1.5 Hz).

D) 3-Methyl-2-[4-(4,4,5,5-tetramethyl-1,3,2-dioxaborolan-2-yl)phenoxy]-3H-imidazo[4,5-b]pyridine A mixture of 4,4,4',4',5,5,5',5'-octamethyl-2,2'-bi(1,3,2-dioxaborolane) (3.8 g), KOAc (2.9 g), 2-(4-bromophenoxy)-3-methyl-3H-imidazo[4,5-b]pyridine (3.0 g) and Pd(dppf)$_2$Cl$_2$ dichloromethane complex (0.41 g) in THF (30 mL) and DMSO (1.5 mL) was stirred at 80° C. for 4 h under Ar atmosphere. The mixture was diluted with AcOEt and filtered on silica gel conditioned with AcOEt. The filtrate was concentrated under reduced pressure. The residue was purified by silica gel column chromatography (AcOEt/hexane) and recrystallization from AcOEt/hexane to give the title compound (1.3 g).

MS (API+): [M+H]$^+$352.1.

E) 1-Ethyl-3-{(4-[(3-methyl-3H-imidazo[4,5-b]pyridin-2-yl)oxy]phenyl}-1H-pyrazolo[4,3-b]pyridine A mixture of 3-methyl-2-[4-(4,4,5,5-tetramethyl-1,3,2-dioxaborolan-2-yl)phenoxy]-3H-imidazo[4,5-b]pyridine (217 mg), 3-bromo-1-ethyl-1H-pyrazolo[4,3-b]pyridine (140 mg), Pd(PPh$_3$)$_4$ (21 mg) and $Na_2CO_3$ (230 mg) in DME (5 mL) and water (1 mL) was refluxed overnight under Ar atmosphere. The reaction mixture was poured into water and extracted with AcOEt. The extract was washed with brine, dried over $Na_2SO_4$, and concentrated under reduced pressure. The residue was purified by silica gel column chromatography (AcOEt/hexane) and recrystallized from AcOEt/hexane to give the title compound (103 mg).

mp 176-177° C.

$^1$H NMR (300 MHz, DMSO-$d_6$) δ 1.49 (3H, t, J=7.2 Hz), 3.78 (3H, s), 4.56 (2H, q, J=7.2 Hz), 7.21 (1H, dd, J=7.9, 4.9 Hz), 7.49 (1H, dd, J=8.7, 4.5 Hz), 7.58-7.65 (2H, m), 7.80 (1H, dd, J=7.9, 1.5 Hz), 8.22 (1H, dd, J=5.1, 1.3 Hz), 8.28 (1H, dd, J=8.7, 1.1 Hz), 8.57-8.63 (2H, m), 8.66 (1H, dd, J=4.3, 1.3 Hz).

MS (API+): [M+H]$^+$371.3.

Anal. Calcd for $C_{21}H_{18}N_6O$: C, 68.09; H, 4.90; N, 22.69. Found: C, 67.83; H, 4.92; N, 22.39.

Example 15

3,3'-Benzene-1,4-diylbis(1-ethyl-1H-pyrazolo[4,3-b]pyridine)

A mixture of 1,4-phenylenediboronic acid (37.0 mg), 3-bromo-1-ethyl-1H-pyrazolo[4,3-b]pyridine (101 mg), Pd(PPh$_3$)$_4$ (25.8 mg) and $Cs_2CO_3$ (0.280 g) in DME/water (3/1, 4 mL) was exposed to microwave irradiation (120° C., 40 min), treated with water, and extracted with AcOEt. The organic layer was dried over MgSO$_4$ and concentrated under reduced pressure. The residue was purified by silica gel column chromatography (AcOEt/hexane). Crystallization from AcOEt/hexane gave the title compound (6.00 mg).

MS (API+): [M+H]$^+$369.2.

Example 16

3-[1-(1H-Benzimidazol-2-yl)-1H-pyrazol-4-yl]-1-ethyl-1H-pyrazolo[4,3-b]pyridine

A mixture of 2-chloro-1-{[2-(trimethylsilyl)ethoxy]methyl}-1H-benzo[d]imidazole (300 mg), 4-bromo-1H-pyrazole (779 mg) and TEA (739 μL) was stirred at 120° C. for 24 h, treated with water, and extracted with AcOEt. The organic layer was dried over MgSO$_4$ and concentrated under reduced pressure. The residue was purified by silica gel column chromatography (AcOEt/hexane). The eluted material was dissolved in 1,4-dioxane (3 mL) and then 4,4,4',4',5,5,5',5'-octamethyl-2,2'-bi(1,3,2-dioxaborolane) (110 mg), Pd(dppf)$_2$Cl$_2$ (31.6 mg) and KOAc (85 mg) were added. The mixture was stirred at 90° C. for 12 h under Ar atmosphere, treated with water, and extracted with AcOEt. The organic layer was dried over MgSO$_4$, passed through a Celite pad covered with activated carbon, and concentrated under reduced pressure. The residue was dissolved in DME (4 mL) and then 3-bromo- 1-ethyl-1H-pyrazolo[4,3-b]pyridine (0.097 g), Pd(PPh$_3$)$_4$ (0.050 g), Cs$_2$CO$_3$ (0.280 g) and water (1 mL) were added. The mixture was exposed to microwave irradiation (120° C., 40 min), treated with water, and extracted with AcOEt. The organic layer was dried over MgSO$_4$ and concentrated under reduced pressure. The residue was purified by silica gel column chromatography (AcOEt/hexane).

The eluted material was dissolved in THF (2 mL) and then 1 M TBAF in THF (2 mL) was added. The mixture was stirred at reflux for 4 h, and then exposed to microwave irradiation at 100° C. for 1 h, treated with water, and extracted with AcOEt. The organic layer was dried over MgSO$_4$ and concentrated under reduced pressure. The residue was purified by silica gel column chromatography (AcOEt/hexane). Crystallization from AcOEt/hexane gave the title compound (14.0 mg).

MS (API+): [M+H]$^+$330.4.

Example 17

1-Ethyl-3-[1-(1-methyl-1H-benzimidazol-2-yl)-1H-pyrazol-4-yl]-1H-pyrazolo[4,3-b]pyridine A mixture of 3-[(1-(1H-benzo[d]imidazol-2-yl)-1H-pyrazol-4-yl]-1-ethyl-1H-pyrazolo[4,3-b]pyridine (8 mg), MeI (2.278 µL) and Cs$_2$CO$_3$ (15.83 mg) in DMF (2 mL) was stirred at room temperature for 3 h, treated with water, and extracted with AcOEt. The organic layer was dried over MgSO$_4$ and concentrated under reduced pressure. The residue was purified by silica gel column chromatography (AcOEt/hexane). Crystallization from AcOEt/hexane gave the title compound (4.80 mg).

MS (API+): [M+H]$^+$344.2.

Example 18

1-(1-Methylethyl)-3-{4-[(3-methyl-3H-imidazo[4,5-b]pyridin-2-yl)oxy]phenyl}-1H-pyrazolo[4,3-b]pyridine A) 3-Bromo-1-(1-methylethyl)-1H-pyrazolo[4,3-b]pyridine To a solution of 3-bromo-1H-pyrazolo[4,3-b]pyridine (200 mg) in DMF (10 mL) were added 2-iodopropane (0.20 mL) and K$_2$CO$_3$ (168 mg) at room temperature. After stirring overnight, the reaction mixture was poured into water and extracted with AcOEt. The extract was washed with water and brine, dried over MgSO$_4$, and concentrated under reduced pressure. The residue was purified by basic silica gel column chromatography (AcOEt/hexane) to give the title compound (147 mg).

MS (ESI+): found: 240.1, 242.0.

$^1$H NMR (300 MHz, CDCl$_3$) δ 1.61 (6H, d, J=6.8 Hz), 4.81 (1H, spt, J=6.7 Hz), 7.34 (1H, dd, J=8.7, 4.5 Hz), 7.79 (1H, dd, J=8.5, 1.3 Hz), 8.63 (1H, dd, J=4.3, 1.3 Hz).

B) 1-(1-Methylethyl)-3-{4-[(3-methyl-3H-imidazo[4,5-b]pyridin-2-yl)oxy]phenyl}-1H-pyrazolo[4,3-b]pyridine A mixture of 3-methyl-2-[4-(4,4,5,5-tetramethyl-1,3,2-dioxaborolan-2-yl)phenoxy]-3H-imidazo[4,5-b]pyridine (215 mg), 3-bromo-1-(1-methylethyl)-1H-pyrazolo[4,3-b]pyridine (147 mg), Pd(PPh$_3$)$_4$ (21 mg) and Na$_2$CO$_3$ (227 mg) in DME (5 mL) and water (1 mL) was refluxed overnight under Ar atmosphere. The reaction mixture was poured into water and extracted with AcOEt. The extract was washed with brine, dried over Na$_2$SO$_4$, and concentrated under reduced pressure. The residue was purified by silica gel column chromatography (AcOEt/hexane) and recrystallized from AcOEt/hexane to give the title compound (225 mg).

MS (ESI+): [M+H]$^+$385.4.

$^1$H NMR (300 MHz, CDCl$_3$) δ 1.66 (6H, d, J=6.9 Hz), 3.85 (3H, s), 4.87 (1H, dt, J=13.3, 6.7 Hz), 7.13 (1H, dd, J=7.7, 5.1 Hz), 7.29 (1H, dd, J=8.5, 4.3 Hz), 7.48-7.55 (2H, m), δ 7.80 (2H, ddd, J=7.3, 5.5, 1.5 Hz), 8.24 (1H, dd, J=5.1, 1.3 Hz), 8.61-8.69 (3H, m).

mp 163-164° C.

Anal. Calcd for C$_{22}$H$_{20}$N$_6$O: C, 68.73; H, 5.24; N, 21.86. Found: C, 68.78; H, 5.28; N, 21.84.

Example 19

1-Cyclobutyl-3-{(4-[(3-methyl-3H-imidazo[4,5-b]pyridin-2-yl)oxy]phenyl}-1H-pyrazolo[4,3-b]pyridine A)
3-Bromo-1-cyclobutyl-1H-pyrazolo[4,3-b]pyridine To a solution of 3-bromo-1H-pyrazolo[4,3-b]pyridine (200 mg) in DMF (10 ml) were added cyclobutyl bromide (0.19 mL) and Cs$_2$CO$_3$ (395 mg) at room temperature. After stirring overnight at 60° C., the reaction mixture was poured into water and extracted with AcOEt. The extract was washed with water and brine, dried over MgSO$_4$, and concentrated under reduced pressure. The residue was purified by basic silica gel column chromatography (AcOEt/hexane) to give the title compound (181 mg).

MS (ESI+): found: 252.1, 254.1.

B) 1-Cyclobutyl-3-{4-[(3-methyl-3H-imidazo[4,5-b]pyridin-2-yl)oxy]phenyl}-1H-pyrazolo[4,3-b]pyridine A mixture of 3-methyl-2-[4-(4,4,5,5-tetramethyl-1,3,2-dioxaborolan-2-yl)phenoxy]-3H-imidazo[4,5-b]pyridine (252 mg), 3-bromo-1-cyclobutyl-1H-pyrazolo[4,3-b]pyridine (181 mg), Pd(PPh$_3$)$_4$ (25 mg) and Na$_2$CO$_3$ (266 mg) in DME (5 mL) and water (1 mL) was refluxed overnight under Ar atmosphere. The reaction mixture was poured into water and extracted with AcOEt. The extract was washed with brine, dried over Na$_2$SO$_4$, and concentrated under reduced pressure. The residue was purified by silica gel column chromatography (AcOEt/hexane) and recrystallized from AcOEt/hexane to give the title compound (282 mg).

MS (ESI+): [M+H]$^+$397.4.

Example 20

1-Ethyl-3-[4-(3H-imidazo[4,5-b]pyridin-2-yloxy)phenyl]-1H-pyrazolo[4,3-b]pyridine A) 2-(Methylsulfanyl)-3H-imidazo[4,5-b]pyridine To a solution of 1H-imidazo[4,5-b]pyridine-2-thiol (5.0 g) in acetone (75 mL) were added MeI (2.3 mL) and K$_2$CO$_3$ (18 g) at room temperature. After stirring for 1 day, the mixture was filtered and concentrated under reduced pressure. The residue was purified by silica gel column chromatography (AcOEt/hexane) to give the title compound (1.2 g).

$^1$H NMR (300 MHz, DMSO-d$_6$) δ 2.71 (3H, s), 7.14 (1H, dd, J=7.9, 4.9 Hz), 7.82 (1H, d, J=7.2 Hz), 8.19 (1H, d, J=3.4 Hz), 13.05 (1H, brs).

B) 2-(Methylsulfonyl)-3H-imidazo[4,5-b]pyridine

To a solution of 2-(methylsulfanyl)-3H-imidazo[4,5-b]pyridine (1.7 g) in AcOEt (100 mL) was added mCPBA (4.6 g) at 0° C. After stirring for 4 h, the mixture was concentrated under reduced pressure. The residual solid was washed with AcOEt to give the title compound (1.8 g).
MS (API+): [M+H]$^+$197.9.

C) 2-(Methylsulfonyl)-1-{([2-(trimethylsilyl)ethoxy]methyl}-1H-imidazo[4,5-b]pyridine To a solution of 2-(methylsulfonyl)-1H-imidazo[4,5-b]pyridine (1.8 g) and SEMCl (1.9 mL) in DMF (30 mL) was added NaH (60% in oil, 0.43 g) at 0° C. After stirring at 0° C. for 1 h, the mixture was partitioned between water and AcOEt. The organic layer was washed with brine, dried over Na$_2$SO$_4$, filtered and concentrated under reduced pressure. The residue was purified by silica gel column chromatography (AcOEt/hexane) to give the title compound (0.45 g).
MS (API+): [M+H]$^+$328.1.

D) 2-(4-Bromophenoxy)-3-{[2-(trimethylsilyl)ethoxy]methyl}-3H-imidazo[4,5-b]pyridine A mixture of 2-(methylsulfonyl)-1-{[2-(trimethylsilyl)ethoxy]methyl}-1H-imidazo[4,5-b]pyridine (315 mg), 4-bromophenol (166 mg) and TEA (268 μL) was stirred at 120° C. for 3 h. To the mixture was added TEA (268 μL), and the mixture was stirred at 120° C. for 3 h. The mixture was partitioned between water and AcOEt. The organic layer was washed with brine, dried over Na$_2$SO$_4$, filtered and concentrated under reduced pressure. The residue was purified by basic silica gel column chromatography (AcOEt/hexane) to give the title compound (212 mg).
MS (API+): found 420.1, 422.0.

E) 2-[4-(4,4,5,5-Tetramethyl-1,3,2-dioxaborolan-2-yl)phenoxy]-3-{[2-(trimethylsilyl)ethoxy]methyl}-3H-imidazo[4,5-b]pyridine A mixture of 2-(4-bromophenoxy)-3-{[2-(trimethylsilyl)ethoxy]methyl}-3H-imidazo[4,5-b]pyridine (212 mg), 4,4,4',4',5,5,5',5'-octamethyl-2,2'-bi(1,3,2-dioxaborolane) (192 mg), Pd(dppf)$_2$Cl$_2$.CH$_2$Cl$_2$ (38 mg) and KOAc (148 mg) in THF (5 mL)-DMSO (0.25 mL) was stirred at 80° C. overnight under Ar atmosphere. The mixture was diluted with AcOEt and filtered through a silica gel pad conditioned with AcOEt. The filtrate was concentrated under reduced pressure. The residue was purified by silica gel column chromatography (AcOEt/hexane) to give the title compound (100 mg).
MS (API+): [M+H]$^+$468.2.

F) 1-Ethyl-3-[(4-(3-{([2-(trimethylsilyl)ethoxy]methyl}-3H-imidazo[4,5-b]pyridin-2-yloxy)phenyl]-1H-pyrazolo[4,3-b]pyridine A mixture of 2-[4-(4,4,5,5-tetramethyl-1,3,2-dioxaborolan-2-yl)phenoxy]-3-{[2-(trimethylsilyl)ethoxy]methyl}-3H-imidazo[4,5-b]pyridine (100 mg), 3-bromo-1-ethyl-1H-pyrazolo[4,3-b]pyridine (140 mg), Pd(PPh$_3$)$_4$ (7 mg), Na$_2$CO$_3$ (79 mg), DME (5 mL), and water (1 mL) was refluxed overnight under Ar atmosphere. The mixture was poured into water and extracted with AcOEt. The extract was washed with brine, dried over Na$_2$SO$_4$, and concentrated under reduced pressure. The residue was purified by silica gel column chromatography (AcOEt/hexane) and recrystallized from AcOEt/hexane to give the title compound (90 mg).
MS (API+): [M+H]$^+$487.1.

G) 1-Ethyl-3-[4-(3H-imidazo[4,5-b]pyridin-2-yloxy)phenyl]-1H-pyrazolo[4,3-b]pyridine A mixture of 1-ethyl-3-[4-(3-{[2-(trimethylsilyl)ethoxy]methyl}-3H-imidazo[4,5-b]pyridin-2-yloxy)phenyl]-1H-pyrazolo[4,3-b]pyridine (90 mg), 1 M TBAF in THF (0.74 mL) and THF (2 ml) was heated at 100° C. for 3 h under microwave irradiation. The mixture was stirred at 80° C. overnight. The mixture was poured into water and extracted with AcOEt. The organic layer was washed with brine, dried over Na$_2$SO$_4$, filtered and concentrated under reduced pressure. The residue was purified by basic silica gel column chromatography (AcOEt/hexane) to give the title compound (18 mg).
MS (API+): [M+H]$^+$357.2.

Example 21

1-Ethyl-3-[4-(pyridin-2-yloxy)phenyl]-1H-pyrazolo[4,3-b]pyridine

A) 2-(4-Bromophenoxy)pyridine

To a stirred solution of 4-bromophenol (200 mg) in DMF (3 mL) was added NaH (60% in oil, 46.2 mg) at room temperature. The mixture was stirred for 30 min, and 2-chloropyridine (131 mg) was added. The mixture was exposed to microwave irradiation at 230° C. for 1 h, treated with water, and extracted with AcOEt. The organic layer was dried over MgSO$_4$ and concentrated under reduced pressure. The residue was purified by silica gel column chromatography (AcOEt/hexane). The product was crystallized from AcOEt/hexane to give the title compound (76 mg).
MS (API+): [M+H]$^+$249.8.

B) 1-Ethyl-3-[4-(pyridin-2-yloxy)phenyl]-1H-pyrazolo[4,3-b]pyridine

A mixture of 2-(4-bromophenoxy)pyridine (76 mg), 4,4,4',4',5,5,5',5'-octamethyl-2,2'-bi(1,3,2-dioxaborolane) (81 mg), Pd(dppf)$_2$Cl$_2$ (22.24 mg) and K$_2$CO$_3$ (59.6 mg) in 1,4-dioxane (3 mL) was stirred at 90° C. for 12 h under Ar atmosphere, treated with water, and extracted with AcOEt. The organic layer was dried over MgSO$_4$ and passed through a Celite pad covered with activated carbon, and concentrated under reduced pressure. The residue was dissolved in DME (4 mL) and 3-bromo-1-ethyl-1H-pyrazolo[4,3-b]pyridine (67.8 mg), Pd(PPh$_3$)$_4$ (34.7 mg), Cs$_2$CO$_3$ (195 mg) and water (1 mL) were added. The mixture was exposed to microwave irradiation at 120° C. for 40 min, treated with water, and extracted with AcOEt. The organic layer was dried over MgSO$_4$ and concentrated under reduced pressure. The residue was purified by silica gel column chromatography (AcOEt/hexane). The product was crystallized from AcOEt/hexane to give the title compound (30.0 mg).
MS (API+): [M+H]$^+$317.0.

Example 22

3-(4-[{5-Chloropyridin-2-yl)oxy]phenyl}-1-ethyl-1H-pyrazolo[4,3-b]pyridine

The title compound was prepared by a similar manner as that of Example 21.
MS (API+): [M+H]'351.1.

Example 23

6-[4-(1-Ethyl-1H-pyrazolo[4,3-b]pyridin-3-yl)phenoxy]pyridine-3-carbonitrile The title compound was prepared by a similar manner as that of Example 21.

MS (API+): [M+H]⁺342.1.

Example 24

3-[4-(1-Ethyl-1H-pyrazolo[4,3-b]pyridin-3-yl)phenyl]-2,3-dihydro-1H-pyrrolo[1,2-a]benzimidazole

A) Ethyl 3-[4-(4,4,5,5-tetramethyl-1,3,2-dioxaborolan-2-yl)phenyl]-3-(1-[{2-(trimethylsilyl)ethoxy}methyl]-1H-benzo[d]imidazol-2-yl)acrylate

[4-(4,4,5,5-Tetramethyl-1,3,2-dioxaborolan-2-yl)phenyl] (1-{[2-(trimethylsilyl)ethoxy]methyl}-1H-benzimidazol-2-yl)methanone (1.0 g) was added to a solution of triethyl phosphonoacetate (0.498 mL) and NaH (60% in oil, 0.109 g) in THF (10 mL) at 0° C. The mixture was stirred at room temperature under a dry atmosphere for 1 h. The mixture was poured into water at room temperature and extracted with AcOEt. The organic layer was separated, washed with water and brine, dried over MgSO₄ and concentrated under reduced pressure. The residue was purified by silica gel column chromatography (hexane/AcOEt) to give the title compound (1.0 g).

¹H NMR (300 MHz, CDCl₃) δ −0.09 (9H, s), 0.72-0.82 (2H, m), 1.16 (3H, t, J=7.2 Hz), 1.35 (12H, s), 3.19-3.30 (2H, m), 4.12 (2H, q, J=7.2 Hz), 5.09 (2H, s), 6.77 (1H, s), 7.28-7.41 (4H, m), 7.42-7.49 (1H, m), 7.77-7.87 (3H, m).

B) Ethyl 3-{4-(1-ethyl-1H-pyrazolo[4,3-b]pyridin-3-yl)phenyl}-3-(1-[{2-(trimethylsilyl)ethoxy}methyl]-1H-benzo[d]imidazol-2-yl)acrylate A mixture of 3-bromo-1-ethyl-1H-pyrazolo[4,3-b]pyridine (300 mg), ethyl 3-{4-(4,4,5,5-tetramethyl-1,3,2-dioxaborolan-2-yl)phenyl}-3-(1-[{2-(trimethylsilyl)ethoxy}methyl]-1H-benzo[d]imidazol-2-yl)acrylate (1456 mg), Pd(PPh₃)₄ (77 mg), 2 M Na₂CO₃ aqueous solution (1.991 mL) and THF (4 mL) was heated at 150° C. for 30 min under microwave irradiation. The reaction mixture was concentrated under reduced pressure. The residue was purified by silica gel column chromatography (hexane/AcOEt) to give the title compound (670 mg).

MS (ESI+): [M+H]⁺568.4.

¹H NMR (300 MHz, CDCl₃) δ −0.19 (9H, s), 0.66-0.80 (2H, m), 1.04 (3H, t, J=7.2 Hz), 1.56 (3H, t, J=7.2 Hz), 3.23-3.36 (2H, m), 4.04 (2H, q, J=7.2 Hz), 4.47 (2H, q, J=7.2 Hz), 5.34 (2H, s), 6.87 (1H, s), 7.29-7.40 (2H, m), 7.42-7.96 (7H, m), 8.47-8.61 (2H, m).

C) Ethyl 3-[4-(1-ethyl-1H-pyrazolo[4,3-b]pyridin-3-yl)phenyl]-3-(1-[{2-(trimethylsilyl)ethoxy}methyl]-1H-benzo[d]imidazol-2-yl)propanoate A mixture of ethyl 3-[4-(1-ethyl-1H-pyrazolo[4,3-b]pyridin-3-yl)phenyl]-3-(1-[{2-(trimethylsilyl)ethoxy}methyl]-1H-benzo[d]imidazol-2-yl)acrylate (100 mg) and 10% Pd—C (18.74 mg) in EtOH (10 mL) was hydrogenated under balloon pressure at room temperature overnight. The catalyst was removed by filtration and the filtrate was concentrated under reduced pressure to give the title compound (91 mg).

MS (ESI+): [M+H]⁺ 570.4.

¹H NMR (300 MHz, DMSO-d₆) δ −0.23 (9H, s), 0.58-0.72 (2H, m), 1.08 (3H, t, J=7.0 Hz), 1.42 (3H, t, J=7.2 Hz), 2.96-3.14 (1H, m), 3.19-3.32 (2H, m), 3.41-3.60 (1H, m), 4.00 (2H, q, J=7.2 Hz), 4.51 (2H, q, J=7.0 Hz), 4.87-5.05 (1H, m), 5.39-5.55 (1H, m), 5.53-5.73 (1H, m), 7.14-7.30 (2H, m), 7.38-7.52 (3H, m), 7.53-7.62 (1H, m), 7.64-7.74 (1H, m), 8.15-8.29 (1H, m), 8.35-8.46 (2H, m), 8.55-8.66 (1H, m).

D) 3-[4-(1-Ethyl-1H-pyrazolo[4,3-b]pyridin-3-yl)phenyl]-3-(1-[{2-(trimethylsilyl)ethoxy]methyl}-1H-benzo[d]imidazol-2-yl)propan-1-ol LiAlH₄ (11.99 mg) was added to a solution of ethyl 3-[4-(1-ethyl-1H-pyrazolo[4,3-b]pyridin-3-yl)phenyl]-3-(1-[{2-(trimethylsilyl)ethoxy}methyl]-1H-benzo[d]imidazol-2-yl)propanoate (90 mg) in THF (10 mL) at 0° C. The mixture was stirred at room temperature under a dry atmosphere for 1 h. The mixture was poured into water at room temperature and extracted with AcOEt. The organic layer was washed with water and brine, dried over MgSO₄ and concentrated under reduced pressure. The residue was purified by silica gel column chromatography (hexane/AcOEt) to give the title compound (80 mg).

MS (ESI+): [M+H]⁺528.4.

¹H NMR (300 MHz, CDCl₃) δ −0.10 (9H, s), 0.76-0.90 (2H, m), 1.51-1.58 (3H, m), 2.40-2.56 (1H, m), 2.57-2.73 (1H, m), 3.32-3.48 (2H, m), 3.62-3.88 (2H, m), 4.27-4.39 (1H, m), 4.39-4.55 (2H, m), 4.62-4.79 (1H, m), 5.22-5.37 (2H, m), 7.26-7.34 (3H, m), 7.36-7.43 (3H, m), 7.71-7.80 (1H, m), 7.79-7.87 (1H, m), 8.33-8.44 (2H, m), 8.59-8.66 (1H, m).

E) 3-[4-{3-Bromo-1-(1-[{2-(trimethylsilyl)ethoxy}methyl]-1H-benzo[d]imidazol-2-yl)propyl}phenyl]-1-ethyl-1H-pyrazolo[4,3-b]pyridine To a solution of 3-{4-(1-ethyl-1H-pyrazolo[4,3-b]pyridin-3-yl)phenyl}-3-(1-[(2-(trimethylsilyl)ethoxy)methyl]-1H-benzo[d]imidazol-2-yl)propan-1-ol (80 mg) and PPh₃ (43.7 mg) in DMF (2 mL) was added NBS (27.0 mg) at room temperature. The mixture was stirred at room temperature under a dry atmosphere for 1 h. The mixture was neutralized with saturated NaHCO₃ aqueous solution at 0° C. and extracted with AcOEt. The organic layer was separated, washed with water and brine, dried over MgSO₄ and concentrated under reduced pressure. The residue was purified by silica gel column chromatography (hexane/AcOEt) to give the title compound (75 mg).

MS (ESI+): [M+H]⁺591.3.

¹H NMR (300 MHz, CDCl₃) δ −0.13 (9H, s), 0.78-0.88 (2H, m), 1.50-1.60 (3H, m), 2.61-2.79 (1H, m), 2.98-3.16 (1H, m), 3.29-3.58 (3H, m), 3.58-3.76 (1H, m), 4.40-4.52 (2H, m), 4.71-4.81 (1H, m), 5.31-5.39 (2H, m), 7.27-7.34 (3H, m), 7.38-7.43 (1H, m), 7.43-7.51 (2H, m), 7.72-7.79 (1H, m), 7.81-7.88 (1H, m), 8.33-8.45 (2H, m), 8.60-8.67 (1H, m).

F) 3-[4-(1-Ethyl-1H-pyrazolo[4,3-b]pyridin-3-yl)phenyl]-2,3-dihydro-1H-benzo[d]pyrrolo[1,2-a]imidazole A mixture of 3-[4-{3-bromo-1-(1-[{2-(trimethylsilyl)ethoxy}methyl]-1H-benzo[d]imidazol-2-yl)propyl]phenyl}-1-ethyl-1H-pyrazolo[4,3-b]pyridine (75 mg) and 2 M HCl in AcOEt (0.063 mL) was stirred at 60° C. under a dry atmosphere overnight. The reaction mixture was concentrated under reduced pressure.

To a solution of the residue in DMF (2 mL) was added NaH (60% in oil, 10.16 mg) at room temperature. The mixture was stirred at room temperature under a dry atmosphere for 1 h. The mixture was poured into MeOH at room temperature and concentrated under reduced pressure. The residue was purified by silica gel column chromatography (hexane/AcOEt) to give the title compound (8.0 mg).

MS (ESI+): [M+H]+380.2.

$^1$H NMR (300 MHz, CDCl$_3$) δ 1.56 (3H, t, J=7.2 Hz), 2.70-2.86 (1H, m), 3.17-3.33 (1H, m), 4.10-4.23 (1H, m), 4.26-4.38 (1H, m), 4.47 (2H, q, J=7.2 Hz), 4.57-4.67 (1H, m), 7.22-7.34 (3H, m), 7.35-7.47 (3H, m), 7.71-7.82 (2H, m), 8.40-8.50 (2H, m), 8.58-8.67 (1H, m).

Example 25

9-[4-(1H-Benzimidazol-2-yloxy)phenyl]-7,8-dihydro-6H-pyrido[2,3-b]pyrrolizine

A) 2-[4-(Methoxymethoxy)phenyl]-4,4,5,5-tetramethyl-1,3,2-dioxaborolane

NaH (60% in oil, 4.00 g) was added portionwise at 0° C. to a solution of 4-(4,4,5,5-tetramethyl-1,3,2-dioxaborolan-2-yl)phenol (11.00 g) in DMF (125 mL). After stirring for 10 min, MOMCl (7.60 mL) was added dropwise, and the mixture was stirred for 1 h. The reaction mixture was poured into water and extracted with AcOEt. The extract was washed with water and brine, dried over MgSO$_4$, and concentrated under reduced pressure. The residue was purified by silica gel column chromatography (hexane/AcOEt) to give the title compound (8.86 g).

$^1$H NMR (300 MHz, CDCl$_3$) δ 1.33 (12H, s), 3.47 (3H, s), 5.20 (2H, s), 7.00-7.04 (2H, m), 7.73-7.77 (2H, m).

B) 3-[4-(Methoxymethoxy)phenyl]-1H-pyrrolo[3,2-b]pyridine

To a suspension of Xphos (0.695 g), 3-bromo-1H-pyrrolo[3,2-b]pyridine (3.59 g), 2-[4-(methoxymethoxy)phenyl]-4,4,5,5-tetramethyl-1,3,2-dioxaborolane (4.81 g) and Cs$_2$CO$_3$ (11.86 g) in DME (50 mL) and water (10 mL) was added Pd$_2$(dba)$_3$ (0.334 g). The mixture was refluxed overnight under Ar atmosphere. The mixture was added to water and extracted with AcOEt. The organic layer was separated, washed with brine, dried over Na$_2$SO$_4$ and concentrated under reduced pressure. The residue was purified by silica gel column Chromatography (AcOEt/hexane) to give the title compound (0.650 g).

MS (API+): [M+H]$^+$255.1.

C) 1-(3-Bromopropyl)-3-[4-(methoxymethoxy)phenyl]-1H-pyrrolo[3,2-b]pyridine

To a solution of 3-[4-(methoxymethoxy)phenyl]-1H-pyrrolo[3,2-b]pyridine (650 mg) was added NaH (60% in oil, 153 mg) at 0° C. After stirring at room temperature for 1 h, the mixture was added dropwise to 1,3-dibromopropane (0.778 mL). The mixture was stirred at room temperature for 2 h. The mixture was added to water and extracted with AcOEt. The organic layer was washed with brine, dried over Na$_2$SO$_4$ and concentrated under reduced pressure. The residue was purified by silica gel column chromatography (AcOEt/hexane) to give the title compound (486 mg).

MS (API+): [M+H]$^+$375.1.

D) 9-[4-(Methoxymethoxy)phenyl]-7,8-dihydro-6H-pyrido[2,3-b]pyrrolizine

A solution of 1-(3-bromopropyl)-3-[4-(methoxymethoxy)phenyl]-1H-pyrrolo[3,2-b]pyridine (486 mg), tri-n-butyltin hydride (0.697 mL), and AIBN (21.27 mg) in toluene (25 mL) was heated at 110° C. overnight. To the mixture was added AIBN (21.27 mg), and the mixture was heated at 110° C. for 2 h. The mixture was added to water and extracted with AcOEt. The organic layer was separated, washed with brine, dried over Na$_2$SO$_4$ and concentrated under reduced pressure. The residue was purified by silica gel column chromatography (AcOEt/hexane) to give the title compound (88 mg).

MS (API+): [M+H]$^+$295.1.

E) 4-(7,8-Dihydro-6H-pyrido[2,3-b]pyrrolizin-9-yl)phenol

To a solution of 9-[4-(methoxymethoxy)phenyl]-7,8-dihydro-6H-pyrido[2,3-b]pyrrolizine (200 mg) in THF (4 mL) was added 1 M HCl aqueous solution (1 mL). The mixture was heated at 70° C. for 2 h. The mixture was neutralized with 1 M NaOH aqueous solution and extracted with AcOEt. The organic layer was separated, washed with brine, dried over Na$_2$SO$_4$ and concentrated under reduced pressure. The precipitate was washed with 50% AcOEt in hexane and collected by filtration to give the title compound (154 mg).

MS (API+): [M+H]$^+$251.0.

F) 9-[4-(1-{([2-(Trimethylsilyl)ethoxy]methyl}-1H-benzo[d]imidazol-2-yloxy)phenyl]-7,8-dihydro-6H-pyrido[2,3-b]pyrrolizine To a solution of 4-(7,8-dihydro-6H-pyrido[2,3-b]pyrrolizin-9-yl)phenol (154 mg) in DMF (2.5 mL) was added NaH (60% in oil, 34.5 mg), and the mixture was stirred at 100° C. for 5 min. 2-Chloro-1-{[2-(trimethylsilyl)ethoxy]methyl}-1H-benzo[d]imidazole (174 mg) was added to the mixture and the mixture was heated at 150° C. under microwave irradiation for 1.5 h. The mixture was partitioned between saturated NaHCO$_3$ aqueous solution and AcOEt. The organic layer was washed with brine, dried over Na$_2$SO$_4$, filtered and concentrated under reduced pressure. The residue was purified by silica gel column chromatography (AcOEt/hexane) to give the title compound (199 mg).

MS (API+): [M+H]$^+$497.2.

G) 9-[4-(1H-Benzimidazol-2-yloxy)phenyl]-7,8-dihydro-6H-pyrido[2,3-b]pyrrolizine To a solution of 9-[4-(1-{[2-(trimethylsilyl)ethoxy]methyl}-1H-benzo[d]imidazol-2-yloxy)phenyl]-7,8-dihydro-6H-pyrido[2,3-b]pyrrolizine (199 mg) in EtOH (2 mL) was added 6 M HCl aqueous solution (2 mL) and the mixture was heated at 70° C. for 2 h. The mixture was neutralized with saturated NaHCO$_3$ aqueous solution and extracted with AcOEt. The organic layer was separated, washed with brine, dried over Na$_2$SO$_4$ and concentrated under reduced pressure. The residue was collected by filtration and washed with AcOEt to give the title compound (135 mg).

MS (API+): [M+H]$^+$367.1.

Example 26

9-{4-[(1-Methyl-1H-benzimidazol-2-yl)oxy]phenyl}-7,8-dihydro-6H-pyrido[2,3-b]pyrrolizine To a mixture of 9-[4-(1H-benzimidazol-2-yloxy)phenyl]-7,8-dihydro-6H-pyrido[2,3-b]pyrrolizine (70 mg) and $K_2CO_3$ (79 mg) in DMF (1 mL) was added MeI (0.024 mL). The mixture was stirred at 40° C. overnight. The mixture was poured into saturated $NaHCO_3$ aqueous solution and extracted with AcOEt. The organic layer was separated, washed with brine, dried over $Na_2SO_4$ and concentrated under reduced pressure. The residue was purified by silica gel column chromatography (AcOEt/hexane) to give the title compound (38.1 mg).

MS (API+): [M+H]$^+$381.2.

Example 27

1-Ethyl-3-{4-[(5-methylpyridin-2-yl)oxy]phenyl}-1H-pyrazolo[4,3-b]pyridine

A mixture of 3-[4-(5-chloropyridin-2-yloxy)phenyl]-1-ethyl-1H-pyrazolo[4,3-b]pyridine (58 mg), methylboronic acid (59.4 mg), Pd(dppf)$_2$Cl$_2$ (18 mg) and Cs$_2$CO$_3$ (766 mg) in DME/H$_2$O (4 mL, 3/1) was exposed to microwave irradiation at 140° C. for 1 h, and then Pd(OAc)$_2$ (3.7 mg), Xphos (15.7 mg) and Cs$_2$CO$_3$ (107 mg) were added. The mixture was exposed to microwave irradiation at 140° C. for 1 h, treated with water, and extracted with AcOEt. The organic layer was dried over MgSO$_4$ and concentrated under reduced pressure. The residue was purified by preparative HPLC (H$_2$O in CH$_3$CN containing 10 mM NH$_4$HCO$_3$). Crystallization from AcOEt/hexane gave title compound (11 mg).

MS (API+): [M+H]$^+$331.1.

Example 28

1-Ethyl-3-{4-[(3-methyl-3H-imidazo[4,5-b]pyridin-2-yl)oxy]phenyl}-1H-pyrazolo[3,4-b]pyrazine A)
3-Chloro-N-methoxy-N-methylpyrazine-2-carboxamide To a suspension of 3-chloropyrazine-2-carboxylic acid (5.46 g) in THF (100 mL) was added CDT (6.14 g) at room temperature, and the mixture was stirred at room temperature for 30 min and heated to 50° C. After stirring at 50° C. for 1 h, the mixture was cooled to room temperature. To the mixture were added N,O-dimethylhydroxylamine hydrochloride (5.04 g) and DIPEA (9.02 mL) at room temperature, and the mixture was stirred at room temperature overnight. The mixture was concentrated under reduced pressure. The residue was purified by silica gel column chromatography (AcOEt/hexane) to give the title compound (3.05 g).

MS (API+): [M+H]$^+$202.1.
$^1$H NMR (300 MHz, CDCl$_3$) δ 3.43 (3H, s), 3.58 (3H, s), 8.44 (1H, d, J=2.3 Hz), 8.52 (1H, d, J=2.3 Hz).

B) [4-(Benzyloxy)phenyl](3-chloropyrazin-2-yl)methanone

To a solution of 3-chloro-N-methoxy-N-methylpyrazine-2-carboxamide (2.05 g) in THF (50 mL) was added dropwise [4-(benzyloxy)phenyl]magnesium bromide in THF (12 mL) at 0° C. After stirring at 0° C. for 2 h, the mixture was quenched with water and extracted with AcOEt. The organic layer was washed with brine, dried over Na$_2$SO$_4$, filtered and concentrated under reduced pressure. The residue was purified by silica gel column chromatography (AcOEt/hexane) to give the title compound (2.47 g).

MS (ESI+): [M+H]$^+$325.2.
$^1$H NMR (300 MHz, CDCl$_3$) δ 5.15 (2H, s), 7.04 (2H, d, J=9.0 Hz), 7.30-7.46 (5H, m), 7.81 (2H, d, J=9.0 Hz), 8.51 (1H, d, J=2.6 Hz), 8.58 (1H, d, J=2.6 Hz).

C)
3-[4-(Benzyloxy)phenyl]-1H-pyrazolo[3,4-b]pyrazine

To a solution of [4-(benzyloxy)phenyl](3-chloropyrazin-2-yl)methanone (1.23 g) in EtOH (20 mL) was added hydrazine hydrate (0.37 mL) at room temperature, and the mixture was refluxed for 2 h. The mixture was concentrated under reduced pressure. The residue was partitioned between AcOEt/THF (1/1) and saturated NaHCO$_3$ aqueous solution. The organic layer was dried over Na$_2$SO$_4$, filtered and concentrated under reduced pressure. The residual crystals were recrystallized from THF/AcOEt to give the title compound (0.60 g).

MS (ESI+): [M+H]$^+$303.2.
$^1$H NMR (300 MHz, DMSO-d$_6$) δ 5.19 (2H, s), 7.20 (2H, d, J=9.1 Hz), 7.30-7.56 (5H, m), 8.38 (2H, d, J=9.1 Hz), 8.63 (1H, d, J=2.3 Hz), 8.70 (1H, d, J=2.3 Hz), 14.05 (1H, brs).

D) 3-[4-(Benzyloxy)phenyl]-1-ethyl-1H-pyrazolo[3,4-b]pyrazine

A suspension of 3-[4-(benzyloxy)phenyl]-1H-pyrazolo[3,4-b]pyrazine (0.58 g), EtI (0.18 ml), and K$_2$CO$_3$ (0.39 g) in DMF (5 mL) was stirred for 3 h at room temperature. The reaction mixture was poured into water and extracted with AcOEt. The extract was washed with water and brine, dried over Na$_2$SO$_4$, and concentrated under reduced pressure. The residue was purified by silica gel column chromatography (AcOEt/hexane) to give the title compound (0.61 g).

MS (API+): [M+H]$^+$331.3.
$^1$H NMR (300 MHz, CDCl$_3$) δ 1.59 (3H, t, J=7.2 Hz), 4.60 (2H, q, J=7.2 Hz), 5.14 (2H, s), 7.12 (2H, d, J=9.1 Hz), 7.29-7.50 (5H, m), 8.40 (2H, d, J=9.1 Hz), 8.44 (1H, d, J=2.3 Hz), 8.59 (1H, d, J=2.3 Hz).

E)
4-(1-Ethyl-1H-pyrazolo[3,4-b]pyrazin-3-yl)phenol

A mixture of 3-[4-(benzyloxy)phenyl]-1-ethyl-1H-pyrazolo[3,4-b]pyrazine (570 mg) and 10% Pd—C (50% wet, 200 mg) in MeOH (8 mL) and AcOEt (8 mL) was hydrogenated under balloon pressure at room temperature for 2 h. The catalyst was removed by filtration and the filtrate was concentrated under reduced pressure. The residue was purified by silica gel column chromatography (AcOEt/hexane) to give the title compound (240 mg).

MS (API+): [M+H]$^+$241.1.
$^1$H NMR (300 MHz, DMSO-d$_6$) δ 1.49 (3H, t, J=7.2 Hz), 4.53 (2H, q, J=7.2 Hz), 6.93 (2H, d, J=9.0 Hz), 8.25 (2H, d, J=9.0 Hz), 8.63 (1H, d, J=2.3 Hz), 8.70 (1H, d, J=2.3 Hz), 9.74 (1H, s).

F) 1-Ethyl-3-{4-[(3-methyl-3H-imidazo[4,5-b]pyridin-2-yl)oxy]phenyl}-1H-pyrazolo[3,4-b]pyrazine To a solution of 4-(1-ethyl-1H-pyrazolo[3,4-b]pyrazin-3-yl)phenol (100 mg) and 3-methyl-2-(methylsulfonyl)-3H-imidazo[4,5-b]pyridine (88 mg) in DMF (3 mL) was added NaH (60% in oil, 17 mg) at room temperature, and the mixture was heated at 150° C. for 1.5 h under microwave irradiation. The mixture was poured into water and extracted with AcOEt. The organic layer was dried over $Na_2SO_4$, filtered and concentrated under reduced pressure. The residue was purified by basic silica gel column chromatography (AcOEt/hexane) and recrystallized from AcOEt/hexane to give the title compound (98 mg).

MS (API+): [M+H]$^+$372.1.

$^1$H NMR (300 MHz, DMSO-d$_6$) δ 1.53 (3H, t, J=7.2 Hz), 3.78 (3H, s), 4.60 (2H, q, J=7.2 Hz), 7.21 (1H, dd, J=7.9, 4.9 Hz), 7.66 (2H, d, J=9.1 Hz), 7.80 (1H, dd, J=7.9, 1.5 Hz), 8.22 (1H, dd, J=4.9, 1.5 Hz), 8.53 (2H, d, J=9.1 Hz), 8.71 (1H, d, J=2.3 Hz), 8.78 (1H, d, J=2.3 Hz).

mp 161-162° C.

Anal. Calcd for $C_{20}H_{17}N_7O$: C, 64.68; H, 4.61; N, 26.40. Found: C, 64.52; H, 4.59; N, 26.39.

Example 29

2-{2-[4-(1-Ethyl-1H-pyrazolo[4,3-b]pyridin-3-yl)phenoxy]-1H-benzimidazol-1-yl}ethanol A) Ethyl (2-chloro-1H-benzimidazol-1-yl)acetate To a solution of 2-chloro-1H-benzo[d]imidazole (10 g) and NaH (60% in oil, 3.15 g) in DMF (150 mL) was added ethyl bromoacetate (11.0 mL) at 0° C. After stirring overnight at room temperature, the reaction mixture was quenched with water and extracted with AcOEt. The extract was washed with water and brine, dried over $MgSO_4$, and concentrated under reduced pressure. The precipitate was crystallized from AcOEt/hexane to give the title compound (12 g).

MS (ESI+): found: 239.1.

$^1$H NMR (300 MHz, CDCl$_3$) δ 1.27 (3H, t, J=7.2 Hz), 4.25 (2H, q, J=7.2 Hz), 4.90 (2H, s), 7.17-7.25 (1H, m), 7.27-7.35 (2H, m), 7.67-7.75 (1H, m).

B) Ethyl[2-(4-bromophenoxy)-1H-benzimidazol-1-yl]acetate

To a mixture of ethyl 2-(2-chloro-1H-benzo[d]imidazol-1-yl)acetate (11.0 g) and p-bromophenol (23.9 g) was added TEA (19.2 mL) at room temperature. After stirring overnight at 120° C., the reaction mixture was quenched with water and extracted with AcOEt. The organic layer was separated, washed with 1 M NaOH aqueous solution and brine, dried over MgSO$_4$ and concentrated under reduced pressure. The residue was purified by basic silica gel column chromatography (AcOEt/hexane) and recrystallized from AcOEt/hexane to give the title compound (11.0 g).

MS (ESI+): found: 375.2, 377.8.

$^1$H NMR (300 MHz, CDCl$_3$) δ 1.27 (3H, t, J=7.2 Hz), 4.25 (2H, q, J=7.2 Hz), 4.85 (2H, s), 7.08-7.34 (5H, m), 7.49-7.63 (3H, m).

C) Ethyl {2-[4-(4,4,5,5-tetramethyl-1,3,2-dioxaborolan-2-yl)phenoxy]-1H-benzimidazol-1-yl}acetate A mixture of ethyl[2-(4-bromophenoxy)-1H-benzimidazol-1-yl]acetate (1.3 g), 4,4,4',4',5,5,5',5'-octamethyl-2,2'-bi (1,3,2-dioxaborolane) (1.3 g), Pd(dppf)$_2$Cl$_2$ (38 mg) and KOAc (1.02 g) in THF (20 mL)-DMSO (1.0 ml) was stirred at 80° C. under N$_2$ atmosphere overnight. The mixture was diluted with AcOEt and filtered on silica gel conditioned with AcOEt. The filtrate was concentrated under reduced pressure. The residue was purified by silica gel column chromatography (AcOEt/hexane) to give the title compound (1.06 g).

$^1$H NMR (300 MHz, CDCl$_3$) δ 1.20-1.29 (3H, m), 1.34 (12H, s), 4.24 (2H, q, J=7.2 Hz), 4.86 (2H, s), 7.11-7.24 (3H, m), 7.36 (2H, d, J=8.3 Hz), 7.53-7.62 (1H, m), 7.88 (2H, d, J=8.3 Hz).

D) Ethyl {2-[4-(1-ethyl-1H-pyrazolo[4,3-b]pyridin-3-yl)phenoxy]-1H-benzimidazol-1-yl}acetate A mixture of ethyl {2-[4-(4,4,5,5-tetramethyl-1,3,2-dioxaborolan-2-yl)phenoxy]-1H-benzimidazol-1-yl}acetate (540 mg), 3-bromo-1-ethyl-1H-pyrazolo[4,3-b]pyridine (289 mg), Pd(PPh$_3$)$_4$ (44.3 mg), Na$_2$CO$_3$ (474 mg) in DME (10 mL) and water (2 ml) was refluxed overnight under Ar atmosphere. The reaction mixture was poured into water and extracted with AcOEt. The extract was washed with brine, dried over Na$_2$SO$_4$, and concentrated under reduced pressure. The residue was purified by silica gel column chromatography (AcOEt/hexane) to give the title compound (105 mg).

MS (ESI+): [M+H]$^+$442.0.

$^1$H NMR (300 MHz, CDCl$_3$) δ 1.28 (3H, t, J=7.2 Hz), 1.54-1.59 (3H, m), 4.27 (2H, q, J=7.2 Hz), 4.49 (2H, q, J=7.2 Hz), 4.90 (2H, s), 7.17-7.24 (3H, m), 7.31 (1H, dd, J=8.5, 4.3 Hz), 7.50 (2H, d, J=9.1 Hz), 7.57-7.63 (1H, m), 7.77 (1H, dd, J=8.5, 1.3 Hz), 8.61 (2H, d, J=9.1 Hz), 8.65 (1H, dd, J=4.3, 1.3 Hz).

E) 2-[(2-[4-(1-Ethyl-1H-pyrazolo[4,3-b]pyridin-3-yl)phenoxy]-1H-benzimidazol-1-yl]ethanol LiAlH$_4$ (24.8 mg) was added to a solution of ethyl 2-{2-[4-(1-ethyl-1H-pyrazolo[4,3-b]pyridin-3-yl)phenoxy]-1H-benzo[d]imidazol-1-yl}acetate (144 mg) in THF (3.5 ml) at 0° C. After stirring for 1 h at the same temperature, Na$_2$SO$_4$.10H$_2$O was added to the reaction mixture at 0° C. and stirred for 30 min. After Na$_2$SO$_4$ was added to this mixture, the precipitate was removed by filtration, and the filtrate was concentrated under reduced pressure. The residue was purified by silica gel column chromatography (AcOEt/hexane). The solid was crystallized from AcOEt/hexane to give the title compound (81 mg).

MS (ESI+): [M+H]$^+$400.1

$^1$H NMR (300 MHz, DMSO-d$_6$) δ 1.48 (3H, t, J=7.2 Hz), 3.80 (2H, q, J=5.5 Hz), 4.27 (2H, t, J=5.5 Hz), 4.55 (2H, q, J=7.2 Hz), 5.01 (1H, t, J=5.7 Hz), 7.08-7.23 (2H, m), 7.37-7.44 (1H, m), 7.44-7.53 (2H, m), 7.56 (2H, d, J=8.7 Hz), 8.27 (1H, dd, J=8.5, 1.3 Hz), 8.57 (2H, d, J=8.7 Hz), 8.66 (1H, dd, J=4.5, 1.1 Hz). mp 183-184° C.

Anal. Calcd for $C_{23}H_{21}N_5O_2$: C, 69.16; H, 5.30; N, 17.53. Found: C, 69.04; H, 5.48; N, 17.13.

Example 30

1-Ethyl-3-{5-[(3-methyl-3H-imidazo[4,5-b]pyridin-2-yl)oxy]pyridin-2-yl}-1H-pyrazolo[4,3-b]pyridine A) 5-Hydroxy-N-methoxy-N-methylpyridine-2-carboxamide A mixture of 5-hydroxypicolinic acid (5.00 g), N,O-dimethylhydroxylamine hydrochloride (3.86 g), TEA (11.1 mL), WSC (7.58 g) and HOBt (5.34 g) in DMF (100 mL) was stirred at room temperature for 24 h. The mixture was poured into 5% NaHCO$_3$ aqueous solution and extracted with AcOEt (10 times). The organic layer was separated, dried over Na$_2$SO$_4$ and concentrated under reduced pressure. The residue was purified by silica gel column chromatography (AcOEt/hexane) to give the title compound (4.13 g).
MS (API+): [M+H]$^+$183.1.

B) 5-(Benzyloxy)-N-methoxy-N-methylpyridine-2-carboxamide

A mixture of 5-hydroxy-N-methoxy-N-methylpicolinamide (7.51 g), $K_2CO_3$ (6.27 g) and benzyl bromide (2.83 mL) in acetone (70 mL) was stirred at 50° C. for 14 h, evaporated, treated with water and extracted with AcOEt. The organic layer was dried over $Na_2SO_4$ and concentrated under reduced pressure. The residue was purified by silica gel column chromatography (AcOEt/hexane) to the title compound (4.87 g).
MS (API+): [M+H]$^+$273.4.

C) [5-(Benzyloxy)pyridin-2-yl](3-fluoropyridin-2-yl)methanone

To a solution of diisopropylamine (2.08 g) in THF (50 mL) was added 1.6 M n-BuLi in hexane (12.3 mL) at −5° C. The mixture was stirred for 15 min. The mixture was cooled to −78° C., and a solution of 3-fluoropyridine (1.74 g) in THF (10 mL) was added. The mixture was stirred for 1 h. To the mixture was added a solution of 5-(benzyloxy)-N-methoxy-N-methylpicolinamide (4.87 g) in THF (5 mL). The mixture was stirred at −78° C. for 2 h. The mixture was quenched with saturated $NH_4Cl$ aqueous solution at −78° C. and extracted with AcOEt. The organic layer was separated, washed with brine, dried over $Na_2SO_4$ and concentrated under reduced pressure. The residue was purified by silica gel column chromatography (AcOEt/hexane) to give the title compound (2.87 g).
MS (API+): [M+H]$^+$309.4.

D) 3-[5-(Benzyloxy)pyridin-2-yl]-1H-pyrazolo[4,3-b]pyridine

A mixture of [5-(benzyloxy)pyridin-2-yl] (3-fluoropyridin-2-yl)methanone (2.85 g) and hydrazine monohydrate (1.348 mL) in EtOH (10 mL) was stirred at 50° C. overnight. After cooling, insoluble material was filtrated and washed with EtOH. The filtrate was evaporated, treated with water and extracted with AcOEt. The organic layer was dried over $Na_2SO_4$ and concentrated under reduced pressure. The residue was purified by silica gel column chromatography (AcOEt/hexane) to give the title compound (0.232 g).
MS (ESI+): [M+H]$^+$303.1.

E) 3-[5-(Benzyloxy)pyridin-2-yl]-1-ethyl-1H-pyrazolo[4,3-b]pyridine

A mixture of $K_2CO_3$ (212 mg, 1.53 mmol), 3-[5-(benzyloxy)pyridin-2-yl]-1H-pyrazolo[4,3-b]pyridine (232 mg) in DMF (3 mL) was added EtI (0.064 mL), and stirred at room temperature overnight. The mixture was added to saturated $NaHCO_3$ aqueous solution and extracted with AcOEt. The organic layer was separated, washed with brine and dried over $Na_2SO_4$ and concentrated under reduced pressure. The residue was purified by silica gel column chromatography (AcOEt/hexane) to give the title compound (224 mg).
MS (API+): [M+H]$^+$331.4.

F) 6-(1-Ethyl-1H-pyrazolo[4,3-b]pyridin-3-yl)pyridin-3-ol

A mixture of 3-[5-(benzyloxy)pyridin-2-yl]-1-ethyl-1H-pyrazolo[4,3-b]pyridine (224 mg) and 10% Pd—C (50% wet, 78 mg) in MeOH (3 mL) and AcOEt (3 mL) was hydrogenated under balloon pressure at room temperature overnight. The solid was filtrated and washed with MeOH (50 mL×3). The filtrate was concentrated under reduced pressure. The precipitate was collected by filtration and washed with 25% AcOEt in hexane to give the title compound (137 mg).
MS (API+): [M+H]$^+$241.3.

G) 1-Ethyl-3-{5-[(3-methyl-3H-imidazo[4,5-b]pyridin-2-yl)oxy]pyridin-2-yl}-1H-pyrazolo[4,3-b]pyridine To a mixture of 3-methyl-2-(methylsulfonyl)-3H-imidazo[4,5-b]pyridine (90 mg) and 6-(1-ethyl-1H-pyrazolo[4,3-b]pyridin-3-yl)pyridin-3-ol (68 mg) in DMF (1 mL) was added NaH (60% in oil, 18.11 mg), and the mixture was stirred at 100° C. for 1 h. The mixture was heated at 180° C. for 30 min under microwave irradiation. The mixture was poured into water and extracted with AcOEt. The organic layer was separated, washed with brine, dried over $Na_2SO_4$ and concentrated under reduced pressure. The residue was purified by basic silica gel column chromatography (AcOEt/hexane). The eluent was evaporated and the residue was crystallized from EtOH/hexane to give the title compound (38.1 mg).
MS (API+): [M+H]$^+$372.1.

Example 31

1-(1-Methylethyl)-3-{6-[(3-methyl-3H-imidazo[4,5-b]pyridin-2-yl)oxy]pyridin-3-yl}-1H-pyrazolo[4,3-b]pyridine A) 3-(6-Methoxypyridin-3-yl)-1-(1-methylethyl)-1H-pyrazolo[4,3-b]pyridine To a mixture of 3-bromo-1-isopropyl-1H-pyrazolo[4,3-b]pyridine (100 mg), 6-methoxypyridin-3-ylboronic acid (96 mg), Pd(OAc)$_2$ (9.35 mg), and Xphos (39.7 mg) in THF (3 mL) was added a solution of $Cs_2CO_3$ (271 mg) in $H_2O$ (1 mL). The mixture was exposed to microwave irradiation at 100° C. for 30 min, treated with water, and extracted with AcOEt. The organic layer was dried over $MgSO_4$ and concentrated under reduced pressure. The residue was purified by silica gel column chromatography (AcOEt/hexane) to give the title compound (100 mg).
MS (API+): [M+H]$^+$269.3.

B) 5-[1-(1-Methylethyl)-1H-pyrazolo[4,3-b]pyridin-3-yl]pyridin-2-ol

A mixture of 3-(6-methoxypyridin-3-yl)-1-(1-methylethyl)-1H-pyrazolo[4,3-b]pyridine (100 mg), MeOH (10 mL) and concentrated HCl (3 mL) was stirred at reflux for 24 h and then evaporated. The residue was treated with saturated $NaHCO_3$ aqueous solution and extracted with AcOEt. The organic layer was dried over $MgSO_4$ and concentrated under reduced pressure. The residue was suspended in IPE and collected by filtration to give the title compound (76 mg).
MS (API+): [M+H]$^+$255.4.

C) 1-(1-Methylethyl)-3-{6-[(3-methyl-3H-imidazo[4,5-b]pyridin-2-yl)oxy]pyridin-3-yl}-1H-pyrazolo[4,3-b]pyridine To a stirred mixture of 5-[1-(1-Methylethyl)-1H-pyrazolo[4,3-b]pyridin-3-yl]pyridin-2-ol (76 mg) in DMF (4 mL) was added NaH (60% in oil, 12.6 mg) at room temperature. The mixture was stirred at room temperature for 30 min and then 3-methyl-2-(methylsulfonyl)-3H-imidazo[4,5-b]pyridine (76 mg) was added. The mixture was exposed to microwave irradiation at 180° C. for 30 min, treated with water, and extracted with AcOEt. The organic layer was dried over MgSO$_4$ and concentrated under reduced pressure. The residue was purified by silica gel column chromatography (AcOEt/hexane). The product was crystallized from AcOEt/hexane to give the title compound (23.0 mg).

MS (API+): [M+H]$^+$386.2.

Example 32

1-Ethyl-3-{(6-[(3-methyl-3H-imidazo[4,5-b]pyridin-2-yl)oxy]pyridin-3-yl}-1H-pyrazolo[4,3-b]pyridine A) 1-Ethyl-3-(6-methoxypyridin-3-yl)-1H-pyrazolo[4,3-b]pyridine To a mixture of 3-bromo-1-ethyl-1H-pyrazolo[4,3-b]pyridine (120 mg), 6-methoxypyridin-3-ylboronic acid (122 mg), Pd(OAc)$_2$ (11.92 mg) and Xphos (50.6 mg) in THF (3 mL) was added a solution of Cs$_2$CO$_3$ (346 mg) in H$_2$O (1 mL). The mixture was exposed to microwave irradiation at 100° C. for 30 min, treated with water, and extracted with AcOEt. The organic layer was dried over MgSO$_4$ and concentrated under reduced pressure. The residue was purified by silica gel column chromatography (AcOEt/hexane) to give the title compound (120 mg).

MS (API+): [M+H]$^+$269.3.

B) 5-(1-Ethyl-1H-pyrazolo[4,3-b]pyridin-3-yl)pyridin-2-ol

A mixture of 1-ethyl-3-(6-methoxypyridin-3-yl)-1H-pyrazolo[4,3-b]pyridine (120 mg), MeOH (10 mL) and concentrated HCl (5 mL) was stirred at reflux for 24 h and then evaporated. The residue was treated with saturated NaHCO$_3$ aqueous solution and extracted with AcOEt. The organic layer was dried over MgSO$_4$ and concentrated under reduced pressure. The residue was suspended in IPE and collected by filtration to give the title compound (90 mg).

MS (API+): [M+H]$^+$241.3.

C) 1-Ethyl-3-[(6-[(3-methyl-3H-imidazo[4,5-b]pyridin-2-yl)oxy]pyridin-3-yl]-1H-pyrazolo[4,3-b]pyridine To a stirred solution of 5-(1-ethyl-1H-pyrazolo[4,3-b]pyridin-3-yl)pyridin-2-ol (80 mg) in DMF (4 mL) was added NaH (60% in oil, 13.98 mg) at room temperature. The mixture was stirred at room temperature for 30 min and then 3-methyl-2-(methylsulfonyl)-3H-imidazo[4,5-b]pyridine (73.9 mg) was added. The mixture was exposed to microwave irradiation at 180° C. for 30 min, treated with water, and extracted with AcOEt. The organic layer was dried over MgSO$_4$ and concentrated under reduced pressure. The residue was purified by silica gel column chromatography (AcOEt/hexane). The product was crystallized from AcOEt/hexane to give the title compound (51.0 mg)

MS (API+): [M+H]$^+$372.4.

Example 33

1-(1-Methylethyl)-3-{5-[(3-methyl-3H-imidazo[4,5-b]pyridin-2-yl)oxy]pyridin-2-yl}-1H-pyrazolo[4,3-b]pyridine A) 3-[5-(Benzyloxy)pyridin-2-yl]-1-(1-methylethyl)-1H-pyrazolo[4,3-b]pyridine A mixture of 3-[5-(benzyloxy)pyridin-2-yl]-1H-pyrazolo[4,3-b]pyridine (237 mg), K$_2$CO$_3$ (217 mg) in DMF (3 mL) was added 2-iodopropane (0.102 mL), and stirred at room temperature for 72 h. The mixture was poured into saturated NaHCO$_3$ aqueous solution and extracted with AcOEt. The organic layer was separated, washed with brine, dried over MgSO$_4$ and concentrated under reduced pressure. The residue was purified by silica gel column chromatography (AcOEt/hexane) to give the title compound (219 mg).

MS (API+): [M+H]$^+$345.1.

B) 6-[1-(1-Methylethyl)-1H-pyrazolo[4,3-b]pyridin-3-yl]pyridin-3-ol

A mixture of 3-[5-(benzyloxy)pyridin-2-yl]-1-(1-methylethyl)-1H-pyrazolo[4,3-b]pyridine (219 mg) and 10% Pd—C (50% wet, 73.1 mg) in MeOH (3 mL) and AcOEt (3 mL) was hydrogenated under balloon pressure at room temperature overnight. The solid was filtrated and washed with MeOH (10 mL). The filtrate was concentrated under reduced pressure to give the title compound (140 mg).

MS (API+): [M+H]$^+$255.2.

C) 1-(1-Methylethyl)-3-{5-[(3-methyl-3H-imidazo[4,5-b]pyridin-2-yl)oxy]pyridin-2-yl}-1H-pyrazolo[4,3-b]pyridine To a mixture of 3-methyl-2-(methylsulfonyl)-3H-imidazo[4,5-b]pyridine (174 mg) and 6-[(1-(1-methylethyl)-1H-pyrazolo[4,3-b]pyridin-3-yl]pyridin-3-ol (140 mg) in DMF (1.5 ml) was added NaH (60% in oil, 35.2 mg), and the mixture was stirred at 100° C. for 1 h. The mixture was heated at 180° C. for 30 min under microwave irradiation. The mixture was poured into water and extracted with AcOEt. The organic layer was separated, washed with brine, dried over Na$_2$SO$_4$ and concentrated under reduced pressure. The residue was purified by basic silica gel column chromatography (AcOEt/hexane) and silica gel column chromatography (AcOEt/hexane). The eluent was evaporated and the residue was purified by preparative HPLC (C18, eluent: H$_2$O/CH$_3$CN (10 mM NH$_4$HCO$_3$)). The eluent was evaporated to give the title compound (68.1 mg).

MS (API+): [M+H]$^+$386.3.

Example 34

1-Ethyl-3-(4-{[3-(2-methoxyethyl)-3H-imidazo[4,5-b]pyridin-2-yl]oxy}phenyl)-1H-pyrazolo[4,3-b]pyridine A) 3-(2-Methoxyethyl)-2-(methylsulfanyl)-3H-imidazo[4,5-b]pyridine A mixture of 2-(methylthio)-3H-imidazo[4,5-b]pyridine (400 mg) and 1-bromo-2-methoxyethane (370 mg) in DMF (7 mL) was stirred at 80° C. for 3 h, treated with water, and extracted with AcOEt. The organic layer was dried over MgSO₄ and concentrated under reduced pressure. The residue was purified by silica gel column chromatography (AcOEt/hexane) to give the title compound (200 mg).
MS (API+): [M+H]⁺224.2.

B) 3-(2-Methoxyethyl)-2-(methylsulfonyl)-3H-imidazo[4,5-b]pyridine

To a stirred solution of 3-(2-methoxyethyl)-2-(methylsulfanyl)-3H-imidazo[4,5-b]pyridine (200 mg) in AcOEt (5 ml) was added mCPBA (423 mg) at room temperature. The mixture was stirred at room temperature for 3 h and then evaporated. The residue was purified by silica gel column chromatography (AcOEt/hexane) to give the title compound (200 mg).
MS (API+): [M+H]⁺256.0.

C) 2-(4-Bromophenoxy)-3-(2-methoxyethyl)-3H-imidazo[4,5-b]pyridine

To a stirred solution of 4-bromophenol (149 mg) in DMF (4 mL) was added NaH (60% in oil, 36.0 mg) at room temperature. The mixture was stirred at room temperature for 30 min. To the mixture was added 3-(2-methoxyethyl)-2-(methylsulfonyl)-3H-imidazo[4,5-b]pyridine (200 mg). The mixture was exposed to microwave irradiation at 180° C. for 30 min, treated with water, and extracted with AcOEt. The organic layer was dried over MgSO₄ and concentrated under reduced pressure. The residue was purified by silica gel column chromatography (AcOEt/hexane) to give the title compound (243 mg).
MS (API+): [M+H]⁺348.2

D) 1-Ethyl-3-(4-{([3-(2-methoxyethyl)-3H-imidazo[4,5-b]pyridin-2-yl]oxy}phenyl)-1H-pyrazolo[4,3-b]pyridine A mixture of 2-(4-bromophenoxy)-3-(2-methoxyethyl)-3H-imidazo[4,5-b]pyridine (120 mg), 4,4,4',4',5,5,5',5'-octamethyl-2,2'-bi(1,3,2-dioxaborolane) (88 mg), Pd(dppf)₂Cl₂ dichloromethane adduct (28.4 mg) and KOAc (50.7 mg) in THF/DMSO (20/1, 3.15 mL) was stirred at 90° C. for 12 h under Ar atmosphere, treated with water, and extracted with AcOEt. The organic layer was dried over MgSO₄ and passed through a celite pad covered with activated carbon, and concentrated under reduced pressure.
To a mixture of the residue, 3-bromo-1-ethyl-1H-pyrazolo[4,3-b]pyridine (77 mg), Pd(PPh₃)₄ (39.3 mg) in THF (3 mL) was added a solution of Cs₂CO₃ (166 mg) in H₂O (1 mL). The mixture was exposed to microwave irradiation at 100° C. for 30 min, treated with water, and extracted with AcOEt. The organic layer was dried over MgSO₄ and concentrated under reduced pressure. The residue was purified by silica gel column chromatography (AcOEt/hexane). Crystallization from AcOEt/hexane gave the title compound (44.0 mg).
MS (API+): [M+H]⁺415.1.
¹H NMR (300 MHz, DMSO-d₆) δ 1.48 (3H, t, J=7.2 Hz), 3.75-3.89 (2H, t, J=5.5 Hz), 4.44 (2H, t, J=5.5 Hz), 4.56 (2H, q, J=7.2 Hz), 7.12-7.31 (1H, m), 7.44-7.66 (3H, m), 7.73-7.88 (1H, m), 8.19-8.37 (2H, m), 8.52-8.74 (3H, m).

Example 35

3-(4-{([3-(2-Methoxyethyl)-3H-imidazo[4,5-b]pyridin-2-yl]oxy}phenyl)-1-(1-methylethyl)-1H-pyrazolo[4,3-b]pyridine A mixture of 2-(4-Bromophenoxy)-3-(2-methoxyethyl)-3H-imidazo[4,5-b]pyridine (120 mg), 4,4,4',4',5,5,5',5'-octamethyl-2,2'-bi(1,3,2-dioxaborolane) (88 mg), Pd(dppf)₂Cl₂ dichloromethane adduct (28.4 mg) and KOAc (50.7 mg) in THF/DMSO (20/1, 3.15 mL) was stirred at 90° C. for 12 h under Ar atmosphere, treated with water, and extracted with AcOEt. The organic layer was dried over MgSO₄ and passed through celite pad covered with activated carbon, and concentrated under reduced pressure.
To a mixture of the residue 3-bromo-1-isopropyl-1H-pyrazolo[4,3-b]pyridine (82 mg), Pd(PPh₃)₄ (39.3 mg) in THF (3 mL) was added a solution of Cs₂CO₃ (166 mg) in H₂O (1 mL). The mixture was exposed to microwave irradiation at 100° C. for 30 min, treated with water, and extracted with AcOEt. The organic layer was dried over MgSO₄ and concentrated under reduced pressure. The residue was purified by silica gel column chromatography (AcOEt/hexane). Crystallization from AcOEt/hexane gave the title compound (48.0 mg).
MS (API+): [M+H]⁺429.2.
¹H NMR (300 MHz, DMSO-d₆) δ 1.58 (6H, d, J=6.8 Hz), 3.83 (2H, t, J=5.5 Hz), 4.44 (2H, t, J=5.5 Hz), 5.11 (1H, spt, J=6.8 Hz), 7.14-7.28 (1H, m), 7.42-7.53 (1H, m), 7.52-7.65 (2H, m), 7.76-7.87 (1H, m), 8.16-8.25 (1H, m), 8.30 (1H, d, J=7.2 Hz), 8.49-8.72 (3H, m).

Example 36

1-{2-[4-(1-Ethyl-1H-pyrazolo[4,3-b]pyridin-3-yl)phenoxy]-1H-benzimidazol-1-yl}-2-methylpropan-2-ol A) 2-(4-Bromophenoxy)-1H-benzimidazole A mixture of 2-chloro-1H-benzo[d]imidazole (10 g), 4-bromophenol (56.7 g) and TEA (45.5 mL) was stirred at 150° C. overnight. The mixture was quenched with water at room temperature and extracted with AcOEt. The extract was washed with 1 M NaOH aqueous solution, dried over Na₂SO₄, and concentrated under reduced pressure. The precipitate was crystallized from AcOEt/hexane to give the title compound (11.9 g).
MS (ESI+): [M+H]⁺291.0.
¹H NMR (300 MHz, DMSO-d₆) δ 7.10 (2H, dd, J=5.9, 3.2 Hz), 7.29-7.45 (4H, m), 7.65 (2H, d, J=8.7 Hz).

B) 1-[2-(4-Bromophenoxy)-1H-benzimidazol-1-yl]propan-2-one

To a solution of 2-(4-bromophenoxy)-1H-benzo[d]imidazole (5.72 g) in DMF (60 mL) was added NaH (60% in oil, 950 mg) at 0° C. After stirring for 5 min, chloroacetone (2.36 mL) was added to the mixture at 0° C. The mixture was stirred at room temperature for 5 h. The mixture was diluted with AcOEt and washed with water. The organic layer was dried over Na₂SO₄, filtered and concentrated under reduced pressure. The residue was purified by silica gel column chromatography (AcOEt in hexane) and recrystallized from THF/Et₂O to give the title compound (3.47 g).
MS (API+): found: 345.2, 347.2
¹H NMR (300 MHz, CDCl₃) δ 2.27 (3H, s), 4.88 (2H, s), 7.03-7.12 (1H, m), 7.15-7.31 (4H, m), 7.48-7.66 (3H, m).

C) 1-{2-[4-(1-Ethyl-1H-pyrazolo[4,3-b]pyridin-3-yl)phenoxy]-1H-benzimidazol-1-yl}-2-methylpropan-2-ol A solution of 1-[2-(4-bromophenoxy)-1H-benzo[d]imidazol-1-yl]propan-2-one (155 mg) in THF (3 mL) was added to a solution of methylmagnesium bromide (3 M solution in diethyl ether, 0.539 mL) and cerium(III) chloride (133 mg) (dried under reduced pressure at 80° C. for 1 h) in THF (2 mL) at −78° C. The mixture was quenched with water at 0° C., filtered and extracted with AcOEt. The organic layer was separated, washed with water and brine, dried over MgSO$_4$ and filtered on silica pad. The mixture of the filtrate, 4,4,4', 4',5,5,5',5'-octamethyl-2,2'-bi(1,3,2-dioxaborolane) (174 mg), Pd(dppf)$_2$Cl$_2$ dichloromethane adduct (4.89 mg) and KOAc (134 mg) in THF (5 mL)-DMSO (0.25 mL) was stirred at 80° C. under N$_2$ atmosphere overnight. The mixture was diluted with AcOEt and filtered on silica gel conditioned with AcOEt. The filtrate was concentrated under reduced pressure.

A mixture of the residue, 3-bromo-1-ethyl-1H-pyrazolo[4,3-b]pyridine (104 mg), Pd(PPh$_3$)$_4$ (16.0 mg), Na$_2$CO$_3$ (171 mg), DME (4 mL), and water (0.8 ml) was refluxed for 6 h under N$_2$ atmosphere. The reaction mixture was poured into water and extracted with AcOEt. The extract was washed with brine, dried over Na$_2$SO$_4$, and concentrated under reduced pressure. The residue was purified by silica gel column chromatography (AcOEt in hexane) and recrystallized from AcOEt/hexane to give the title compound (120 mg). The solid was crystallized from AcOEt/hexane.

MS (API+): [M+H]$^+$428.3.

mp 152-153° C.

$^1$H NMR (300 MHz, DMSO-d$_6$) δ 1.48 (3H, t, J=7.2 Hz), 3.31 (6H, s), 4.11 (2H, s), 4.55 (2H, q, J=7.2 Hz), 4.78 (1H, s), 7.05-7.20 (2H, m), 7.35-7.43 (1H, m), 7.49 (1H, dd, J=8.7, 4.2 Hz), 7.56 (3H, d, J=9.1 Hz), 8.27 (1H, d, J=7.2 Hz), 8.57 (2H, d, J=9.1 Hz), 8.66 (1H, d, J=3.0 Hz).

Example 37

1-Ethyl-6-fluoro-3-{4-[(3-methyl-3H-imidazo[4,5-b]pyridin-2-yl)oxy]phenyl}-1H-pyrazolo[4,3-b]pyridine A) 3,5-Difluoro-N-methoxy-N-methylpyridine-2-carboxamide To a suspension of 3,5-difluoropicolinic acid (3.5 g) in THF (70 ml) was added CDI (3.92 g) at room temperature. The mixture was stirred at room temperature for 30 min and at 50° C. for 1 h. After cooling to room temperature, N,O-dimethylhydroxylamine hydrochloride (3.22 g) and DIPEA (5.76 mL) were added. The mixture was stirred at room temperature for 12 h, and then concentrated under reduced pressure. The residue was purified by silica gel column chromatography (hexane/AcOEt) to give the title compound (2.5 g).

$^1$H NMR (300 MHz, DMSO-d$_6$) δ 3.31 (3H, s), 3.52 (3H, s), 8.03-8.17 (1H, m), 8.58 (1H, d, J=2.3 Hz).

B) [4-(Benzyloxy)phenyl](3,5-difluoropyridin-2-yl)methanone

To a stirred solution of 3,5-difluoro-N-methoxy-N-methylpyridine-2-carboxamide (2.5 g) in THF (50 mL) was added [4-(benzyloxy)phenyl](bromo)magnesium (1 M solution in THF, 12.3 mL) at −78° C. The mixture was stirred at −78° C. for 3 h, treated with saturated NH$_4$Cl aqueous solution and extracted with AcOEt. The organic layer was dried over MgSO$_4$ and concentrated under reduced pressure. The residue was purified by silica gel column chromatography (AcOEt/hexane). The product was crystallized from AcOEt/hexane to give the title compound (2.3 g).

$^1$H NMR (300 MHz, DMSO-d$_6$) δ 5.24 (2H, s), 7.10-7.25 (2H, m), 7.27-7.54 (5H, m), 7.76-7.92 (2H, m), 8.10-8.26 (1H, m), 8.64 (1H, d, J=2.3 Hz).

C) 4-(1-Ethyl-6-fluoro-1H-pyrazolo[4,3-b]pyridin-3-yl)phenol

A mixture of [4-(benzyloxy)phenyl](3,5-difluoropyridin-2-yl)methanone (400 mg), ethylhydrazine (369 mg) and 2-propanol (5 mL) was stirred at room temperature for 30 min, and at 90° C. for 12 h, treated with water, and extracted with AcOEt. The organic layer was dried over MgSO$_4$ and concentrated under reduced pressure. The residue was dissolved in EtOH (40 mL) and 10% Pd—C (50% wet, 400 mg) was added. The mixture was stirred at room temperature for 1 h under H$_2$ atmosphere, filtered and evaporated. The residue was suspended in AcOEt/IPE and collected by filtration to give the title compound (220 mg).

MS (API+): [M+H]$^+$258.1.

D) 1-Ethyl-6-fluoro-3-{(4-[(3-methyl-3H-imidazo[4,5-b]pyridin-2-yl)oxy]phenyl}-1H-pyrazolo[4,3-b]pyridine To a stirred solution of 4-(1-ethyl-6-fluoro-1H-pyrazolo[4,3-b]pyridin-3-yl)phenol (200 mg) in DMF (4 mL) was added NaH (60% in oil, 31.1 mg) at room temperature. The mixture was stirred at room temperature for 30 min and then 3-methyl-2-(methylsulfonyl)-3H-imidazo[4,5-b]pyridine (164 mg) was added. The mixture was exposed to microwave irradiation at 180° C. for 30 min, treated with water, and extracted with AcOEt. The organic layer was dried over MgSO$_4$ and concentrated under reduced pressure. The residue was purified by basic silica gel column chromatography (AcOEt/Hexane). The product was crystallized from EtOH/hexane to give the title compound (165 mg).

MS (API+): [M+H]$^+$389.3.

$^1$H NMR (300 MHz, DMSO-d$_6$) δ 1.47 (3H, t, J=7.2 Hz), 3.77 (3H, s), 4.52 (2H, q, J=7.2 Hz), 7.14-7.25 (1H, m), 7.62 (2H, d, J=8.7 Hz), 7.75-7.84 (1H, m), 8.18-8.25 (1H, m), 8.26-8.33 (1H, m), 8.48-8.58 (2H, m), 8.67 (1H, s).

Example 38

1-Ethyl-3-{4-[(3-methyl-3H-imidazo[4,5-b]pyridin-2-yl)oxy]phenyl}-1H-pyrazolo[4,3-d]pyrimidine A) Methyl 1-ethyl-4-nitro-1H-pyrazole-5-carboxylate A mixture of methyl 4-nitro-1H-pyrazole-3-carboxylate (5.0 g), EtI (2.8 mL) and K$_2$CO$_3$ (8.1 g) in acetone (50 mL) was stirred at 50° C. for 4 h. After stirring at room temperature overnight, the mixture was filtered and the filtrate was concentrated under reduced pressure. The residue was purified by silica gel column chromatography (AcOEt/hexane) to give the title compound (2.2 g).

$^1$H NMR (300 MHz, CDCl$_3$) δ 1.50 (3H, t, J=7.2 Hz), 4.03 (3H, s), 4.32 (2H, q, J=7.2 Hz), 8.03 (1H, s).

B) Methyl 4-amino-1-ethyl-1H-pyrazole-5-carboxylate

A mixture of methyl 1-ethyl-4-nitro-1H-pyrazole-5-carboxylate (2.2 g) and 10% Pd—C (0.60 g) in MeOH (30 mL) was hydrogenated under balloon pressure at room temperature overnight. The catalyst was removed by filtration and the filtrate was concentrated under reduced pressure to give the title compound (1.8 g).

MS (API+): [M+H]$^+$170.3.

$^1$H NMR (300 MHz, CDCl$_3$) δ 1.36 (3H, t, J=7.2 Hz), 3.92 (3H, s), 4.09 (2H, brs), 4.45 (2H, q, J=7.2 Hz), 7.09 (1H, s).

C) 1-Ethyl-1H-pyrazolo[4,3-d]pyrimidin-7-ol

A mixture of methyl 4-amino-1-ethyl-1H-pyrazole-5-carboxylate (1.75 g), formamidine acetate (1.615 g), n-butanol (20 mL) and DIPEA (20 mL) was stirred at 120° C. for 3 h. The mixture was concentrated under reduced pressure, and the residual crystals were washed with AcOEt/hexane to give the title compound (1.47 g).

MS (API+): [M+H]$^+$165.1.

$^1$H NMR (300 MHz, DMSO-d$_6$) δ 1.38 (3H, t, J=7.2 Hz), 4.57 (2H, q, J=7.2 Hz), 7.86 (1H, s), 7.97 (1H, s), 12.04 (1H, brs).

D) 7-Chloro-1-ethyl-1H-pyrazolo[4,3-d]pyrimidine

A mixture of 1-ethyl-1H-pyrazolo[4,3-d]pyrimidin-7-ol (2.91 g) and POCl$_3$ (30 mL) was stirred at 100° C. overnight. The mixture was concentrated under reduced pressure. The residue was neutralized with saturated NaHCO$_3$ aqueous solution and extracted with AcOEt. The organic layer was dried over Na$_2$SO$_4$, filtered and concentrated under reduced pressure. The residue was purified by silica gel column chromatography (AcOEt/hexane) to give the title compound (2.14 g).

1H NMR (300 MHz, CDCl$_3$) δ 1.57 (3H, t, J=7.4 Hz), 4.81 (2H, q, J=7.4 Hz), 8.29 (1H, s), 8.81 (1H, s).

E) 1-Ethyl-1H-pyrazolo[4,3-d]pyrimidine

A mixture of 7-chloro-1-ethyl-1H-pyrazolo[4,3-d]pyrimidine (105 mg), TEA (0.088 mL) and 10% Pd—C (30 mg) in AcOEt (5 mL) was hydrogenated under balloon pressure at room temperature for 2 h. The catalyst was removed by filtration and the filtrate was concentrated under reduced pressure to give the title compound (80 mg).

MS (ESI+): [M+H]$^+$149.0.

1H NMR (300 MHz, CDCl$_3$) δ 1.60 (3H, t, J=7.2 Hz), 4.55 (2H, q, J=7.2 Hz), 8.26 (1H, s), 9.12 (1H, s), 9.15 (1H, s).

F) 3-Bromo-1-ethyl-1H-pyrazolo[4,3-d]pyrimidine

To a solution of 1-ethyl-1H-pyrazolo[4,3-d]pyrimidine (300 mg) in DMF (6 mL) was added NBS (721 mg) at room temperature, and the mixture was stirred at 80° C. overnight. The mixture was poured into water and extracted with AcOEt. The organic layer was washed with brine, dried over Na$_2$SO$_4$, filtered and concentrated under reduced pressure. The residue was purified by silica gel column chromatography (AcOEt/hexane) to give the title compound (310 mg). $^1$H NMR (300 MHz, CDCl$_3$) δ 1.62 (3H, t, J=7.3 Hz), 4.54 (2H, q, J=7.3 Hz), 9.14 (1H, s), 9.17 (1H, s).

G) 1-Ethyl-3-{(4-[(3-methyl-3H-imidazo[4,5-b]pyridin-2-yl)oxy]phenyl}-1H-pyrazolo[4,3-d]pyrimidine A mixture of 3-methyl-2-(4-(4,4,5,5-tetramethyl-1,3,2-dioxaborolan-2-yl)phenoxy)-3H-imidazo[4,5-b]pyridine (309 mg), 3-bromo-1-ethyl-1H-pyrazolo[4,3-d]pyrimidine (200 mg), Pd(PPh$_3$)$_4$ (61 mg), Na$_2$CO$_3$ (327 mg), DME (4 mL), and water (0.8 mL) was refluxed overnight under Ar atmosphere. The reaction mixture was poured into water and extracted with AcOEt. The extract was washed with brine, dried over Na$_2$SO$_4$, and concentrated under reduced pressure. The residual crystals were washed with AcOEt and recrystallized from AcOEt/hexane to give the title compound (71.0 mg).

MS (API+): [M+H]$^+$372.2.

$^1$H NMR (300 MHz, DMSO-d$_6$) δ 1.54 (3H, t, J=7.2 Hz), 3.78 (3H, s), 4.67 (2H, q, J=7.2 Hz), 7.21 (1H, dd, J=7.9, 4.9 Hz), 7.66 (2H, d, J=8.7 Hz), 7.80 (1H, dd, J=7.9, 1.1 Hz), 8.22 (1H, dd, J=4.9, 1.1 Hz), 8.54 (2H, d, J=8.7 Hz), 9.17 (1H, s), 9.60 (1H, s).

mp 218-220° C.

Anal. Calcd for C$_{20}$H$_{17}$N$_7$O: C, 64.68; H, 4.61; N, 26.40. Found: C, 64.58; H, 4.70; N, 26.12.

Example 39

1-(2,2-Difluoroethyl)-3-{4-[(3-methyl-3H-imidazo[4,5-b]pyridin-2-yl)oxy]phenyl}-1H-pyrazolo[4,3-b]pyridine A)
3-Fluoro-N-methoxy-N-methylpyridine-2-carboxamide To a suspension of 3-fluoropicolinic acid (17.7 g) in THF (300 mL) was added CDI (22.4 g) at room temperature, and the mixture was stirred at room temperature for 30 min and heated to 50° C. After stirring at 50° C. for 1 h, the mixture was cooled to room temperature. To the mixture were added N,O-dimethylhydroxylamine hydrochloride (18.4 g) and DIPEA (32.9 mL) at room temperature, and the mixture was stirred at room temperature for 12 h. The mixture was concentrated under reduced pressure. The residue was purified by silica gel column chromatography (AcOEt) to give the title compound (21.8 g).

$^1$H NMR (300 MHz, CDCl$_3$) δ 3.40 (3H, s), 3.59 (3H, s), 7.34-7.44 (1H, m), 7.44-7.56 (1H, m), 8.42-8.50 (1H, m).

B) [4-(Benzyloxy)phenyl](3-fluoropyridin-2-yl) methanone

To a solution of 3-fluoro-N-methoxy-N-methylpyridine-2-carboxamide (4.8 g) in THF (100 mL) was added dropwise [4-(benzyloxy)phenyl]magnesium bromide (1 M solution in THF, 27.4 mL) at 0° C. After stirring at 0° C. for 2 h, the mixture was warmed to room temperature and stirred at room temperature overnight. The mixture was quenched with water and extracted with AcOEt. The organic layer was washed with brine, dried over Na$_2$SO$_4$, filtered and concentrated under reduced pressure. The residue was purified by silica gel column chromatography (AcOEt/hexane) to give the title compound (3.0 g).

MS (API+): [M+H]$^+$308.3.

C)
3-[4-(Benzyloxy)phenyl]-1H-pyrazolo[4,3-b]pyridine

A mixture of [4-(benzyloxy)phenyl](3-fluoropyridin-2-yl) methanone (3.0 g) and hydrazine hydrate (5.0 mL) in EtOH (90 mL) was refluxed for 4 days. The mixture was concentrated under reduced pressure. The residue was partitioned between water and AcOEt. The organic layer was washed with brine, dried over Na$_2$SO$_4$ and concentrated under reduced pressure. The residue was purified by silica gel column chromatography (AcOEt/hexane) to give the title compound (0.83 g).

MS (API+): [M+H]$^+$302.3.

D) 4-[1-(2,2-Difluoroethyl)-1H-pyrazolo[4,3-b]pyridin-3-yl]phenol

To a stirred mixture of 3-[4-(benzyloxy)phenyl]-1H-pyrazolo[4,3-b]pyridine (300 mg) and Cs₂CO₃ (649 mg) in DMF (4 ml) was added 2,2-difluoroethyl trifluoromethanesulfonate (234 mg) at 0° C. The mixture was stirred at room temperature for 12 h, treated with water, and extracted with AcOEt. The organic layer was dried over MgSO₄ and concentrated under reduced pressure. The residue was dissolved in EtOH (8 mL) and 10% Pd—C (200 mg) was added. The mixture was stirred at room temperature for 30 min under H₂ atmosphere, filtered and evaporated. The residue was purified by silica gel column chromatography (hexane/AcOEt) to give the title compound (142 mg).
MS (API+): [M+H]⁺276.1.

E) 1-(2,2-Difluoroethyl)-3-{4-[(3-methyl-3H-imidazo[4,5-b]pyridin-2-yl)oxy]phenyl}-1H-pyrazolo[4,3-b]pyridine To a stirred solution of 4-[1-(2,2-difluoroethyl)-1H-pyrazolo[4,3-b]pyridin-3-yl]phenol (142 mg) in DMF (4 mL) was added NaH (60% in oil, 20.63 mg) at room temperature. The mixture was stirred at room temperature for 30 min and then 3-methyl-2-(methylsulfonyl)-3H-imidazo[4,5-b]pyridine (109 mg) was added. The mixture was exposed to microwave irradiation at 180° C. for 30 min, treated with water, and extracted with AcOEt. The organic layer was dried over MgSO₄ and concentrated under reduced pressure. The residue was purified by silica gel column chromatography (AcOEt/hexane). The product was crystallized from AcOEt/hexane to give the title compound (90 mg)
MS (API+): [M+H]⁺407.2.
¹H NMR (300 MHz, DMSO-d₆) δ 3.78 (3H, s), 5.08 (2H, td, J=15.4, 3.4 Hz), 6.29-6.77 (1H, m), 7.21 (1H, dd, J=7.7, 5.1 Hz), 7.53-7.59 (1H, m), 7.60-7.67 (2H, m), 7.80 (1H, dd, J=7.9, 1.5 Hz), 8.20-8.24 (1H, m), 8.31 (1H, d, J=7.5 Hz), 8.56-8.63 (2H, m), 8.69-8.73 (1H, m).

Example 40

6-Fluoro-1-(1-methylethyl)-3-{4-[(3-methyl-3H-imidazo[4,5-b]pyridin-2-yl)oxy]phenyl}-1H-pyrazolo[4,3-b]pyridine

A) 3-[4-(Benzyloxy)phenyl]-6-fluoro-1-(1-methylethyl)-1H-pyrazolo[4,3-b]pyridine A mixture of [4-(benzyloxy)phenyl](3,5-difluoropyridin-2-yl)methanone (100 mg) and hydrazine hydrate (77 mg) in 2-propanol (5 mL) was stirred at room temperature for 30 min and at 90° C. for 12 h, treated with water, and extracted with AcOEt. The organic layer was dried over MgSO₄ and concentrated under reduced pressure. The residue was dissolved in DMF (5 mL), and then Cs₂CO₃ (150 mg, 0.46 mmol) and 2-bromopropane (50.5 mg) were added successively. The mixture was stirred for 12 h, treated with water, and extracted with AcOEt. The organic layer was dried over MgSO₄ and concentrated under reduced pressure. The residue was purified by silica gel column chromatography (AcOEt/hexane) to give the title compound (70.0 mg).
MS (API+): [M+H]⁺362.2.

B) 4-[6-Fluoro-1-(1-methylethyl)-1H-pyrazolo[4,3-b]pyridin-3-yl]phenol

A mixture of 3-[4-(benzyloxy)phenyl]-6-fluoro-1-(1-methylethyl)-1H-pyrazolo[4,3-b]pyridine (130 mg) and 10% Pd—C (100 mg) in EtOH (20 mL) was stirred at room temperature for 1 h under H₂ atmosphere, filtered and evaporated. The residue was purified by silica gel column chromatography (hexane/AcOEt) to give the title compound (76 mg).
MS (API+): [M+H]⁺272.0.

C) 6-Fluoro-1-(1-methylethyl)-3-{4-[(3-methyl-3H-imidazo[4,5-b]pyridin-2-yl)oxy]phenyl}-1H-pyrazolo[4,3-b]pyridine To a stirred solution of 4-[6-fluoro-1-(1-methylethyl)-1H-pyrazolo[4,3-b]pyridin-3-yl]phenol (76 mg) in DMF (4 mL) was added NaH (60% in oil, 11.2 mg) at room temperature. The mixture was stirred at room temperature for 30 min and then 3-methyl-2-(methylsulfonyl)-3H-imidazo[4,5-b]pyridine (59.2 mg) was added. The mixture was exposed to microwave irradiation at 180° C. for 30 min, treated with water, and extracted with AcOEt. The organic layer was dried over MgSO₄ and concentrated under reduced pressure. The residue was purified by basic silica gel column chromatography (AcOEt/hexane). The product was crystallized from AcOEt/hexane to give the title compound (60.0 mg).
MS (API+): [M+H]⁺403.3.
¹H NMR (300 MHz, DMSO-d₆) δ 1.57 (6H, d, J=6.8 Hz), 3.77 (3H, s), 5.05 (1H, spt, J=6.8 Hz), 7.15-7.26 (1H, m), 7.57-7.65 (2H, m), 7.77-7.83 (1H, m), 8.18-8.25 (1H, m), 8.28-8.36 (1H, m), 8.50-8.57 (2H, m), 8.67 (1H, s).

Example 41

3-(4-{[3-(2,2-Difluoroethyl)-3H-imidazo[4,5-b]pyridin-2-yl]oxy}phenyl)-1-ethyl-1H-pyrazolo[4,3-b]pyridine

A) 3-(2,2-Difluoroethyl)-2-(methylsulfanyl)-3H-imidazo[4,5-b]pyridine

A mixture of 2-(methylsulfanyl)-3H-imidazo[4,5-b]pyridine (600 mg) and 2,2-difluoroethyl trifluoromethanesulfonate (816 mg) in DMF (7 mL) was stirred at 80° C. for 3 h, treated with water, and extracted with AcOEt. The organic layer was dried over MgSO₄ and concentrated under reduced pressure to give the title compound (400 mg).
MS (API+): [M+H]⁺230.2.

B) 3-(2,2-Difluoroethyl)-2-(methylsulfonyl)-3H-imidazo[4,5-b]pyridine

To a stirred solution of 3-(2,2-difluoroethyl)-2-(methylsulfanyl)-3H-imidazo[4,5-b]pyridine (400 mg) in AcOEt (5 mL) was added mCPBA (825 mg) at room temperature. The mixture was stirred at room temperature for 3 h and then evaporated. The residue was purified by silica gel column chromatography (AcOEt/hexane) to give the title compound (360 mg).
¹H NMR (300 MHz, DMSO-d₆) δ 3.63 (3H, s), 5.08 (2H, td, J=14.6, 3.6 Hz), 6.29-6.76 (1H, m), 7.56 (1H, dd, J=8.1, 4.7 Hz), 8.33-8.43 (1H, m), 8.59-8.75 (1H, m).

C) 2-(4-Bromophenoxy)-3-(2,2-difluoroethyl)-3H-imidazo[4,5-b]pyridine

To a stirred solution of 4-bromophenol (238 mg) in DMF (4 mL) was added NaH (60% in oil, 55.1 mg) at room temperature. The mixture was stirred at room temperature for 30 min and then 3-(2,2-difluoroethyl)-2-(methylsulfonyl)-3H-imidazo[4,5-b]pyridine (360 mg) was added. The mixture was exposed to microwave irradiation at 180° C. for 30 min, treated with water, and extracted with AcOEt. The organic layer was dried over MgSO$_4$ and concentrated under reduced pressure. The residue was purified by silica gel column chromatography (AcOEt/hexane) to give the title compound (387 mg).

$^1$H NMR (300 MHz, DMSO-d$_6$) δ 4.69 (2H, td, J=15.5, 3.2 Hz), 6.31-6.78 (1H, m), 7.21-7.30 (1H, m), 7.41-7.50 (2H, m), 7.66-7.73 (2H, m), 7.81-7.89 (1H, m), 8.19-8.27 (1H, m).

D) 3-(4-{[3-(2,2-Difluoroethyl)-3H-imidazo[4,5-b]pyridin-2-yl]oxy}phenyl)-1-ethyl-1H-pyrazolo[4,3-b]pyridine A mixture of 2-(4-bromophenoxy)-3-(2,2-difluoroethyl)-3H-imidazo[4,5-b]pyridine (180 mg), 4,4,4',4',5,5,5',5'-octamethyl-2,2'-bi(1,3,2-dioxaborolane) (129 mg), Pd(dppf)$_2$Cl$_2$ dichloromethane adduct (41.8 mg) and K$_2$CO$_3$ (74.8 mg) in THF/DMSO (20/1, 3.15 mL) was stirred at 100° C. for 12 h under Ar atmosphere, treated with water, and extracted with AcOEt. The organic layer was dried over MgSO$_4$ and passed through a celite pad covered with activated carbon, and concentrated under reduced pressure.

To a mixture of the residue, 3-bromo-1-ethyl-1H-pyrazolo[4,3-b]pyridine (115 mg), and Pd(PPh$_3$)$_4$ (58.9 mg) in THF (3 mL) was added a solution of Cs$_2$CO$_3$ (249 mg) in H$_2$O (1 mL). The mixture was exposed to microwave irradiation at 100° C. for min, treated with water, and extracted with AcOEt. The organic layer was dried over MgSO$_4$ and concentrated under reduced pressure. The residue was purified by basic silica gel column chromatography (AcOEt/hexane). Crystallization from AcOEt/hexane gave the title compound (65.0 mg).

MS (API+): [M+H]$^+$421.3.

$^1$H NMR (300 MHz, DMSO-d$_6$) δ 1.48 (3H, t, J=7.2 Hz), 4.56 (2H, q, J=7.2 Hz), 4.74 (2H, td, J=15.6, 3.2, Hz), 6.35-6.81 (1H, m), 7.20-7.29 (1H, m), 7.45-7.55 (1H, m), 7.57-7.65 (2H, m), 7.79-7.91 (1H, m), 8.21-8.34 (2H, m), 8.57-8.71 (3H, m).

Example 42

3-(4-{[3-(2,2-Difluoroethyl)-3H-imidazo[4,5-b]pyridin-2-yl]oxy}phenyl)-1-(1-methylethyl)-1H-pyrazolo[4,3-b]pyridine A mixture of 2-(4-bromophenoxy)-3-(2,2-difluoroethyl)-3H-imidazo[4,5-b]pyridine (180 mg), 4,4,4',4',5,5,5',5'-octamethyl-2,2'-bi(1,3,2-dioxaborolane) (129 mg), Pd(dppf)$_2$Cl$_2$ dichloromethane adduct (41.8 mg) and K$_2$CO$_3$ (74.8 mg) in THF/DMSO (20/1, 3.15 ml) was stirred at 100° C. for 12 h under Ar atmosphere, treated with water, and extracted with AcOEt. The organic layer was dried over MgSO$_4$ and passed through a celite pad covered with activated carbon, and concentrated under reduced pressure.

To a mixture of the residue, 3-bromo-1-(1-methylethyl)-1H-pyrazolo[4,3-b]pyridine (122 mg), Pd(PPh$_3$)$_4$ (58.9 mg) in THF (3 mL) was added a solution of Cs$_2$CO$_3$ (249 mg) in H$_2$O (1 mL). The mixture was exposed to microwave irradiation at 100° C. for min, treated with water, and extracted with AcOEt. The organic layer was dried over MgSO$_4$ and concentrated under reduced pressure. The residue was purified by basic silica gel column chromatography (AcOEt/hexane). Crystallization from AcOEt/hexane gave the title compound (43.0 mg).

MS (API+): [M+H]$^+$435.4.

$^1$H NMR (300 MHz, DMSO-d$_6$) δ 1.58 (6H, d, J=6.4 Hz), 4.74 (2H, td, J=15.6, 3.2 Hz), 5.11 (1H, spt), 6.34-6.81 (1H, m), 7.26 (1H, dd, J=7.9, 4.9 Hz), 7.44-7.51 (1H, m), 7.57-7.64 (2H, m), 7.81-7.89 (1H, m), 8.20-8.27 (1H, m), 8.27-8.34 (1H, m), 8.56-8.70 (3H, m).

Example 43

2-Methyl-1-(2-{4-[1-(1-methylethyl)-1H-pyrazolo[4,3-b]pyridin-3-yl]phenoxy}-1H-benzimidazol-1-yl)propan-2-ol A mixture of 2-methyl-1-{2-[4-(4,4,5,5-tetramethyl-1,3,2-dioxaborolan-2-yl)phenoxy]-1H-benzimidazol-1-yl}propan-2-ol (237 mg), 3-bromo-1-(1-methylethyl)-1H-pyrazolo[4,3-b]pyridine (139 mg), Cs$_2$CO$_3$ (378 mg), Pd(PPh$_3$)$_4$ (20.1 mg), DME (5 mL), and water (1 mL) was stirred at 140° C. for 30 min under microwave irradiation. The reaction mixture was poured into water and extracted with AcOEt. The extract was washed with brine, dried over Na$_2$SO$_4$, and concentrated under reduced pressure. The residue was purified by silica gel column chromatography (AcOEt/hexane) and recrystallized from AcOEt/hexane to give the title compound (175 mg).

MS (API+): [M+H]$^+$442.4.

Example 44

1-Methyl-3-{4-[(3-methyl-3H-imidazo[4,5-b]pyridin-2-yl)oxy]phenyl}-1H-pyrazolo[4,3-b]pyridine A)
4-(1-Methyl-1H-pyrazolo[4,3-b]pyridin-3-yl)phenol To a stirred mixture of 3-[4-(benzyloxy)phenyl]-1H-pyrazolo[4,3-b]pyridine (300 mg) and Cs$_2$CO$_3$ (649 mg) in DMF (4 mL) was added MeI (0.093 mL) at 0° C. The mixture was stirred at room temperature for 12 h, treated with water, and extracted with AcOEt. The organic layer was dried over MgSO$_4$ and concentrated under reduced pressure. The residue was dissolved in EtOH (20 mL) and 10% Pd—C (50% wet, 200 mg) was added. The mixture was stirred for 1 h under H$_2$ atmosphere, filtered and evaporated. The residue was purified by silica gel column chromatography (AcOEt/hexane) to give the title compound (160 mg).

MS (API+): [M+H]$^+$226.3.

B) 1-Methyl-3-{(4-[(3-methyl-3H-imidazo[4,5-b]pyridin-2-yl)oxy]phenyl}-1H-pyrazolo[4,3-b]pyridine To a stirred solution of 4-(1-methyl-1H-pyrazolo[4,3-b]pyridin-3-yl)phenol (76 mg) in DMF (4 mL) was added NaH (60% in oil, 13.5 mg) at room temperature. The mixture was stirred at room temperature for 30 min, and then 3-methyl-2-(methylsulfonyl)-3H-imidazo[4,5-b]pyridine (71.3 mg) was added. The mixture was exposed to microwave irradiation at 180° C. for min, treated with water, and extracted with AcOEt. The organic layer was dried over MgSO$_4$ and concentrated under reduced pressure. The residue was purified, by basic silica gel column chromatography (AcOEt/hexane). The product was crystallized from AcOEt/hexane to give the title compound (40.0 mg).

MS (API+): [M+H]$^+$357.4.

$^1$H NMR (300 MHz, DMSO-d$_6$) δ 3.77 (3H, s), 4.17 (3H, s), 7.21 (1H, dd, J=7.9, 4.9 Hz), 7.45-7.55 (1H, m), 7.58-7.65 (2H, m), 7.76-7.86 (1H, m), 8.17-8.27 (2H, m), 8.54-8.64 (2H, m), 8.65-8.70 (1H, m).

Example 45

6-Fluoro-1-methyl-3-{4-[(3-methyl-3H-imidazo[4,5-b]pyridin-2-yl)oxy]phenyl}-1H-pyrazolo[4,3-b]pyridine

A) 4-(6-Fluoro-1-methyl-1H-pyrazolo[4,3-b]pyridin-3-yl)phenol

A mixture of [4-(benzyloxy)phenyl](3,5-difluoropyridin-2-yl)methanone (300 mg), methylhydrazine (212 mg) and 2-propanol (5 mL) was stirred at room temperature for 30 min, and then at 90° C. for 12 h, treated with water, and extracted with AcOEt. The organic layer was dried over MgSO$_4$ and concentrated under reduced pressure. The crude material was dissolved in EtOH (20 mL) and 10% Pd—C (50% wet, 98 mg) was added. The mixture was stirred for 1 h under H$_2$ atmosphere, filtered and evaporated. The residue was purified by silica gel column chromatography (AcOEt/hexane) to give the title compound (125 mg).

MS (API+): [M+H]$^+$244.1.

B) 6-Fluoro-1-methyl-3-{4-[(3-methyl-3H-imidazo[4,5-b]pyridin-2-yl)oxy]phenyl}-1H-pyrazolo[4,3-b]pyridine To a stirred solution of 4-(6-fluoro-1-methyl-1H-pyrazolo[4,3-b]pyridin-3-yl)phenol (120 mg) in DMF (4 mL) was added NaH (60% in oil, 11.84 mg) at room temperature. The mixture was stirred at room temperature for 30 min, and then 3-methyl-2-(methylsulfonyl)-3H-imidazo[4,5-b]pyridine (104 mg) was added. The mixture was exposed to microwave irradiation at 180° C. for 30 min, treated with water, and extracted with AcOEt. The organic layer was dried over MgSO$_4$ and concentrated under reduced pressure. The residue was purified by basic silica gel column chromatography (AcOEt/hexane). The product was crystallized from EtOH/hexane to give the title compound (80 mg).

MS (API+): [M+H]$^+$375.4.

$^1$H NMR (300 MHz, DMSO-d$_6$) δ 3.77 (3H, s), 4.13 (3H, s), 7.21 (1H, dd, J=7.9, 4.9 Hz), 7.62 (2H, d, J=8.7 Hz), 7.73-7.86 (1H, m), 8.16-8.32 (2H, m), 8.49-8.58 (2H, m), 8.68 (1H, d, J=2.6 Hz).

Example 46

1-Ethyl-3-{3-fluoro-4-[(3-methyl-3H-imidazo[4,5-b]pyridin-2-yl)oxy]phenyl}-1H-pyrazolo[4,3-b]pyridine

A) 2-(4-Bromo-2-fluorophenoxy)-3-methyl-3H-imidazo[4,5-b]pyridine

A suspension of 3-methyl-2-(methylsulfonyl)-3H-imidazo[4,5-b]pyridine (700 mg), 4-bromo-2-fluorophenol (0.399 mL) and NaH (60% in oil, 159 mg) was heated at 180° C. for 30 min under microwave irradiation. The mixture was quenched with water at room temperature and extracted with AcOEt. The organic layer was separated, washed with water and brine, dried over MgSO$_4$ and concentrated under reduced pressure. The residue was purified by silica gel column chromatography (AcOEt/hexane) to give the title compound (691 mg).

MS (ESI+): found: 322.3, 324.2.

B) 2-[2-Fluoro-4-(4,4,5,5-tetramethyl-1,3,2-dioxaborolan-2-yl)phenoxy]-3-methyl-3H-imidazo[4,5-b]pyridine The mixture of 2-(4-bromo-2-fluorophenoxy)-3-methyl-3H-imidazo[4,5-b]pyridine (685 mg), 4,4,4',4',5,5,5',5'-octamethyl-2,2'-bi(1,3,2-dioxaborolane) (810 mg), Pd(dppf)$_2$Cl$_2$ (22.7 mg) and KOAc (626 mg) in THF (10 mL)-DMSO (0.5 mL) was stirred at 80° C. under N$_2$ atmosphere for 5 h. The mixture was diluted with AcOEt and filtered on silica gel conditioned with AcOEt. The filtrate was concentrated under reduced pressure. The residue was purified by silica gel column chromatography (AcOEt in hexane) to give the title compound (781 mg).

MS (API+): [M+H]$^+$370.1.

C) 1-Ethyl-3-{3-fluoro-4-[(3-methyl-3H-imidazo[4,5-b]pyridin-2-yl)oxy]phenyl}-1H-pyrazolo[4,3-b]pyridine A mixture of 2-[2-fluoro-4-(4,4,5,5-tetramethyl-1,3,2-dioxaborolan-2-yl)phenoxy]-3-methyl-3H-imidazo[4,5-b]pyridine (350 mg), 3-bromo-1-ethyl-1H-pyrazolo[4,3-b]pyridine (214 mg), Pd(PPh$_3$)$_4$ (32.9 mg), Cs$_2$CO$_3$ (618 mg), DME (5 mL), and water (1 mL) was stirred at 140° C. for 30 min under microwave irradiation. The reaction mixture was poured into water and extracted with AcOEt. The extract was washed with brine, dried over Na$_2$SO$_4$, and concentrated under reduced pressure. The residue was purified by silica gel column chromatography (AcOEt/hexane) and recrystallized from AcOEt/hexane to give the title compound (264 mg).

MS (API+): [M+H]$^+$389.2.

Example 47

3-{3-Fluoro-4-[(3-methyl-3H-imidazo[4,5-b]pyridin-2-yl)oxy]phenyl}-1-(1-methylethyl)-1H-pyrazolo[4,3-b]pyridine The title compound was prepared by a similar manner as that of Example 46.

MS (API+): [M+H]$^+$403.1.

Example 48

1-Ethyl-6-fluoro-3-(4-{[3-(2-methoxyethyl)-3H-imidazo[4,5-b]pyridin-2-yl]oxy}phenyl)-1H-pyrazolo[4,3-b]pyridine To a stirred solution of 4-(1-ethyl-6-fluoro-1H-pyrazolo[4,3-b]pyridin-3-yl)phenol (57.6 mg) in DMF (4 mL) was added NaH (60% in oil, 5.38 mg) at room temperature. The mixture was stirred at room temperature for 30 min and then 3-(2-methoxyethyl)-2-(methylsulfonyl)-3H-imidazo[4,5-b]pyridine (52 mg) was added. The mixture was exposed to microwave irradiation at 180° C. for 30 min, treated with water, and extracted with AcOEt. The organic layer was dried over MgSO$_4$ and concentrated under reduced pressure. The residue was purified by basic silica gel column chromatography (AcOEt/hexane). The product was crystallized from EtOH/hexane to give the title compound (38.0 mg).

MS (API+): [M+H]$^+$433.3.

$^1$H NMR (300 MHz, DMSO-d$_6$) δ 1.47 (3H, t, J=7.0 Hz), 3.28 (3H, s), 3.82 (2H, t, J=5.5 Hz), 4.39-4.57 (4H, m), 7.21 (1H, dd, J=8.0, 4.9 Hz), 7.55-7.62 (2H, m), 7.76-7.83 (1H, m), 8.19-8.24 (1H, m), 8.30 (1H, dd, J=9.5, 2.7 Hz), 8.51-8.57 (2H, m), 8.65-8.69 (1H, m).

Example 49

1-(2,2-Difluoroethyl)-6-fluoro-3-(4-{[3-(2-methoxyethyl)-3H-imidazo[4,5-b]pyridin-2-yl]oxy}phenyl)-1H-pyrazolo[4,3-b]pyridine A) 3-[4-(Benzyloxy)phenyl]-6-fluoro-1H-pyrazolo[4,3-b]pyridine A mixture of [4-(benzyloxy)phenyl](3,5-difluoropyridin-2-yl)methanone (41 mg), hydrazine hydrate (31.5 mg) and 2-propanol (10 mL) was stirred at 90° C. for 12 h, treated with saturated NaHCO$_3$ aqueous solution, and extracted with AcOEt. The organic layer was dried over MgSO$_4$ and concentrated under reduced pressure. The residue was purified by silica gel column chromatography (AcOEt/hexane) to give the title compound (32.0 mg).

$^1$H NMR (300 MHz, DMSO-d$_6$) δ 5.18 (2H, s), 7.17 (2H, d, J=9.1 Hz), 7.28-7.56 (5H, m), 7.86-8.00 (1H, m), 8.34-8.42 (2H, m), 8.60 (1H, s), 13.39 (1H, brs).

B) 4-[1-(2,2-Difluoroethyl)-6-fluoro-1H-pyrazolo[4,3-b]pyridin-3-yl]phenol

To a stirred mixture of 3-[4-(benzyloxy)phenyl]-6-fluoro-1H-pyrazolo[4,3-b]pyridine (100 mg) and Cs$_2$CO$_3$ (204 mg) in DMF (4 mL) was added 2,2-difluoroethyl trifluoromethanesulfonate (73.8 mg) at 0° C. The mixture was stirred at room temperature for 12 h, treated with water, and extracted with AcOEt. The organic layer was dried over MgSO$_4$ and concentrated under reduced pressure. The residue was dissolved in EtOH (8 mL) and 10% Pd—C (50% wet, 100 mg) was added. The mixture was stirred at room temperature for 1 h under H$_2$ atmosphere, filtered and evaporated. The residue was purified by silica gel column chromatography (AcOEt/hexane) to give the title compound (47.0 mg).

MS (API+): [M+H]$^+$294.2.

C) 1-(2,2-Difluoroethyl)-6-fluoro-3-(4-{[3-(2-methoxyethyl)-3H-imidazo[4,5-b]pyridin-2-yl]oxy}phenyl)-1H-pyrazolo[4,3-b]pyridine To a stirred solution of 4-[1-(2,2-difluoroethyl)-6-fluoro-1H-pyrazolo[4,3-b]pyridin-3-yl]phenol (47 mg) in DMF (4 mL) was added NaH (60% in oil, 4.23 mg) at room temperature. The mixture was stirred at room temperature for 30 min, and then 3-(2-methoxyethyl)-2-(methylsulfonyl)-3H-imidazo[4,5-b]pyridine (52 mg) was added. The mixture was exposed to microwave irradiation at 180° C. for 30 min, treated with water, and extracted with AcOEt. The organic layer was dried over MgSO$_4$ and concentrated under reduced pressure. The residue was purified by basic silica gel column chromatography (AcOEt/hexane). The product was crystallized from EtOH/hexane to give the title compound (32.0 mg).

MS (API+): [M+H]$^+$469.1.

$^1$H NMR (300 MHz, DMSO-d$_6$) δ 3.28 (3H, s), 3.82 (2H, t, J=5.5 Hz), 4.44 (2H, t, J=5.5 Hz), 5.05 (2H, td, J=15.3, 3.4 Hz), 6.32-6.74 (1H, m), 7.22 (1H, dd, J=8.0, 4.9 Hz), 7.58-7.65 (2H, m), 7.77-7.84 (1H, m), 8.22 (1H, dd, J=4.9, 1.5 Hz), 8.28-8.35 (1H, m), 8.51-8.57 (2H, m), 8.72-8.75 (1H, m).

Example 50

6-Fluoro-3-(4-{[3-(2-methoxyethyl)-3H-imidazo[4,5-b]pyridin-2-yl]oxy}phenyl)-1-methyl-1H-pyrazolo[4,3-b]pyridine To a stirred solution of 4-(6-fluoro-1-methyl-1H-pyrazolo[4,3-b]pyridin-3-yl)phenol (37 mg) in DMF (4 mL) was added NaH (60% in oil, 4.02 mg) at room temperature. The mixture was stirred at room temperature for 30 min, and then 3-(2-methoxyethyl)-2-(methylsulfonyl)-3H-imidazo[4,5-b]pyridine (52 mg) was added. The mixture was exposed to microwave irradiation at 180° C. for 30 min, treated with water, and extracted with AcOEt. The organic layer was dried over MgSO$_4$ and concentrated under reduced pressure. The residue was purified by basic silica gel column chromatography (AcOEt/hexane). The product was crystallized from EtOH/hexane to give the title compound (28.0 mg).

MS (API+): [M+H]$^+$419.3.

$^1$H NMR (300 MHz, DMSO-d$_6$) δ 3.28 (3H, s), 3.82 (2H, t, J=5.5 Hz), 4.13 (3H, s), 4.44 (2H, t, J=5.5 Hz), 7.21 (1H, dd, J=8.0, 4.9 Hz), 7.59 (2H, d, J=8.7 Hz), 7.78-7.84 (1H, m), 8.19-8.28 (2H, m), 8.50-8.58 (2H, m), 8.66-8.70 (1H, m).

Example 51

1-(2,2-Difluoroethyl)-6-fluoro-3-{(4-[(3-methyl-3H-imidazo[4,5-b]pyridin-2-yl)oxy]phenyl}-1H-pyrazolo[4,3-b]pyridine To a stirred solution of 4-[1-(2,2-difluoroethyl)-6-fluoro-1H-pyrazolo[4,3-b]pyridin-3-yl]phenol (114 mg) in DMF (4 ml) was added NaH (60% in oil, 10.2 mg) at room temperature. The mixture was stirred at room temperature for 30 min, and then 3-methyl-2-(methylsulfonyl)-3H-imidazo[4,5-b]pyridine (82 mg) was added. The mixture was exposed to microwave irradiation at 180° C. for 30 min, treated with water, and extracted with AcOEt. The organic layer was dried over MgSO$_4$ and concentrated under reduced pressure. The residue was purified by basic silica gel column chromatography (AcOEt/hexane). The product was crystallized from EtOH/hexane to give the title compound (83 mg).

MS (API+): [M+H]$^+$425.3.

$^1$H NMR (300 MHz, DMSO-d$_6$) δ 3.77 (3H, s), 5.05 (2H, td, J=15.3, 3.4 Hz), 6.30-6.77 (1H, m), 7.21 (1H, dd, J=7.9, 4.9 Hz), 7.59-7.68 (2H, m), 7.76-7.83 (1H, m), 8.20-8.25 (1H, m), 8.29-8.36 (1H, m), 8.50-8.58 (2H, m), 8.73 (1H, d, J=1.5 Hz).

Example 52

1-(2,2-Difluoroethyl)-3-(4-{[3-(2-methoxyethyl)-3H-imidazo[4,5-b]pyridin-2-yl]oxy}phenyl)-1H-pyrazolo[4,3-b]pyridine To a stirred solution of 4-(1-(2,2-difluoroethyl)-1H-pyrazolo[4,3-b]pyridin-3-yl)phenol (50 mg) in DMF (4 mL) was added NaH (60% in oil, 4.80 mg) at room temperature. The mixture was stirred at room temperature for 30 min and then 3-(2-methoxyethyl)-2-(methylsulfonyl)-3H-imidazo[4,5-b]pyridine (52 mg) was added. The mixture was exposed to microwave irradiation at 180° C. for 30 min, treated with water, and extracted with AcOEt. The organic layer was dried over MgSO$_4$ and concentrated under reduced pressure. The residue was purified by basic silica gel column chromatography (AcOEt/hexane). The product was crystallized from AcOEt/hexane to give the title compound (24.0 mg).

MS (API+): [M+H]$^+$451.1.

$^1$H NMR (300 MHz, DMSO-d$_6$) δ 3.29 (3H, s), 3.82 (2H, t, J=5.5 Hz), 4.44 (2H, t, J=5.5 Hz), 5.08 (2H, td, J=15.5, 3.4 Hz), 6.32-6.75 (1H, m), 7.22 (1H, dd, J=7.9, 4.9 Hz), 7.52-7.65 (3H, m), 7.78-7.85 (1H, m), 8.18-8.24 (1H, m), 8.31 (1H, d, J=9.1 Hz), 8.60 (2H, d, J=9.1 Hz), 8.69-8.73 (1H, m).

Example 53

1-(2-{4-[1-(2,2-Difluoroethyl)-1H-pyrazolo[4,3-b]pyridin-3-yl]phenoxy}-1H-benzimidazol-1-yl)-2-methylpropan-2-ol The title compound was prepared by a similar manner as that of Example 43.
MS (API+): [M+H]$^+$ 464.2.
Example compounds are listed in Tables 1-9.

TABLE 1

| Example | Structure | Additive | MS [M + H]$^+$ |
|---|---|---|---|
| 1 | 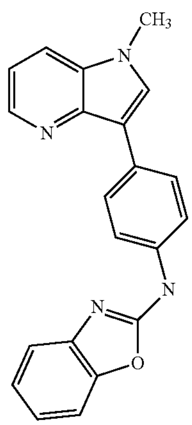 [SMILES: Cn1cc(-c2ccc(Nc3nc4ccccc4o3)cc2)c2ncccc21] | HCl | 341.0 |
| 2 | 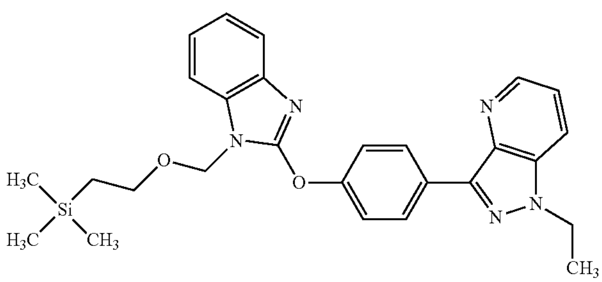 [SMILES: CCn1nc(-c2ccc(Oc3nc4ccccc4n3COCC[Si](C)(C)C)cc2)c2ncccc21] | | 486.6 |
| 3 | 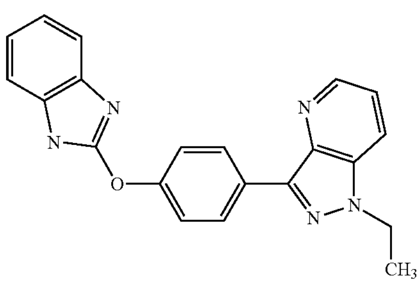 [SMILES: CCn1nc(-c2ccc(Oc3nc4ccccc4[nH]3)cc2)c2ncccc21] | | 356.1 |
| 4 | 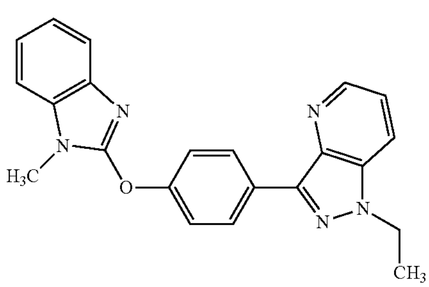 [SMILES: CCn1nc(-c2ccc(Oc3nc4ccccc4n3C)cc2)c2ncccc21] | | 370.2 |

TABLE 1-continued

| Example | Structure | Additive | MS [M + H]⁺ |
|---|---|---|---|
| 5 | 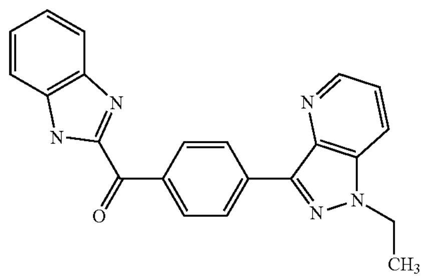 [SMILES: CCn1nc(-c2ccc(C(=O)c3nc4ccccc4[nH]3)cc2)c2ncccc21] | | 368.2 |
| 6 | 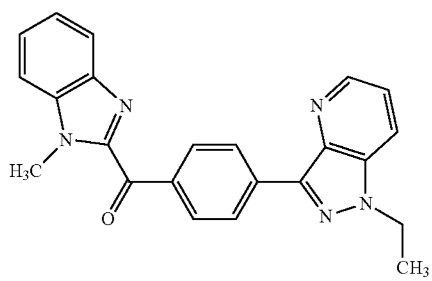 [SMILES: CCn1nc(-c2ccc(C(=O)c3nc4ccccc4n3C)cc2)c2ncccc21] | | 382.2 |

TABLE 2

| Example | Structure | Additive | MS [M + H]⁺ |
|---|---|---|---|
| 7 | 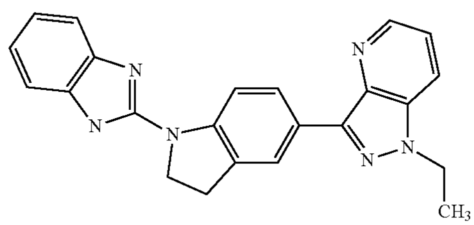 [SMILES: CCn1nc(-c2ccc3c(c2)CCN3c2nc3ccccc3[nH]2)c2ncccc21] | | 381.2 |
| 8 | 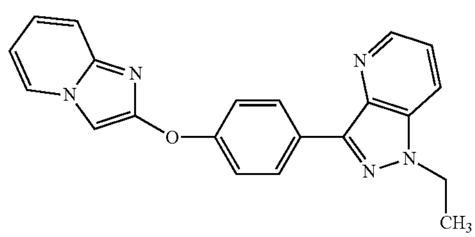 [SMILES: CCn1nc(-c2ccc(Oc3cn4ccccc4n3)cc2)c2ncccc21] | HCl | 356.2 |
| 9 | 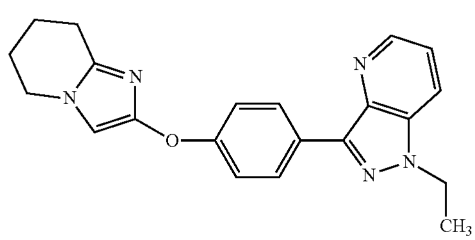 [SMILES: CCn1nc(-c2ccc(Oc3cn4c(n3)CCCC4)cc2)c2ncccc21] | HCl | 360.2 |

TABLE 2-continued

| Example | Structure | Additive | MS [M + H]+ |
|---|---|---|---|
| 10 | 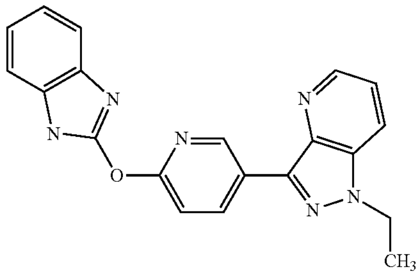 [SMILES: CCn1nc(-c2ccc(Oc3nc4ccccc4[nH]3)nc2)c2ncccc21] | | 357.4 |
| 11 | 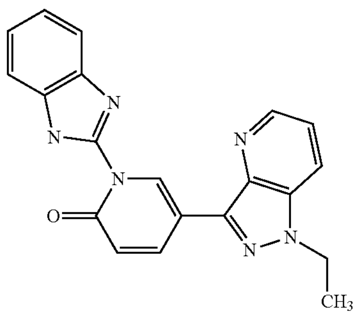 [SMILES: CCn1nc(-c2ccc(=O)n(-c3nc4ccccc4[nH]3)c2)c2ncccc21] | | 357.4 |
| 12 | 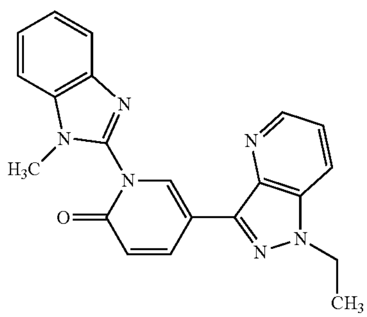 [SMILES: CCn1nc(-c2ccc(=O)n(-c3nc4ccccc4n3C)c2)c2ncccc21] | | 371.3 |

TABLE 3

| Example | Structure | Additive | MS [M + H]+ |
|---|---|---|---|
| 13 | 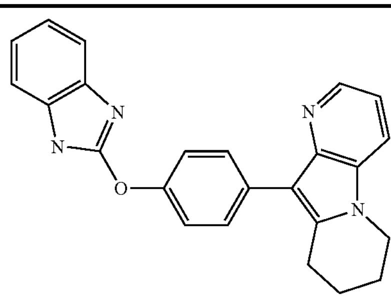 | | 381.2 |
| 14 | 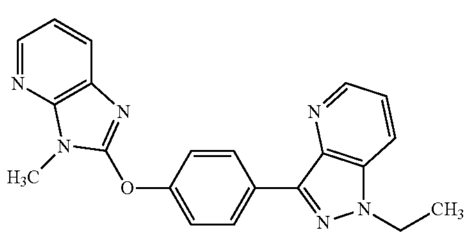 [SMILES: CCn1nc(-c2ccc(Oc3nc4cccnc4n3C)cc2)c2ncccc21] | | 371.3 |

TABLE 3-continued
| Example | Structure | Additive | MS [M + H]+ |
|---|---|---|---|
| 15 | 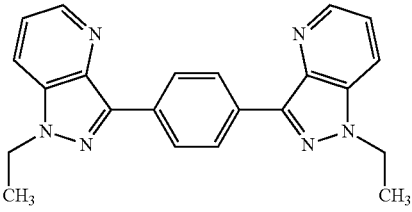 [SMILES: CCn1nc(-c2ccc(-c3nn(CC)c4cccnc34)cc2)c2ncccc21] | | 369.2 |
| 16 | 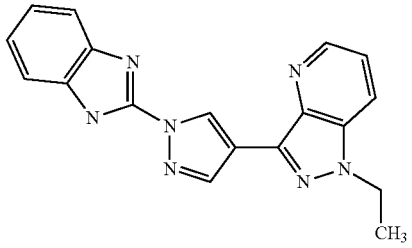 [SMILES: CCn1nc(-c2cnn(-c3nc4ccccc4[nH]3)c2)c2ncccc21] | | 330.4 |
| 17 | 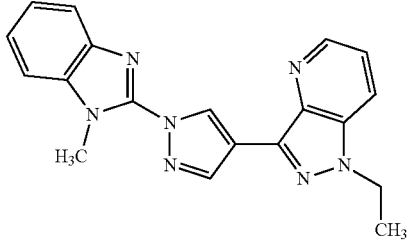 [SMILES: CCn1nc(-c2cnn(-c3nc4ccccc4n3C)c2)c2ncccc21] | | 344.2 |
| 18 | 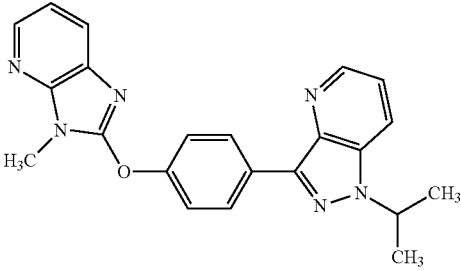 [SMILES: CC(C)n1nc(-c2ccc(Oc3nc4cccnc4n3C)cc2)c2ncccc21] | | 385.4 |
TABLE 4
| Example | Structure | Additive | MS [M + H]+ |
|---|---|---|---|
| 19 | 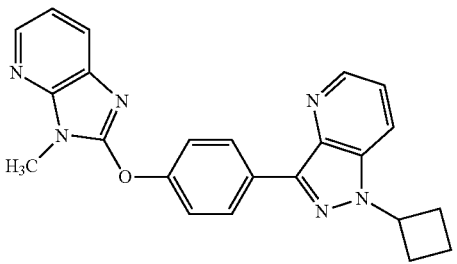 [SMILES: Cn1c(Oc2ccc(-c3nn(C4CCC4)c4cccnc34)cc2)nc2cccnc21] | | 397.4 |

TABLE 4-continued

| Example | Structure | Additive | MS [M + H]+ |
|---------|-----------|----------|-------------|
| 20 | 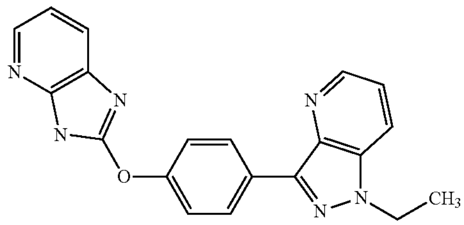 [SMILES: CCn1nc(-c2ccc(Oc3nc4cccnc4[nH]3)cc2)c2ncccc21] | | 357.2 |
| 21 | 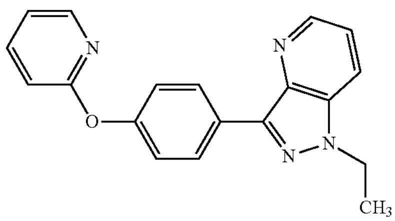 [SMILES: CCn1nc(-c2ccc(Oc3ccccn3)cc2)c2ncccc21] | | 317.0 |
| 22 | 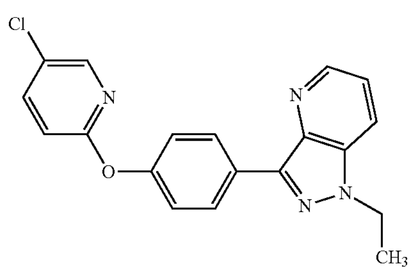 [SMILES: CCn1nc(-c2ccc(Oc3ccc(Cl)cn3)cc2)c2ncccc21] | | 351.1 |
| 23 | 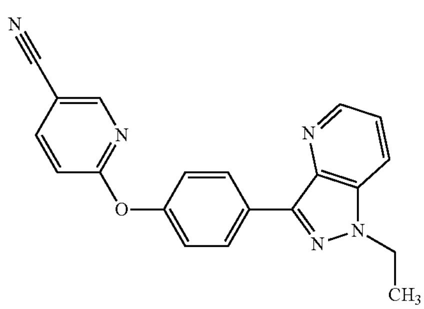 [SMILES: CCn1nc(-c2ccc(Oc3ccc(C#N)cn3)cc2)c2ncccc21] | | 342.1 |
| 24 | 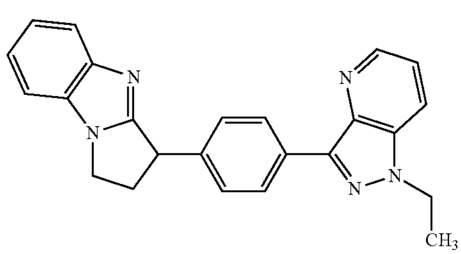 [SMILES: CCn1nc(-c2ccc(C3CCn4c3nc3ccccc34)cc2)c2ncccc21] | | 380.2 |

TABLE 5
| Example | Structure | Additive | MS [M + H]+ |
|---------|-----------|----------|-------------|
| 25 | 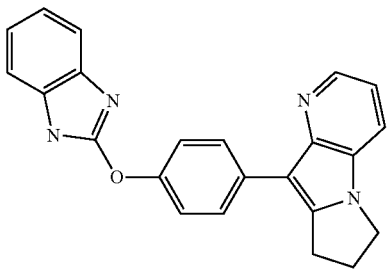 [SMILES: c1ccc2[nH]c(Oc3ccc(-c4c5n(c6cccnc46)CCC5)cc3)nc2c1] | | 367.1 |
| 26 | 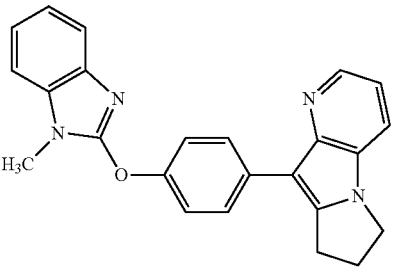 [SMILES: Cn1c(Oc2ccc(-c3c4n(c5cccnc35)CCC4)cc2)nc2ccccc21] | | 381.2 |
| 27 | 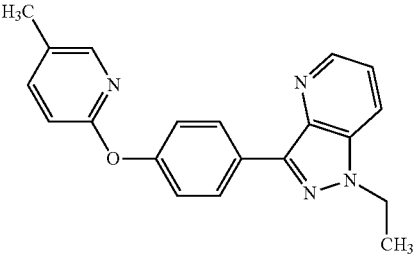 [SMILES: CCn1nc(-c2ccc(Oc3ccc(C)cn3)cc2)c2ncccc21] | | 331.1 |
| 28 | 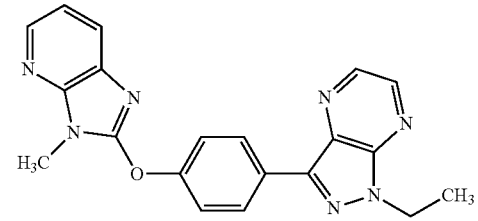 [SMILES: CCn1nc(-c2ccc(Oc3nc4cccnc4n3C)cc2)c2nccnc21] | | 372.1 |
| 29 | 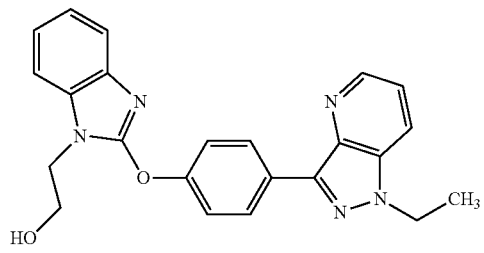 [SMILES: CCn1nc(-c2ccc(Oc3nc4ccccc4n3CCO)cc2)c2ncccc21] | | 400.1 |
| 30 | 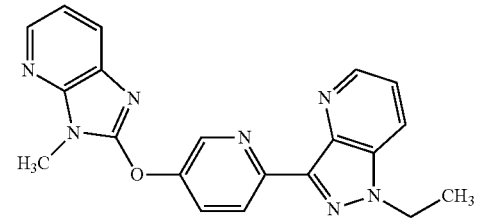 [SMILES: CCn1nc(-c2ccc(Oc3nc4cccnc4n3C)cn2)c2ncccc21] | | 372.1 |

TABLE 6
| Example | Structure | Additive | MS [M + H]+ |
|---|---|---|---|
| 31 | 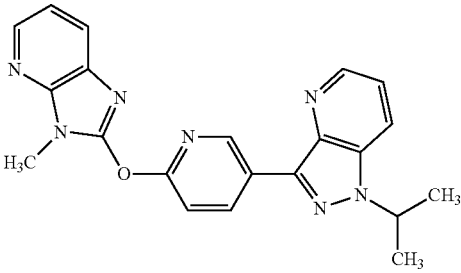 [SMILES: CC(C)n1nc(-c2ccc(Oc3nc4cccnc4n3C)nc2)c2ncccc21] | | 386.2 |
| 32 | 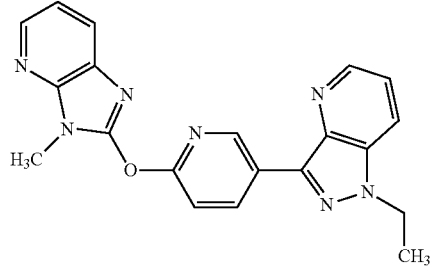 [SMILES: CCn1nc(-c2ccc(Oc3nc4cccnc4n3C)nc2)c2ncccc21] | | 372.4 |
| 33 | 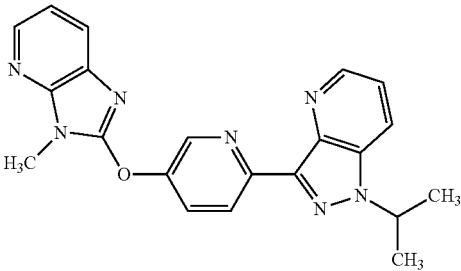 [SMILES: CC(C)n1nc(-c2ccc(Oc3nc4cccnc4n3C)cn2)c2ncccc21] | | 386.3 |
| 34 | 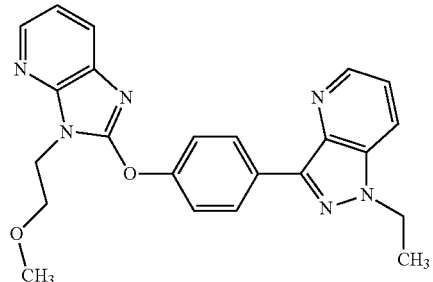 | | 415.1 |
| 35 | 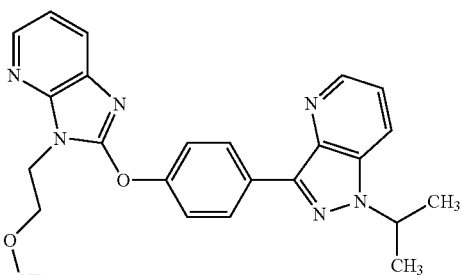 | | 429.2 |

TABLE 6-continued

| Example | Structure | Additive | MS [M + H]+ |
|---|---|---|---|
| 36 | 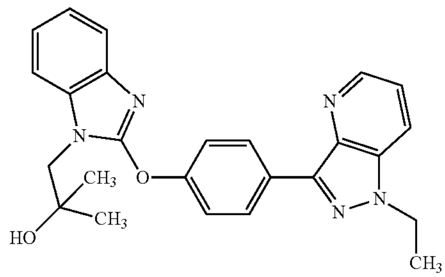 [SMILES: CCn1nc(-c2ccc(Oc3nc4ccccc4n3CC(C)(C)O)cc2)c2ncccc21] | | 428.3 |

TABLE 7

| Example | Structure | Additive | MS [M + H]+ |
|---|---|---|---|
| 37 | 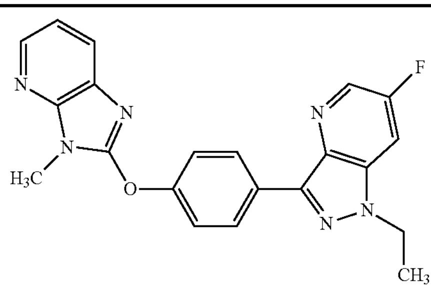 | | 389.3 |
| 38 | 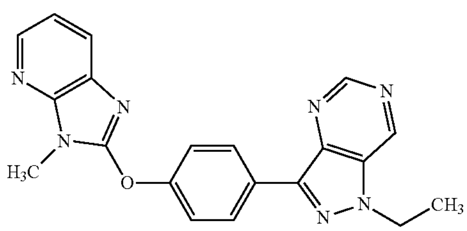 [SMILES: CCn1nc(-c2ccc(Oc3nc4cccnc4n3C)cc2)c2ncncc21] | | 372.2 |
| 39 | 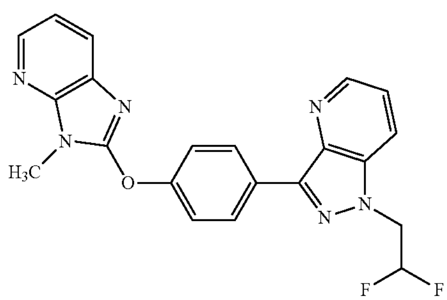 [SMILES: Cn1c(Oc2ccc(-c3nn(CC(F)F)c4cccnc34)cc2)nc2cccnc21] | | 407.2 |
| 40 | 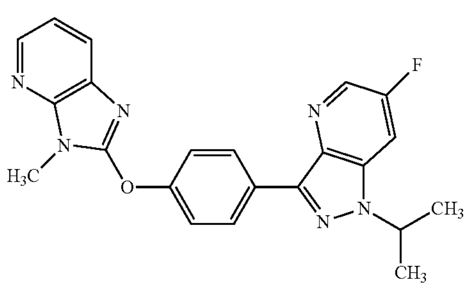 [SMILES: CC(C)n1nc(-c2ccc(Oc3nc4cccnc4n3C)cc2)c2ncc(F)cc21] | | 403.3 |

TABLE 7-continued

| Example | Structure | Additive | MS [M + H]+ |
|---|---|---|---|
| 41 | 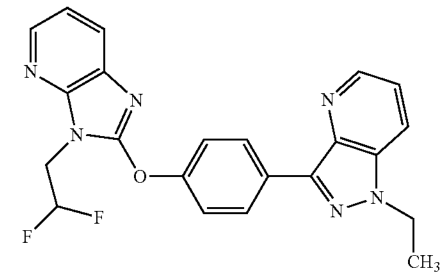 [SMILES: CCn1nc(-c2ccc(Oc3nc4cccnc4n3CC(F)F)cc2)c2ncccc21] | | 421.3 |
| 42 | 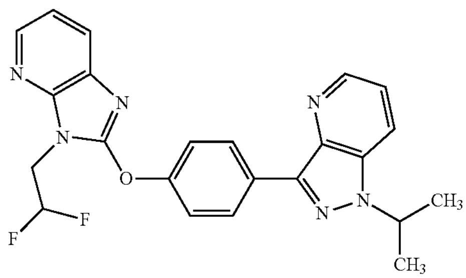 [SMILES: CC(C)n1nc(-c2ccc(Oc3nc4cccnc4n3CC(F)F)cc2)c2ncccc21] | | 435.4 |

TABLE 8

| Example | Structure | Additive | MS [M + H]+ |
|---|---|---|---|
| 43 | 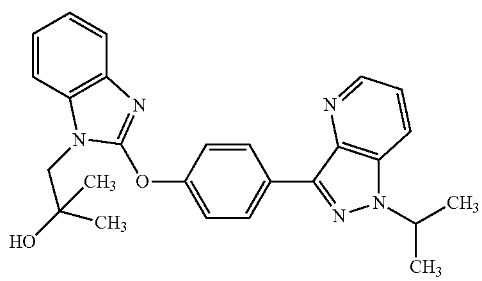 [SMILES: CC(C)n1nc(-c2ccc(Oc3nc4ccccc4n3CC(C)(C)O)cc2)c2ncccc21] | | 442.4 |
| 44 | 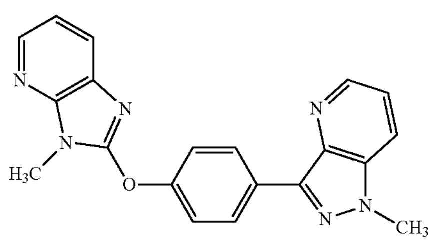 [SMILES: Cn1nc(-c2ccc(Oc3nc4cccnc4n3C)cc2)c2ncccc21] | | 357.4 |
| 45 | 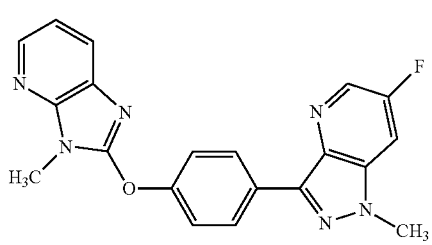 [SMILES: Cn1nc(-c2ccc(Oc3nc4cccnc4n3C)cc2)c2ncc(F)cc21] | | 375.4 |

TABLE 8-continued

| Example | Structure | Additive | MS [M + H]+ |
|---------|-----------|----------|-------------|
| 46 | 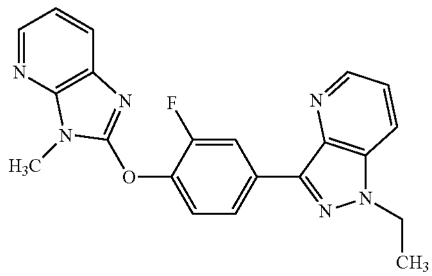 [SMILES: CCn1nc(-c2ccc(Oc3nc4cccnc4n3C)c(F)c2)c2ncccc21] | | 389.2 |
| 47 | 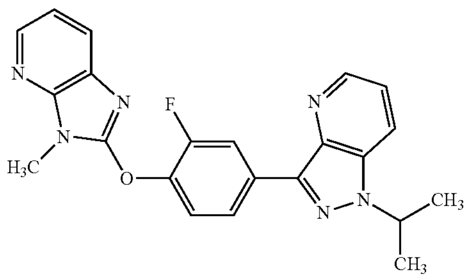 [SMILES: CC(C)n1nc(-c2ccc(Oc3nc4cccnc4n3C)c(F)c2)c2ncccc21] | | 403.1 |
| 48 | 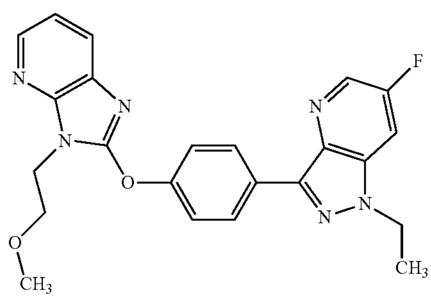 [SMILES: CCn1nc(-c2ccc(Oc3nc4cccnc4n3CCOC)cc2)c2ncc(F)cc21] | | 433.3 |

TABLE 9

| Example | Structure | Additive | MS [M + H]+ |
|---------|-----------|----------|-------------|
| 49 | 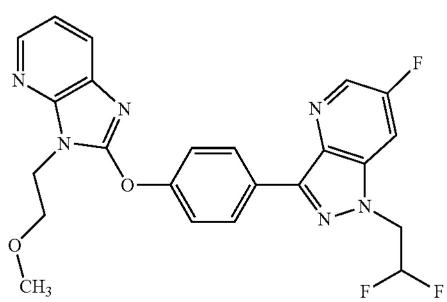 [SMILES: COCCn1c(Oc2ccc(-c3nn(CC(F)F)c4cc(F)cnc34)cc2)nc2cccnc21] | | 469.1 |

TABLE 9-continued

| Example | Structure | Additive | MS [M + H]+ |
|---------|-----------|----------|-------------|
| 50 | 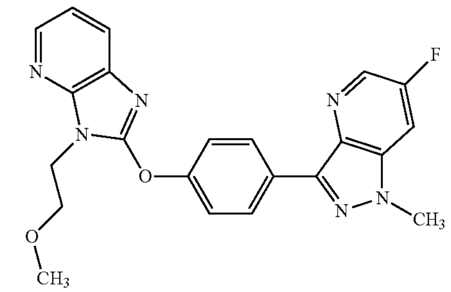 [SMILES: COCCn1c(Oc2ccc(-c3nn(C)c4cc(F)cnc34)cc2)nc2cccnc21] | | 419.3 |
| 51 | 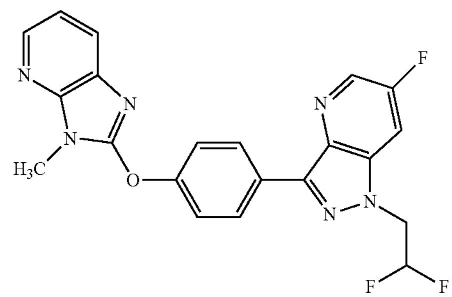 [SMILES: Cn1c(Oc2ccc(-c3nn(CC(F)F)c4cc(F)cnc34)cc2)nc2cccnc21] | | 425.3 |
| 52 | 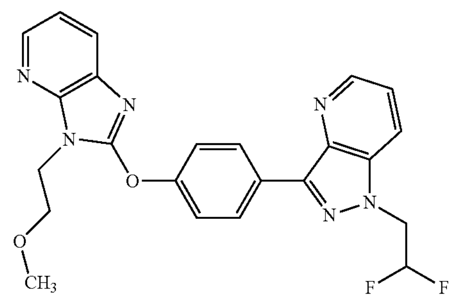 [SMILES: COCCn1c(Oc2ccc(-c3nn(CC(F)F)c4cccnc34)cc2)nc2cccnc21] | | 451.1 |
| 53 | 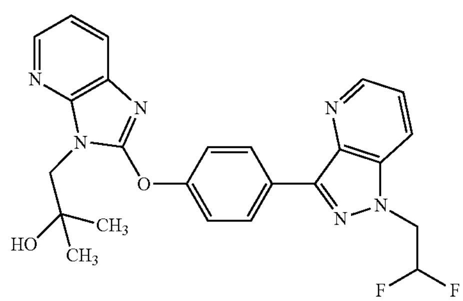 [SMILES: CC(C)(O)Cn1c(Oc2ccc(-c3nn(CC(F)F)c4cccnc34)cc2)nc2cccnc21] | | 464.2 |

Test Example 1

PDE Enzyme Inhibition

Human PDE10A enzyme was generated from Sf9 or COS-7 cells transfected with the full-length gene. Cloned enzyme was extracted from homogenized cell pellets. The extracted enzyme from sf9 cells was partially purified using His-tag affinity column. The enzyme was stored at −70° C. until use. PDE activity was measured using a SPA (Scintillation Proximity Assay) (GE Healthcare). To evaluate the inhibitory activity, 10 μL of serial diluted compounds were incubated with 20 μL of PDE enzyme in assay buffer (50 mM HEPES-NaOH, 8.3 mM $MgCl_2$, 1.7 mM EGTA, 0.1% BSA (pH 7.4)) for 30 min. at room temperature. Final concentration of DMSO in the assay was 1 percent as compounds were tested in duplicate in 96-well half-area plates (Corning). To start the reaction, 10 μL of substrate [$^3$H] cGMP (25 or 50 nM; enclosed in SPA kits from GE Healthcare or purchased from PerkinElmer, respectively) was added for a final assay volume of 40 μL. After 60 min incubation at room temperature, yttrium SPA beads containing Zinc sulphate were added (20 μL at 6 mg/mL) to terminate the PDE reaction. After being settled for 60 min, assay plates were counted in a scintillation counter (PerkinElmer) to allow calculation of inhibition rate. Inhibition rate was calculated on the basis of 0% control wells with DMSO and 100% control wells without enzyme. The results are shown in Table 10.

TABLE 10

| Example No. | % inhibition at 1 μM |
|---|---|
| 1 | 97.6 |
| 3 | 97.7 |
| 4 | 98.7 |
| 6 | 95 |
| 7 | 101 |
| 8 | 100 |
| 10 | 99 |
| 13 | 103 |
| 18 | 100 |
| 24 | 99 |
| 28 | 101 |
| 34 | 105 |
| 35 | 93 |
| 36 | 99 |
| 37 | 101 |
| 38 | 103 |
| 39 | 102 |
| 40 | 101 |
| 44 | 107 |
| 45 | 95 |
| 48 | 104 |
| 49 | 103 |
| 50 | 100 |
| 51 | 102 |
| 52 | 101 |

Test Example 2

Inhibition of MK-801-Induced Hyperlocomotion

Animals

Male ICR mice were supplied by CLEA Japan, Inc (Japan). After arrival to the vivarium, animals were allowed more than 1 week for acclimation. They were housed under a 12 h-12 h light/dark cycle in a temperature- and humidity-controlled laboratory and allowed food and water ad libitum. The care and use of the animals and the experimental protocols used in this research were approved by the Experimental Animal Care and Use Committee of Takeda Pharmaceutical Company, Ltd (Osaka, Japan).

Drug Administration

The compounds were suspended in 0.5% (w/v) methylcellulose in distilled water, and administered by orally. (+)-MK-801 hydrogen maleate (Sigma-Aldrich, St Louis, Mo.) was dissolved in saline, and administered subcutaneously (s.c.). All drugs were dosed in a volume of 20 mL/kg body weight for mice.

Inhibition of MK-801-Induced Hyperlocomotion

The widely used animal models of psychosis have been the measurement of the extent of hyperlocomotion induced by psychostimulants (e.g., amphetamine, cocaine, methamphetamine, MK-801 and phencyclidine) in rodents (Schizophrenia Bulletin 2010, vol. 36: 1066-1072; Psychopharmacology 1999, vol. 145: 237-250). The compounds were tested for its ability to antagonize MK-801-induced hyperlocomotion in mice. Male ICR mice (30-43 g) were habituated to the locomotor chambers with infrared sensors (Brain Science Idea Co., Ltd. Japan) for more than 60 min. Animals were removed from each chamber and treated with either vehicle or test compounds (p.o.) and immediately returned to the chamber. After 60 min, animals were again removed from the chambers and treated with either saline or MK-801 (0.3 mg/kg, s.c.), and then immediately returned to the test chamber. Activity count was recorded every 1 min bins. Total amounts of activity were measured during 120 min after MK-801 treatment. Data are represented as means plus the standard errors of the means (n=10-12). Statistical analysis was performed with the Welch's t-test for comparison between control group and MK-801+vehicle treated group with significance set at ***$P<0.001$ and the Steel's test for comparisons with vehicle-treated group with significance set at #$P<0.05$.

The Results are shown in FIG. 1.

Compounds in figures (FIG. 1) correspond to the following example.

Compound A (Example 36)
Compound B (Example 37)
Compound C (Example 39)
Compound D (Example 45)
Compound E (Example 48)

By orally administered 60 min before MK-801 (0.3 mg/kg, s.c.) treatment, compounds produced the inhibition of MK-801-induced hyperlocomotion.

Formulation Example 1

| | |
|---|---|
| (1) Compound of the Example 1 | 10.0 g |
| (2) Lactose | 70.0 g |
| (3) Cornstarch | 50.0 g |
| (4) Soluble starch | 7.0 g |
| (5) Magnesium stearate | 3.0 g |

After 10.0 g of the compound in Embodiment 1 and 3.0 g of magnesium stearate are granulated in 70 mL aqueous solution of soluble starch (7.0 g as soluble starch) and then dried, the resulting mixture is mixed with 70.0 g of lactose and 50.0 g of cornstarch (lactose, cornstarch, soluble starch and magnesium stearate are all products in compliance with Japanese Pharmacopoeia $14^{th}$ Edition). The mixture is compressed to obtain a tablet.

INDUSTRIAL APPLICABILITY

The compound of the present invention is useful as a prophylactic or therapeutic drug for schizophrenia and the like.

This application is based on provisional patent application Nos. 61/370,566 and 61/427,271 filed in U.S.A., the contents of which are hereby incorporated by reference.

Although the present invention have been presented or described by referring to preferred embodiments of this invention, it will, however, be understood by those of ordinary skill in the art that various modifications may be made to the forms and details without departing from the scope of the invention as set forth in the appended claims. All patents, patent publications and other publications indicated or cited in the Specification are hereby incorporated in their entireties by reference.

CITATION LIST

Patent Documents patent document 1: WO2008/004117
patent document 2: WO2010/0057121
patent document 3: WO2010/057126
patent document 4: WO2006/072828
patent document 5: WO2008/001182
patent document 6: WO2010/063610
patent document 7: WO2006/044821
patent document 8: JP-A-2010-111624
patent document 9: WO2010/051781
patent document 10: US 2008/0045561 A1
patent document 11: WO2010/090737

Non-Patent Documents non-patent document 1: Nat. Rev. Drug Disc. 2006, vol. 5: 660-670
non-patent document 2: Circ. Res. 2007, vol. 100(7): 950-966
non-patent document 3: Proc. Natl. Acad. Sci. USA 1999, vol. 96: 8991-8996,
non-patent document 4: J. Biol. Chem. 1999, vol. 274: 18438-18445, Gene 1999, vol. 234: 109-117
non-patent document 5: Eur. J. Biochem. 1999, vol. 266: 1118-1127
non-patent document 6: J. Biol. Chem. 1999, vol. 274: 18438-18445
non-patent document 7: Eur. J. Biochem. 1999, vol. 266: 1118-1127
non-patent document 8: Brain Res. 2003, vol. 985: 113-126

The invention claimed is:

1. A compound represented by the formula (1'):

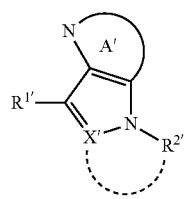

(1')

wherein,
Ring A' represents (1) an optionally substituted pyridine ring wherein the 4-position is unsubstituted, (2) an optionally substituted pyridazine ring, (3) an unsubstituted pyrimidine ring, or (4) an unsubstituted pyrazine ring,
$R^{1'}$ represents a group represented by

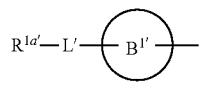

wherein,
$R^{1a'}$ represents a 5- to 10-membered heterocyclic group which may be substituted by 1 to 3 substituents selected from a group consisting of
(1) a $C_{1-6}$ alkyl group which may be substituted by 1-3 substituents selected from the group consisting of (a) a 2-(trimethylsilyl)ethoxy group, (b) a hydroxy group, (c) a $C_{1-6}$ alkoxy group and (d) a halogen atom;
(2) a halogen atom; and
(3) a cyano group,
L' represents bond, —O—, —CO— or —NH, and
Ring B$^{1'}$ represents
(1) a benzene ring which may be substituted by a halogen atom,
(2) an unsubstituted pyridine ring,
(3) a dihydropyridine ring which may be substituted by an oxo group, or (4) an unsubstituted pyrazole ring, or
alternatively, L' and $R^{1a'}$ may be taken together to form

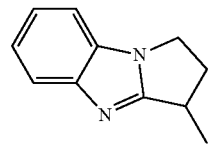

$R^{2'}$ represents a hydrogen atom, or a substituent,
X' represents =N— or =$CR^{b'}$— ($R^{b'}$ represents a hydrogen atom, or a substituent),
- - - - - represents that $R^{b'}$ and $R^{2'}$ may form, taken together with the carbon atom and the nitrogen atom to which they are each adjacent, an optionally substituted 5- to 7-membered ring when X' is =$CR^{b'}$—,
provided that:
5-ethoxy-3-[3-(morpholin-4-ylcarbonyl)phenyl]-1H-pyrazolo[4,3-b]pyridine
is excluded;
or a salt thereof.

2. A compound represented by the formula (1):

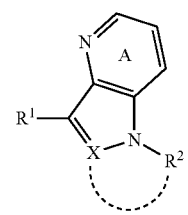

(1)

wherein,
Ring A represents an optionally substituted pyridine ring wherein the 4-position is unsubstituted,
$R^1$ represents a group represented by

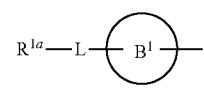

wherein,
$R^{1a}$ represents a 5- to 10-membered heterocyclic group which may be substituted by 1 to 3 substituents selected from a group consisting of
(1) a $C_{1-6}$ alkyl group which may be substituted by 1-3 substituents selected from the group consisting of (a) a 2-(trimethylsilyl)ethoxy group, (b) a hydroxy group, (c) a $C_{1-6}$ alkoxy group and (d) a halogen atom;
(2) a halogen atom; and
(3) a cyano group,
L represents bond, —O—, —CO— or —NH, and
Ring B$^1$ represents
(1) a benzene ring which may be substituted by a halogen atom,
(2) an unsubstituted pyridine ring,
(3) a dihydropyridine ring which may be substituted by an oxo group, or (4) an unsubstituted pyrazole ring, or
alternatively, L' and $R^{1a}$ may be taken together to form

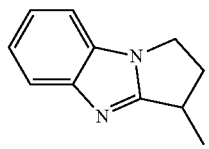

$R^2$ represents a hydrogen atom, or a substituent,
X represents =N— or =$CR^b$— ($R^b$ represents a hydrogen atom, or a substituent),
- - - - - represents that $R^b$ and $R^2$ may form, taken together with the carbon atom and the nitrogen atom to which they are each adjacent, an optionally substituted 5- to 7-membered ring when X is =$CR^b$—,
provided that
5-ethoxy-3-[3-(morpholin-4-ylcarbonyl)phenyl]-1H-pyrazolo[4,3-b]pyridine
is excluded;
or a salt thereof.

3. The compound according to claim 2, wherein Ring A is a pyridine ring wherein the 4-position is unsubstituted, and the other positions may be substituted by substituent(s) selected from the group consisting of (i) an optionally substituted $C_{1-6}$ alkyl group, (ii) an optionally substituted $C_{1-6}$ alkoxy group, (iii) a halogen atom and (iv) a cyano group, or a salt thereof.

4. The compound according to claim 2, wherein Ring A is a pyridine ring wherein the 4-position is unsubstituted, and the other positions may be substituted by a halogen atom, or a salt thereof.

5. The compound according to claim 2, or a salt thereof, wherein $R^2$ is an optionally substituted $C_{1-6}$ alkyl group.

6. The compound according to claim 2, wherein L is —O—, or a salt thereof.

7. 1-(2,2-Difluoroethyl)-3-{4-[(3-methyl-3H-imidazo[4,5-b]pyridin-2-yl)oxy]phenyl}-1H-pyrazolo[4,3-b]pyridine, or a salt thereof.

8. 6-Fluoro-1-methyl-3-{4-[(3-methyl-3H-imidazo[4,5-b]pyridin-2-yl)oxy]phenyl}-1H-pyrazolo[4,3-b]pyridine, or a salt thereof.

9. 1-Ethyl-6-fluoro-3-(4-{[3-(2-methoxyethyl)-3H-imidazo[4,5-b]pyridin-2-yl]oxy}phenyl)-1H-pyrazolo[4,3-b]pyridine, or a salt thereof.

10. A medicament comprising the compound according to claim 1 or 2, or a salt thereof.

11. The medicament according to claim 10 which is an agent for inhibiting phosphodiesterase 10A.

* * * * *

UNITED STATES PATENT AND TRADEMARK OFFICE
CERTIFICATE OF CORRECTION

PATENT NO. : 9,029,536 B2  
APPLICATION NO. : 13/814073  
DATED : May 12, 2015  
INVENTOR(S) : Joseph Raker Page 1 of 1

It is certified that error appears in the above-identified patent and that said Letters Patent is hereby corrected as shown below:

In the claims

Column 151, line 60, in claim 1 change "L' represents bond, -O-, -CO- or –NH, and" to --L' represents bond, -O-, -CO- or -NH-, and--.

Column 152, line 13, in claim 1 change "X' represents =N-or=CR$^{b'\text{-}(Rb'}$ represents a hydrogen" to --X' represents =N- or =CR$^{b'}$- (R$^{b'}$ represents a hydrogen--.

Column 152, line 60, in claim 2 change "L represents bond, -O-, -CO- or –NH, and" to --L represents bond, -O-, -CO- or -NH-, and--.

Signed and Sealed this  
Tenth Day of November, 2015

Michelle K. Lee  
*Director of the United States Patent and Trademark Office*